(12) United States Patent
Moyle

(10) Patent No.: US 8,603,974 B2
(45) Date of Patent: Dec. 10, 2013

(54) SALMON FOLLITROPIN HORMONE ANALOGS

(76) Inventor: William R. Moyle, Piscataway, NJ (US)

( * ) Notice: Subject to any disclaimer, the term of this patent is extended or adjusted under 35 U.S.C. 154(b) by 0 days.

(21) Appl. No.: 13/114,861

(22) Filed: May 24, 2011

(65) Prior Publication Data

US 2012/0021984 A1    Jan. 26, 2012

Related U.S. Application Data

(63) Continuation of application No. 11/911,571, filed as application No. PCT/US2006/014103 on Apr. 13, 2006, now abandoned.

(60) Provisional application No. 60/671,117, filed on Apr. 13, 2005.

(51) Int. Cl.
    *A61K 38/24*    (2006.01)
    *C07K 14/00*    (2006.01)
    *C07K 14/59*    (2006.01)

(52) U.S. Cl.
    USPC ........................... 514/9.9; 530/350; 530/398

(58) Field of Classification Search
    None
    See application file for complete search history.

(56) References Cited

PUBLICATIONS

Wells, J. A. "Additivity of mutational effects in proteins." Biochemistry 29(37): 8509-17. (1990).
Ngo, et al. "Computational complexity, protein structure prediction, and the Levinthal Paradox." In Merz, K., Jr., and LeGrand, S., eds., The Protein Folding Problem and Tertiary Structure Prediction, chap. 14, pp. 492-495. Birkhauser, Boston, MA. (1994).
Bork, P. "Powers and Pitfalls in Sequence Analysis: The 70% Hurdle." Genome Res. 10: 398-400. (2000).
Skolnick et al. "From genes to protein structure and function: novel applications of computational approaches in the genomic era." Trends in Biotechnology 18: 34-39. (2000).
Doerks et al. "Protein annotation: detective work for function prediction." Trends Genet. 14(6):248-50. (1998).
Smith et al. "The challenges of genome sequence annotation or 'The devil is in the details.'" Nature Biotechnology 15: 1222-1223 (1997).
Brenner SE. "Errors in genome annotation." Trends in Genetics 15: 132-133. (1999).
Bork et al. "Go hunting in sequence databases but watch out for the traps." Trends in Genetics 12 : 425-427. (1996).
Lapthorn et al. "Crystal structure of human chorionic gonadotropin." Nature 369, 455-461. (1994).
Xing et al. "Glycoprotein Hormone Assembly in the Endoplasmic Reticulum. III. The Seatbelt and Its Latch Site Determine the Assembly Pathway." J Biol Chem. 279:35449-35457. (2004).
Sastre et al. "Current trends in the treatment of polycystic ovary syndrome with desire for children." Therapeutics and Clinical Risk Management 5: 353-360. (2009).
Wang et al. "Rapid analysis of gene expression (RAGE) facilitates universal expression profiling." Nucleic Acids Res. 27(23):4609-18. (1999).
Kaufman et al. "Transgenic Analysis of a 100-kb Human ?-Globin Cluster-Containing DNA Fragment Propagated as a Bacterial Artificial Chromosome." Blood 94: 3178-3184. (1999).
Phillips, J. A. "The challenge of gene therapy and DNA delivery." J. Pharm. Pharmacology 53: 1169-1174. (2001).
Tokuriki et al. "Stability effects of mutations and protein evolvability." Current Opinion in Structural Biology 19(5): 596-604. (2009).
Xing et al. "Glycoprotein Hormone Assembly in the Endoplasmic Reticulum. IV. Probable Mechanism of Subunit Docking and Completion of Assembly." J Biol Chem.279:35458-35468. (2004).
Xing et al. "Glycoprotein Hormone Assembly in the Endoplasmic Reticulum. I. The Glycosylated End of Human ?-Subunit Loop 2 Is Threaded through a ?-Subunit Hole." J Biol Chem. 279:35426-35436. (2004).
Xing et al. "Alternatively Folded Choriogonadotropin Analogs." J. Biol. Chem. 276(50): 46953-46960. (2001.
Bernard et al. "Only a Portion of the Small Seatbelt Loop in Human Choriogonadotropin Appears Capable of Contacting the Lutropin Receptor." J. Biol. Chem. 279(43): 44438-44441. (2004).
Hillier, S. G. "The Parkes Lecture: Controlled ovarian stimulation in women." Journal of Reproduction and Fertility 120: 201-210. (2000).
Schally et al. "New approaches to treatment of various cancers based on cytotoxic analogs of LHRH, somatostatin and Bombesin." Life Sciences 72(21): 2305-2320. (2003).
Xing et al. "Threading of a glycosylated protein loop through a protein hole: Implications for combination of human chorionic gonadotropin subunits." Protein Science 10(2): 226-235. (2001).
Related U.S. Appl. No. 11/911,571, filed Oct. 15, 2007.

*Primary Examiner* — Elizabeth C Kemmerer
*Assistant Examiner* — Christina Borgeest
(74) *Attorney, Agent, or Firm* — Fox Rothschild LLP

(57) ABSTRACT

This invention relates to the field of glycoprotein hormone analogs and their uses as agonists, antagonists, targeting vectors, and immunogens. In particular, this invention describes a method for stabilizing a heterodimer that permits the preparation of functional glycoprotein hormone analogs. The analogs of present invention comprise at least one alpha subunit polypeptide and at least one beta subunit polypeptide, wherein the seatbelt region of the beta subunit is linked to the alpha subunit. The invention also provides for a beta subunit polypeptide wherein the C-terminal amino acid is from residue 10 to residue 20 of the seatbelt region.

14 Claims, 47 Drawing Sheets

Overview of glycoprotein hormone structure in most vertebrates.

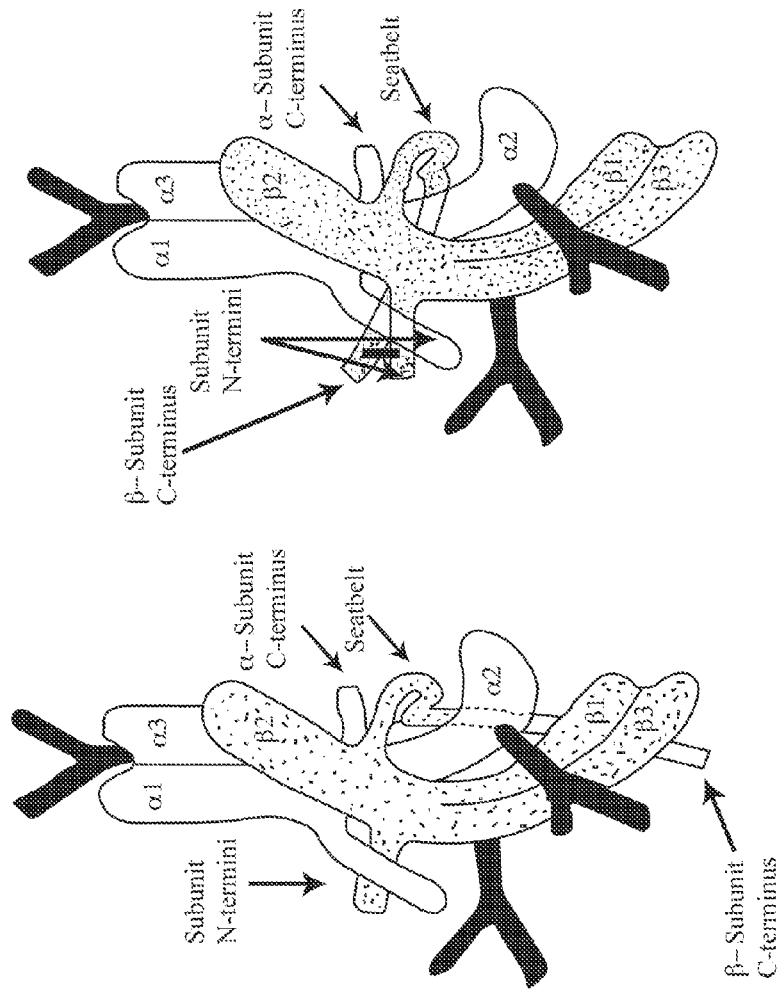
Overview of glycoprotein hormone structure in some teleost fish.

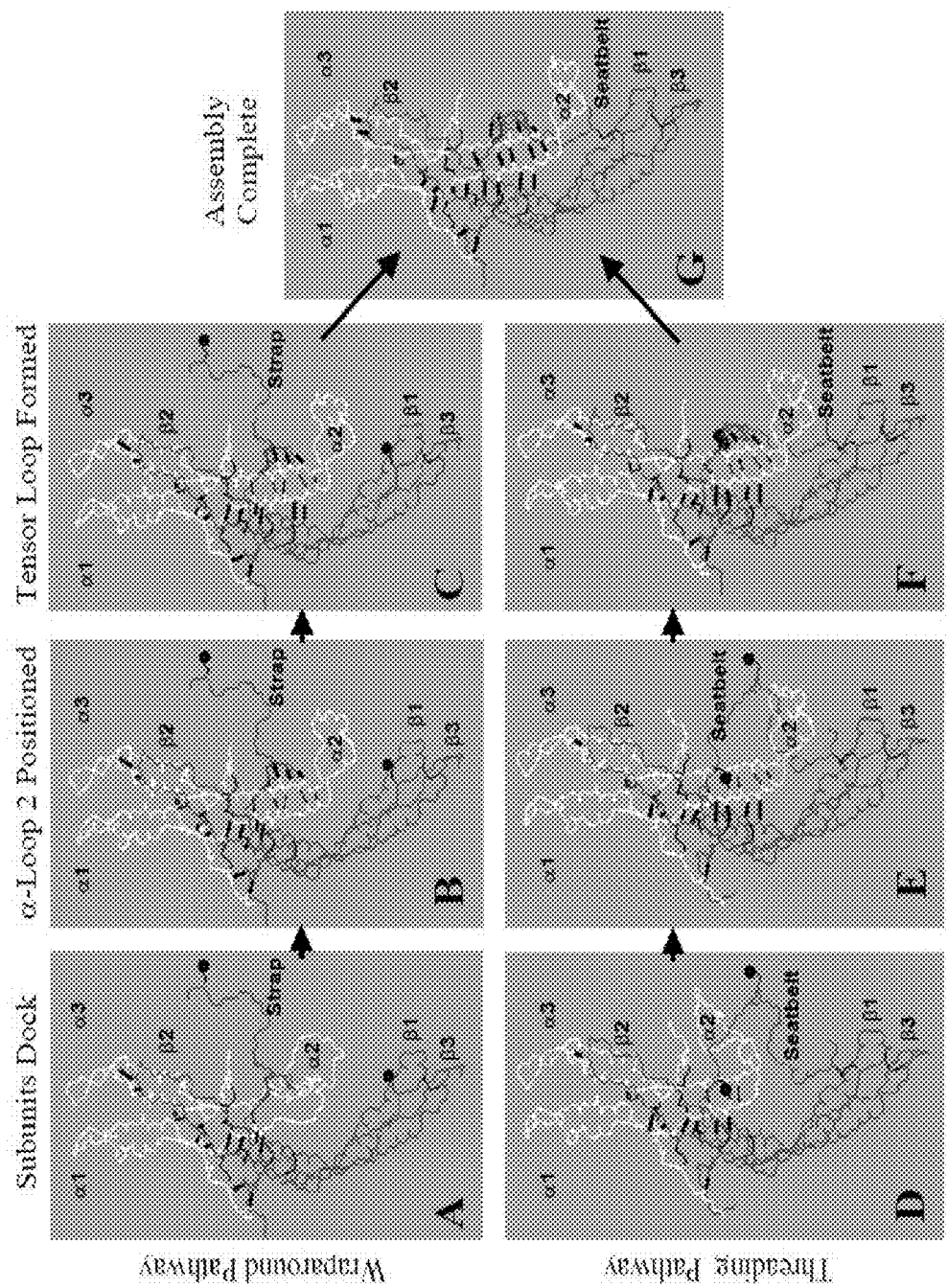
Fig. 3. Pathways of heterodimer assembly

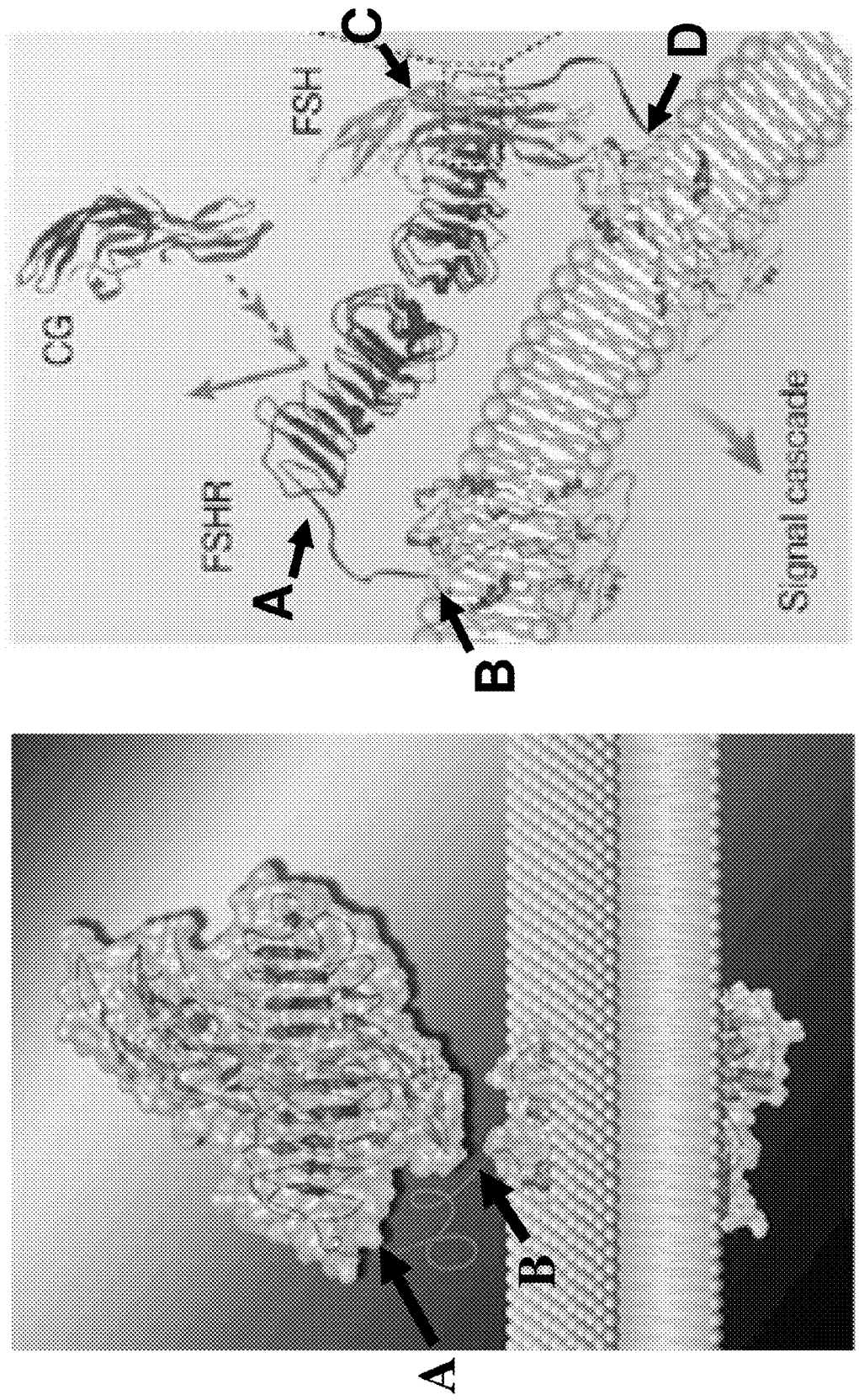
Fig. 4. Most widely viewed structures of glycoprotein hormones

Fig. 5. Models describing alternate view of glycoprotein hormone receptor.
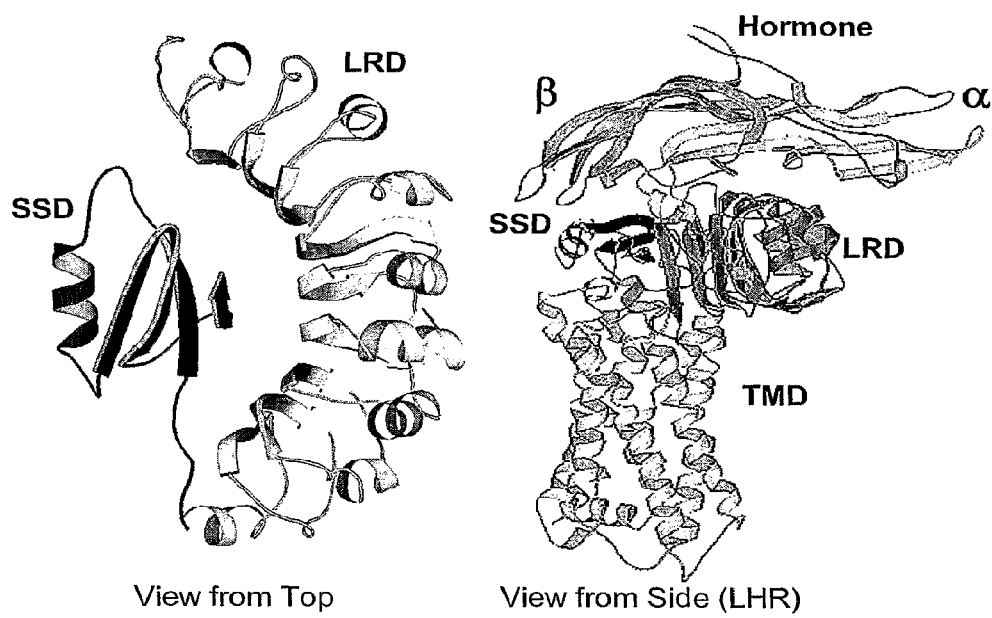
View from Top    View from Side (LHR)
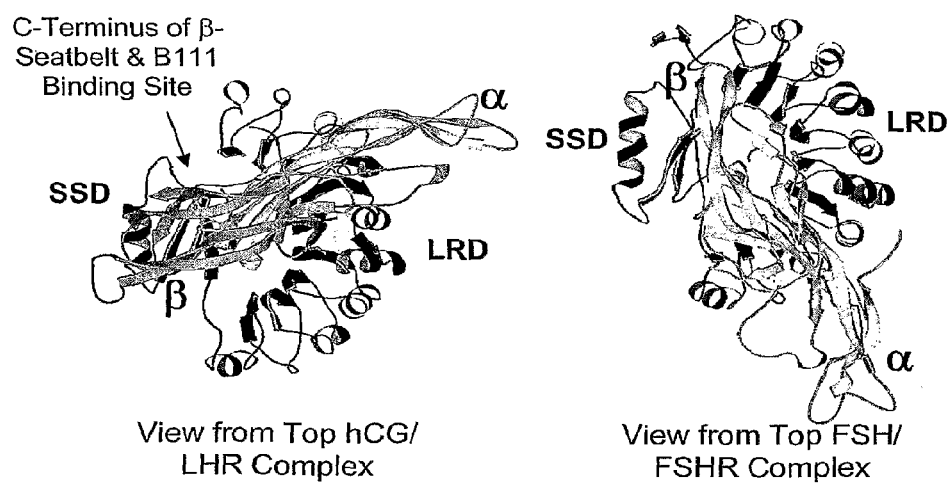
View from Top hCG/LHR Complex    View from Top FSH/FSHR Complex

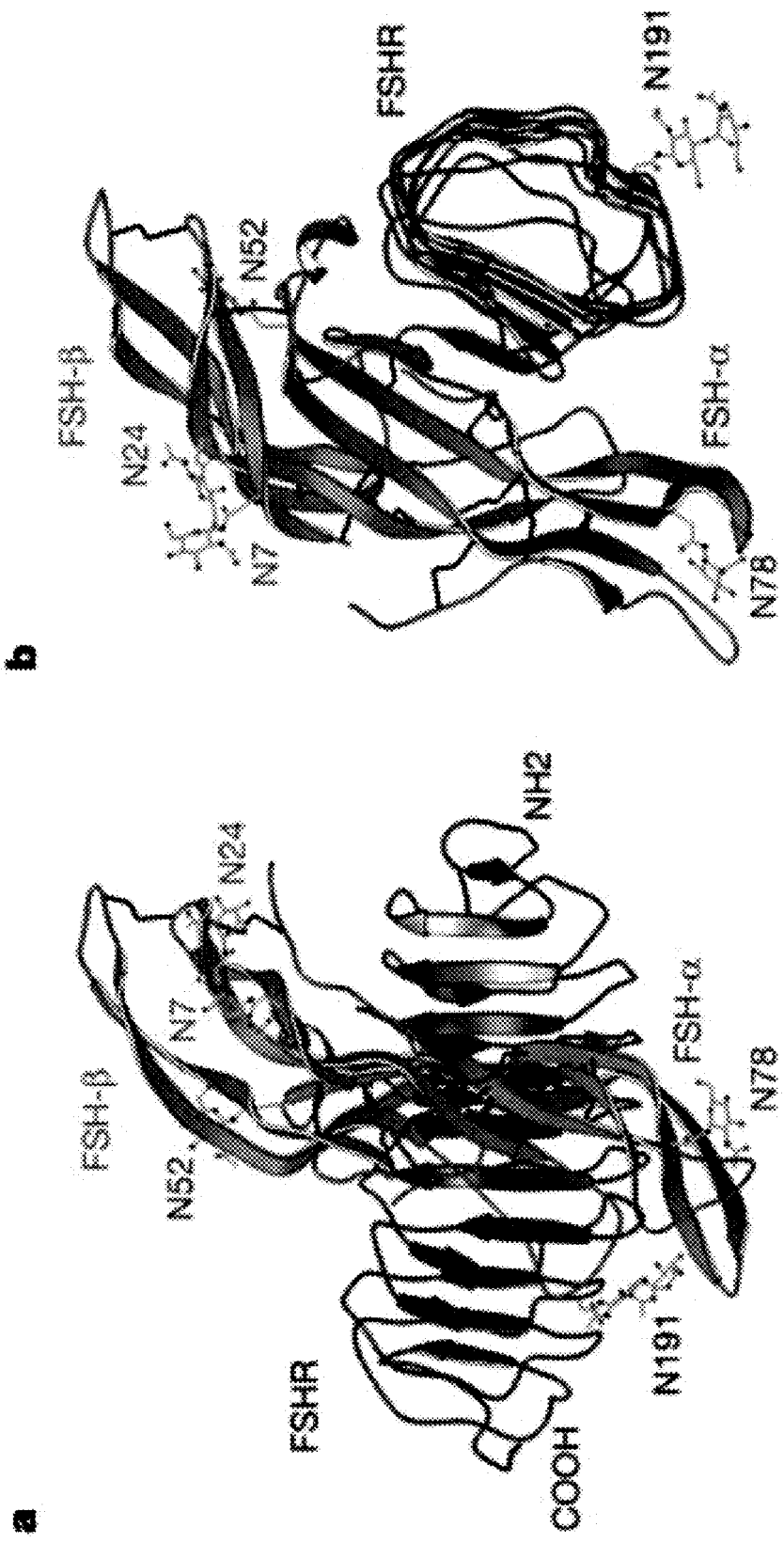
Fig. 6. Crystal Structure of the hFSH-hFSH Receptor Fragment.

Fig. 7. Mechanism of Signal Transduction based on the Crystal Structure
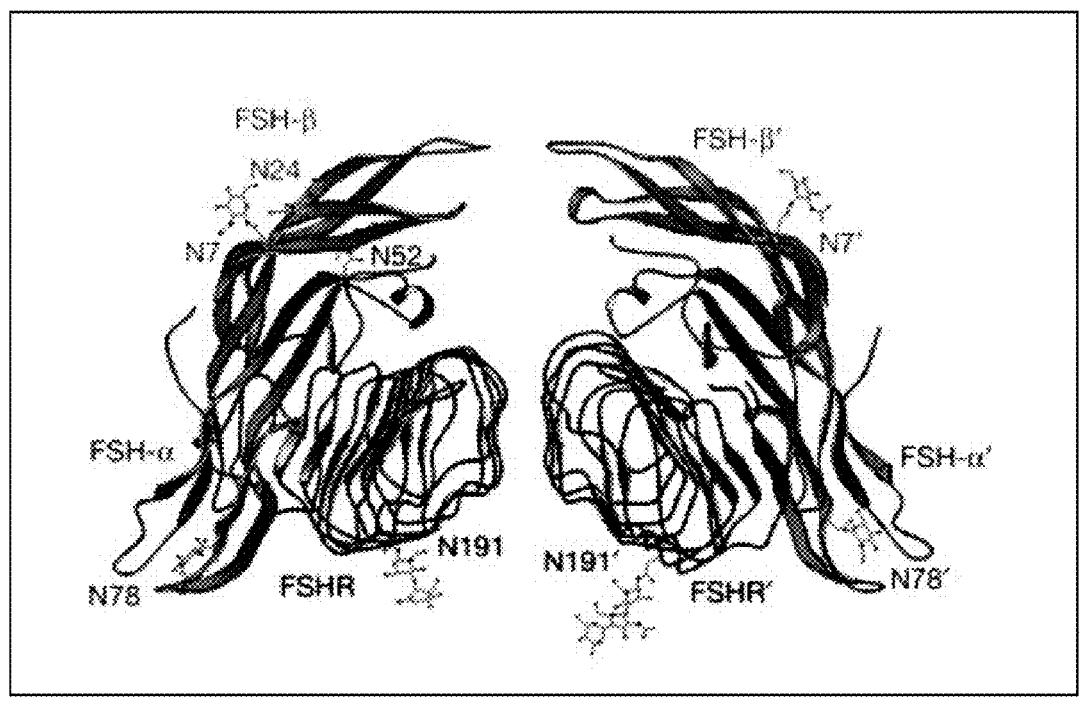
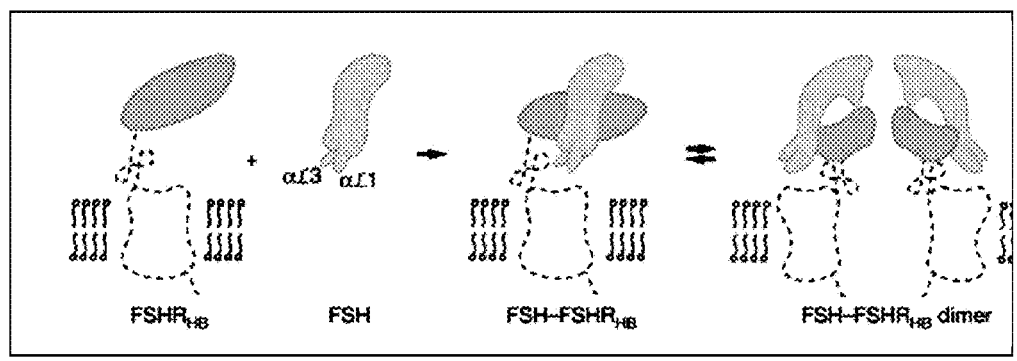

Fig. 8. Sequences of Constructs used in these studies.

SEQ ID NO: 1 pEX1. Amino acid sequence encoded by a chimera salmon-human α-subunit analog.

MDYYRKYAAIFLVTLSVFLHVLHSAPDVCDCPECTLQENPFFSQPGAPILQCMGCCFSRAY
PTPLRSKQTMLVPKNITSEATCCVAKSYNRVTVMGGFKVENHTACHCSCCYYHKS

SEQ ID NO: 2 pEX2. Amino acid sequence encoded by a chimeric salmon-human α-subunit analog that has positive residues in α-subunit loop 1.

MDYYRKYAAIFLVTLSVFLHVLHSAPDVCDCPECKLKENKFFSKPGAPILQCMGCCFSRAY
PTPLRSKQTMLVPKNITSEATCCVAKSYNRVTVMGGFKVENHTACHCSCCYYHKS

SEQ ID NO: 3 pEX3. Amino acid sequence encoded by a chimeric salmon FSH hCG β-subunit analog that has residues derived from hCG in loop 2.

METDTLLLWVLLLWVPGSTGDYKAKELASGTDCRYGCRLNNMTITVEREDCHGSITITTCA
GLCPTMTRVLQGVLPALPQVVCNFKEWSYEKVYLEGCPSGVDPFFIPVAKSCDCIKCKTDN
TDCDCISMATPGSFEQT

SEQ ID NO: 4 pEX4. Amino acid sequence encoded by a chimeric salmon FSH - hCG β-subunit analog that has residues derived from hCG in loop 3.

METDTLLLWVLLLWVPGSTGDYKAKELASGTDCRYGCRLNNMTITVEREDCHGSITITTCA
GLCETTDLNYQSTWLPRSQGVCNFKEWSYESIRLPGCPRGVNPVFIPVAKSCDCIKCKTDN
TDCDCISMATPGSFEQT

SEQ ID NO: 5 pEX5. sequence an αβ construct containing a chimeric human/salmon α-subunit linked to a truncated salmon FSIIβ subunit by the hCG β-subunit carboxyterminus and a Furin cleavage site.

MDYYRKYAAIFLVTLSVFLHVLHSAPDVQDCPECTLQENPFFSQPGAPILQCMGCCFSRAY
PTPLRSKQTMLVPKNITSEATCCVAKSYNRVTVMGGFKVENHTACHCSCCYYHKSDDPRFQ
DSSSSKAPPPSLPSPSRLPGPSDTPILPQRRFKRPRCRLNNMTITVEREDCHGSITITTCA
GLCETTDLNYQSTWLPRSQGVCNFKEWSYEKVYLEGCPSGVDPFFIPVAKSCDCIKCKTDN
TDCDC

SEQ ID NO: 6 pEX6. Amino acid sequence encoded by a Flag salmon FSH β-subunit analog that has an additional glycosylation signal on loop 3 and can be expressed with pRM917 to form a doubly crosslinked heterodimer.

METDTLLLWVLLLWVPGSTGDYKAKELASGTDCRYGCRLNNMTITVEREDCHGSITITTCA
GLCETTDLNYQSTWLPRSQGVCNFKEWSYEKVYLEGCPSGVNSTFIPVAKSCDCIKCKTDN
TDCDCISMATPGSFEQT

Fig. 8 (cont.)
SEQ ID NO: 7 pMB574 Amino acid sequence encoded by the human α-subunit construct.

MDYYRKYAAIFLVTLSVFLHVLHSAPDVQDCPECTLQENPFFSQPGAPILQCMGCCFSRAY
PTPLRSKKTMLVQKNVTSESTCCVAKSYNRVTVMGGFKVENHTACHCSTCYYHKS

SEQ ID NO: 8 pMB584 Amino acid sequence encoded by the hCG β-subunit construct.

MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCGG
PKDHPLTCDDPRFQDSSSSKAPPPSLPSPSRLPGPSDTPILPQ

SEQ ID NO: 9 pMB1010 Amino acid sequence encoded by the α-subunit construct used to express α-T86C.

MDYYRKYAAIFLVTLSVFLHVLHSAPDVQDCPECTLQENPFFSQPGAPILQCMGCCFSRAY
PTPLRSKKTMLVQKNVTSESTCCVAKSYNRVTVMGGFKVENHTACHCSCCYYHKS

SEQ ID NO: 10 pMB1197 Amino acid sequence encoded by the α-subunit construct used to express Fos-α.

MEMFQGLLLLLLLSMGGTWASGLTDTLQAETDQLEDKKSALQTEIANLLKEKEKLEFILAGQDCPEC
TLQENPFFSQPGAPILQCMGCCFSRAYPTPLRSKKTMLVQKNVTSESTCCVAKSYNRVTVMGGFKVE
NHTACHCSTCYYHKS

SEQ ID NO: 11 pMB1243 Amino acid sequence encoded by the human α-subunit construct α-R35C,N52D.

MDYYRKYAAIFLVTLSVFLHVLHSAPDVQDCPECTLQENPFFSQPGAPILQCMGCCFSCAY
PTPLRSKKTMLVQKDVTSESTCCVAKSYNRVTVMGGFKVENHTACHCSTCYYHKS

SEQ ID NO: 12 pMB1244 Amino acid sequence encoded by the human α-subunit construct α-Y37C,N52D.

MDYYRKYAAIFLVTLSVFLHVLHSAPDVQDCPECTLQENPFFSQPGAPILQCMGCCFSRAC
PTPLRSKKTMLVQKDVTSESTCCVAKSYNRVTVMGGFKVENHTACHCSTCYYHKS

SEQ ID NO: 13 pMB1326 Amino acid sequence encoded by the hCG-hFSH β-subunit chimera construct hCF(101-109)β-I33C,δ115.

MEMFQGLLLLLLLSMGGTWASKEPLRPRCRPINATLAVEKEGCPVCITVNTTCAGYCPTM
TRVLQGVLPALPQVVCNYRDVRFESIRLPGCPRGVNPVVSYAVALSCQCALCRRSTTDCTV
RGLGPSYCDDPR

Fig. 8 (cont.)
SEQ ID NO: 14 pMB1328 Amino acid sequence encoded by the hCG-hFSH β-subunit chimera construct hCF(101-109)β-A35C,δ115.

MEMFQGLLLLLLLSMGGTWASKEPLRPRCRPINATLAVEKEGCPVCITVNTTICCGYCPTM
TRVLQGVLPALPQVVCNYRDVRFESIRLPGCPRGVNPVVSYAVALSCQCALCRRSTTDCTV
RGLGPSYCDDPR

SEQ ID NO: 15 pMB2376 Amino acid sequence encoded by the β-subunit construct used to express salmon FSHβ,CG-tail MEMFQGLLLLLLLSMGGTWASGTDCRYGCRLNNMTITVEREDCHGSITITTCAGLCETTDL
NYQSTWLPRSQGVCNFKEWSYEKVYLEGCPSGVDPFFIPVAKSCDCIKCKTDNTDCDRISM
ATPSCIVNPLEFQDSSSSKAPPPSLPSPSRLPGPSDTPILPQ SEQ ID NO: 16 pMB2419 Amino acid sequence encoded by the β-subunit construct used to express hCGβ-C26A, G102C,δ103.

MEMFQGLLLLLLLSMGGTWASKEPLRPRCRPINATLAVEKEGCPVAITVNTTICAGYCPTM
TRVLQGVLPALPQVVCNYRDVRFESIRLPGCPRGVNPVVSYAVALSCQCALCRRSTTDCGC

SEQ ID NO: 17 pMB2472 Amino acid sequence encoded by the α-subunit construct used to express α-N52D, T86C MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKS SEQ ID NO: 18 pMB2480 Amino acid sequence encoded by the β-subunit construct used to express salmon β-C4A, CG-tail MEMFQGLLLLLLLSMGGTWASGTDARYGCRLNNMTITVEREDCHGSITITTCAGLCETTDL
NYQSTWLPRSQGVCNFKEWSYEKVYLEGCPSGVDPFFIPVAKSCDCIKCKTDNTDCDRISM
ATPSCIVNPLEFQDSSSSKAPPPSLPSPSRLPGPSDTPILPQ SEQ ID NO: 19 pMB2484 Amino acid sequence encoded by the β-subunit construct used to express hCGβ-K2N,P4T,N13D,C26A,N30D,G102C,δ103

MEMFQGLLLLLLLSMGGTWASNETLRPRCRPIDATLAVEKEGCPVAITVDTTICAGYCPTM
TRVLQGVLPALPQVVCNYRDVRFESIRLPGCPRGVNPVVSYAVALSCQCALCRRSTTDCGC

SEQ ID NO: 20 pMB2487 Amino acid sequence encoded by the β-subunit construct used to express Flag-Salmon-FSHβ-C4A, CG-tail METDTLLLWVLLLWVPGSTGDYKAKELASGTDARYGCRLNNMTITVEREDCHGSITITTCA
GLCETTDLNYQSTWLPRSQGVCNFKEWSYEKVYLEGCPSGVDPFFIPVAKSCDCIKCKTDN
TDCDRISMATPSCIVNPLEFQDSSSSKAPPPSLPSPSRLPGPSDTPILPQ Fig. 8 (cont.)
SEQ ID NO: 21 pMB2497 Amino acid sequence encoded by the β-subunit construct used to express Flag Salmon-FSHβ-C4A, R102C δ103

METDTLLLWVLLLWVPGSTGDYKAKELASGTDARYGCRLNNMTITVEREDCHGSITITTCA
GLCETTDLNYQSTWLPRSQGVCNFKEWSYEKVYLEGCPSGVDPFFIPVAKSCDCIKCKTDN
TDCDC

SEQ ID NO: 22 pMB2498 Amino acid sequence encoded by the β-subunit construct used to express hCGβ-C26A, G102C, C110A MEMFQGLLLLLLLSMGGTWASKEPLRPRCRPINATLAVEKEGCPVAITVNTTICAGYCPTM
TRVLQGVLPALPQVVCNYRDVRFESIRLPGCPRGVNPVVSYAVALSCQCALCRRSTTDCGC
PKDHPLTADDPRFQDSSSSKAPPPSLPSPSRLPGPSDTPILPQ SEQ ID NO: 23 pMB2501 Amino acid sequence encoded by the α-subunit construct used to express human α-N52D, T86C, CG-tail, S143C, βla MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDDPRFQ
DSSSSKAPPPSLPSPSRLGPCDTPILPQHPETLVKVKDAEDQLGARVGYIELDLNSGKILE
SFRPEERFPMMSTFKVLLCGAVLSRIDAGQEQLGRRIHYSQNDLVEYSPVTEKHLTDGMTV
RELCSAAITMSDNTAANLLLTTIGGPKELTAFLHNMGDHVTRLDRWEPELNEAIPNDERDT
TMPVAMATTLRKLLTGELLTLASRQQLIDWMEADKVAGPLLRSALPAGWFIADKSGAGERG
SRGIIAALGPDGKPSRIVVIYTTGSQATMDERNRQIAEIGASLIKHW SEQ ID NO: 24 pMB2531 Amino acid sequence encoded by the α-subunit construct used to express human α-N52D, T86C, CG-tail, βla MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDDPRFQ
DSSSSKAPPPSLPSPSRLGPSDTPILPQHPETLVKVKDAEDQLGARVGYIELDLNSGKILE
SFRPEERFPMMSTFKVLLCGAVLSRIDAGQEQLGRRIHYSQNDLVEYSPVTEKHLTDGMTV
RELCSAAITMSDNTAANLLLTTIGGPKELTAFLHNMGDHVTRLDRWEPELNEAIPNDERDT
TMPVAMATTLRKLLTGELLTLASRQQLIDWMEADKVAGPLLRSALPAGWFIADKSGAGERG
SRGIIAALGPDGKPSRIVVIYTTGSQATMDERNRQIAEIGASLIKHW SEQ ID NO: 25 pMB2537 Amino acid sequence encoded by the β-subunit construct used to express hCGβ-C26A, N13D, G102C, δ103

MEMFQGLLLLLLLSMGGTWASKEPLRPRCRPIDATLAVEKEGCPVAITVNTTICAGYCPTM
TRVLQGVLPALPQVVCNYRDVRFESIRLPGCPRGVNPVVSYAVALSCQCALCRRSTTDCGC

SEQ ID NO: 26 pMB2538 Amino acid sequence encoded by the α-subunit construct used to express human α- A1S (δ2-5) N52D,T86C.

MEMFQGLLLLLLLSMGGTWASDCPECTLQENPFFSQPGAPILQCMGCCFSRAYPTPLRSKK
TMLVQKDVTSESTCCVAKSYNRVTVMGGFKVENHTACHCSCCYYHKS

Fig. 8 (cont.)
SEQ ID NO: 27 pMB2543 Amino acid sequence encoded by the α-subunit construct used to express human α-N52D, E56C MDYYRKYAAIFLVTLSVFLHVLHSAPDVQDCPECTLQENPFFSQPGAPILQCMGCCFSRAY
PTPLRSKKTMLVQKDVTSCSTCCVAKSYNRVTVMGGFKVENHTACHCSTCYYHKS SEQ ID NO: 28 pMB2544#1 Amino acid sequence encoded by the α-subunit construct used to express human α-N52D,T54C MDYYRKYAAIFLVTLSVFLHVLHSAPDVQDCPECTLQENPFFSQPGAPILQCMGCCFSRAY
PTPLRSKKTMLVQKDVCSESTCCVAKSYNRVTVMGGFKVENHTACHCSTCYYHKS SEQ ID NO: 29 pMB2544#11 Amino acid sequence encoded by the α-subunit construct used to express human α-T54C MDYYRKYAAIFLVTLSVFLHVLHSAPDVQDCPECTLQENPFFSQPGAPILQCMGCCFSRAY
PTPLRSKKTMLVQKNVCSESTCCVAKSYNRVTVMGGFKVENHTACHCSTCYYHKS SEQ ID NO: 30 pMB2545 Amino acid sequence encoded by the β-subunit construct used to express hCGβ-(δ2-5) R8C, C26A, G102C, δ103.

MEMFQGLLLLLLLSMGGTWASRPCCRPINATLAVEKEGCPVAITVNTTICAGYCPTMTRVL
QGVLPALPQVVCNYRDVRFESIRLPGCPRGVNPVVSYAVALSCQCALCRRSTTDCGC

SEQ ID NO: 31 pMB2546 Amino acid sequence encoded by the β-subunit construct used to express hCGβ-(δ2-4) L5C, C26A, G102C, δ103.

MEMFQGLLLLLLLSMGGTWASCRPRCRPINATLAVEKEGCPVAITVNTTICAGYCPTMTRV
LQGVLPALPQVVCNYRDVRFESIRLPGCPRGVNPVVSYAVALSCQCALCRRSTTDCGC

SEQ ID NO: 32 pMB2548 Amino acid sequence encoded by the β-subunit construct used to express hCG/hFSH chimera CF(94-97)β-C26A,G102C,δ103.

MEMFQGLLLLLLLSMGGTWASKEPLRPRCRPINATLAVEKEGCPVAITVNTTICAGYCPTM
TRVLQGVLPALPQVVCNYRDVRFESIRLPGCPRGVNPVVSYAVALSCQCALCDSDSTDCGC

SEQ ID NO: 33 pMB2552 Amino acid sequence encoded by the construct used to express the hCG-hFSH β-subunit chimera hCF(101-109)β-N13D,I33C,δ111.

MEMFQGLLLLLLLSMGGTWASKEPLRPRCRPIDATLAVEKEGCPVCITVNTTCCAGYCPTM
TRVLQGVLPALPQVVCNYRDVRFESIRLPGCPRGVNPVVSYAVALSCQCALCRRSTTDCTV
RGLGPSYC

Fig. 8 (cont.)
SEQ ID NO: 34 pMB2553 Amino acid sequence encoded by the αβ-subunit construct used to express human α-N52D,T86C,CG-tail'-(FURIN)-β-C26A,G102C,δ103

MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDEPRFQ
DSSSSKAPPPSLPSPSRLPGPSDTPILPQRRFKRPRCRPINATLAVEKEGCPVAITVNTTI
CAGYCPTMTRVLQGVLPALPQVVCNYRDVRFESIRLPGCPRGVNPVVSYAVALSCQCALCR
RSTTDCGC

SEQ ID NO: 35 pMB2567 Amino acid sequence encoded by the β-subunit construct used to express hCGβ-E19C, G102C, δ103.

MEMFQGLLLLLLLSMGGTWASKEPLRPRCRPINATLAVCKEGCPVCITVNTTICAGYCPTM
TRVLQGVLPALPQVVCNYRDVRFESIRLPGCPRGVNPVVSYAVALSCQCALCRRSTTDCGC

SEQ ID NO: 36 pMB2568 Amino acid sequence encoded by the β-subunit construct used to express hCGβ-A17C, G102C, δ103.

MEMFQGLLLLLLLSMGGTWASKEPLRPRCRPINATLCVEKEGCPVCITVNTTICAGYCPTM
TRVLQGVLPALPQVVCNYRDVRFESIRLPGCPRGVNPVVSYAVALSCQCALCRRSTTDCGC

SEQ ID NO: 37 pMB2571 Amino acid sequence encoded by the β-subunit construct used to express hCG/hFSH chimera CF (101-109)β-V102C,δ111

MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCDSDSTDCGC
RGLGPSYC

SEQ ID NO: 38 pMB2578 Amino acid sequence encoded by the αβ-subunit construct used to express
human α-N52D,T86C,CG-tail',β-C26A,(δ74,75),G102C,δ103

MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDEPRFQ
DSSSSKAPPPSLPSPSRLPGPSDTPILPSKEPLRPRCRPINATLAVEKEGCPVAITVNTTI
CAGYCPTMTRVLQGVLPALPQVVCNYRDVRFESIRLPGCPVNPVVSYAVALSCQCALCRRS
TTDCGC

SEQ ID NO: 39 pMB2588#1 Amino acid sequence encoded by the α-subunit construct used to express α-K45T,N52D,T86C.

MDYYRKYAAIFLVTLSVFLHVLHSAPDVQDCPECTLQENPFFSQPGAPILQCMGCCFSRAY
PTPLRSKTTMLVQKDVTSESTCCVAKSYNRVTVMGGFKVENHTACHCSCCYYHKS

Fig. 8 (cont.)
SEQ ID NO: 40 pMB2588#12 Amino acid sequence encoded by the α-subunit construct used to express α-K45A,N52D,T86C MDYYRKYAAIFLVTLSVFLHVLHSAPDVQDCPECTLQENPFFSQPGAPILQCMGCCFSRAY
PTPLRSKATMLVQKDVTSESTCCVAKSYNRVTVMGGFKVENHTACHCSCCYYHKS SEQ ID NO: 41 pMB2591 Amino acid sequence encoded by the α-subunit construct used to express α-N52D,T86C,Y88D MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCDYHKS SEQ ID NO: 42 pMB2616 Amino acid sequence encoded by the αβ-subunit construct used to express the hCG/hFSH chimera human α-N52D,T86C,CG-tail'-(FURIN)-CF(94-97)β-C26A,G102C,δ103

MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDEPRFQ
DSSSSKAPPPSLPSPSRLPGPSDTPILPQRRFKRPRCRPINATLAVEKEGCPVAITVNTTI
CAGYCPTMTRVLQGVLPALPQVVCNYRDVRFESIRLPGCPRGVNPVVSYAVALSCQCALCD
SDSTDCGC

SEQ ID NO: 43 pMB2617 Amino acid sequence encoded by the αβ-subunit construct used to express human α-K45T,N52D,T86C,CG-tail'-(FURIN)-β-C26A,G102C,δ103

MDYYRKYAAIFLVTLSVFLHVLHSAPDVQDCPECTLQENPFFSQPGAPILQCMGCCFSRAY
PTPLRSKTTMLVQKDVTSESTCCVAKSYNRVTVMGGFKVENHTACHCSCCYYHKSDEPRFQ
DSSSSKAPPPSLPSPSRLPGPSDTPILPQRRFKRPRCRPINATLAVEKEGCPVAITVNTTI
CAGYCPTMTRVLQGVLPALPQVVCNYRDVRFESIRLPGCPRGVNPVVSYAVALSCQCALCR
RSTTDCGC

SEQ ID NO: 44 pMB2618 Amino acid sequence encoded by the αβ-subunit construct used to express human α-K45A,N52D,T86C,CG-tail-(FURIN)-β-C26A,G102C,δ103

MDYYRKYAAIFLVTLSVFLHVLHSAPDVQDCPECTLQENPFFSQPGAPILQCMGCCFSRAY
PTPLRSKATMLVQKDVTSESTCCVAKSYNRVTVMGGFKVENHTACHCSCCYYHKSDEPRFQ
DSSSSKAPPPSLPSPSRLPGPSDTPILPQRRFKRPRCRPINATLAVEKEGCPVAITVNTTI
CAGYCPTMTRVLQGVLPALPQVVCNYRDVRFESIRLPGCPRGVNPVVSYAVALSCQCALCR
RSTTDCGC

SEQ ID NO: 45 pMB2619 Amino acid sequence encoded by the αβ-subunit construct used to express human α-(δ48,49)N52D,T86C,CG-tail'-β-C26A,G102C,δ103

MDYYRKYAAIFLVTLSVFLHVLHSAPDVQDCPECTLQENPFFSQPGAPILQCMGCCFSRAY
PTPLRSKKTMQKDVTSESTCCVAKSYNRVTVMGGFKVENHTACHCSCCYYHKSDEPRFQDS
SSSKAPPPSLPSPSRLPGPSDTPILPSKEPLRPRCRPINATLAVEKEGCPVAITVNTTICA
GYCPTMTRVLQGVLPALPQVVCNYRDVRFESIRLPGCPRGVNPVVSYAVALSCQCALCRRS
TTDCGC

Fig. 8 (cont.)
SEQ ID NO: 46 pMB2672 Amino acid Seq. ID encoded by the β-subunit construct used to express hCGβ-H106C,δ107.

MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCGG
PKDC

SEQ ID NO: 47 pMB2673 Amino acid Seq. ID encoded by the β-subunit construct used to express hCGβ-L108C,δ109.

MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCGG
PKDHPC

SEQ ID NO: 48 pMB2674 Amino acid Seq. ID encoded by the β-subunit construct used to express hCGβ-P103C,δ104.

MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCGG
C

SEQ ID NO: 49 pMB2783 Amino acid Seq. ID encoded by the βα-subunit construct used to express a chimera of salmonFSH/hCG/salmonLHβ-human α

MEMFQGLLLLLLLSMGGTWASGTECGYGRCRPINATLAVEKEGCPVCITVNTTICAGYCPT
MTRVLQGVLPALPQVVCNYRDVRFESIRLPGCPRGVNPVVSYAVALSCQCSLCNMSTSDCT
IESLQPDFCITPRFQDSSSSKAPPPSLPSPSRLPGPSDTPILPQAPDVQDCPECTLQENPF
FSQPGAPILQCMGCCFSRAYPTPLRSKKTMLVQKNVTSESTCCVAKSYNRVTVMGGFKVEN
HTACHCSTCYYHKS

SEQ ID NO: 50 pMB2811 Amino acid Seq. ID encoded by the construct used to express a chimera of the salmon FSH receptor, the rat LH receptor, and Neo'

MMKMKKIMKMLLCVLGCVSMSQAEVAMVNSGTTFTYLCMGNTITHMPTHIPKNTTDLEFKQ
THIRVFPQEAFTNLQQLTAIVLTENGMLESIGAFAFANLPRLTEITITKSKHLVIIHHQAF
IGLPKLSHLTICNTGLRVLPNFSRIHSAAMTFLLDLQDNVHIVIIPSNAFLGLTTNTIDEL
RLTKNGISEVESHAFNGTKIHKLYLMGNLQLSHMHNNSFKGAEGPGFLDTSRTALSSLPES
VLGEVEHLSAVSVFSLRTLPPLSLFTKLRQANLTYPSHCCAFHKHQRNRTFRMTSACFKPG
AQNNLHFFMDFCLNWTSVACSPAPDAFNPCEDIMGSAPLRVLIWLINILAIFGNLTVLFVL
LTSRYKLTVPRFLMCNLSFADFCMGLYLLLIASVDSQTKGQYYNHAIDWQTGSGCGAAGFF
TVFASELSVYTLTVITLERWHTITYAVQLDQKLRLRHAIPIMLGGWLFSTLIATMPLVGIS
NYMKVSICLPMDVESTLSQVYILSILILNVVAFVVICACYIRIYFAVQNPELTAPNKDTKI
AKKMAILIFTDFTCMAPISFFAISAAFKVPLITVTNSKILLVLFYPVNSCANPFLYAIFTK
AFQRDFLLLLSRFGCCKRRAELYRRKEFSAYTSNCKNGFPGASKPSQATLKLSTVHCQQPI
PPRALTHGQFCRYPAQWRPLEFMIEQDGLHAGSPAAWVERLFGYDWAQQTIGCSDAAVFRL
SAQGRPVLFVKTDLSGALNELQDEAARLSWLATTGVPCAAVLDVVTEAGRDWLLLGEVPGQ
DLLSSHLAPAEKVSIMADAMRRLHTLDPATCPFDHQAKHRIERARTRMEAGLVDQDDLDEE
HQGLAPAELFARLKARMPDGEDLVVTHGDACLPNIMVENGRFSGFIDCGRLGVADRYQDIA
LATRDIAEELGGEWADRFLVLYGIAAPDSQRIAFYRLLGEFF

Fig. 8 (cont.)
SEQ ID NO: 51 pMB2813 Amino acid Seq. ID encoded by the β-subunit construct used to express Flag-salmon FSHβ-C4S,R98C,C106S-long METDTLLLWVLLLWVPGSTGDYKAKELASGTDSRYGCRLNNMTITVEREDCHGSITITTCA
GLCETTDLNYQSTWLPRSQGVCNFKEWSYEKVYLEGCPSGVDPFFIPVAKSCDCIKCKTDN
TDCDCISMATPGSIVNPLEFQDSSSSKAPPPSLPSPSRLPGPSDTPILPQ SEQ ID NO: 52 pMB2826 Amino acid Seq. ID encoded by the βα-subunit construct used to express a chimera of hCG/salmonLHβ-human α chimera MEMFQGLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCTI
ESLQPDFCITPRFQDSSSSKAPPPSLPSPSRLPGPSDTPILPQAPDVQDCPECTLQENPFF
SQPGAPILQCMGCCFSRAYPTPLRSKKTMLVQKNVTSESTCCVAKSYNRVTVMGGFKVENH
TACHCSTCYYHKS SEQ ID NO: 53 pMB2827 Amino acid Seq. ID encoded by the β-subunit construct used to express Flag-salmon FSHβ,R98C,C106S-short METDTLLLWVLLLWVPGSTGDYKAKELASGTDCRYGCRLNNMTITVEREDCHGSITITTCA
GLCETTDLNYQSTWLPRSQGVCNFKEWSYEKVYLEGCPSGVDPFFIPVAKSCDCIKCKTDN
TDCDCISMATPGSFEQT SEQ ID NO: 54 pMB2860 Amino acid Seq. ID encoded by the α-subunit construct used to express α-Q5C,T86C MDYYRKYAAIFLVTLSVFLHVLHSAPDVCDCPECTLQENPFFSQPGAPILQCMGCCFSRAY
PTPLRSKKTMLVQKNVTSESTCCVAKSYNRVTVMGGFKVENHTACHCSCCYYHKS SEQ ID NO: 55 PS1 Amino acid Seq. ID encoded by the β-subunit construct used to express salmon FSHβ (original coding Seq. ID obtained from Dr. Penny Swanson)

MYCTHLKTLQLVVMATLWVTPVRAGTDCRYGCRLNNMTITVEREDCHGSITITTCAGLCE
TTDLNYQSTWLPRSQGVCNFKEWSYEKVYLEGCPSGVDPFFIPVAKSCDCIKCKTDNTDC
DRISMATPSCIVNPLEM

SEQ ID NO: 56 PS2 Amino acid Seq. ID encoded by the α-subunit construct used to express salmon αII (original coding Seq. ID obtained from Dr. Penny Swanson)

MCLLKSTGLSLILSALLVIGDSYPNSDKTNMGCEECTLKPNTIFPNIMQCTGCCFSRAYPT
PLRSKQTMLVPKNITSEATCCVAKEGERVTTKDGFPVTNHTECHCSTCYYHKS

Fig. 8 (cont.)
SEQ ID NO: 57 pRM783 Amino acid Seq. ID encoded by the β-subunit construct used to express Flag-salmon FSHβ-CGtail METDTLLLWVLLLWVPGSTGDYKAKELASGTDCRYGCRLNNMTITVEREDCHGSITITTCA
GLCETTDLNYQSTWLPRSQGVCNFKEWSYEKVYLEGCPSGVDPFFIPVAKSCDCIKCKTDN
TDCDRISMATPSCIVNPLEFQDSSSSKAPPPSLPSPSRLPGPSDTPILPQ SEQ ID NO: 58 pRM784 Amino acid Seq. ID encoded by the βα-subunit construct used to express Flag-salmon FSHβ-CGtail-human α-N52D METDTLLLWVLLLWVPGSTGDYKAKELASGTDCRYGCRLNNMTITVEREDCHGSITITTCA
GLCETTDLNYQSTWLPRSQGVCNFKEWSYEKVYLEGCPSGVDPFFIPVAKSCDCIKCKTDN
TDCDRISMATPSCIVNPLEFQDSSSSKAPPPSLPSPSRLPGPSDTPILPQAPDVQDCPECT
LQENPFFSQPGAPILQCMGCCFSRAYPTPLRSKKTMLVQKDVTSESTCCVAKSYNRVTVMG
GFKVENHTACHCSTCYYHKS SEQ ID NO: 59 pRM787 Amino acid Seq. ID encoded by the βα-subunit construct used to express Flag-salmon FSHβ-CGtail-human α

METDTLLLWVLLLWVPGSTGDYKAKELASGTDCRYGCRLNNMTITVEREDCHGSITITTCA
GLCETTDLNYQSTWLPRSQGVCNFKEWSYEKVYLEGCPSGVDPFFIPVAKSCDCIKCKTDN
TDCDRISMATPSCIVNPLEFQDSSSSKAPPPSLPSPSRLPGPSDTPILPQAPDVQDCPECT
LQENPFFSQPGAPILQCMGCCFSRAYPTPLRSKKTMLVQKNVTSESTCCVAKSYNRVTVMG
GFKVENHTACHCSTCYYHKS

SEQ ID NO: 60 pRM794 Amino acid Seq. ID encoded by the β-subunit construct used to express Jun-salmon FSHβ-CGtail MEMFQGLLLLLLLSMGGTWASGRIARLEEKVKTLKAQNSELASTANMLREQVAQLKQKVMG
LRPSGTDCRYGCRLNNMTITVEREDCHGSITITTCAGLCETTDLNYQSTWLPRSQGVCNFK
EWSYEKVYLEGCPSGVDPFFIPVAKSCDCIKCKTDNTDCDRISMATPSCIVNPLEFQDSSS
SKAPPPSLPSPSRLPGPSDTPILPQ SEQ ID NO: 61 pRM796 Amino acid Seq. ID encoded by the α-subunit construct used to express Flag-salmon αII METDTLLLWVLLLWVPGSTGDYKAKELYPNSDKTNMGCEECTLKPNTIFPNIMQCTGCCFS
RAYPTPLRSKQTMLVPKNITSEATCCVAKEGERVTTKDGFPVTNHTECHCSTCYYHKS SEQ ID NO: 62 pRM798 Amino acid Seq. ID encoded by the αβ-subunit construct used to express human α-CGtail(partial)-salmonFSHβ-CGtail MDYYRKYAAIFLVTLSVFLHVLHSAPDVQDCPECTLQENPFFSQPGAPILQCMGCCFSRAY
PTPLRSKKTMLVQKNVTSESTCCVAKSYNRVTVMGGFKVENHTACHCSTCYYHKSDDPRFQ
DSSSAKAPPPSLPSPSSGTDCRYGCRLNNMTITVEREDCHGSITITTCAGLCETTDLNYQS
TWLPRSQGVCNFKEWSYEKVYLEGCPSGVDPFFIPVAKSCDCIKCKTDNTDCDRISMATPS
CIVNPLEFQDSSSSKAPPPSLPSPSRLPGPSDTPILPQ Fig. 8 (cont.)
SEQ ID NO: 63 pRM799 Amino acid Seq. ID encoded by the βα-subunit construct used to express hCGβ-salmon αII MEMFQGLLLLLLLLSMGGTWASKEPLRPRCRPINATLAVEKEGCPVCITVNTTICAGYCPTM
TRVLQGVLPALPQVVCNYRDVRFESIRLPGCPRGVNPVVSYAVALSCQCALCRRSTTDCGG
PKDHPLTCDDPRFQDSSSSKAPPPSLPSPSRLPGPSDTPILPQKDELYPNSDKTNMGCEECTLKPNTIFP
NIMQCTGCCFSRAYPTPLRSKQTMLVPKNITSEATCCVAKEGERVTTKDGFPVTNHTECHCSTCYYH
KS SEQ ID NO: 64 pRM902 Amino acid Seq. ID encoded by the α-subunit construct used to express human α-N52D,T86C,CG-tail MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDEPRFQ
DSSSSKAPPPSLPSPSRLPGPSDTPILPQ SEQ ID NO: 65 pRM903 Amino acid Seq. ID encoded by the αβ-subunit construct used to express human α-N52D,T86C,CG-tail',β-C26A,G102C,δ103

MDYYRKYAAIFLVTLSVFLHVLHSAPDVQDCPECTLQENPFFSQPGAPILQCMGCCFSRAY
PTPLRSKKTMLVQKDVTSESTCCVAKSYNRVTVMGGFKVENHTACHCSCCYYHKSDEPRFQ
DSSSSKAPPPSLPSPSRLPGPSDTPILPSKEPLRPRCRPINATLAVEKEGCPVAITVNTTI
CAGYCPTMTRVLQGVLPALPQVVCNYRDVRFESIRLPGCPRGVNPVVSYAVALSCQCALCR
RSTTDCGC

SEQ ID NO: 66 pRM917 Amino acid Seq. ID encoded by the α-subunit construct used to express α-Q5C,N52D,T86C MDYYRKYAAIFLVTLSVFLHVLHSAPDVCDCPECTLQENPFFSQPGAPILQCMGCCFSRAY
PTPLRSKKTMLVQKDVTSESTCCVAKSYNRVTVMGGFKVENHTACHCSCCYYHKS Binding of $^{125}$I-hCG and pRM917+pMB2545

Binding of $^{125}$I-hCG and pRM917 and pMB2546

Fig. 25. Strategy To Prepare Fusion Proteins Containing An LH Receptor Targeting Domain human α-N52D,T86C,CG-tail-[Apoptosis Inducing or Other Protein]-linker-(FURIN)-β-C26A,G102C,δ103

↓ human α-N52D,T86C,CG-tail-[Apoptosis Inducing or Other Protein]-linker-(FURIN)-β

β-C26A,G102C,δ103

Response to αδ52 T86C-βK2N, P4T, C26A, δ13,30, G102C, δ103

Fig. 30. Alpha subunit alignment

| SEQ ID NO: | | 7 10 | 28 31 32 | | | 59 60 | | 82 84 87 | |
|---|---|---|---|---|---|---|---|---|---|
| 7 | Human | APDVQDCPEC | TLQENPFFSQ | PGAPILQCMG | CCFSRAYPTP | LRSKKTMLVQ | KNVTSESTCC | VAKSYNRVTV | MGGFKVENHT ACHCSTCYYH KS |
| 277 | Ovine | FPDGEFTMQGCPEC | KLKENKYFSK | PDAPIYQCMG | CCFSRAYPTP | ARSKKTMLVP | KNITSEATCC | VAKAFTKATV | MGNVRVENHT ECHCSTCYYH KS |
| 278 | Porcine | FPDGEFTMQGCPEC | KLKENKYFSK | LGAPIYQCMG | CCFSRAYPTP | ARSKKTMLVP | KNITSEATCC | VAKAFTKATV | MGNARVENHT ECHCSTCYYH KS |
| 279 | Bovine | FPDGEFTMQGCPEC | KLKENKYFSK | PDAPIYQCMG | CCFSRAYPTP | ARSKKTMLVP | KNITSEATCC | VAKAFTKATV | MGNVRVENHT ECHCSTCYYH KS |
| 280 | Equine | FPDGEFTQDCPEC | KLRENKYFFK | LGVPIYQCKG | CCFSRAYPTP | ARSRKTMLVP | KNITSESTCC | VAKAFIRVTV | MGNIKLENHT QCYCSTCYHH KI |
| 281 | Goldfish | YPRNYMNNFGCEEC | ELKENNIFSK | PGAPVYQCMG | CCFSRAYPTP | LRSKKTMLVP | KNITSEATCC | VAKEVKRVLV | N-DVRLVNHT DCHCSTCYYH KS |
| 282 | Sturgeon | YPDGDM-TQGCHEC | KLKLNKYFST | PRDQIFQCVG | CCFSRAYPTP | LRSKKTMLVP | KNITSEATCC | VAKDFKRI-- | --NQKLENHT DCHCSTCYYH KT |
| 283 | Zebrafish | YSRNDVSNYGCEEC | KLMNERFSK | PGAPVYQCVG | CCFSRAYPTP | LRSKKTMLVP | KNITSEATCC | VAKESKMVAT | --NIPLYNHT DCHCSTCYYH KS |
| 284 | Catfish | YPNNDF---GCEEC | KLKENNIFSK | PGAPVYQCMG | CCFSRAYPTP | LRSKKTMLVP | KNITSEATCC | VAKEVKRVIV | N-DVKLVNHT DCHCSTCYYH KF |
| 285 | Salmon I | YPNSDMTNVGCEEC | KLKENKLFSN | PGAPVYQCTG | CCFSRAYPTP | LQSKKAMLVP | KNITSEATCC | VAKEGERVVV | D-NIKLTNHT ECMCNTCYYH KS |
| 286 | Salmon II | YPNSDKTNMGCEEC | TLKPNTIF-- | ---PNIMQCTG | CCFSRAYPTP | LRSKKQTMLVP | KNITSEATCC | VAKEGERVTT | KDGFPVTNHT ECHCSTCYYH KS |

Figure 31. Seatbelt Alignment

| hormone | | species | | | | SEQ ID NO |
|---|---|---|---|---|---|---|
| cg | AAK84307 | cavia porcellus guinea pig | gtc | rlsnsdc | gglrgqpsac | 71 |
| cg | aaa53287 | human | alc | rrsttdc | ggpkdhpltc | 72 |
| cg | AAL69704 | human | alc | rrsttdc | ggpkdhpltc | 73 |
| cg | AAL69730 | Macaca mulatta | alc | rrstsdc | ggpkdhplac | 74 |
| cg | P51500 | marmoset Callithrix jacchus | glc | rrsysdc | gslrneplgc | 75 |
| cg | AAL69732 | monkey Aotus trivirgatus primate | alc | rrsysdc | gnlkseplgc | 76 |
| cg | AAL69731 | monkey Callicebus moloch primate | glc | rrsysdc | gslrneplgc | 77 |
| cg | AAL69726 | monkey colobus guereza | glc | rrstsdc | ggpkdhpltc | 78 |
| cg | AAL69727 | monkey colobus guereza | glc | rrsttdc | ggpkdhpltc | 79 |
| cg | AAL69724 | monkey colobus guereza | glc | rrstsdc | ggpkdhpltc | 80 |
| cg | AAL69725 | monkey colobus guereza | glc | rrsttdc | ggpkdhpltc | 81 |
| cg | AAK08644 | monkey Macaca fascicularis | glc | rrstscc | ggpkdhpltc | 82 |
| cg | AAK08643 | monkey Macaca fascicularis | glc | rrstscc | ggpkdhpltc | 83 |
| cg | AAL69729 | monkey Macaca mulatta | alc | rrsttdc | ggpkdhpltc | 84 |
| cg | AAL69728 | monkey Macaca mulatta | alc | rrstscc | ggpkdhpltc | 85 |
| cg | P07434 | monkey Papio cynocephalus anubis | alc | rrsttcc | ggpkdhpltc | 86 |
| cg | AAL69712 | monkey Pongo pygmaeus | alc | rrsttcc | ggpkdhpltc | 87 |
| cg | AAL69710 | monkey Pongo pygmaeus | alc | rrsttcc | ggpkdhpltc | 88 |
| cg | AAL69714 | monkey Presbytis obscura | glc | rrsttcc | ggpkdhpltc | 89 |
| cg | AAL69715 | monkey Presbytis obscura | glc | rrsttcc | ggpkdhpltc | 90 |
| cg | AAL69717 | monkey Presbytis obscura | glc | rrsttcc | ggpkdhpltc | 91 |
| cg | AAL69718 | monkey Presbytis obscura | glc | rrsttdc | ggpkdhpltc | 92 |
| cg | AAL69716 | monkeyPresbytis obscura | glc | rrsttdc | ggpkdrpltc | 93 |
| cg | AAL69711 | orangutan: Pongo pygmaeus orangutan | alc | rrsttdc | ggpkdrpltc | 94 |
| cg3 | NP_000728 | human | alc | rrsttdc | ggpkdhpltc | 95 |
| cg7 | np_149133 | human | alc | rrsttdc | ggpkdhpltc | 96 |
| fsh-f | P48250 | Arctic cisco omul Coregonus autumnalis Baikal omul | ikc | ktdntdc | drismatpsc | 97 |
| fsh-f | AAC38035 | bass Morone saxatilis stripped bass | ttc | ntentdc | grfpedipsc | 98 |
| fsh-f | AAB25412 | bonito Katsuwonus pelamis bonito | tvc | ntgntyc | grlpgytpsc | 99 |
| fsh-m | p04937 | bovine | skc | dsdstdc | tvrglgpsyc | 100 |

Fig. 31 (cont.)

| | | | | | | |
|---|---|---|---|---|---|---|
| fsh-f | BAB18563 | bream Pagrus major red sea bream | tvc | dtgnmdc | grfpgnipkc | 101 |
| fsh-f | | african catfish | sqc | nteitdc | gafsmqpssc | 102 |
| fsh-f | aak07415 | carp black carp Mylopharyngodon piceus | skc | nsdiadc | gvlsqqtssc | 103 |
| fsh-f | o13050 | carp cyprinus carpio | skc | nsditdc | galsqqtlsc | 104 |
| fsh-f | q9dg81 | Channel catfish Actinopterygii; Neopterygii; Teleostei; Ostariophysi; Siluriformes Ictalurus punctatus | sqc | nteitdc | gafsmqpssc | 105 |
| fsh-b | aa199279 | chicken Gallus gallus | etc | dtdstdc | tvrglgpsyc | 106 |
| fsh-f | cAB93518 | eel conger conger Teleostei; Anguilliformes; congridae | src | ntnstdc | gqlnteasgc | 107 |
| fsh-f | bab97390 | eel conger myriaster | src | ntnstdc | gqlnteasgc | 108 |
| fsh-f | q9ykt3 | eel Japanese eel Anguilla japonica | skc | ntdstdc | gplntevsgc | 109 |
| fsh-a | q9ps36 | frog Rana catesbeiana | grc | dsettdc | tvralgptyc | 110 |
| fsh-a | cac39253 | frog Rana ridibunda marsh frog | grc | nsettdc | tvralgptyc | 111 |
| fsh-f | p30971 | Fundulus heteroclitus Atlantic killifish | sac | ntkdtyc | trlyahipsc | 112 |
| fsh-m | aam81325 | goat capra hircus | gkc | drdstdc | tvrglgpsyc | 113 |
| fsh-f | q98848 | goldfish carassius auratus | skc | nsditdc | gvlsqqtlgc | 114 |
| fsh-f | baa36975 | goldfish carassius auratus | skc | nsdvtdc | gvlsqqtisc | 115 |
| fsh-f | Q9PW99 | gourami Trichogaster trichopterus : three spot gourami | tac | nagntyc | ghfhgyipsc | 116 |
| fsh-m | q9jk69 | guinea pig cavia porcellus | gkc | dsdstdc | tvrglgpsyc | 117 |
| fsh-f | CAD10501 | halibut Hippoglossus hippoglossus Atlantic halibut | sic | nlddtdc | spfpgdipgc | 118 |
| fsh-f | BAB47387 | halibut Paralichthys olivaceus bastard halibut | | | | |
| fsh-m | p01226 | horse | gkc | nsdstdc | tvrglgpsyc | 119 |
| fsh-m | 1f17b | human | gkc | dsdstdc | tvrglgpsyc | 120 |
| fsh-m | np0005501 | human | gkc | dsdstdc | tvrglgpsyc | 121 |
| fsh-f | | lungfish | GTC | HTETTDC | TVGGLGPSYC | 122 |
| fsh-b | baco7314 | ibis Japanese crested Ibis Nipponia nippon | etc | dtdstdc | tvrglgpsyc | 123 |
| fsh-m | aak92541 | marsupial Monodelphis domestica | gsc | dtdstdc | tvrglgpsyc | 124 |
| fsh-m | AAM09904 | monkey Macaca mulatta | gkc | dsds | | 125 |
| fsh-m | np032071 | mouse | gkc | dsdstdc | tvrglgpsyc | 126 |
| fsh-a | bab92958 | newt Red-Bellied Newt cynops pyrrhogaster | gac | dtdhtdc | tvrglgpnyc | 127 |
| fsh-f | P48252 | Oncorhynchus masou cherry salmon | ikc | ktdntdc | drksmatpsc | 128 |
| fsh-f | BAB17686 | Oncorhynchus mykiss rainbow trout | ikc | ktdntdc | drismatpsc | 129 |
| fsh-b | p80665 | ostrich Struthio camelus | etc | dtdstdc | tvrglgpsyc | 130 |
| fsh-m | af448454-1 | panda giant panda Ailuropoda melanoleuca | gkc | dsdstdc | tvrglgpsyc | 131 |
| fsh-m | po1228 | pig | gkc | dsdstdc | tvrglgpsyc | 132 |

Fig. 31 (cont.)

| | | | | | | |
|---|---|---|---|---|---|---|
| fsh-m | o46430 | possum brushtail possum | | gsc | dtdstdc | tvrglgpsyc | 133 |
| fsh-b | bac01164 | quail Japanese quail coturnix japonica | | etc | dtdstdc | tvrglgpsyc | 134 |
| fsh-m | p18427 | rat | | gkc | dsdstdc | tvrglgpsyc | 135 |
| fsh-f | P10257 | salmon Oncorhynchus keta chum salmon | | ikc | ktdntdc | drismatpsc | 136 |
| fsh-f | AAM92269 | salmon Plecoglossus altivelis Protacanthopterygii; Salmoniformes; Osmeridae ayu | | ttc | siastec | dpmhmdmasc | 137 |
| fsh-f | AAD34594 | salmon Salmo salar atlantic salmon | | ikc | etdntdc | drismatpsc | 138 |
| fsh-f | cac43235 | shark smaller spotted catshark gnathostomes Scyliorhinus canicula | | gmc | ntettdc | tvsamepthc | 139 |
| fsh-m | p01227 | sheep | | gkc | drdstdc | tvrglgpsyc | 140 |
| fsh-m | q9qyb0 | siberian hamster Paodopus sungorus | | gkc | dsdstdc | tvrglgpsyc | 141 |
| fsh-f | cab93504 | sturgeon Siberian sturgeon Acipenser baerii | | ggc | atdytdc | gtlslgpsdc | 142 |
| fsh-m | AAK30588 | tiger Panthera tigris altaica | | gkc | dsdstdc | tvqglgpsyc | 143 |
| fsh-f | AAK83079 | tilapia Oreochromis mossambicus tilapia | | tac | nantdc | gtlsgyipsc | 144 |
| fsh-a | bab93558 | toad Japanese toad Bufo japonicus | | grc | nsettdc | tvrglgpthc | 145 |
| fsh-f | P37205 | tuna Thunnus obesus tuna | | tac | ntgntyc | grlpgyvpsc | 146 |
| fsh-r | bab92948 | turtle japanese chinemys reevesii | | esc | dtdntdc | tvrglgpsyc | 147 |
| fsh-f | ay424303 | zebra fish | | nqv | nsdttdw | gaispqttsc | 148 |
| lh-f | Q90225 | Acanthopagrus latus Teleostei | | glc | amdtsdc | tfeslqpnfc | 149 |
| lh-m | AAL41022 | Ailuropoda melanoleuca giant panda | | gpc | rlsnsdc | ggpraqplac | 150 |
| lh-f | AAL37629 | Anguilla anguilla | | nlc | tmdtsdc | aiqslrpdfc | 151 |
| lh-f | AAL37630 | Anguilla bicolor bicolor | | nlc | tmdtsdc | aiqslrpdfc | 152 |
| lh-f | AAL37633 | Anguilla celebesensis | | nlc | tmdtsdc | aiqslrpdfc | 153 |
| lh-f | AF395604_1 | Anguilla marmorata | | nlc | tmdtsdc | aiqslrpdfc | 154 |
| lh-f | P48251 | Arctic cisco Baikal omul coregonus autumnalis | | slc | nmdtsdc | tieslqpdlc | 155 |
| lh-f | AAM92270 | Ayu Plecoglossus altivelis Protacanthopterygii; Salmoniformes; Osmeridae | | nmc | tmdtsdc | tiqslnpdfc | 156 |
| lh-m | P33088 | Balaenoptera acutorostrata minke whale | | gpc | rlsssbc | gpgrazplac | 157 |
| lh-f | i50994 | bass striped bass Morone saxatilis | | grc | amdtsdc | tfeslqpnfc | 158 |
| lh-f | Q91121 | bass striped bass Morone saxatilis | | grc | amdtsdc | tfeslqpnfc | 159 |
| lh-f | g9pw98 | Blue gourami Trichogaster trichopterus | | src | vmdtsdc | tfeslqpdfc | 160 |
| lh-f | AAB25413 | bonito Katsuwonus plelamis Teleostei | | grc | amdtsdc | tfeslqpdfc | 161 |
| lh-m | P04651 | bovine | | gpc | rlsstdc | ggprtqplac | 162 |
| lh-m | AAA30623 | bovine bos taurus | | gsc | rlsstdc | ggprtqplac | 163 |
| lh-m | 16015133 | camel Arabian camel | | | | | |
| lh-m | P18842 | Canis familiaris dog | | gpc | rlsnsdc | ggpraqslac | 164 |

Fig. 31 (cont.)

| | | | | | | |
|---|---|---|---|---|---|---|
| lh-f | aak07414 | carp black carp Myiopharyngodon piceus | slc | tmdtsdc | tieslqpdyc | 165 |
| lh-f | CAA66359 | Clarias gariepinus African catfish | slc | tmdtsdc | tieslnpdfc | 166 |
| lh-f | P01235 | carp cyprinus carpio | slc | tmdtsdc | tieslqpdfc | 167 |
| lh-f | P37038 | carp silver carp Hypophthalmichthys molitrix | slc | tmdtsdc | tieslqpdyc | 168 |
| lh-f | P53543 | catfish African catfish clarias gariepinus | slc | tmdtsdc | tieslnpdfc | 169 |
| lh-f | AAB24037 | catfish African catfish clarias gariepinus | slc | tmdtsdc | tieslnpdfc | 170 |
| lh | AAC04365 | Ceratotherium simum simum Perissodactyla | gpc | rlsssdc | ggpraqplac | 171 |
| lk-f | Q9DG80 | Channel catfish Ictalurus punctatus Actinopterygii; Neopterygii; Teleostei; Ostariophysi; Siluriformes | tlc | tmdtsdc | tieslnpdfc | 172 |
| lh-b | a61091 | chicken Gallus gallus | arc | pnatsdc | tvgglgpafc | 173 |
| lh-f | P30984 | ctenopharyngodon idella Teleostei; Ostariophysi cypriniformes; cyprinidae; ctenopharyngodon | slc | tmdtsdc | tieslqpdfc | 174 |
| lh-m | AAL69738 | Cynocephalus variegatus primate | gpc | rlsssdc | ggprtqplac | 175 |
| lh-m | AAL69734 | Daubentonia madagascariensis aye-aye primate | gac | rlsssdc | ggpraqpfac | 176 |
| lh-m | P19794 | donkey chorionic gonadctrophin-beta Equus asinus | gpc | rlkttdc | ggprdhplac | 177 |
| lh-f | P27767 | eel Anguilla anguilla European eel | nlc | tmdtsdc | aiqslrpdfc | 178 |
| lr-f | AAL37636 | eel Anguilla marmorata | nlc | tmdtsdc | aiqslrpdfc | 179 |
| lh-f | BAB97391 | eel conger myriaster | nlc | tmetsdc | tiqslrpdfc | 180 |
| lh | aam28896 | Epinephelus coioides induced precocious sex change | grc | amdtsdc | tfeslqpnfc | 181 |
| lh-m | 046641 | Equus burchellii zebra | gpc | rlkttdc | ggprdhplac | 182 |
| lh-m | O77805 | Felis cattus | gpc | rlsssdc | ggpraqplac | 183 |
| lh-f | BAB47388 | flounder Japanese flounder Paralichthys olivaceus | grc | alntsdc | tfqslqpdfc | 184 |
| lh-a | P80071 | frof Rana catesbeiana Amphibia | dlc | kmdysdc | tvessepdvc | 185 |
| lh-a | cac39252 | frog marsh frog Rana ridibunda | dfc | kmdysdc | tvessepdvc | 186 |
| lh-m | AAL69736 | Galago senegalensis primate | gpc | rlsssdc | ggpraqplac | 187 |
| lh-f | q98849 | goldfish carassius auratus | slc | tmdtsdc | tieslqpdfc | 188 |
| lh-m | AAK84305 | guinea pig cavia porcellus guinea pig | gtc | rlsnsdc | gglrgqpsac | 189 |
| lh-m | AAK84306 | guinea pig cavia porcellus guinea pig | gtc | rlsnsdc | gglrgqpsac | 190 |
| lh-f | cAD10502 | halibut Atlantic halibut | grc | alntsdc | tfeslqpdfc | 191 |
| lh-m | Q9QYA9 | hamster Phodopus sungorus siberian hamster | gpc | rlstsdc | ggprtqpm | 192 |
| lh-f | q9yqh2 | herring Pacific herring clupea pallasi | slc | smdtsdc | tiesvepdfc | 193 |
| lh-m | P08751 | horse | gpc | qikttdc | gvfrdqplac | 194 |
| lh-m | AAC04362 | horse Equus caballus horse | gpc | qikttdc | gvfrdqplac | 195 |
| lr-m | AAC04361 | horse? Equus hemionus kulan | gpc | rlkttdc | ggprdhplac | 196 |
| lh-m | NP_000885 | human | gpc | rrstsdc | ggpkchpltc | 197 |

Fig. 31 (cont.)

| | | | | | | |
|---|---|---|---|---|---|---|
| lh-m | AAL69719 | human | gpc | rrstsdc | ggpkdhpltc | 198 |
| lh-m | O46483 | kangaroo Macropus rufus red kangaroo | gsc | rlshsdc | ggpraqphlc | 199 |
| lh-f | P30972 | Killifish Fundulus heteroclitus | ggc | amatsdc | tfeslqpdfc | 200 |
| lh-f | 1819439A | killifish Fundulus heteroclitus killifish | ggg | amatsdc | tfeslqpdfc | 201 |
| lh | AAL69737 | Loris tardigradus | gpc | rlsssdc | ggpraqalac | 202 |
| lh-m | AAL69723 | monkey colobus guereza | gpc | rrstsdc | ggpkdhpltc | 203 |
| lh-m | AAL69721 | monkey Macaca mulatta | gpc | hrstsdc | ggpkdhpltc | 204 |
| lh-m | AAL69722 | monkey Presbytis obscura | gpc | rrstsdc | ggprdhpltc | 205 |
| lh-m | AAL13337 | Monodelphis domestica | gsc | rlshsdc | ggprarphlc | 206 |
| lh-m | NP_032523 | mouse | gpc | rlsssdc | ggprtqpmac | 207 |
| lh-a | bab92959 | newt Amphibia Salamandridae cynops pyrrhogaster Red-Bellied Newt | nmc | kmdysdc | tvqsigpefc | 208 |
| lh-b | p80664 | ostrich Struthio camelus | arc | pmatadc | tvaglgpafc | 209 |
| lh-m | AAK30589 | Panthera tigris altaica tiger | gpc | rlsssdc | ggpraqplac | 210 |
| lh-f | AAK58602 | Paralichthys olivaceus flounder | grc | alntsdc | tfqslqpdfc | 211 |
| lh-m | P01232 | pig | cpc | rlsssdc | ggpraqplac | 212 |
| .h | AAL69720 | Pongo pygmaeus | glc | rrstsdc | ggpkdhpltc | 213 |
| lh-m | O46482 | possum Trichosurus vulpecula brushtail possum | gsc | rlshsdc | ggprarphlc | 214 |
| lh-m | AAL69739 | primate Pteropus lylei | cpc | rlsssdc | gcpraqslac | 215 |
| lh-b | p45657 | quail Japanese quail coturnix japonica | arc | piatsdc | tvqglgpafc | 216 |
| lh-m | A61465 | rabbit Oryctolagus cuniculus rabbit | gpc | rlsssdc | ggpraeplac | 217 |
| lh-m | NP_036990 | rat | cpc | rlsssdc | ggprtqpmtc | 218 |
| lh-m | O77835 | rhinoceros Ceratotherium simum white rhinoceros | gpc | rlsssdc | ggpraqplac | 219 |
| lh-f | P10256 | salmon chum salmon Oncorhynchus keta | slc | nmdtsdc | tieslqpdfc | 220 |
| lh-f | P48253 | salmon masu salmon Oncorhynchus masou | slc | nmdtsdc | tieslqpdfc | 221 |
| lh-f | P07732 | salmon Oncorhynchus tshawytscha | slc | nmdtsdc | tieslqpdfc | 222 |
| lh-f | BAB18564 | seabream Pagrus major red seabream | glc | amdtsdc | tfeslepnfc | 223 |
| lh-f | cac43236 | shark smaller spotted catshark Scyliorhinus canicula | rlc | rmdytdc | tvqsikpdfc | 224 |
| lh-m | U7SHB | sheep | gpc | rlsstdc | ggprtqplac | 225 |
| lh-m | F01231 | sheep | gpc | rlsstdc | ggprtqplac | 226 |
| lh-m | I46949 | sheep | cpc | rlsstdc | ggprtqplac | 227 |
| lh-f | cAB93502 | sturgeon Siberian sturgeon Acipenser baerii | slc | rmessdc | tiqsvgpsdc | 228 |
| lh-f | cAB93503 | sturgeon Siberian sturgeon Acipenser baerii | slc | rmessdc | tiqvgpsdc | 229 |
| lh-m | AAL69733 | Tarsius bancanus primate | cpc | rlsssdc | ggpraqplac | 230 |

Fig. 31 (cont.)

| | | | | | | | |
|---|---|---|---|---|---|---|---|
| lh-f | AAP49576 | tilapia (nile) Creochromis niloticus | grc | amdtsdc | tfesmqpdfc | 231 |
| lh-a | BAB93557 | toad Bufo japonicus Japanese toad | dlc | kmdysdc | tvesssepdvc | 232 |
| lh-a | BAB93553 | toad Bufo japonicus Japanese toad | dlc | kmdysdc | tvesssepdvc | 233 |
| lh-a | BAB93552 | toad Japanese toad Bufo japonicus | dlc | kmdysdc | tvesssepdvc | 234 |
| lh-f | BAB17687 | trout rainbow trout Oncorhynchus mykiss | slc | nmdtsdc | tieslqpdfc | 235 |
| lh-f | P37206 | tuna Thunnus obesus | grc | amdtsdc | tfeslqpdfc | 236 |
| lh-r | P45646 | turkey LH Meleagris gallopavo | arc | piatsdc | tvqglqpafc | 237 |
| lh-r | bab92949 | turtle Reeves's turtle chinemys reevesii | slc | pmdssdc | tvhsigpdfc | 238 |
| lh-m | AAL69735 | Varecia variegata primate | gac | rlsssdc | ggpraqpfac | 239 |
| lh-m | P25330 | whale Physeter catodon sperm whale | gpc | rlsssdc | gpgraqplac | 240 |
| lh-m | 1103192A | whale Physeter catodon sperm whale | gpc | rlsssdc | gpgraqplac | 241 |
| lh-a | aak49986 | xenopus | ngc | kmdysdc | tvqsigpdfc | 242 |
| lh-a | AAC04360 | zebra Equus zebra hartmannae | gpc | rlkttdc | ggprdhplac | 243 |
| lh | AAD34593 | | slc | nmdtsdc | tieslqpefc | 244 |
| lh-f | P12837 | eel daggertooth pike conger Pike eel Muraenesox cinereus | nlc | tmdtsdc | aiqslrpdfc | 245 |
| lh-m | S09344 | salmon chum salmon | slc | nmdtsdc | tieslqpdfc | 246 |
| tsh-f | o73824 | Atlantic salmon Salmo salar Protacanthopterygii; Salmoniformes; Salmonidae; Salmo | gtc | ntdsdec | ahkassdgarc | 247 |
| tsh-m | p01223 | bovine | gkc | ntdysdc | iheaiktnyc | 248 |
| tsh-f | AAD51753 | carp bighead carp Aristichthys nobilis | stc | nthsdec | ahktsnaarkc | 249 |
| tsh-b | o57340 | chicken Gallus gallus | gkc | ntdysdc | vhekvrtnyc | 250 |
| tsh-f | BAA20003 | ctenopharyngodon idella Teleostei; Ostariophysi cypriniformes; cyprinidae; ctenopharyngodon | stc | nthsdec | ahktsnaarkc | 251 |
| tsh-f | baa20002 | cyprinus carpio | stc | nthsdec | ahrtsnagmkc | 252 |
| tsh-f | p54828 | dog canis familiaris Mammalia; Eutheria; carnivora; Fissipedia; canidae; canis | gkc | ntdysdc | iheaiktnyc | 253 |
| tsh-f | Q08127 | eel Anguilla anguilla eel | rac | dpardec | thrasadgdrc | 254 |
| tsh-f | S34148 | eel Anguilla anguilla European eel | rac | dpardec | thrasadgdrc | 255 |
| tsh-f | BAA85183 | goldfish carassius auratus | stc | ntnsdec | ahktnnagmkc | 256 |
| tsh-f | BAA20081 | goldfish carassius auratus | stc | ntnsdec | ahktnnagmkc | 257 |
| tsh-m | Q62590 | hamster Phodopus sungorus hamster | gkc | ntdysdc | iheavktnyc | 258 |
| tsh-m | Q28376 | horse | gkc | ntdysdc | iheaikanyc | 259 |
| tsh-m | aab30828 | human | gkc | ntdysdc | iheaiktnyc | 260 |
| tsh-m | np000540 | human | gkc | ntdysdc | iheaiktnyc | 261 |
| tsh-m | aab24571 | human | gkc | ntdysdc | theavktnyc | 262 |
| tsh-b | bac07313 | ibis Japanese crested ibis Aves; Neognathae; ciconiformes; Threskiornithidae Nipponia nippon | gkc | ntdysdc | vhekvrtnyc | 263 |

Fig. 31 (cont.)

| | | | | | | |
|---|---|---|---|---|---|---|
| tsh-m | p79357 | Lama glama camelidae | | gkc | dtdysdc | iqeavkmnyc | 264 |
| tsh-m | AAK67820 | Litocranius walleri gerenuk rumen | | gkc | ntdyidc | ihesvttnyc | 265 |
| tsh-m | AAL05938 | marsupial Monodelphis domestica | | gkc | ntdnsdc | iheavrtnyc | 266 |
| tsh-m | NP_033458 | mouse | | | | | |
| tsh | AAK67825 | Oreotragus oreotragus ruminant klipspringer | | | | | |
| tsh-m | 760571b | pig | | gkc | dtdysdc | iheaiktnyc | 267 |
| tsh-m | p01224 | pig | | gkc | ntdysdc | iheaiktnyc | 268 |
| tsh-m | CAA10519 | pig | | | | | |
| tsh-f | p37240 | Rainbow trout Oncorhynchus mykiss Protacanthopterygii; Salmoniformes; Salmonidae; Oncorhynchus | | gtc | ntdsdec ahkassgdgarc | 269 |
| tsh-m | AAB59720 | rat | | gkc | ntdysdc | theavktnyc | 270 |
| tsh-m | np037248 | rat | | gkc | ntdysdc | theavktnyc | 271 |
| tsh-m | BAA00456 | rat | | gkc | ntdysdc | theavktnyc | 272 |
| tsh-f | cab93505 | sturgeon Siberian sturgeon Acipenser baerii | | rkc | ntdysec | tmeplrpspc | 273 |
| tsh | AAK67807 | Syncerus caffer | | | | | |
| tsh-a | bab93560 | toad Japanese toad Bufo japonicus | | ekc | nteyidc | vqdridsnyc | 274 |
| tsh-a | bab93563 | toad Japanese toad Bufo japonicus | | ekc | nteyidc | vqdridsnyc | 275 |
| tsh-a | bab93562 | toad Japanese toad Bufo japonicus | | ekc | nteyidc | vqdridsnyc | 276 |

SALMON FOLLITROPIN HORMONE ANALOGS

CROSS-REFERENCE TO RELATED APPLICATIONS

This application is a Continuation Application claiming priority under 35 U.S.C. §120 of U.S. patent application Ser. No. 11/911,571, filed Oct. 15, 2007, which is a National Stage filing under 35 U.S.C. §371 of International Application No. PCT/US2006/014103, filed Apr. 13, 2006. The International Application claims priority under 35 U.S.C. §119(e) to U.S. Provisional Application No. 60/671,117, filed Apr. 13, 2005. The disclosures of all three applications are incorporated herein by reference.

STATEMENT REGARDING FEDERALLY SPONSORED RESEARCH OR DEVELOPMENT

This research has been funded by NIH Grant HD14907. The U.S. government has certain rights to the invention.

FIELD OF THE INVENTION

The present invention relates to the field of glycoprotein hormone analogs and their uses as agonists, antagonists, targeting vectors, and immunogens. In particular, this invention describes a method for stabilizing a heterodimer that permits the preparation of functional glycoprotein hormone analogs. Glycoprotein hormones control the functions of the gonads and the thyroid gland. These hormones are $\alpha\beta$ heterodimers that are stabilized by a portion of the $\beta$-subunit known commonly as the "seatbelt." The seatbelt contains a cysteine at its carboxyterminus that enables it to form a disulfide bond with another cysteine in the $\beta$-subunit. In most vertebrates the seatbelt is disulfide bridged to a cysteine in $\beta$-subunit loop 1. The seatbelt is bridged to a cysteine in the aminoterminal end of $\beta$-subunit loop 1 in several teleost fish follitropins. The present invention describes a method for stabilizing a heterodimer that permits the preparation of glycoprotein hormone analogs that lack portions of the seatbelt.

BACKGROUND OF THE INVENTION

The Glycoprotein Hormone Family

The glycoprotein hormone family contains three members, namely lutropin (LH, which is also known a luteinizing hormone or interstitial cell stimulating hormone), follitropin (FSH, which is also known as follicle stimulating hormone), and thyrotropin (TSH, which is also known as thyroid stimulating hormone). Lutropins and follitropins of fish are also known as gonadotropin II (GTHII) and gonadotropin I (GTHI), respectively. These glycoprotein hormones are made in the anterior pituitary gland. The placentas of humans, other primates, and some mammals—e.g., horses—also make a glycoprotein hormone known as choriogonadotropin (CG) that has a similar or identical amino acid sequence as that of lutropin. CG interacts with lutropin receptors and, in some cases—e.g., equine CG—can interact with lutropin and follitropin receptors of many species (Murphy and Martinuk, 1991). CG has a role in the maintenance of pregnancy and that of humans (hCG) is essential for maintaining early pregnancy. Its presence in the urine of pregnant women is the basis of most pregnancy tests. hCG is also produced by many tumors and its presence in men and non-pregnant women is an indication of malignancy.

$\alpha$ and $\beta$ Subunits

Glycoprotein hormones are composed of two subunits termed $\alpha$ and $\beta$ (Pierce and Parsons, 1981). A single gene encodes the $\alpha$-subunit in most vertebrate species and this subunit is common to lutropins, follitropins, thyrotropins, and choriogonadotropins. Post-translational modifications of the glycoprotein hormones can create differences in their $\alpha$-subunits such as the finding that the $\alpha$-subunit of LH usually contains a higher ratio of sulfate to sialic acid than that of FSH (Baenziger and Green, 1988). Some fish have two $\alpha$-subunit genes that encode sequences that differ primarily in loops $\alpha$1 and $\alpha$3. The $\beta$-subunits of lutropins, follitropins, and thyrotropins are encoded by separate genes. Similarities in the locations of the cysteines and other residues in the $\beta$-subunits of all glycoprotein hormones suggest that genes encoding the $\beta$-subunits arose by gene duplication and then diverged during early vertebrate evolution (Li and Ford, 1998). The evolution of the primate CG genes occurred much later, most likely by read-through and duplication of the LH gene (Fiddes and Talmadge, 1984). Although the $\beta$-subunit controls the biological properties of each hormone (Pierce and Parsons, 1981), both hormone subunits are required for full activity in most assays.

Heterodimer Formation

Heterodimer formation and dissociation in vitro requires that the glycosylated end of $\alpha$2 pass beneath the seatbelt through a hole in the $\beta$-subunit. The seatbelt presents a significant impediment to heterodimer dissociation and assembly at physiological temperature and pH (Xing et al., 2001b). This is due largely to the presence of the oligosaccharide on $\alpha$2 as shown by the fact that its removal facilitates assembly (Xing and Moyle, 2003), a phenomenon that can be used as a method for preparing heterodimers lacking this oligosaccharide. Normally, the heterodimer is stable at pH 3-4 and above. Removal of the $\alpha$-2 oligosaccharide decreases heterodimer stability significantly and, with the exception of heterodimers in which the seatbelt is latched to a cysteine in the aminoterminal end of the $\beta$-subunit, the absence of the $\alpha$2 oligosaccharide renders the heterodimer unstable at pH 5. Heterodimers in which the seatbelt is latched to a cysteine in the aminoterminal end of the $\beta$-subunit are usually much more stable than those in which the seatbelt is latched to a cysteine in $\beta$-subunit loop 1.

Due to the role of the seatbelt in heterodimer stability, it was thought that the heterodimer was assembled before the seatbelt became latched. This notion was supported by studies using pulse chase analyses (Ruddon et al., 1996). Extensive studies of heterodimer formation in the endoplasmic reticulum (Xing et al., 2004a; Xing et al., 2004b; Xing et al., 2004c; Xing et al., 2004d), the major site of glycoprotein hormone assembly, revealed that it occurs by two mechanisms (FIG. 3). In one termed the "wraparound" pathway, the subunits dock before the seatbelt is latched, the seatbelt is wrapped around $\alpha$2, and assembly is completed when the seatbelt becomes latched. Although this process is required for assembly of salmon FSH and other piscine follitropins in which the seatbelt is latched to a cysteine in the aminoterminal region of the $\beta$-subunit (Xing et al., 2004c), it is inefficient for at least two reasons. First, the $\beta$-subunit has a tendency to fold completely prior to heterodimer assembly unless it is prevented from doing so by the composition of the seatbelt or by a chaperone that interferes with seatbelt latching. Mammalian cells have a chaperone that impedes latching of the human LH seatbelt before the subunits dock, a phenomenon that facilitates the assembly of human LH by the wraparound pathway. The second impediment to assembly by the wraparound pathway stems from the fact that the unlatched seatbelt destabilizes the transient complex composed of the α-subunit and the unlatched β-subunit (Xing et al., 2004d). These factors appear to be largely responsible for the difficulty of producing salmon FSH and many other piscine follitropins that have similar folding patterns. Since FSH is required for producing the female gametes of all vertebrates, methods that are capable of overcoming this difficulty of assembly or that are capable of producing active follitropin analogs would be desirable.

The heterodimer can also be assembled by a "threading pathway" in which the glycosylated end of α-subunit loop 2 passes beneath the seatbelt. This process is facilitated substantially by the presence of small concentrations of reducing agents (Xing et al., 2001b). Originally, it was thought that reduction disrupted the seatbelt latch disulfide, which enabled the heterodimer to form by the wraparound pathway. Reducing agents are now known to enhance assembly by disrupting the disulfide that stabilizes the small loop in the aminoterminal half of the seatbelt (Xing et al., 2001b). The redox potential of the endoplasmic reticulum promotes disruption of this disulfide in cells during the assembly of most choriogonadotropins, follitropins, and thyrotropins (Xing et al., 2004a). The ability of 1-3 mM (3-mercaptoethanol to promote assembly in vitro is due to the fact that the disulfide that stabilizes the small seatbelt loop is much more stable in the heterodimer than in the free β-subunit. Its stability in the heterodimer is due largely to interactions between the α- and β-subunits that stabilize the positions of β-subunit cysteines 10 and 11 near one another (FIG. 3). Disruption of the disulfide formed by these cysteines lengthens the seatbelt, which facilitates the passage of the glycosylated end of α2 between the seatbelt and the remainder of the β-subunit. This process, termed "threading" (Xing et al., 2001b; Xing et al., 2004a; Xing et al., 2004b; Xing et al., 2004d), is driven by the formation of a hydrogen bond network between α2 and the β-subunit that drags the glycosylated end of α2 beneath the seatbelt (FIG. 3, lower pathway). Once threading is complete, the proximity of α2 to the residues that form the small seatbelt loop promotes reformation of the disulfide that stabilizes the small seatbelt loop and that stabilizes the heterodimer (Xing et al., 2004a; Xing et al., 2004b; Xing et al., 2004d). This is why concentrations of reducing agents that are sufficient to promote assembly do not cause heterodimer dissociation. Due to the fact that the disruption and formation of the small seatbelt loop lengthens and shortens the seatbelt, this loop can be viewed as a "tensor" and the disulfide that stabilizes this loop can be viewed as "the tensor disulfide" (Xing et al., 2004a; Xing et al., 2004b; Xing et al., 2004d). Threading promotes the efficient assembly of heterodimers such as hCG, hFSH, and hTSH in which the seatbelt is latched to a cysteine in β1. It appears unable to facilitate assembly of heterodimers in which the seatbelt is latched to a cysteine in the aminoterminal end of the β-subunit—e.g., salmon FSH.

Receptor Binding Specificity

In addition to its role in stabilizing the heterodimer, the seatbelt has a substantial influence on receptor binding specificity. Indeed, the seatbelt is responsible for much of the influence of the hormone β-subunit on receptor binding specificity (Moyle et al., 1994; Han et al., 1996; Dias et al., 1994; Grossmann et al., 1997). Remarkably, the aminoterminal and carboxyterminal halves of the seatbelt appear to have separate influences on receptor binding specificity. The aminoterminal half has a much greater influence on binding to LH receptors than the carboxyterminal half. Conversely, the carboxyterminal half of the seatbelt has a much greater influence on binding to FSH receptors than the aminoterminal half. By changing the composition of the seatbelt, one can produce hormone analogs that interact with multiple receptors. Replacing hCG β-subunit residues between cysteines 11 and 12 with their FSH β-subunit counterparts led to a hormone analog that had the same high affinity for LH receptors as hCG and about half the affinity of FSH receptors for FSH (Moyle et al., 1994). By manipulating the composition of the seatbelt loop in this analog, one can alter the ratio of LH/FSH activity more than 100-fold (Han et al., 1996).

Glycoprotein Hormone Agonists and Antagonists

Efforts to design glycoprotein hormone agonists and antagonists would be facilitated by knowledge of the structures of their receptors and these membrane glycoproteins have been studied extensively. Receptors for all three hormone classes have similar components, namely a large extracellular domain, a rhodopsin-like (Palczewski et al., 2000) transmembrane domain (TMD), and a short cytoplasmic carboxyterminal domain. The cytoplasmic carboxyterminus is not needed for receptor expression or signaling (Sanchez-Yague et al., 1992; Zhu et al., 1993). The extracellular domain contains two subdomains. The largest of these contains approximately 250 residues and is composed of leucine-rich repeats (McFarland et al., 1989; Sprengel et al., 1990; Nagayama et al., 1989). The leucine-rich repeat domain (LRD) was modeled several years ago (Moyle et al., 1995; Kajava et al., 1995; Jiang et al., 1995) based on its similarity to ribonuclease inhibitor, the first leucine-rich repeat protein of known structure (Kobe and Deisenhofer, 1993). The LRD creates at least a part of the ligand binding site (Braun et al., 1991) and a crystal structure of hFSH bound to a fragment of the LRD has been determined (Fan and Hendrickson, 2005), although there is some doubt as to relevance of this structure to the manner in which the glycoprotein hormone ligands dock with their cell surface receptors (Moyle et al., 2005). Depending on the receptor, the remainder of the extracellular domain contains approximately 60-150 residues. This portion of the extracellular domain has been more difficult to model, however, since its amino acid sequence is not similar to proteins of known structure. It connects the LRD to the TMD and is often considered a hinge (Jiang et al., 1995; Ji et al., 2002; Rapoport et al., 1998; Dias, 2005; Fan and Hendrickson, 2005) and many diagrams suggest that it is disordered (FIG. 4). It has also been termed the signaling-specificity domain (SSD) to reflect its roles in ligand binding and signal transduction (Moyle et al., 2004). The SSD may make essential contacts with the LRD and TMD (FIG. 5a,b), a phenomenon that would permit the receptor domains to function as an integrated unit. The SSD—i.e., the "hinge region"—is considered to be highly ordered in these models.

Models for Hormone-Receptor Interactions

Two models have been proposed to explain hormone receptor interactions. That favored by most investigators was devised several years ago (Jiang et al., 1995) and is supported by the crystal structure of hFSH bound to a fragment in the human FSH receptor (Fan and Hendrickson, 2005). In the crystal structure hFSH is oriented perpendicular to the concave surface of the LRD (FIGS. 4 and 6), an orientation proposed to explain binding of all glycoprotein hormones to their receptors (Fan and Hendrickson, 2005). In this model the role of the SSD is merely to link the LRD to the TMD in a fashion that permits bound ligand to contact the extracellular loops of the TMD (Fan and Hendrickson, 2005; Remy et al., 1996; Dias, 2005). This widely perceived model served as the logo for the latest international meeting of glycoprotein hormone biologists that was held Apr. 13-17, 2005 (FIG. 5a). Signal transduction is thought to be initiated by dimerization of the LRD through contacts between its convex surface (FIG. 7).

A contrasting view of the receptor (Moyle et al., 2004) maintains that ligands contact the glycosylated surfaces of the LRD and SSD, not the TMD or the concave surface of the LRD as is seen in the crystal structure (Fan and Hendrickson, 2005). Indeed, since the SSD would block access of the ligand to the concave surface of the LRD, both models of ligand binding are mutually exclusive. In the alternate view of the receptor (FIG. 5), the SSD has a compact shape and does not function as a hinge. It has been modeled on the structure of the KH domain (Moyle et al., 2004) and aligned with the concave surface of the LRD and TMD (FIG. 5). Signal transduction depends on interactions between the LRD, SSD, and TMD. Although the LRD has an important role in ligand binding affinity and specificity (Moyle et al., 1994; Segaloff and Ascoli, 1993; Nagayama et al., 1991; Thomas et al., 1996; Xie et al., 1990; Braun et al., 1991), interactions between all three domains contribute to ligand binding specificity and signaling. This explains why the LRD is not the only part of the receptor known to influence binding of most ligands (Abell et al., 1996; Moyle et al., 1994; Bernard et al., 1998; Nagayama et al., 1991; Moyle et al., 2004).

Problems in Attempts to Design Agonists and Antagonists

The lack of structural knowledge has hampered development of glycoprotein hormone agonists and antagonists. Although methods for producing glycoprotein hormones were developed in 1985 (Reddy et al., 1985), these are not applicable to all ligands. For example, it has been particularly difficult to produce hormones and hormone analogs in which the seatbelt is latched to a cysteine in the N-terminal region of the β-subunit. This has limited the development of analogs that can be used to stimulate fertility in not only mammalian systems but also those of salmon, trout, and other fish that express follitropins (in which the seatbelt is latched to a cysteine in the aminoterminal region of the β-subunit).

SUMMARY OF THE INVENTION

In accordance with the present invention, it has now been shown for the first time a glycoprotein hormone analog capable of binding to a receptor selected from the group consisting of luteinizing hormone receptor, follicle stimulating hormone receptor, and thyroid stimulating hormone receptor, the analog comprising at least one α subunit polypeptide and at least one β subunit polypeptide. The β subunit comprises a seatbelt region comprising 1 to 20 consecutive amino acid residues. The α subunit comprises a first amino acid residue, and the seatbelt region comprises a second amino acid residue. The first second amino acid residues are covalently linked by a first covalent bond. The first amino acid residue corresponds to an amino acid residue selected from the group consisting of Glu 10, Thr 11, Leu12, Phe33, Arg35, Tyr37, Thr39, Thr40, Leu41, Thr54, Arg42, Ser43, Val53, Ser55, Glu56, Ser57, Thr58, His83, Ser85, Thr86, Tyr89, and Ser92 of a SEQ ID NO: 7. The second amino acid residue is selected from the group consisting of seatbelt residues 11 to 18.

According to one aspect of the present invention provides a glycoprotein hormone analog capable of binding to a receptor selected from the group consisting of luteinizing hormone receptor, follicle stimulating hormone receptor, and thyroid stimulating hormone receptor, comprising at least one α subunit polypeptide and at least one β subunit polypeptide, wherein the α subunit comprises a first amino acid residue, the seatbelt region comprises a second amino acid residue, and wherein the first and second amino acid residues are covalently linked by a first covalent bond and wherein the C-terminal amino acid of the β subunit polypeptide is from seatbelt residue 10 to seatbelt residue 20.

Other aspects of the present invention include targeting compounds comprising the analogs of the present invention, nucleic acids encoding the analogs of the present invention, and methods of treating a disease or condition in a subject comprising administering the analogs of the present invention.

BRIEF DESCRIPTION OF THE DRAWINGS

FIG. 2. This cartoon compares the structures of the two folding patterns found in vertebrate glycoprotein hormones. All vertebrate lutropins and thyrotropins have the folding pattern seen in the left panel, as do most follitropins. Some teleost fish follitropins have the folding pattern seen in the right panel.

FIG. 3. Glycoprotein Hormone Assembly: These diagrams illustrate the wrapping (top row) and threading (bottom row) pathways of glycoprotein hormone assembly. They were prepared from the crystal structure of hCG by opening the seatbelt latch or tensor disulfides and moving the seatbelt and α-subunit loop 2 to create panels A and D. The positions of the sulfur residues in each of these disrupted disulfides are shown as large black balls. The relative positions of the α- and β-subunits in these docked complexes were identified in crosslinking studies. The short black bars represent the positions of hydrogen bonds and are a few of those that are observed in the crystal structures of hCG and hFSH. Wrapping pathway: Contacts between the tensor loop in the seatbelt and α-subunit loop 2 (panel B) constrain this part of the α-subunit near the β-subunit cystine knot. This facilitates the formation of additional hydrogen bonds that hold α-subunit loop 2 and the N-terminal half of the seatbelt in the position shown in panel C. The C-terminal half of the seatbelt, which we term the strap because it connects the remainder of the seatbelt to the core of the β-subunit, is restrained in positions wherein it can be latched to βCys26, its normal site, or to cysteines added to the α-subunit. Elimination of both βCys26 and βCys110 by replacing them with alanine prevents the seatbelt from being latched but does not prevent docking. When the docked complex is stabilized by an intersubunit disulfide bond between the N-terminal ends of each subunit, it can be recognized reasonably well by antibodies to an epitope that is formed when the seatbelt is normally latched. This shows that the end of the seatbelt has an innate tendency to be located near β-subunit residue 26, a phenomenon that we ascribe to the hydrogen bonds between the tensor loop and α-subunit loop 2. Threading pathway: Disruption of the tensor disulfide elongates the seatbelt substantially as shown by the model in panel D. This permits the formation of hydrogen bonds between α-subunit loop 2 and the β-subunit cystine knot, a phenomenon that drags the glycosylated end of α-subunit loop 2 beneath the seatbelt through the β-subunit hole (panel E). The β-sheet structure that is formed stabilizes hydrogen bonds between the tensor loop and α-subunit loop 2, which brings βCys100 near βCys93 (panel F). This causes the tensor disulfide to reform, which stabilizes the heterodimer (panel G). This view is supported by our finding that the tensor disulfide is much more stable in the heterodimer than the free β-subunit. The α-subunit docks readily with the β-subunit in the ER when its seatbelt is latched or unlatched. Docking is highly reversible in both cases, however. Threading is more efficient than wrapping due to the destabilizing influence of the unlatched seatbelt on the complex. Threading appears to be more efficient than wrapping for all hormones other than those with the folding pattern of salmon FSH or in which seatbelt latching is prevented—e.g., by a cellular chaperone, as is the case for human LH.

FIG. 4. Legend: The common view of the structure of the glycoprotein hormone receptors as of Apr. 13, 2005 was that the receptor extracellular domain consisted of a ligand binding domain composed of leucine-rich repeats—i.e., the leucine-rich repeat domain or LRD—and a disordered domain. The LRD is indicated by the structure at the ends of arrow A (left panel) and by the structures at the ends of arrows A and C (right panel). The remainder of the extracellular domain is indicated by the structures between arrows A and B (left panel) and the structures between arrows A and B and between arrows C and D (right panel). Both suggest that the LRD is coupled to the transmembrane domain by a disordered linker. Note that in this view of the hormone-receptor complexes, the SSD has a clearly defined shape and is not disordered. Left Panel: Logo from the meeting of the International Congress of Gonadotropins and Receptors, Athens Ga., Apr. 13-17, 2005; Right Panel, Figure from the discussion by James Dias in his News and Views article in Nature (Jan. 20, 2005)

FIG. 5. The receptors are thought to consist of three domains, namely a curved leucine-rich repeat domain (LRD), a small signaling-specificity domain (SSD) that is aligned more or less with the concave surface of the LRD (upper left panel), and a transmembrane domain (TMD). The TMD occupies the space directly under the SSD and can make contacts with the lower rim of the LRD nearest the SSD (upper right panel). The hormones contact both the LRD and SSD, but the SSD is not needed for high affinity hCG binding. Most other lutropins, follitropins, and thyrotropins bind only when both the LRD and SSD are present. Note, the position of FSH (and TSH) in the receptor complex differs from that of hCG and most mammalian lutropins. This explains why FSHR and TSHR can be engineered to bind both hFSH and hCG and hTSH and hCG, respectively. Signaling requires a subtle change in the positions of the LRD and SSD that is then transmitted via contacts of each domain with the TMD. Figure taken from Moyle, et al. (2004) J. Biol. Chem. volume 279 pages 44442-44459.

FIG. 6. Figure illustrating two views of hFSH bound to a fragment of the LRD of the human FSH receptor. In crystals containing a fragment of the human FSHR LRD, hFSH is seen to interact with the concave face of the LRD (right panel) in a fashion roughly perpendicular to its major axis (left panel). Loops α1 and α3 of the hFSH α-subunit and loop (32 of the hFSH β-subunit are nearest the bottom of the figure in each panel. Loops al of the α-subunit and loops β1 and β3 of the hFSH β-subunit are above the plane of the LRD in both panels. In this complex, the seatbelt makes only a minor contribution to ligand receptor interactions. Figure from Fan and Hendrickson (2005) Nature volume 433, pages 269-277.

FIG. 7. Signaling transduction is thought to depend on the ability of the hormone receptor complex to dimerize as shown in the top panel, which shows the two molecules of hFSH bound to two molecules of the hFSH receptor LRD juxtaposed to one another. Contacts between the LRD are presumed to be necessary for dimerization. Dimerization is thought to cause the transmembrane domains (areas surrounded by broken lines in the lower panel) to become located within a defined distance of one another. The process of dimerization is induced by hFSH as seen by analyzing the bottom panel from left to right. Binding of hFSH to the receptor (left side of bottom panel) leads to the formation of a complex that can form a reversible dimer (right side of bottom panel). The dimer is thought to form the key aspect needed for signal transduction. No mention is made of the need for the seatbelt in this process. Figures from Fan and Hendrickson (2005) Nature volume 433, pages 269-277.

FIG. 8. Examples of the amino acid and nucleotide sequence of the α and β subunits of the are depicted.

FIG. 25. Strategy To Prepare Fusion Proteins Containing An LH Receptor Targeting Domain. The basic design of this protein is similar to that of pMB2553 except that codons for the protein whose activity is to be expressed in tandem with the LH receptor targeting portion of the protein are inserted between the junction between the CG-tail' and the protease site (e.g., Furin). This will create a single chain construct that is outlined in the upper panel of this figure. Following translation of the fusion protein in an appropriate cell (e.g., CHO cells), it will fold such that its domains derived from the α- and β-subunits will associate with one another and be stabilized by a disulfide bond that is formed between α-subunit residue 86 and β-subunit residue 102. This will create a domain that will bind to LH receptors. When the furin cleavage site is used during expression of the protein, it will be cleaved to yield the species illustrated diagrammatically during secretion. When it is desirable to cleave the protein after the protein is secreted from the cell one should use a cleavage site that is not present in the secretory pathway of the cell being used to make the protein.

AMP accumulation in assays employing CHO cells that over express the rat LH receptor. The oligosaccharide at the N-terminal end of the β-subunit in this analog was not removed prior to assay.

Figure 10:
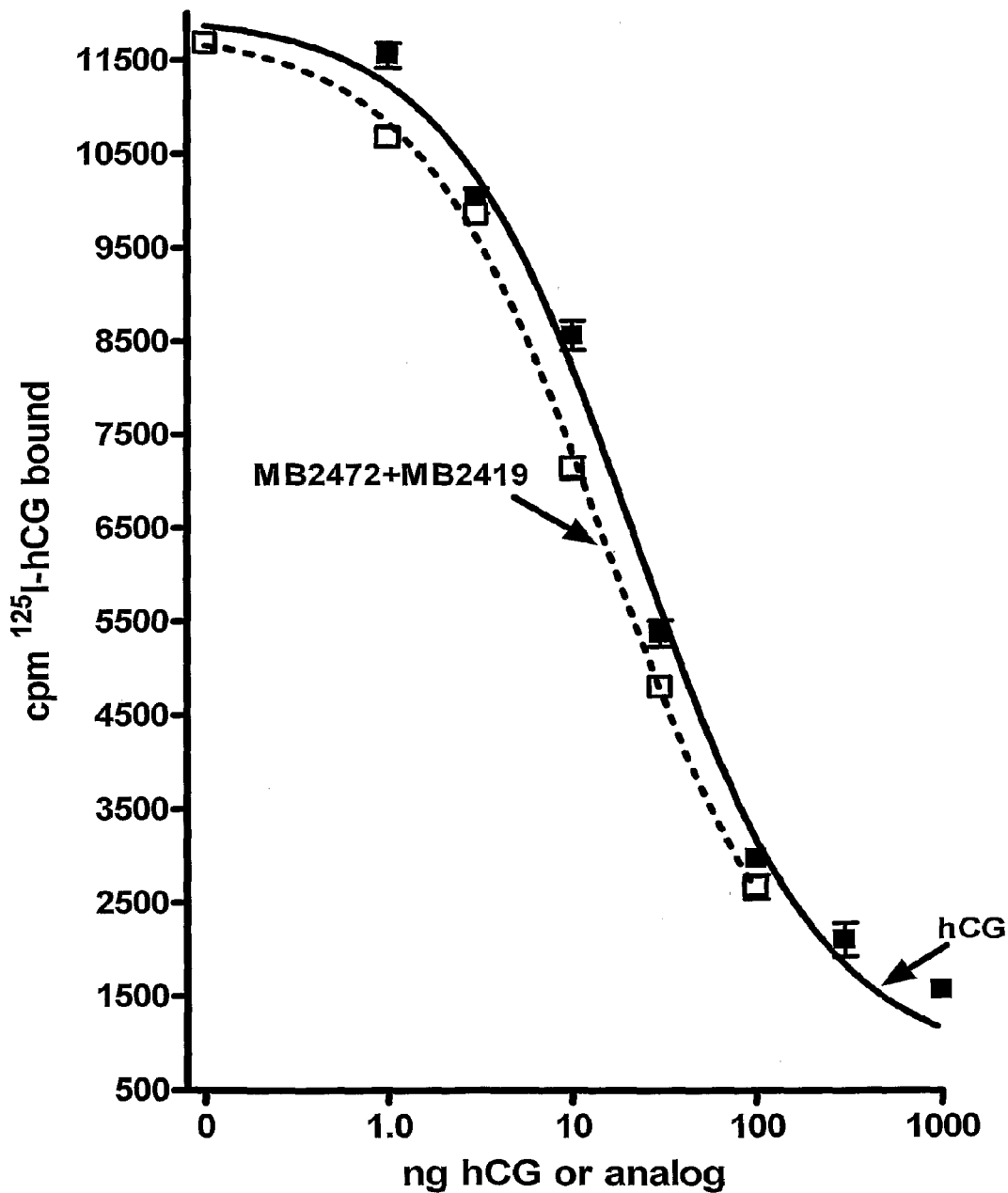
FIG. 10. Ability of pMB2472+pMB2419 to inhibit binding of radioiodinated hCG to CHO cells that express the rat LH receptor. This figure shows that the crosslinked pMB2472+pMB2419 heterodimer has similar affinity for the rat LH receptor as hCG. It also shows that it is equally or slightly more potent than hCG in this receptor binding assay.
Figure 27:
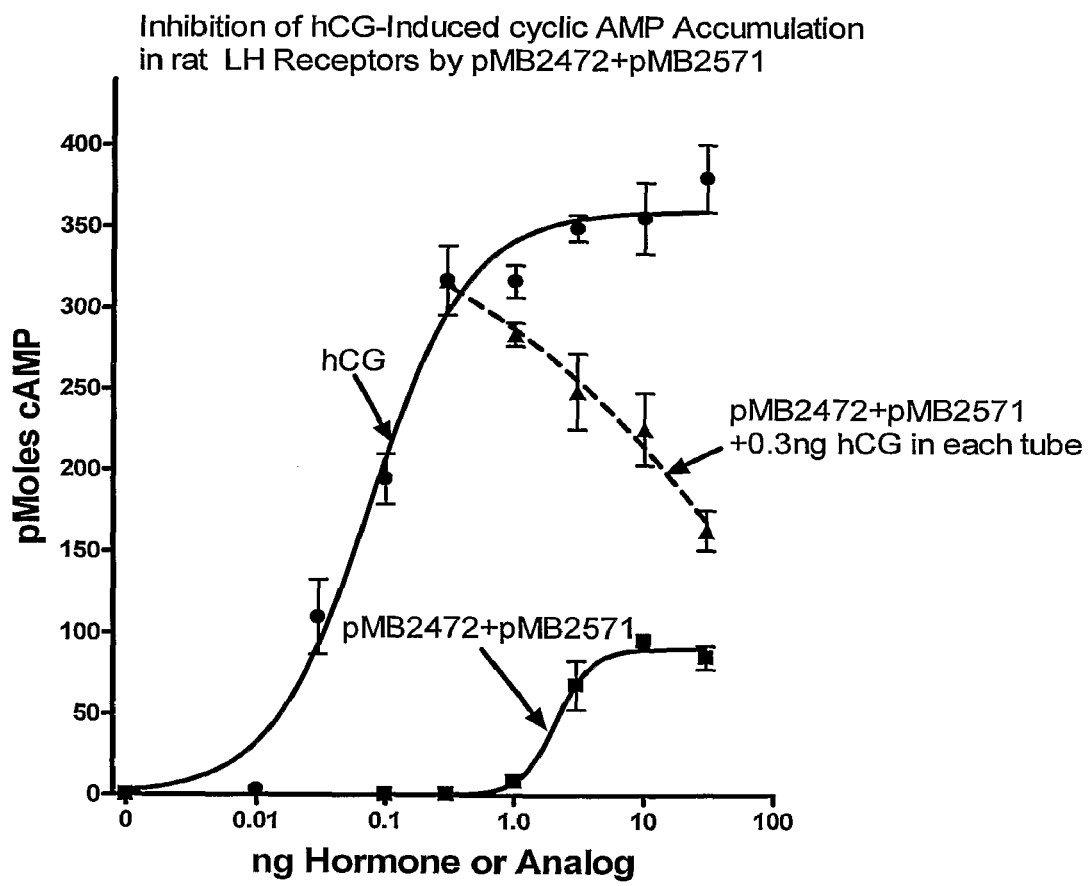

FIG. 27. Relative abilities of hCG and pMB2472+ pMB2571 to stimulate cyclic AMP accumulation in LH receptor assays. Note that the presence of a disulfide crosslink between α-subunit residue 86 and β-subunit residue did not reduce hormone efficacy to nearly the same extent as a crosslink in an analog that cannot latch its seatbelt naturally—e.g., pMB2472+pMB2419 (FIG. 10). Further, the additional residues in the seatbelt of pMB2472+pMB2571 also appeared to reduce its affinity of the receptor (compare this figure with FIG. 11).

Figure 28:
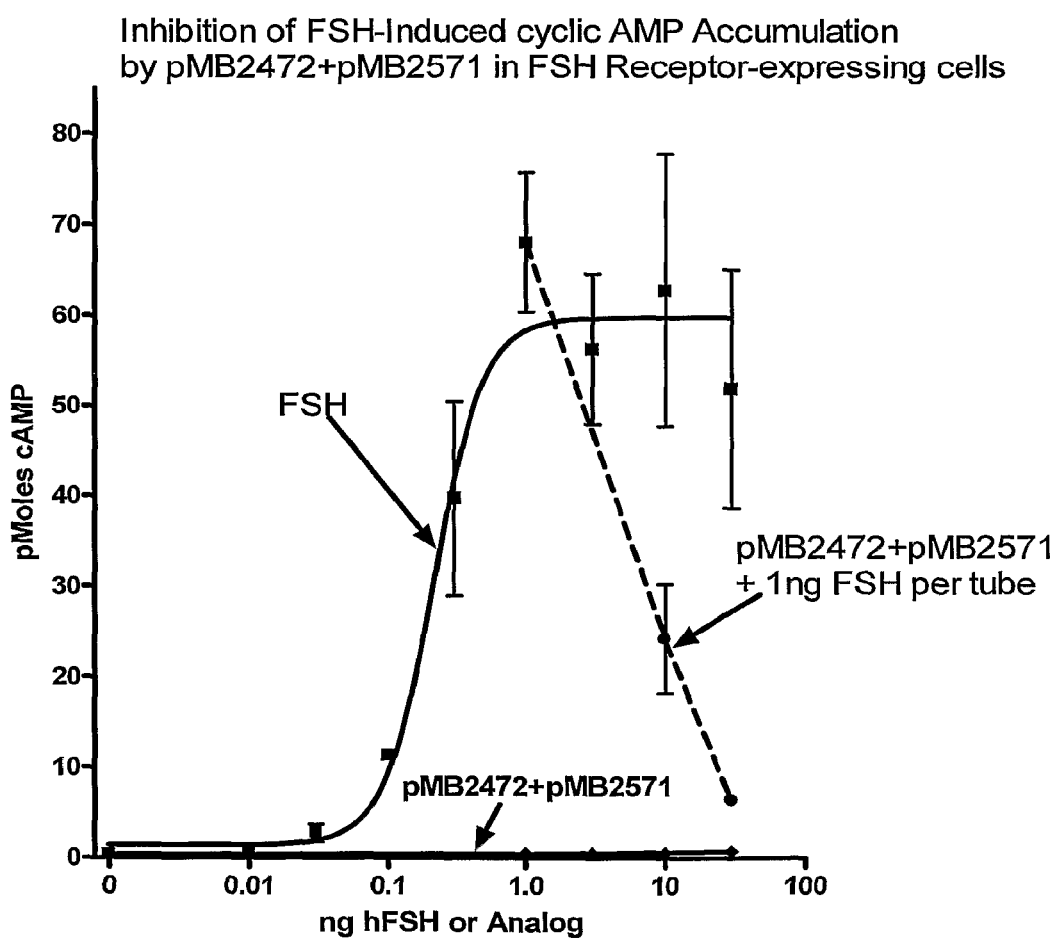

FIG. 28. Relative abilities of hFSH and pMB2472+ pMB2571 to stimulate cyclic AMP accumulation in FSH receptor assays. Note that the presence of the additional seatbelt residues of this analog enabled it to bind FSH receptors although it did not promote hormone efficacy. The analog appeared to bind FSH receptors well since it inhibited the ability of hFSH to stimulate signal transduction.

Figure 29:
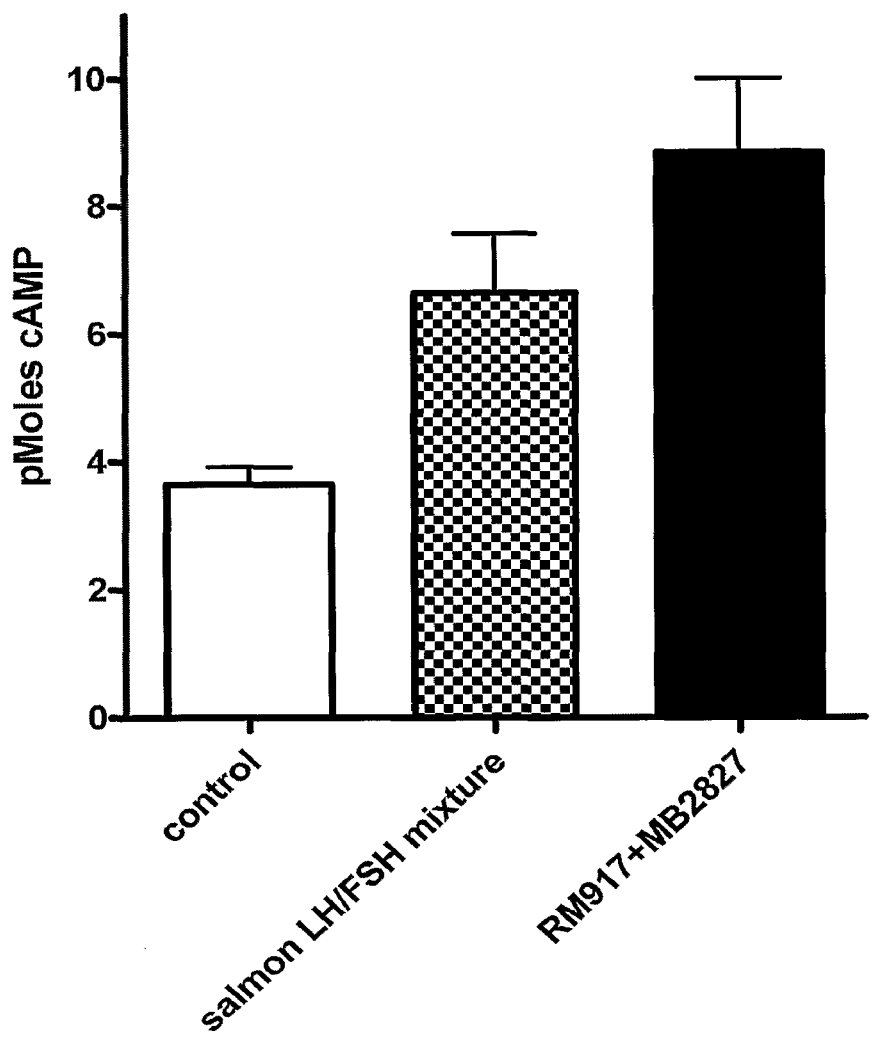

FIG. 29. Stimulation of a salmon FSH receptor—rat LH receptor chimera—neo' fusion protein (pMB2811) that is expressed stably in CHO cells by a mixture of salmon LH and FSH and by pRM917+pMB2827.

FIG. 30. The alignment of α subunits from various species is shown. Numbers at the top show the amino acid number of consensus cysteines relative to the human sequence.

FIG. 31. The alignment of seatbelt regions for different species is shown. The seatbelt region for a majority of species is 20 amino acids long.

DETAILED DESCRIPTION OF THE INVENTION

In one aspect, the present invention relates to a glycoprotein hormone analog capable of binding to a receptor selected from the group consisting of luteinizing hormone receptor, follicle stimulating hormone receptor, and thyroid stimulating hormone receptor, the analog comprising at least one α subunit polypeptide and at least one β subunit polypeptide. The β subunit comprises a seatbelt region comprising 1 to 20 consecutive amino acid residues. The α subunit comprises a first amino acid residue, and the seatbelt region comprises a second amino acid residue. The first second amino acid residues are covalently linked by a first covalent bond. The first amino acid residue corresponds to an amino acid residue selected from the group consisting of Glu9, Thr11, Leu12, Phe33, Arg35, Tyr37, Thr39, Pro40, Leu41, Arg42, Ser43, Val53, Thr54, Ser55, Glu56, Ser57, Thr58, His83, Ser85, Thr86, Tyr89, and Ser92 of SEQ ID NO: 7. The second amino acid residue is selected from the group consisting of seatbelt residues 11 to 18. In an especially preferred embodiment the first amino acid residue corresponds to Thr86 of SEQ ID NO: 7 and the second amino acid residue is seatbelt residue 12. In other preferred embodiments the α subunit polypeptide has an amino acid sequence comprising a sequence selected from the group consisting of SEQ ID NO: 1, 2, 9, 10, 11, 12, 17, 23, 24, 26, 27, 28, 29, 39, 40, 41, 54, 56, 61, 64, and 66 and the β subunit polypeptide has an amino acid comprising a sequence selected from the group consisting of SEQ ID NO: 3, 4, 6, 13, 14, 15, 16, 18, 19, 20, 21, 22, 25, 30, 31, 32, 33, 35, 36, 37 46, 47, 48, 51, 53, 55, 57, and 60.

As used herein, the term "glycoprotein hormone analog" refers to a molecule that possesses a similar structural configuration as a native or wildtype glycoprotein hormone. The analog does not necessarily have a similar activity or function as the native glycoprotein hormone. In some instances the analog comprises a similar amino acid sequence the native glycoprotein hormone. In one embodiment the analog is an agonist, or activator, of a glycoprotein hormone receptor. In other embodiments, the analog is an antagonist, or inhibitor, of a glycoprotein hormone receptor.

Structures in Detail—The "Seatbelt" Region

The seatbelt region of the analog is located on the β subunit. The seatbelt region is generally 20 consecutive amino acids in length (see FIG. 31), with a few species having a seatbelt region of 21 or 22 amino acids. In a preferred embodiment, the seatbelt according to the present invention comprises 20 amino acid residues and these residues are referred to as seatbelt residues 1, 2, 3, 4, 5, 6, 7, 8, 9, 10, 11, 12, 13, 14, 15, 16, 17, 18, 19 and 20. In those embodiments where the seatbelt is 21 amino acids, the seatbelt also comprises seatbelt residue 21. In those embodiments where the seatbelt is 22 amino acids, the seatbelt also comprises seatbelt residues 21 and 22. An analog that is said to have a deleted seatbelt residue(s) or is a truncated seatbelt refers to an analog that lacks certain seatbelt residues in its primary polypeptide sequence. An analog that "lacks" a seatbelt region or a portion of a seatbelt region contains at least a portion of the primary polypeptide sequence of the seatbelt region, but the seatbelt region or a portion of a seatbelt region of such an analog is not "latched". A "latched" seatbelt region refers to a seatbelt region that is wrapped around the α2 loop of the α subunit so as to stabilize heterodimer formation.

Figure 1:
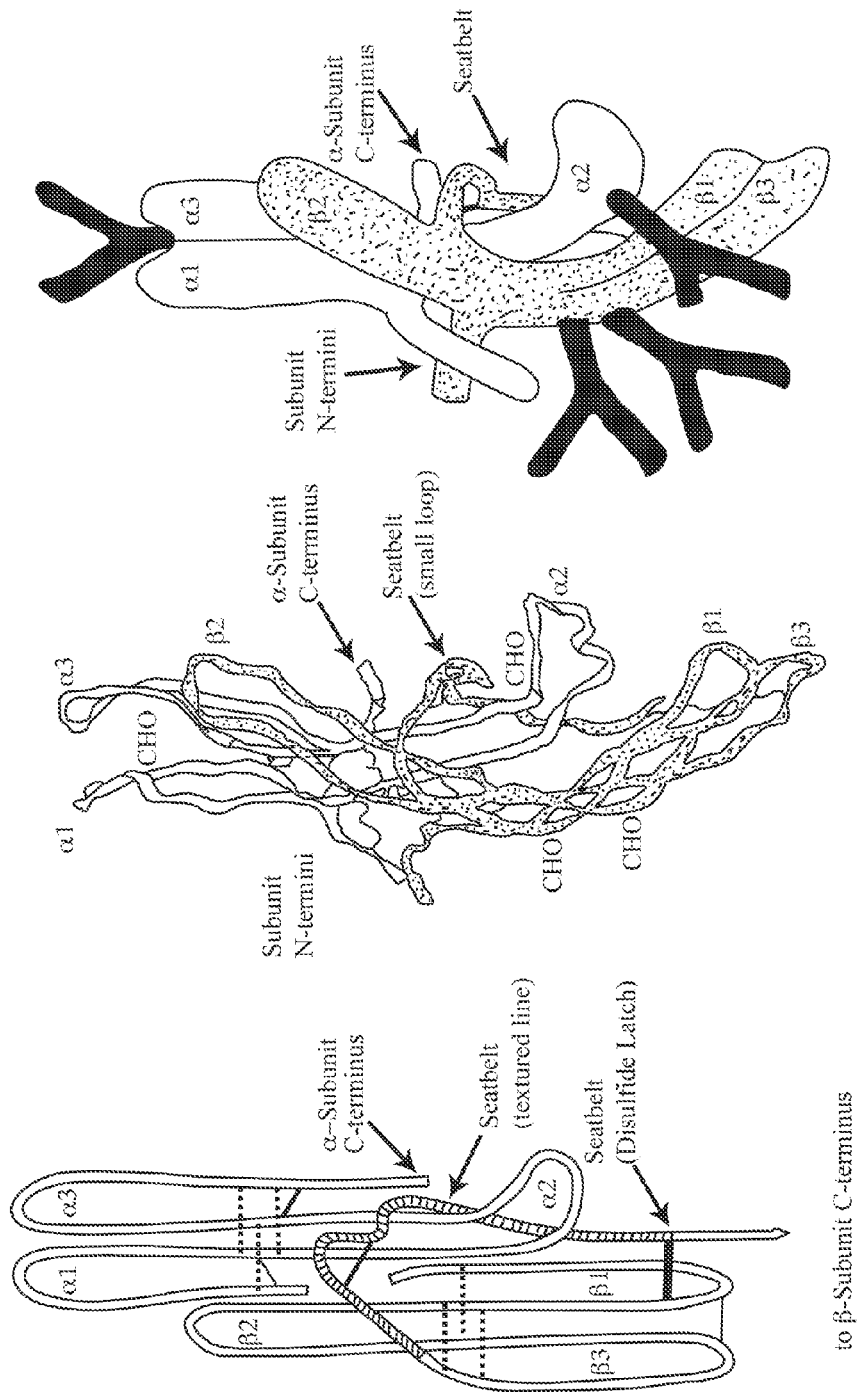
FIG. 1. Cartoons (left, right) and Ribbon diagram (center) illustrating the structure of hCG. Each subunit (α, light gray; β, dark gray) is divided into three large loops labeled α1, α2, α3 and β1, β2, β3. These abbreviations will be used throughout this document to describe parts of the α- and β-subunits. The subunits are held together by a portion of the β-subunit termed the "seatbelt" (textured line in the left cartoon). The amino terminal half of the seatbelt contains a small loop that is known to influence binding to LH and TSH receptors when it contains positively and negatively charged amino acids, respectively. This loop has a key role in heterodimer formation and we refer to it as the "tensor" due to the fact that it regulates the length of the seatbelt during assembly in the endoplasmic reticulum. When the disulfide that stabilizes the small seatbelt loop—i.e., the tensor disulfide—is disrupted, the seatbelt is elongated, which facilitates assembly. Reformation of the tensor disulfide stabilizes the heterodimer. The carboxyterminal half of the seatbelt, which is shown behind α2 in the central panel, connects it to the β-subunit. Due to its elongated nature, we term this region the strap. As a rule, residues in the tensor loop have a more important influence on ligand binding to LH receptors whereas those in the strap region have important roles in binding to FSH receptors. Loops α1, α3, β1, and β3 have similar conformations when the subunits are dissociated and are likely to have similar conformations in all three glycoprotein hormones. In the heterodimer loop α2 is stabilized by being sandwiched between the seatbelt and the β-subunit cysteine knot and parts of loops β1 and β3. We found that the seatbelt does not open during subunit combination in oxidizing conditions in vitro. The locations of the oligosaccharides in the ribbon diagram are denoted by the abbreviation "CHO" and in the right cartoon by the "Y" shapes. Note, when the seatbelt is latched during heterodimer assembly or disassembly, the α2 oligosaccharide must pass through the small opening created by the latched seatbelt. This oligosaccharide is needed to prevent heterodimer dissociation at the mildly acidic pH present in the Golgi, a major reason that it is required for efficient heterodimer secretion.

The structures of hCG and human follitropin (hFSH) have been determined by crystallography (Lapthorn et al., 1994; Wu et al., 1994; Fox et al., 2001). Each subunit of all glycoprotein hormones contains a cystine knot that is responsible for the formation of the three large loops—i.e., α1, α2, α3 and β1, β2, β3—that are seen in their structures (FIG. 1). In the heterodimer, the subunits are oriented such that α1 and α3 contact in and that β1 and β3 are near α2. The stabilities of the natural hormone heterodimers depend on 20 β-subunit residues at the end of its cystine knot that form a part of the β-subunit termed the "seatbelt" (Lapthorn et al., 1994; see FIG. 31). The seatbelt is wrapped around α2 and stabilized by a disulfide bond to a cysteine in β1 of most glycoprotein hormones (FIG. 1, center panel) or to a cysteine in the aminoterminal end of the β-subunit in some piscine follitropins (FIG. 2, right panel). The disulfide bridge that latches the seatbelt constitutes a "latch" that stabilizes the position of its carboxyterminal end. The seatbelts of all vertebrate glycoprotein hormones contain a small 8 residue loop in their aminoterminal halves that has roles in both hormone action (Campbell et al., 1991; Moyle et al., 1994; Han et al., 1996) and heterodimer assembly (Xing et al., 2004b). The amino acid composition of the seatbelt differs widely among glycoprotein hormones, but with the exception of some piscine thyrotropins in which the seatbelt has 1 or 2 additional residues in its carboxyterminal half and some piscine follitropins in which it is latched to a cysteine in the aminoterminal portion of the β-subunit, its structural features appear to be remarkably uniform.

The seatbelt is a critical portion of all glycoprotein hormones and is essential for their biological activities. It originates at the end of the β-subunit cystine knot and its carboxyterminal end is latched to a cysteine in the β subunit. A key feature of all seatbelts is that they are wrapped around the α-subunit loop 2. Indeed, the observation that the hCG seatbelt begins at the end of the β-subunit cystine knot, that it is wrapped around α-subunit loop 2, and that it forms a disulfide bond with a cysteine in the remainder of the β-subunit was responsible for the origin of the name "seatbelt" (Lapthorn et al., 1994). This arrangement of the seatbelt is observed in all the vertebrate glycoprotein hormones. The third and tenth residues of the seatbelts of all vertebrate glycoprotein hormones except that in Zebrafish FSH are cysteines. These cysteines form a disulfide stabilized small loop that is important for the activities of mammalian lutropins (Campbell et al., 1991; Moyle et al., 1994) and for formation of the natural heterodimer (Xing et al., 2004d). It is not known why the Zebrafish FSH β-subunit lacks these two cysteines, but it is presumed that the hydrophobic residues that replace them enable the small loop to form in a manner that is sufficient to stabilize the heterodimer. The cysteine that constitutes the twentieth residue of most vertebrate glycoprotein hormone β-subunits and the twenty-first or twenty-second residues of some piscine thyrotropins forms a disulfide with a cysteine in the β-subunit that latches the carboxyterminal end of the seatbelt to the β-subunit. In most vertebrate glycoprotein hormones, the cysteine that forms the seatbelt latch site is found in β-subunit loop 1 and is the third cysteine in the mature β-subunit. In some piscine follitropins, the seatbelt latch site is found in the aminoterminal end of the β-subunit and is the first cysteine in the mature β-subunit. Changes in the composition of the seatbelt alter hormone activity (Campbell et al., 1991; Moyle et al., 1994; Dias et al., 1994; Grossmann et al., 1997). Seatbelt residues 1-10 are more important for mammalian lutropin activity. Seatbelt residues 10-20 contain a determinant that is more important for mammalian follitropin activity (Moyle et al., 1994).

The seatbelt must be kept latched for the heterodimer to remain intact; disruption of the seatbelt latch disulfide prevents its stable heterodimer formation. It is not essential for the seatbelt to be latched to the β-subunit for the heterodimer to be stabilized, however, and some glycoprotein hormone analogs can be stabilized by forcing the seatbelt to be latched to the α-subunit (Xing et al., 2001a). Some glycoprotein hormone analogs that lack the disulfide bond that latches the end of the seatbelt to the β-subunit can be stabilized by expressing them as a single chain βα fusion protein in which the α-subunit is fused to the end of the β-subunit. In this format, contacts between the α- and β-subunits stabilize the end of the seatbelt near its natural latch site even when the cysteines that form the normal seatbelt latch—i.e., β-subunit Cys26 and Cys110 are both replaced by alanine. B111 is an antibody that recognizes an epitope that contains residues in the vicinity of the natural hCG seatbelt disulfide latch site—i.e., β-subunit Cys26 and Cys110. B111 fails to recognize the β-subunit of human LH, a molecule that is very similar to hCG. Furthermore, B111 also fails to recognize hCG analogs in which the seatbelt is latched to the α-subunit or to a cysteine present in any part of the β-subunit other than to Cys26 (Xing et al., 2001a; Xing et al., 2004a; Xing et al., 2004b; Xing et al., 2004c; Xing et al., 2004d). B111 also fails to recognize the free hCG β-subunit in which Cys26 and Cys110 are both replaced by alanine, which enables the seatbelt to move in a much less restricted fashion than the β-subunit in βα fusion proteins. The fact that B111 recognizes hCG βα fusion proteins in which β-subunit Cys26 and Cys110 are both replaced by alanine (Xing et al., 2001a) shows that the seatbelt of this hormone analog has formed, even though it is not stabilized by a disulfide.

Subunits can be covalently linked by any type of chemical bond. Such bonds include but are not limited to disulfide and peptide bonds. In a preferred embodiment the bond is a disulfide bond.

SEQ ID NO: 7 (FIGS. 8 and 30) is the primary amino acid sequence for the α subunit of human choriogonadotropin (α-hCG). As shown in FIG. 30, there is high homology of α-CG across species. An amino acid of an α subunit sequence corresponds to amino acid of SEQ ID NO: 7 when upon alignment of the α subunit sequence with SEQ ID NO: 7 based on identity or homology, the amino acids are in the same position. For example, Glu13 of ovine α-CG corresponds to Glu9 of SEQ ID NO: 7; Arg15 of ovine α-CG corresponds to Thr11 of SEQ ID NO: 7; Ala45 of ovine α-CG corresponds to Leu41 of SEQ ID NO: 7, etc. Two designations for amino acids are used interchangeably throughout this application, as is common practice in the art: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

In another embodiment the analog comprises at least one α subunit polypeptide and at least one β subunit polypeptide, wherein the α subunit comprises a first amino acid residue, the seatbelt region comprises a second amino acid residue, wherein the first and the second amino acid residues are covalently linked by a first covalent bond, and wherein the C-terminal amino acid of the β subunit polypeptide is from seatbelt residue 10 to seatbelt residue 20. The C-terminal amino acid of a polypeptide according to the present invention is the last amino acid of the polypeptide. Accordingly, a β subunit wherein the C-terminal amino acid of the β subunit polypeptide is from seatbelt residue 10 to seatbelt residue 20 has as its last amino acid seatbelt residue 10, 11, 12, 13, 14, 15, 16, 17, 18, 19, or 20. In certain embodiments the first amino acid residue corresponds to an amino acid residue selected from the group consisting of Glu9, Thr11, Leu12, Phe33, Arg35, Tyr37, Thr39, Pro40, Leu41, Arg42, Ser43, Val53, Thr54, Ser55, Glu56, Ser57, Thr58, His83, Ser85, Thr86, Tyr89, and Ser92 of SEQ ID NO: 7; and the second amino acid residue is selected from the group consisting of seatbelt residues 11 to 18. In an especially preferred embodiment the first amino acid residue corresponds to Thr86 of SEQ ID NO: 7 and the second amino acid residue is seatbelt residue 12.

In a preferred embodiment, the first amino acid residue and the second amino acid residue are both mutated. The first and second amino acid residues can be mutated to any amino acid, including any of the so-called rare or modified amino acids may also be incorporated into a peptide of the invention, including but not limited to the following: 2-Aminoadipic acid, 3-Aminoadipic acid, beta-Alanine (beta-Aminopropionic acid), 2-Aminobutyric acid, 4-Aminobutyric acid (piperidinic acid), 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isodesmosine, allo-Isoleucine, N-Methylglycine (sarcosine), N-Methylisoleucine, N-Methylvaline, Norvaline, Norleucine, Ornithine, 2-Napthylalanine, Threoninol, Tetrahydroisoquinoline 3-carboxlic acid, 4-Indoyl alanine, beta-Tryptophan, cyclo-Leucine. Methods of mutating amino acids are well known. In a preferred embodiment the mutations are generated using PCR-based site-directed mutagenesis.

In an especially preferred embodiment the first amino acid residue and the second amino acid residue are both mutated to cysteine residues and the first covalent bond is a disulfide bond.

In another preferred embodiment, residue 20 of the seatbelt region is not covalently linked to a distal portion of the β subunit. In native glycoprotein hormone β subunits, seatbelt residue 20 is a cysteine residue that forms a disulfide bond with another cysteine of the 3 subunit. In this embodiment seatbelt residue 20 is either absent, or it is only bound to the β subunit via its peptide bond with seatbelt residue 19 on its N-terminal side and possibly an another adjacent amino on its C-terminal side. Accordingly, a "distal portion" refers to binding to any amino acid except the two adjacent amino acids of seatbelt residue 20. In an especially preferred embodiment, seatbelt residue 20 is mutated from a cysteine residue to another amino acid residue, which can be any amino acid except cysteine.

In another embodiment the second amino acid residue of the β subunit polypeptide is the C-terminal residue of the β subunit polypeptide. In this embodiment the β subunit amino acid which is linked to the α subunit is also the last amino acid of the β subunit polypeptide.

In another embodiment the β subunit polypeptide and the α subunit polypeptide are covalently linked via a second covalent bond. In one embodiment the analogs of the present invention comprise a fusion protein of α and β subunits. The α subunit polypeptide and β subunit polypeptide are linked by a peptide bond. In a preferred embodiment the peptide bond is between the C-terminus of the α subunit polypeptide and the N-terminus of the β subunit polypeptide. In an especially preferred embodiment the wherein the analog comprises a cleavage site in between the α subunit and the β subunit. Possible cleavage sites include, but are not limited to a furin cleavage site, a thrombin cleavage site, a Factor Xa cleavage site, and an enterokinase cleavage site.

In another embodiment the α subunit comprises a third amino acid residue, the β subunit polypeptide comprises a fourth amino acid residue, and the third and the fourth amino acid residue are covalently linked via a the second covalent bond. In a preferred embodiment the third amino acid residue and the fourth amino acid residue are both mutated. In an especially preferred embodiment the third amino acid residue and the fourth amino acid residue are both mutated to cysteine residues and the second covalent bond is a disulfide bond.

In a preferred embodiment the third residue of the α subunit polypeptide is selected from the group consisting of Gln5, Arg35, and Tyr37. In a preferred embodiment the fourth residue of the β subunit polypeptide is selected from the group consisting of Leu5, Arg6, Arg8, Ile33, and Ala35.

Role of Glycosylation

The oligosaccharides have a substantial influence on hormone efficacy, but the reason for this remains unexplained (Moyle et al., 1975; Sairam and Bhargavi, 1985; Matzuk et al., 1989; Valove et al., 1994; Fares et al., 1996; Trout et al., 1999; Flack et al., 1994; Min et al., 1996). The oligosaccharides of hCG were found to be essential for its full efficacy; enzymatic deglycosylation reduced its efficacy by 90% in cyclic AMP accumulation assays (Moyle et al., 1975). Subsequent studies using chemical deglycosylation revealed that the oligosaccharides on the α-subunit were more important than those on the β-subunit (Sairam and Bhargavi, 1985). The use of genetic engineering methods to remove the oligosaccharides showed that the α2 oligosaccharide was the most important of all (Matzuk et al., 1989). Removal of this oligosaccharide by itself reduced the efficacy of hCG by half or more. Removal of all the oligosaccharides reduced the efficacy of hCG considerably more (Matzuk et al., 1989), but this also made the heterodimers harder to produce (Matzuk and Boime, 1988).

The contributions of the oligosaccharides to heterodimer production (Matzuk and Boime, 1989), hormone clearance (Baenziger et al., 1992; Cassels et al., 1989; Rosa et al., 1984), and efficacy (Matzuk et al., 1989) confound efforts to use deglycosylated hormone analogs as therapeutics and it is likely that the most useful antagonist analogs will retain most of their oligosaccharides. The presence of sialic acid at the terminal end of the oligosaccharides will also increase the half-life in circulation. This is due to the fact that sulfated and desialylated hormones have long been known to be cleared rapidly (Baenziger et al., 1992; Morell et al., 1971). Thus, it would be best to prepare antagonist analogs that have as much sialylated oligosaccharides as possible.

In another embodiment, the α subunit polypeptide has reduced glycosylation relative to a native α subunit polypeptide. In a one embodiment, the α subunit polypeptide comprises an α2 loop which has reduced glycosylation relative to an α2 loop of a native α subunit polypeptide. In a preferred embodiment the α subunit polypeptide comprises a mutation of at least one asparagine residue relative to a native α subunit polypeptide. In another embodiment the serine/threonine residue of the Asn-Xaa-(Ser/Thr) glycosylation consensus sequence (wherein Xaa is any amino acid exept proline) is mutated. In an especially preferred embodiment the asparagine corresponds to Asn52 of SEQ ID NO: 7

Nucleic Acids

Another aspect of the invention provides a nucleic acid comprising a nucleic acid encoding α and β subunits of the analogs. It is within the scope of the invention that such nucleic acid sequences can be RNA, DNA, or a hybrid of either.

It is well recognized that the genetic code is degenerate, i.e., an amino acid may be coded for by more than one codon. Degenerate codons encode the same amino acid residue, but contain different triplets of nucleotides. Accordingly, for a given nucleic acid sequence encoding an amino acid sequence of the present invention, there will be many degenerate nucleic acid sequences encoding that modulator. These degenerate nucleic acid sequences are considered within the scope of this invention.

In addition, it will also be appreciated by one of skill in the art that different organisms, cells, and cellular compartments may utilize different genetic codes. Thus, a single nucleic acid sequence may encode different polypeptides depending on its cellular context. Accordingly, in addition to the standard genetic code, polypeptides encoded by non-standard genetic codes are also considered within the scope of this invention. These non-standard genetic codes include, but are not limited to, the vertebrate mitochondrial code, the yeast mitochondrial code, the mold, protozoan, and coelenterate mitochondrial code, the mycoplasma/spiroplasma code, the invertebrate mitochondrial code, the ciliate, dasycladacean and hexamita nuclear code, the echinoderm mitochondrial code, the euplotid nuclear code, the bacterial and plant plastid code, the alternative yeast nuclear code, the ascidian mitochondrial code, the flatworm mitochondrial code, blepharisma nuclear code, chlorophycean mitochondrial code, trematode mitochondrial code, scenedesmus obliquus mitochondrial code, and the thraustochytrium mitochondrial code.

The nucleic acid is preferably included within a vector. The nucleic acid is operably linked to signals enabling expression of the nucleic acid sequence and is introduced into a cell utilizing, preferably, recombinant vector constructs, which will express the nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express nucleic acid sequence encoding the analogs of the present invention.

Preferably, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In the vector construction, the nucleic acid agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. Among the promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals.

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of nucleic acid agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker. The use of cationic lipids may promote encapsulation of negatively charged nucleic acids, and also promote fusion with negatively charged cell membranes. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide, peptides derived from DNA binding proteins, or a cationic polymer.

It is also possible to introduce a DNA vector in vivo as a naked DNA plasmid. Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter.

Another aspect of the present invention provides a cell transformed with a nucleic acid of the present invention. Also included in the scope of the present invention is a transgenic organism comprising a recombinant nucleic acid of the present invention. A transgenic animal is an animal into which has been introduced, by human manipulation, one or more genes not native to the animal.

Also included in the scope of the present invention, is a method for producing an analog of the present invention, the method comprising:

a) transforming a cell with a recombinant nucleic acid, and the recombinant nucleic acid comprises a promoter sequence operably linked to a nucleic acid encoding a analog of the present invention, and b) culturing the cell under conditions suitable for expression of the analog, and c) recovering the analog so expressed.

The analogs of the present invention may be prepared by recombinant technology methods, isolated from natural sources, or prepared synthetically, and may be, of prokaryotic or eukaryotic origin. The analogs of the present invention may be unglycosylated or modified subsequent to translation. Such modifications include glycosylation, phosphorylation, acetylation, myristoylation, methylation, isoprenylation, and palmitoylation. Glycosylated analogs are produced in mammalian cells. Using recombinant DNA technology, the nucleic acid encoding the analog is inserted into a suitable vector, which is inserted into a suitable host cell. The analog produced by the resulting host cell is recovered and purified. The analogs are characterized by amino acid composition and sequence, and biological activity.

Use of Glycoprotein Hormone Analogs to Deliver Toxins and Other Agents

Glycoprotein hormone analogs can be used to deliver toxins or other agents to LH receptor bearing cells. Sairam et al. attached the potent toxin gelonin to hCG (Marcil et al., 1993; Singh and Sairam, 1989; Singh et al., 1989). Hansel et al. (Hansel et al., 2001) attached toxic peptides to synthetic hLH analogs during efforts to target receptors in ovarian and prostate carcinomas. While it would be possible to attach these toxins to the antagonists, this approach per se is not likely to be desirable for targeting the cystic follicles in polycystic ovary syndrome (PCOS) patients. Toxins such as gelonin are likely to be antigenic, which would reduce the attractiveness of the approach for repeated use. Furthermore, since gelonin works inside the cell, it must enter the cell to function. Since hCG antagonists have reduced cellular entry (Hoelscher et al., 1991), use of proteins similar to gelonin might reduce their activities. Toxins delivered in liposomes may have significant "bystander" effects, i.e., the abilities to kill cells that are nearby those that are being targeted. Thus, they would have the potential to reduce the ovarian reserve. They may also have serious side effects on the kidney and liver, tissues that participate in hormone clearance (Ascoli et al., 1976; Wehmann et al., 1984). Fusion proteins containing clinically approved drugs—i.e., interferon γ—would be more useful. Fusion proteins containing sphingomyelinase linked to the antagonists might also be useful since they would be likely to produce ceramide only in sufficient quantity to kill cells to which the proteins are bound, i.e., only those cells that have LH receptors. Also, since androgens have been shown to promote the early events in follicle formation, but retard full follicle development (Vendola et al., 1998), the use of gonadotropin antagonists to deliver high local concentrations of drugs that inhibit steroidogenesis—e.g., in liposomal vesicles—would also be very attractive. Only those granulosa cells that require LH and/or steroids for survival would be expected to undergo apoptosis. Turnover of these cells would reverse the symptoms of PCOS.

Another aspect of the invention provides for a targeting compound comprising an analog of the present invention. The targeting compound utilizes the ability of an analog of the present invention to direct an active agent to the specific target cell population in a subject, for example, cystic follicles of an ovary. In one embodiment the targeting compound is complexed with an active agent. An "active agent", as used herein, includes any diagnostic, prophylactic or therapeutic agent that can be used in an animal, including a human. An "active particle", as used herein is a particle into which one or more active agents have been loaded. "Complexed to", as used herein, includes adsorption, noncovalent coupling and covalent coupling of a targeting compound to an active agent or to an active particle.

The active agent used depends on the pathological condition to be diagnosed, prevented or treated, the individual to whom it is to be administered, and the route of administration. Active agents include, but are not limited to, imaging agents, antigens, antibodies, oligonucleotides, antisense oligonucleotides, genes, gene correcting hybrid oligonucleotides, aptameric oligonucleotides, triple-helix forming oligonucleotides, ribozymes, signal transduction pathway inhibitors, tyrosine kinase inhibitors, DNA-modifying agents, therapeutic genes, and systems for therapeutic gene delivery. Also included are drugs; hormones; analgesics; anti-migraine agents; anti-coagulant agents; cardiovascular, anti-hypertensive and vasodilator agents; sedatives; narcotic antagonists; chelating agents; anti-diuretic agents; chemotherapeutic agents; apoptosis-inducing agents; and other agents including, but not limited to, those listed in the United States Pharmacopeia and in other known pharmacopeias.

Drugs include, but are not limited to, peptides, proteins, hormones and analgesics, cardiovascular, narcotic, antagonist, chelating, chemotherapeutic, sedative, anti-hypertensive, anti-anginal, anti-migraine, anti-coagulant, anti-emetic anti-neoplastic and anti-diuretic agents. Hormones include, but are not limited to, insulin, calcitonin, calcitonin gene regulating protein, atrial natriuretic protein, colony stimulating factor, erythropoietin (EPO), interferons, somatotropin, somatostatin, somatomedin, luteinizing hormone releasing hormone (LHRH), tissue plasminogen activator (TPA), growth hormone releasing hormone (GHRH), oxytocin, estradiol, growth hormones, leuprolide acetate, factor VIII, testosterone and analogs thereof. Analgesics include, but are not limited to, fentanyl, sufentanil, butorphanol, buprenorphine, levorphanol, morphine, hydromorphone, hydrocodeine, oxymorphone, methadone, lidocaine, bupivacaine, diclofenac, naproxen, paverin, and analogs thereof. Anti-migraine agents include, but are not limited to heparin, hirudin, and analogs thereof. Anti-coagulant agents include, but are not limited to, scopolamine, ondansetron, domperidone, etoclopramide, and analogs thereof. Cardiovascular, anti-hypertensive and vasodilator agents include, but are not limited to, diltiazem, clonidine, nifedipine, verapamil, isosorbide-5-mononitrate, organic nitrates, nitroglycerine and analogs thereof. Sedatives include, but are not limited to, benzodiazeines, phenothiozines and analogs thereof. Narcotic antagonists include, but are not limited to, naltrexone, naloxone and analogs thereof. Chelating agents include, but are not limited to deferoxamine and analogs thereof. Anti-diuretic agents include, but are not limited to, desmopressin, vasopressin and analogs thereof. Chemotherapeutic agents include any chemical compound useful in the treatment of cancer, including but not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlore-thamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Apoptosis-inducing agents include but are not limited to the TNFα family of ligands An active agent can be formulated in neutral or salt form. Pharmaceutically acceptable salts include, but are not limited to, those formed with free amino groups; those formed with free carboxyl groups; and, those derived from sodium, potassium, ammonium, calcium, ferric hydroxide, isopropylamine, triethylamine, 2-ethylaminoethanol, histidine and procaine. An active agent can be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

Methods of making a targeting compound-active agent complex include, but are not limited to, covalent coupling of a targeting compound and an active agent and noncovalent coupling of a targeting compound and an active agent.

Methods of making a targeting compound-active particle complex include, but are not limited to, incorporating an active agent into a particle including, but not limited to, a nanoparticle, a microparticle, a capsule, a liposome, a non-viral vector system and a viral vector system. The targeting compound can be complexed to the active particle by methods including, but not limited to, adsorption to the active particle, noncovalent coupling to the active particle and covalent coupling, either directly or via a linker, to the active particle, to the polymer or polymers used to synthesize the active particle, to the monomer or monomers used to synthesize the polymer, and to other components comprising the active particle.

Another aspect of the invention provides a pharmaceutical composition comprising an analog of the present invention in admixture with a pharmaceutically acceptable carrier. The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as TWEEN™, polyethylene glycol (PEG), and PLURONICS™.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining analogs with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of analog, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the analogs may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

The analogs may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery.

Therapeutic Uses of Analogs

Another aspect of the invention provides a method of treating a disease or condition in a subject comprising administering an effective dose of a formulation comprising an analog of the present invention to the subject. In a preferred embodiment the disease or condition infertility and in particular infertility caused by polycystic ovary syndrome (PCOS).

Gonadotropin antagonists would have substantial uses for the treatment of PCOS. This syndrome is seen in approximately 5% of women of reproductive age and accounts for roughly a third or more of human infertility. PCOS patients have oligomenorrhea and fail to ovulate or ovulate less frequently than women who have regular menstrual cycles. Although the etiology of PCOS is poorly understood, the cystic follicles that are present in the ovaries of these patients are almost certainly responsible for their infertility; surgical removal of these follicles usually results in reduction of androgen levels and the resumption of ovulatory menstrual cycles (Stein and Leventhal, 1935; Greenblatt and Casper, 1987; Liguori et al., 1996). Removal of the cystic follicles does not "cure" PCOS, however, and these patients become infertile when the cystic follicles re-accumulate. The association between cystic follicles and infertility in PCOS patients implies that development of a non-surgical method for removing the cysts would restore fertility to these women, at least until new cystic follicles accumulate in the ovary. Furthermore, since elimination of the cystic follicles promotes ovulation with little risk of ovarian hyperstimulation or multiple pregnancy (Shanti and Murphy, 1997), a non-surgical procedure that had the same effect as wedge resection would have significant advantages relative to gonadotropin therapy. In principle, it could be attained with only a single injection of an agent that is targeted to LHR or LHR/FSHR expressing cells that has the ability to promote apoptosis of these cells. Furthermore, it could be explored without the danger of creating adhesions and other unwanted side effects of surgery. Adhesions themselves are thought to interfere with fertility if they restrict access of the ovulated egg to the fallopian tube or restrict movements of its fimbriated end.

PCOS is universally associated with hyper secretion of ovarian androgens (Balen et al., 1995), a phenomenon that may have several etiologies and that becomes self sustaining once established. Factors that contribute to PCOS include hyperinsulinemia, which is particularly noticeable in obese patients, but often observed in lean patients (Dunaif, 1997; Dunaif et al., 1996), and aberrant gonadotropin secretion, which is manifested as an increased ratio of LH to FSH (Hall et al., 1998). The latter may be a response to the increased production of ovarian or adrenal androgens. These can become converted to estradiol, a potent inhibitor of FSH secretion. Since LH can enhance androgen production and since this can be augmented by insulin (Franks et al., 1999), elevated ratios of LH/FSH or increased insulin secretion would tend to produce more ovarian androgens and thereby contribute to the self-sustaining nature of PCOS. PCOS may also be exacerbated by the manner in which androgens are made in the adrenal and ovary (Rosenfield, 1999). The gene for CYP17 encodes a protein that has two activities, i.e., 17 hydroxylase and 17,20 lyase (Zhang et al., 1995). This enables the enzyme to hydroxylate pregnenolone and progesterone and then cleave the products to C19 steroids, i.e., androgens and androgen precursors. While only the hydroxylase is needed for the production of adrenal steroids, both activities are required for production of androgens and estrogens. The activities of the lyase appear to be controlled differently than those of the hydroxylase, probably by serine phosphorylation or cytochrome b5 expression (Zhang et al., 1995; Lee-Robichaud et al., 2004). Excessive lyase activity has been proposed to be responsible for the unwanted androgens associated with PCOS.

Most ovarian androgens are produced by cells that have LH receptors. Ovarian androgens are thought to promote the survival of small follicles in the primate ovary and to prevent them from developing fully (Vendola et al., 1998). Thus, once initiated, the production of ovarian androgens would be expected to sustain PCOS. This notion is supported by the observation that treatments of monkeys with testosterone or dihydrotestosterone, an androgen that cannot be converted to estradiol, develop "cystic follicles" (Vendola et al., 1998). Thus antagonists that reduce the abilities of LH to promote androgen production by these cells would be expected to mitigate PCOS.

The influence of dihydrotestosterone on cystic follicle production suggests that conversion of androgens to estradiol is not required for the development of PCOS. Nonetheless, the abilities of anti-estrogens to induce ovulation in a majority of PCOS patients suggest that inappropriate aromatization of estradiol, one of the most potent inhibitors of FSH secretion, may also have a role in this process (Homburg, 2003). Indeed, the effectiveness of clomiphene citrate, the most commonly used therapeutic for ovulation induction (Yildiz et al., 2003), rests on its ability to block the feedback inhibition of FSH secretion by estradiol. The enhanced pituitary gland FSH secretion then stimulates follicular growth in PCOS patients. The advantage of clomiphene therapy for ovulation induction is that it can be used without extensive patient monitoring and has a relatively low incidence of multiple pregnancies (Homburg, 2004). The downside of this therapy is that clomiphene can inhibit endometrial development, which may explain why many clomiphene treated PCOS patients fail to become pregnant, even after multiple treatment cycles. Combination of clomiphene or other anti-estrogen treatment with an LH receptor antagonist would be expected to facilitate the activity of the anti-estrogen and thereby reduce the amount of drug needed to promote ovulation. This would also reduce the likelihood that anti-estrogen therapy would have unwanted effects on the endometrium and fallopian tubes that could interfere with their abilities to enhance fertility.

Patients who fail to become pregnant after repeated clomiphene therapy are usually treated with FSH and/or mixtures of FSH and LH or hCG (Homburg, 2004), gonadotropins that stimulate follicle growth and ovulation. Unfortunately, this therapy can cause ovarian hyperstimulation and often results in multiple pregnancies. Considerable attention has been focused on procedures that might reduce the potential for multiple pregnancies, including the way the hormone is given (Buvat et al., 1989). Gonadotropin therapy may also be combined with GnRH antagonists and agonists (Cardone, 2003). Treatments that promote the turnover of ovarian PCOS tissues would also be expected to enhance the efficacy of gonadotropin therapy and may reduce the incidence of multiple pregnancy.

The role of insulin sensitivity in PCOS has also been studied extensively. Many PCOS patients become pregnant after they lose weight (Homburg, 2004) or after they are treated with insulin potentiating agents such as metformin (Homburg, 2004). The notion that insulin may have a role in the development of PCOS is supported by a case report showing that the PCOS in a patient with an insulinoma disappeared after the tumor was removed (Murray et al., 2000). The use of metformin for ovulation induction remains controversial (Ehrmann et al., 1997; De et al., 1999) although long term treatment may have some benefit for non obese patients (Maciel et al., 2004). Combination of metformin with other therapy may also be beneficial (Homburg, 2004). This would include combination with an inhibitor of LH activity that promotes the turnover of PCOS tissues or that suppresses the production of ovarian androgens.

The earliest method of treating infertility in PCOS patients involved removing their cystic follicles by wedge resection surgery (Stein and Leventhal, 1935). Several other modifications of this procedure have been introduced during the ensuing years (Campo, 1998), but these have largely been replaced by anti-estrogen and gonadotropin therapies, which do not have risks associated with surgery. Most PCOS patients resume menstrual cycles shortly after their cystic follicles have been removed. Since follicle development is then controlled by the intrinsic feedback regulation inherent in the hypothalamic/pituitary/ovarian axis, this procedure does not cause ovarian hyperstimulation or multiple pregnancies (Campo, 1998). Wedge resection and related surgeries do not eliminate the underlying factors that cause the development of cystic follicles, however, and the condition usually returns. Whereas it is not practical to do multiple wedge resection surgeries to remove the follicles, repeat treatments would not be a problem for a non-surgical method such as that involving the use of an antagonist that blocked androgen secretion or an antagonist coupled to an apoptosis inducing agent. The apoptosis inducing agent in the latter therapeutic would facilitate turnover and removal of the unwanted ovarian cells.

The incidence of PCOS usually falls with age (Elting et al., 2000), a decline that appears to parallel the reduction in ovarian reserve. This supports the notion that the self-sustaining aspect of PCOS requires a continued input of follicular tissue and that the accumulation of cystic follicles depends on a balance between follicle production and atresia. Since ovarian androgen production may exert a positive feedback effect on cystic follicle development, even a small reduction in ovarian androgen production would be expected to facilitate the turnover of cystic follicles. Therefore, brief treatments with agents capable of blocking gonadotropin induced steroidogenesis and/or initiating apoptosis would be expected to increase the removal of cystic follicles from the ovaries of PCOS patients in a synergistic fashion.

Another aspect of the invention provides a method of inducing follicle development in fish comprising administering an effective dose of a formulation comprising an analog of the present invention to said fish. Species of fish that can be treated using this method include, but are not limited to, those species listed in FIG. 31.

An effective dose means that amount of active agent which ameliorates the symptoms or condition. Therapeutic efficacy and toxicity of such active agents can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such active agents lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

All patents and publications cited above are herein incorporated by reference. The various aspects of the present invention are further described in the following non-limiting examples.

EXAMPLE 1

Development of a Lutropin Antagonist

The wraparound pathway can be used to prepare hCG analogs in which the seatbelt is latched to the α-subunit rather than to the β-subunit (Xing et al., 2001a). The efficiency of this process depends on the location of the seatbelt latch site. Seatbelt latch sites that are located on α-subunit loop 2 are usually the most efficient and, when the seatbelt is latched to some of these, the heterodimer retains its biological activity. The hCG seatbelt can be forced to latch to a cysteine added to the α-subunit when the normal seatbelt latch site—i.e., Cys26 in β-subunit loop 1—is disrupted. Using this approach (Xing et al., 2001a) prepared heterodimers in which the seatbelt became latched to cysteines that had been substituted for several α-subunit residues. With the exception of hCG analogs in which the seatbelt was latched to cysteines nearby the normal seatbelt latch site—e.g., α-subunit residues Leu41 and Ser43—this approach to crosslinking the heterodimer led to a loss in LH receptor recognition. Although it was possible to latch the seatbelt to α-subunit residue 86 by replacing the threonine normally found at this site with cysteine, the resulting analog was nearly unable to bind to LH receptors (Xing et al., 2001a). Furthermore, it was not possible to obtain active FSH analogs using this approach, most likely because the carboxyterminal half of the seatbelt has a much more important role in the activities of follitropins than lutropins (Campbell et al., 1991; Moyle et al., 1994; Campbell et al., 1997).

Studies of the interaction of hCG, bovine LH, and glycoprotein hormone analogs with rat lutropin receptors and receptor analogs suggested that parts of the seatbelt near its carboxyterminal end are important for hormone efficacy. This portion of the hormone contains the primary epitope for monoclonal antibody B111 (Moyle et al., 1990; Xing et al., 2004a; Moyle et al., 2004). Binding of B111 and to a lesser degree B110, an antibody to an overlapping epitope, restored the efficacy of an hCG analog that lacked an oligosaccharide on α2 (Moyle et al., 2004). Monoclonal antibodies to other sites of the hormone did not restore efficacy to this hCG analog, indicating that they recognized sites that that are distant from those that have an influence on efficacy (Moyle et al., 2004).

The region of the SSD encoded by exon 10 also appears to be important for efficacy. human LHR residues derived from the region of the SSD encoded by exon 10 are needed for full LH responsiveness; their absence leads to infertility (Gromoll et al., 2000). Exon 10 is missing in the marmoset LHR (Zhang et al., 1997; Gromoll et al., 2003) and its ability to respond much better to CG than LH will explain why the marmoset pituitary produces a CG-like hormone rather than LH (Muller et al., 2004b). SSD residues derived from rat LHR exon 10 are not essential for hCG binding, but contribute to the binding of bovine LH and several hCG analogs (Moyle et al., 2004). Analyses of these observations suggest that residues from exon 10 are likely to contact the β-subunit near its seatbelt latch site (Muller et al., 2004a; Moyle et al., 2004). Furthermore, removal of the residues encoded by exon 10 from the rat LH receptor created a receptor that is much less able to respond to hCG analogs that lack the α2 oligosaccharide (Moyle et al., 2004). Removal of the β-subunit carboxyterminus reduced the efficacy of hCG by roughly half (Moyle et al., 2004), indicating that this portion of the hormone is likely to interact with residues derived from exon 10 or nearby sites of the receptor. This also revealed that these contacts may have a role in signal transduction.

Consideration of these observations suggested that it might be possible to prepare hCG analogs that had greatly reduced efficacy for the full-length receptor by removing portions of the seatbelt near the normal seatbelt latch site. Unfortunately, efforts to remove the seatbelt latch site per se destabilize the heterodimer, making it impossible to simply truncate all or part of the seatbelt. There are two ways to produce heterodimers lacking the disulfide that stabilizes the seatbelt, but neither of these would be expected to create a useful antagonist. One of these methods involves production of hCG analogs in a single chain format in which the codons for the α-subunit are fused to codons for the β-subunit or vice versa, codons for the β-subunit are fused to codons for the α-subunit. This type of analog has been prepared and found to have full (Sugahara et al., 1996a; Sugahara et al., 1996b; Sugahara et al., 1995) or significant (Heikoop et al., 1997a) efficacy. Apparently, the single chain format can stabilize the carboxyterminal end of the seatbelt close enough to its natural site that it retains its ability to interact with the receptor to initiate signal transduction, even when the sequences of this region of the seatbelt are altered (Heikoop et al., 1997a). Therefore, it seemed less likely that single chain fusion proteins in which the α-subunit is coupled to the carboxyterminus of the β-subunit can be used to create a useful antagonist, even if the seatbelt latch disulfide is removed. The second method for producing an analog that lacks the seatbelt latch disulfide involves the use of an aminoterminal stabilization domain. This type of domain can be either a disulfide crosslink at the aminoterminal end of the hormone, such as one between α-subunit residue 5 and β-subunit residue 8 (Heikoop et al., 1997b) or other nearby β-subunit residue such as β-subunit residues 6 or 7. Other α-subunit residues in this region can also be crosslinked to the β-subunit including residues 6 and 7. Use of the latter for crosslinking is facilitated by replacing α-subunit residue cysteine 31 with alanine. Heterodimers lacking the seatbelt latch disulfide can also be stabilized by addition of a Fos-Jun dimerization domain (Lin et al., 1999). Unfortunately, analogs lacking the seatbelt latch site that are stabilized in this fashion have very little ability to bind to the receptor, most likely because the carboxyterminal end of the seatbelt is free to move and may destabilize the hormone-receptor complex.

To assemble heterodimers that lack parts of the carboxyterminal region of the seatbelt that are likely to contribute to efficacy and act as LH receptor antagonists, it was necessary to devise methods that would 1) prevent dissociation of the heterodimer after the seatbelt latch disulfide was removed, 2) restrain the region of the small seatbelt loop in a position similar to that seen in the heterodimer, and 3) minimize the amount of seatbelt and other nearby parts of the β-subunit. Since the small seatbelt loop is required for lutropin activity, retention of this part of the β-subunit in a conformation that approximates that seen in hCG or hLH was considered to be important.

Figure 9:
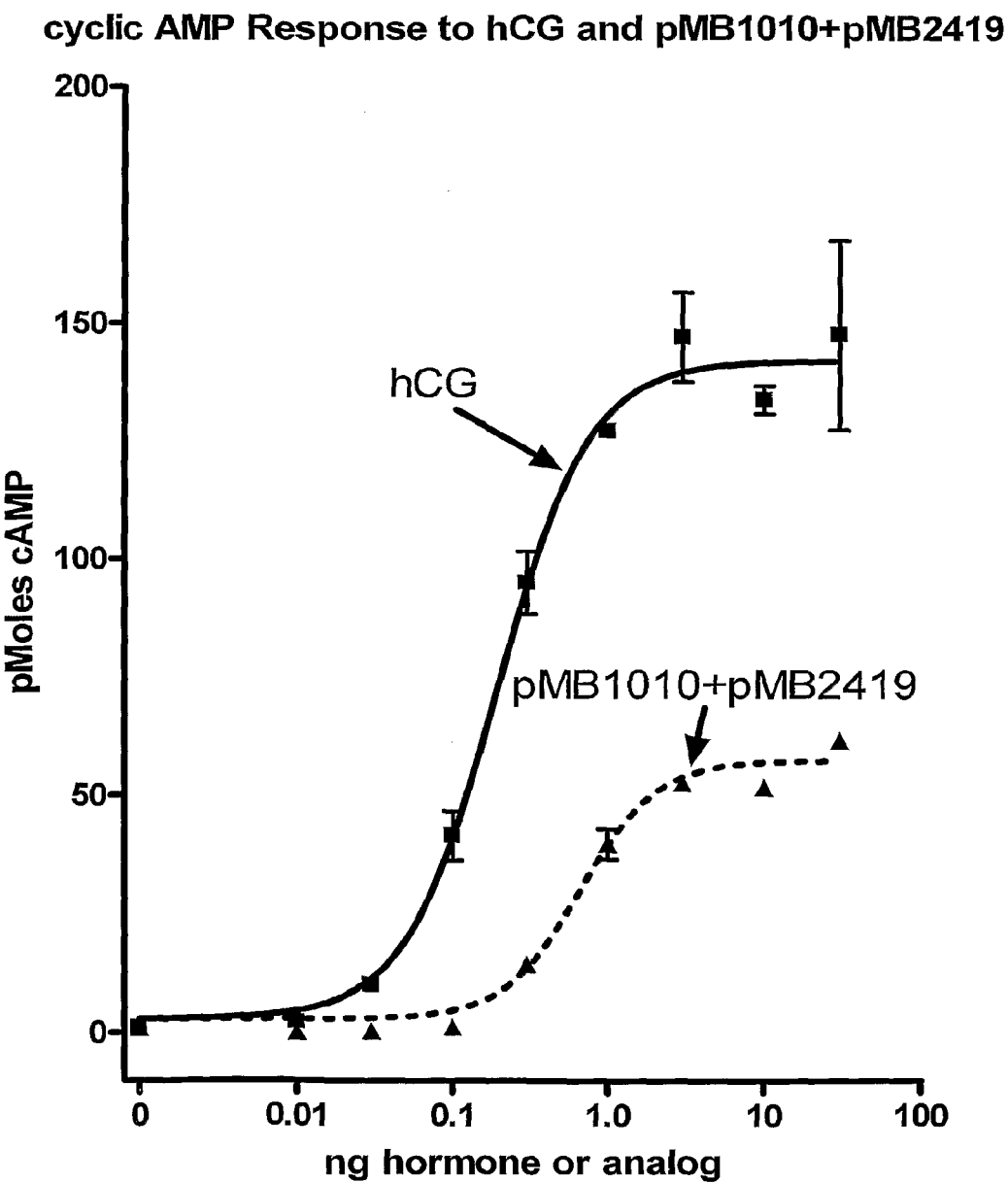
FIG. 9. This figure shows the ability of a crosslinked heterodimer that four N-linked oligosaccharides to stimulate cyclic AMP accumulation in CHO cells that express the rat LH receptor. This analog contains a disulfide crosslink between seatbelt residue #12 and α-subunit residue 86. Cys26 of the β-subunit has been replaced by alanine, seatbelt residues 13-20 have been deleted, and the β-subunit carboxyterminal end has also been deleted. Note that the efficacy of pMB1010+pMB2419 has been reduced relative to that of hCG.

Molecular modeling suggested that introduction of a disulfide crosslink between α-subunit residue 86 and seatbelt residue 102 had the potential to stabilize the small seatbelt loop in a position needed for LH receptor interaction. Since the resulting disulfide would crosslink the heterodimer, it would also stabilize heterodimers that lack the seatbelt. Starting with constructs that encode the native human α-subunit sequence (pMB574, FIG. 8) and the native hCG β-subunit sequence (pMB584, FIG. 8), analogs were built to test this possibility. These analogs were made using standard polymerase chain reaction (PCR) and cassette mutagenesis procedures that are familiar to anyone skilled in the art of making and expressing glycoprotein hormone or other protein analogs in COS-7 and Chinese hamster ovary (CHO) cells. The oligonucleotides needed for mutagenesis were purchased from Integrated DNA Technologies, Inc, Coralville, Iowa. Co-transfection of COS-7 cells with constructs encoding a human α-subunit analog in which Thr86 was replaced by the codon for cysteine (Sequence pMB1010, FIG. 8) and an hCG β-subunit analog that contained a cysteine in place of residue Gly102 and a termination codon in place of Pro103 (Sequence pMB2419, FIG. 8) yielded a disulfide crosslinked heterodimer that was secreted into the culture medium. This analog was stable when treated at pH 2 for 30 minutes at 37° C. and was detected readily using a sandwich immunoassay employing an antibody to the human α-subunit (A113, obtained from Hybritech Inc., San Diego, Calif.) and a radio-iodinated antibody to the hCG β-subunit [B110, that had been prepared in this laboratory (Moyle et al., 1987)]. Note that any of the antagonist analogs described here can be quantified using commercially available antibodies to the α-subunit that recognize hCG and a commercially available antibodies to the hCG β-subunit that recognize epitopes on loops β1 or β3 using sandwich immunoassay procedures or radioimmunoassay procedures. Both types of antibodies are among the most common antibodies that recognize hCG. Furthermore, since the heterodimer that lacks a crosslink is unstable and dissociates into its subunits readily, this type of assay will readily distinguish material that contains a crosslink from material that lacks a crosslink after pH 2 treatment for 30 minutes at 37° C. It is not necessary to use monoclonal or polyclonal antibodies that distinguish hCG and human LH (hLH) in these assays. The resulting crosslinked heterodimer bound formed by co-transfection of COS-7 cells with pMN1010+pMB2419 bound to CHO cells that had been engineered to express the rat LH receptor with high affinity and stimulated cyclic AMP accumulation to only half the extent as hCG (FIG. 9).

Figure 11:
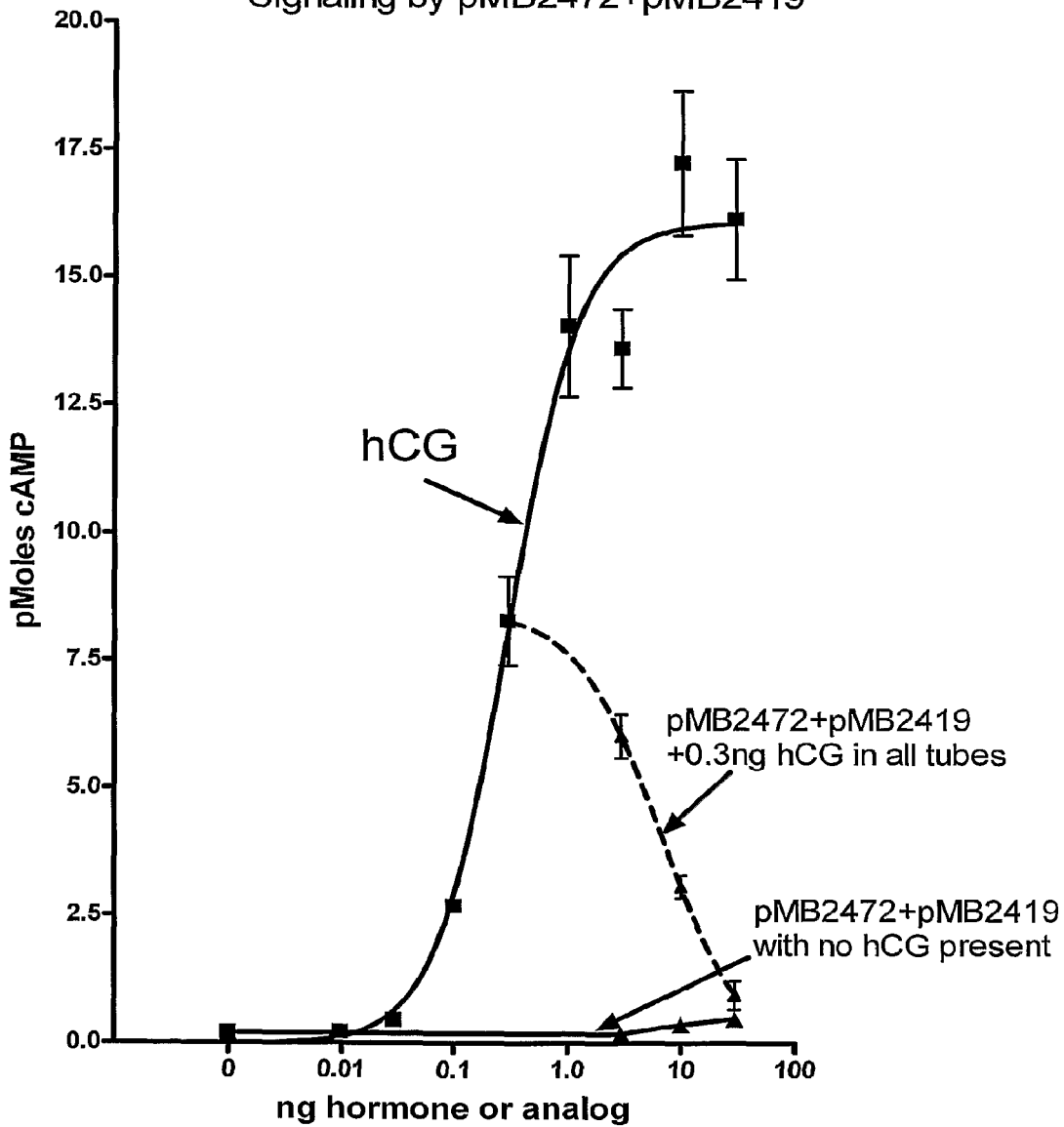
FIG. 11. Influence of removing the oligosaccharide from α-subunit loop 2 from pMB1010 to create pMB2472. When this analog was expressed with pMB2419, it led to the formation of a heterodimer termed pMB2472+pMB2419 that had very little ability to stimulate cyclic AMP accumulation in CHO cells that over express the rat LH receptor. This disulfide crosslinked analog bound to the LH receptor with high affinity and blocked the ability of hCG to stimulate cyclic AMP accumulation.

This analog contained all the N-linked glycosylation signals normally found on hCG, including that at α-subunit residue Asn52 required for full hormone efficacy reduce efficacy (Matzuk et al., 1989). Removal of this oligosaccharide by replacing the codon for α-subunit residue Asn$^{52}$ with one for aspartic acid created a construct that encoded the α-subunit sequence pMB2472 (FIG. 8). Transfection of COS-7 cells with constructs that encode amino acid sequences pMB2472 (FIG. 8) and pMB2419 (FIG. 8) resulted in the secretion of a crosslinked heterodimer that was readily detected in the A113-$^{125}$I-B110 sandwich immunoassay. Although this analog bound to the rat LHR similar to hCG (FIG. 10), it produced trace amounts of cyclic AMP accumulation that were barely detectable in the cyclic AMP radioimmunoassay (RIA) used (Brooker et al., 1979) and was a potent inhibitor of $^{125}$I-hCG binding to CHO cells that over express the rat LH receptor (FIGS. 10 and 11). The change in the amount of cyclic AMP produced in response to stimulation by the antagonist was difficult to measure in the absence of 0.2 mM isobutylmethylxanthine, a potent inhibitor of cyclic AMP degradation. This hCG derived analog was a potent inhibitor of hCG action in CHO cells that over express the rat LH receptor and, its efficacy was 2-5 fold lower that that observed using the other highly potent antagonists (Bernard et al., 2005). The latter consisted of heterodimers that contain a disulfide crosslink between α-subunit residue 37 (sequence pMB1244, FIG. 8) and β-subunit residue 33 (sequence pMB1326, FIG. 8) or between α-subunit residue 35 (sequence pMB1243, FIG. 8) and β -subunit residue 35 (sequence pMB1328, FIG. 8). Sequences pMB1244 and pMB1243 lacked the glycosylation signal at α-subunit residue 52. Sequences pMB1326 and pMB1328 are based on an hCG/hFSH β-subunit chimera that is truncated at residue 115 and have human FSH β-subunit residues 95-103 substituted for hCG β-subunit residues 101-109. These analogs and their activities have been described (Bernard et al., 2005). The analog containing amino acid sequences pMB2472 and pMB2419 was a potent inhibitor of hCG induced cyclic AMP accumulation in CHO cells that over express rat LH receptors (FIG. 10).

Figure 12:
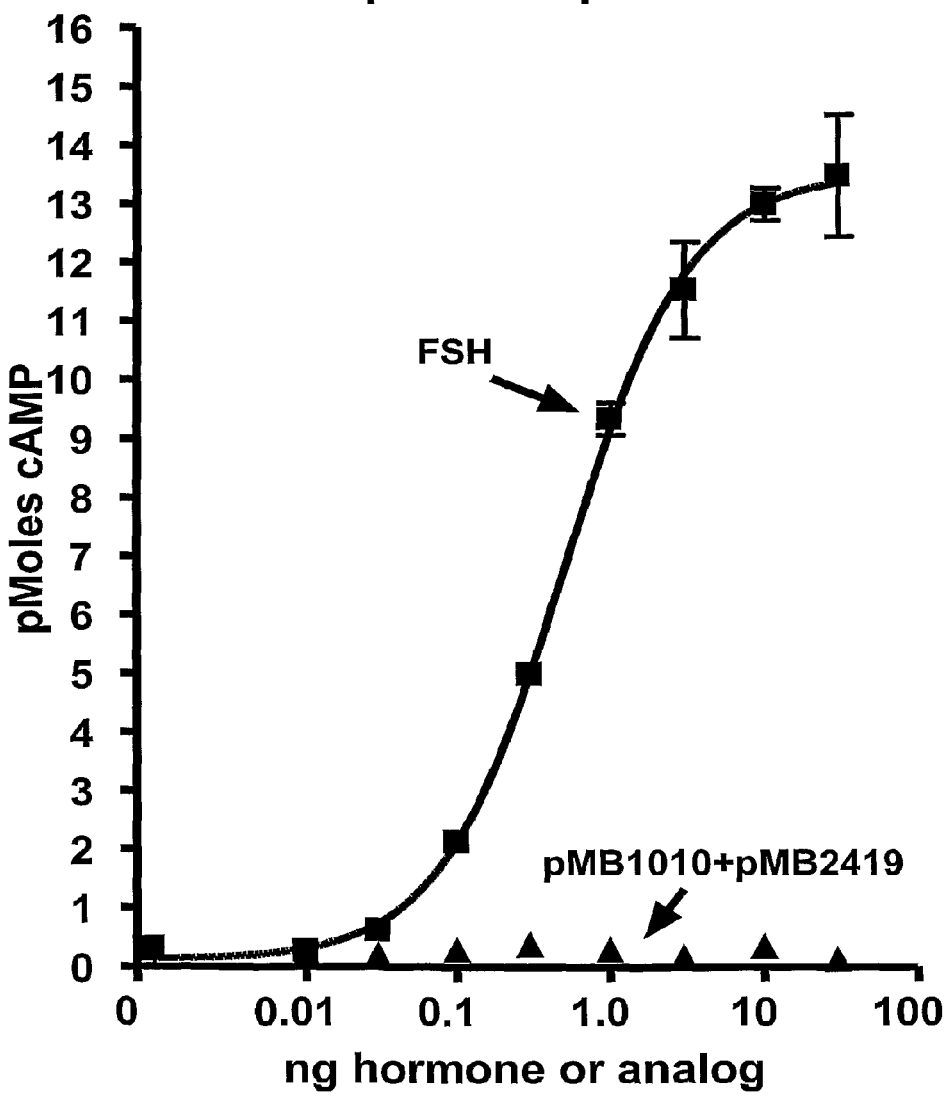
FIG. 12. Inability of pMB1010+pMB2419 heterodimer to initiate signal transduction in CHO cells that over express the FSH receptor. This analog elicited cyclic AMP accumulation in cells that over express the LH receptor (FIG. 9).

Some procedures for preparing lutropin antagonists yield compounds that cross react with follitropin receptors as well as lutropin receptors (Bernard et al., 2005). In contrast, the analog containing sequences pMB2472 and pMB2419 did not interact with FSH receptors and was unable to inhibit the binding of 1251-hFSH to cells that over express human FSH receptor. Neither it, nor its precursor (pMB1010+pMB2419), which has a much greater efficacy, were able to initiate signaling in CHO cells that overexpress the FSH receptor (FIG. 12). It did not inhibit the influence of hFSH on the ability of these cells to illicit cyclic AMP accumulation. This showed that the analog did not bind to FSH receptors, most likely a consequence of the absence of residues in the carboxyterminal half of its seatbelt. This region of the seatbelt is known to influence FSH receptor binding (Moyle et al., 1994).

The analogs illustrated in Example 1 are assembled by the wraparound pathway. This is because the seatbelt cannot be latched before the subunits dock, a phenomenon that will prevent premature latching of the seatbelt. Premature latching of the seatbelt can disrupt the formation of some heterodimers (Xing et al., 2004c), notably those between salmon FSH α and β subunits as well as those of related species of fish. Thus, the approach to produce the heterodimers described in this example is expected to create analogs of salmon FSH that are formed efficiently because they lack the ability to latch their seatbelts before the subunits dock—i.e., prematurely.

EXAMPLE 2

Figure 13:
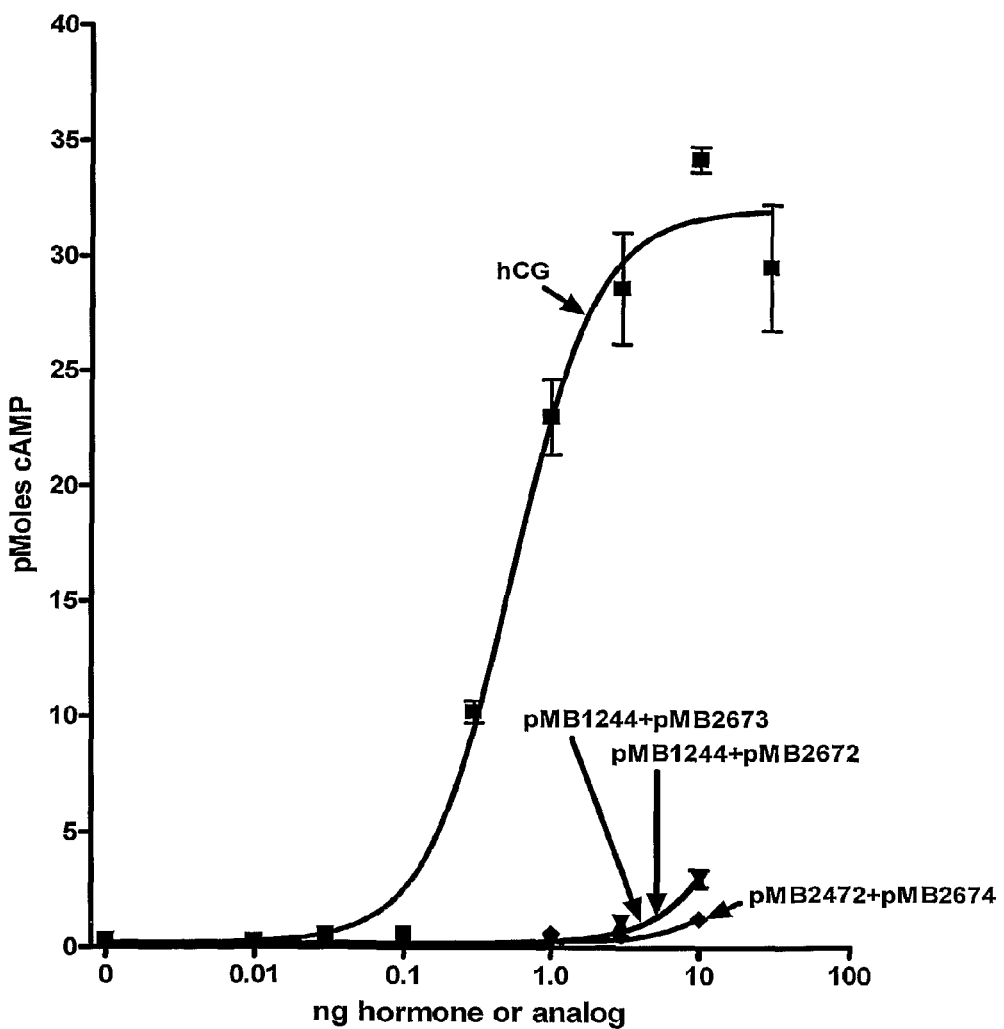
FIG. 13. This figure shows the ability of three heterodimers that contain disulfide crosslinks that differs from those shown described earlier. All of these crosslinks resulted in analogs that had lower affinities and higher efficacies for the rat LH receptor than the heterodimer composed of pMB2472+ pMB2419. Thus, although these crosslinks were found to form, these analogs appear not to be as useful as pMB2472+ pMB2419 for useful as an LH receptor inhibitor.
Figure 14:
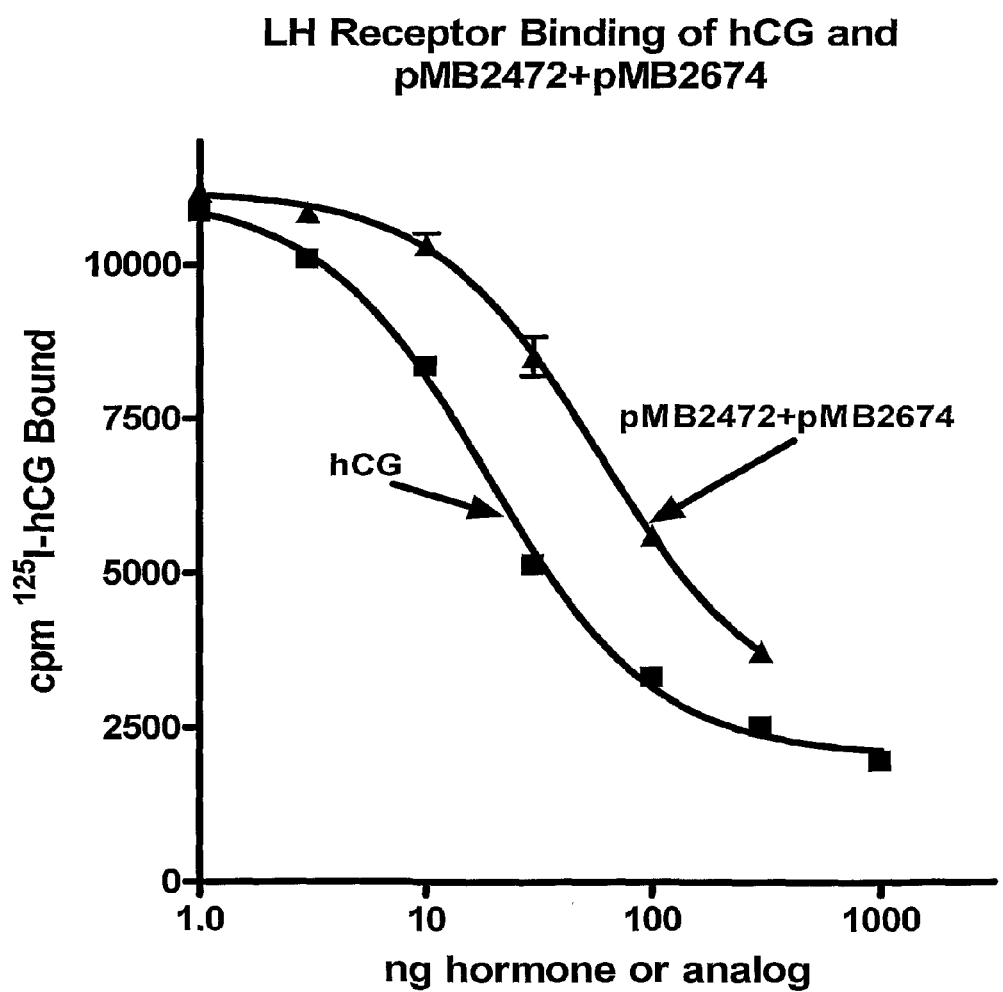
FIG. 14. Ability of pMB2472+pMB2674 to compete with radioiodinated hCG for rat LH receptors. Note that the activity of pMB2472+pMB2674 in this assay is somewhat lower than that of pMB2472+pMB2419 (FIG. 11).
Figure 15:
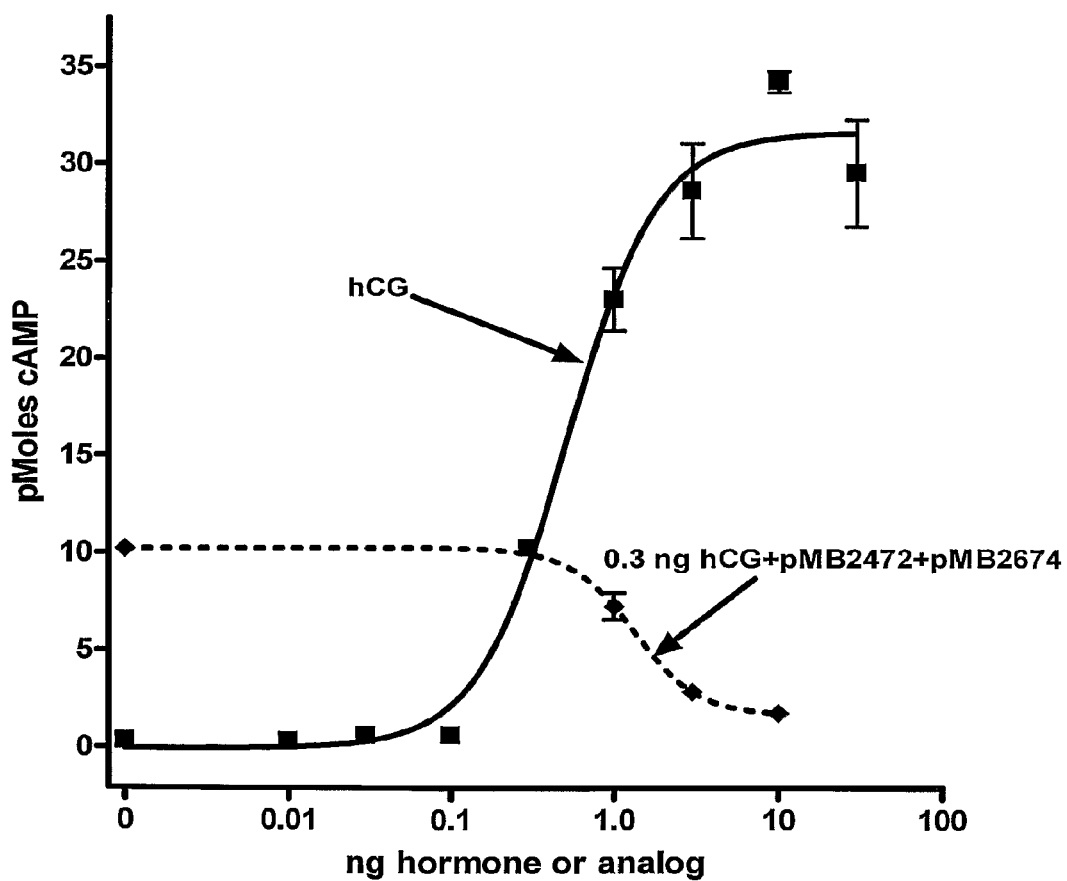
FIG. 15. Ability of pMB2472+pMB2674 to inhibit hCG induced cyclic AMP accumulation in assays employing CHO cells that over express rat LH receptors. The broken line represents the presence of 0.3 ng of hCG plus the indicated amount of pMB2472+pMB2674.

Abilities of Additional Disulfide Crosslinks to Stabilize the Heterodimer Containing a Truncated Seatbelt in a Functional Fashion Crosslinks between α86-β103 that were produced by co-expressing pMB2472 and pMB2674, (FIG. 8), α86-β106 pMB2472 and pMB2672, (FIG. 8) and α86-β108 (pMB2472 and pMB2673, (FIG. 8) permitted the formation of heterodimers containing a truncated seatbelt. These were prepared by expressing a construct that encodes sequences pMB1244 or pMB2472 with constructs that encode sequences pMB2674, pMB2672, or pMB2673 transiently in COST cells. These had the ability to inhibit binding of 125I-hCG to rat LH receptors and had low efficacies in cAMP accumulation signal transduction assays (FIG. 13). Of the three types of crosslink, that between α86 and β102 led to an analog that had the lowest efficacy (FIG. 13). This analog blocked the binding of 125I-hCG to rat LH receptors (FIG. 14) and inhibited hCG stimulated cyclic AMP accumulation (FIG. 15). Its ability to compete with hCG for binding to the rat LH receptor was not as good as that of pMB2472+pMB2419 and, as a result, its ability to block the signal transduction activity of hCG was tested at lower hCG concentrations (FIG. 15).

Figure 16:
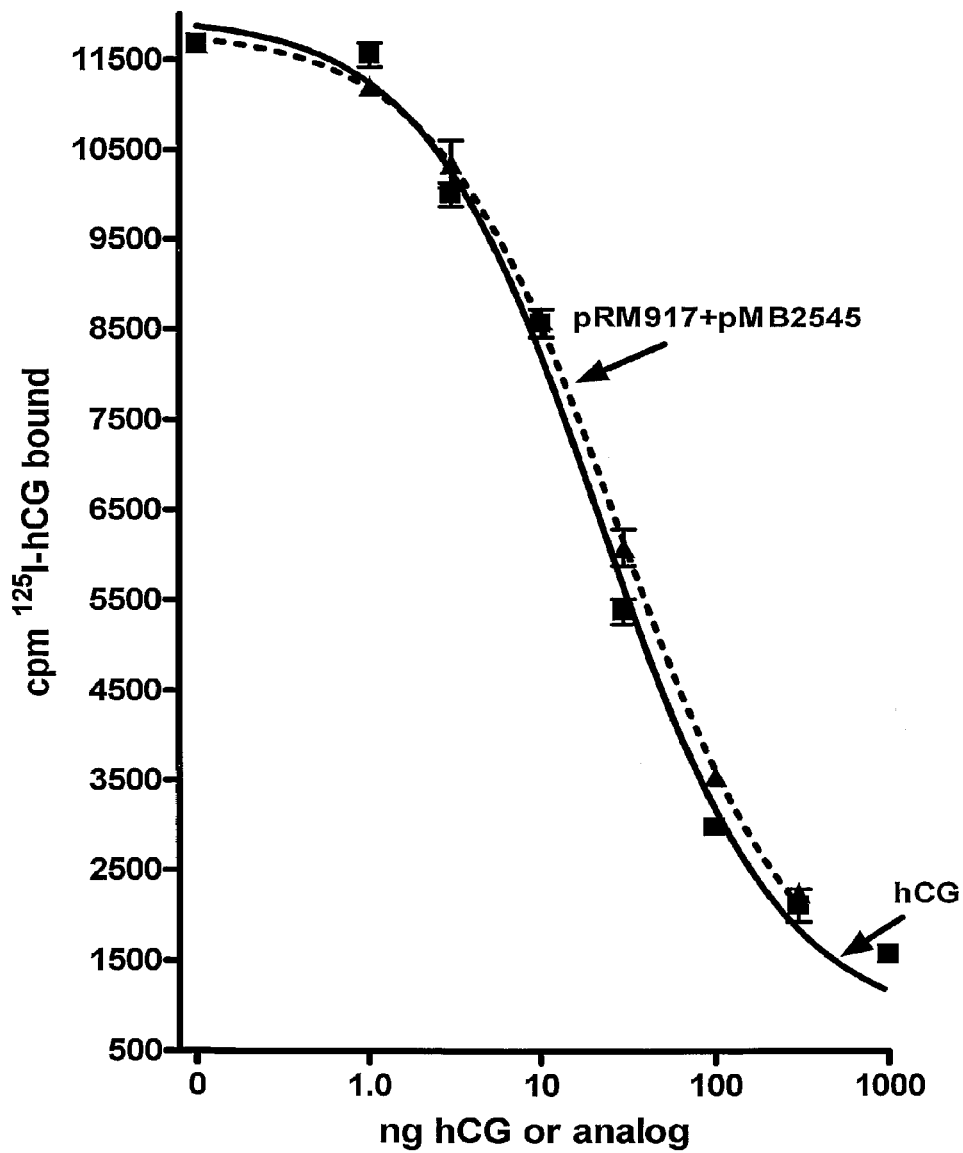
FIG. 16. Relative abilities of hCG and pRM917+pMB2545 to compete with radioiodinated hCG for binding to rat LH receptors. This figure shows that the analog and hCG had similar abilities to block binding of radioiodinated hCG to the rat LH receptor.
Figure 17:
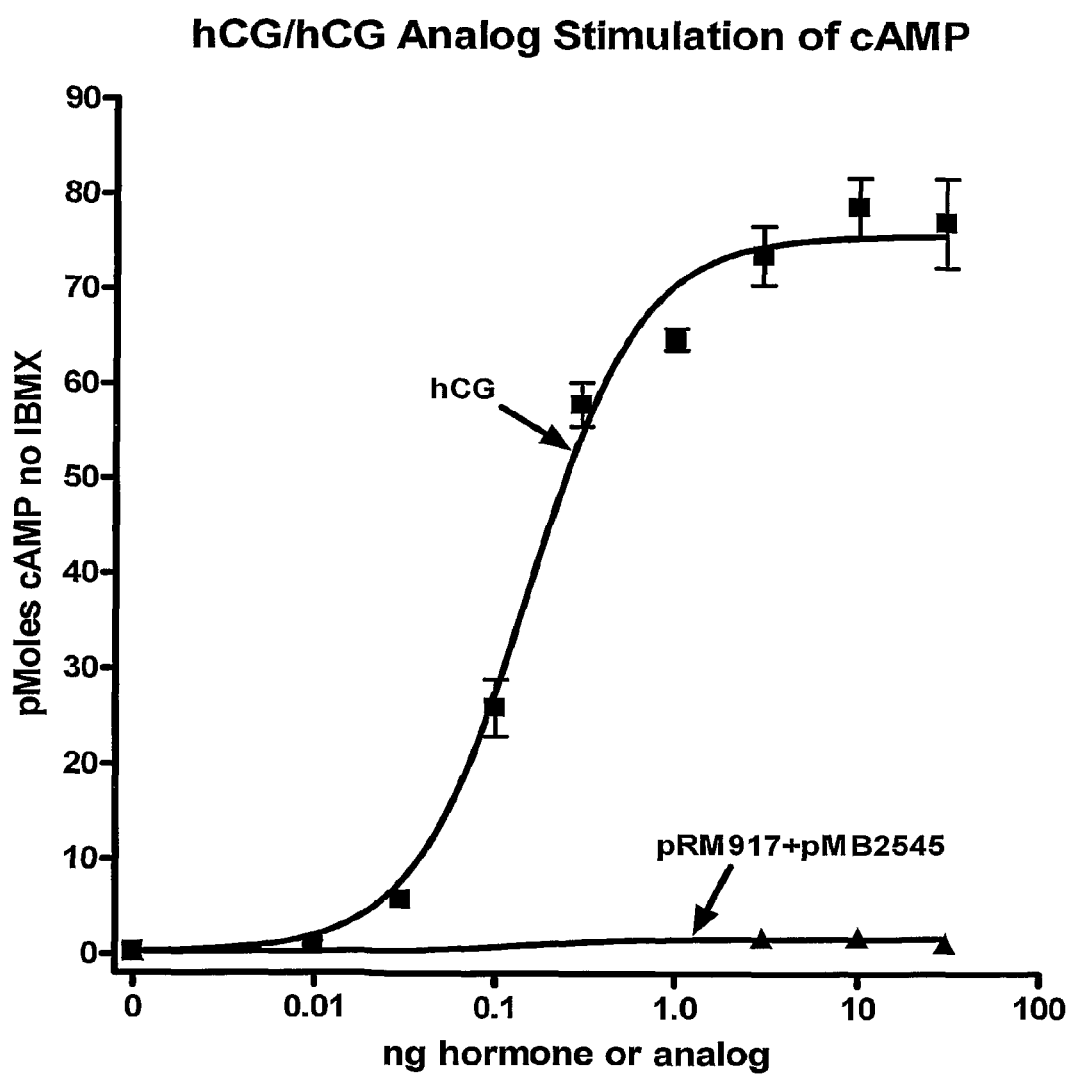
FIG. 17. Relative abilities of hCG and pRM917+pMB2545 to stimulate cyclic AMP accumulation in assays employing CHO cells that over express the rat LH receptor. This figure shows that the analog had much lower efficacy than hCG in this assay.
Figure 18:
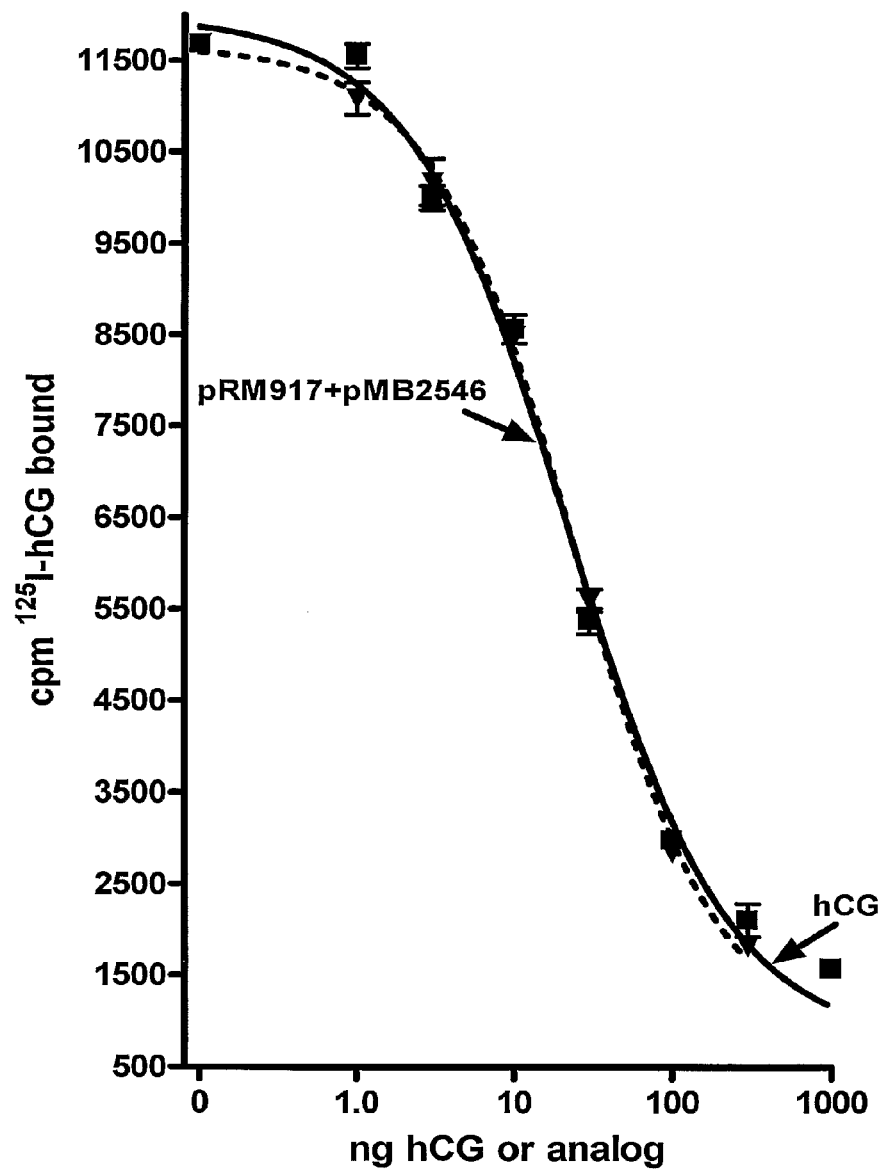
FIG. 18. Relative abilities of hCG and pRM917+pMB2546 to compete with radioiodinated hCG for binding to rat LH receptors. This figure shows that the analog and hCG had similar abilities to block binding of radioiodinated hCG to the rat LH receptor.
Figure 19:
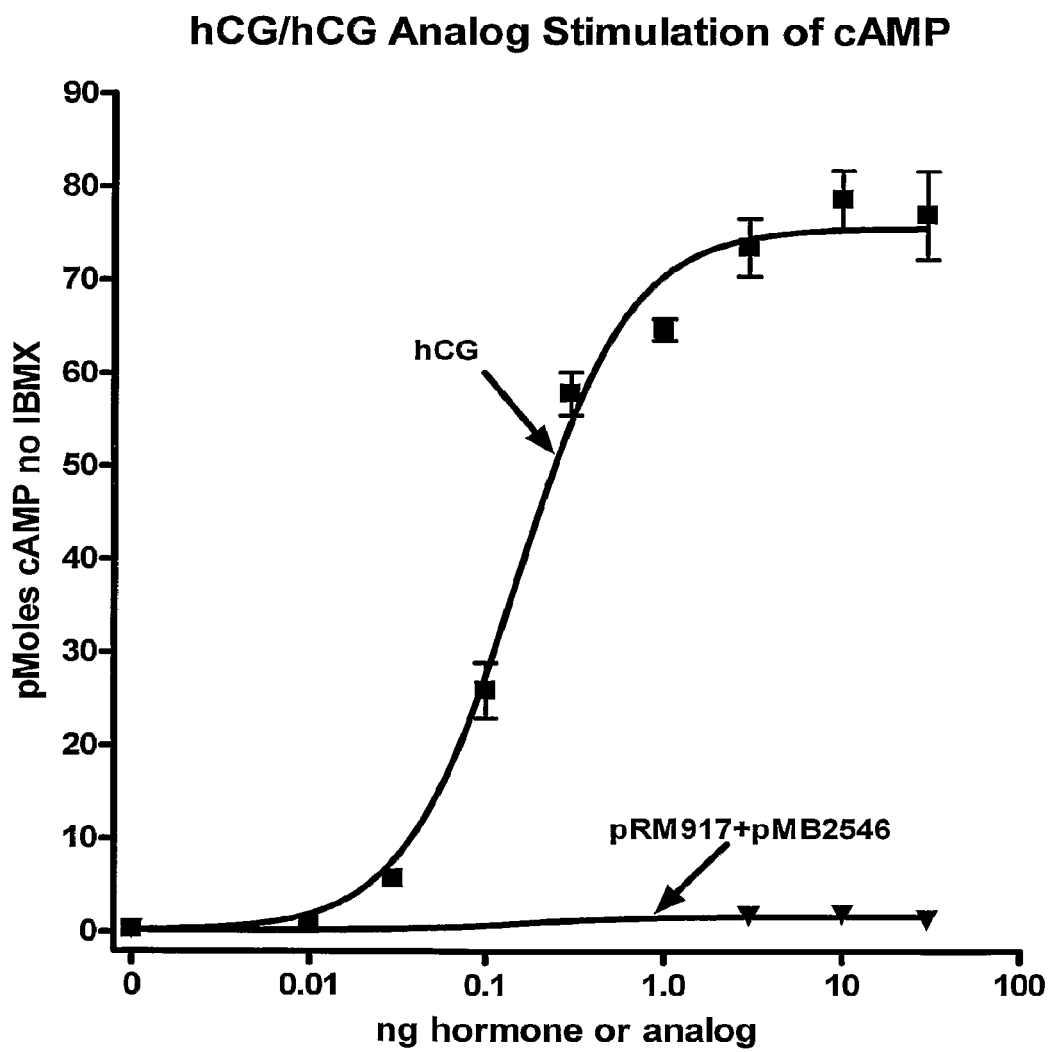
FIG. 19. Relative abilities of hCG and pRM917+pMB2546 to stimulate cyclic AMP accumulation in assays employing CHO cells that over express the rat LH receptor. This figure shows that the analog had much lower efficacy than hCG in this assay.
Figure 20:
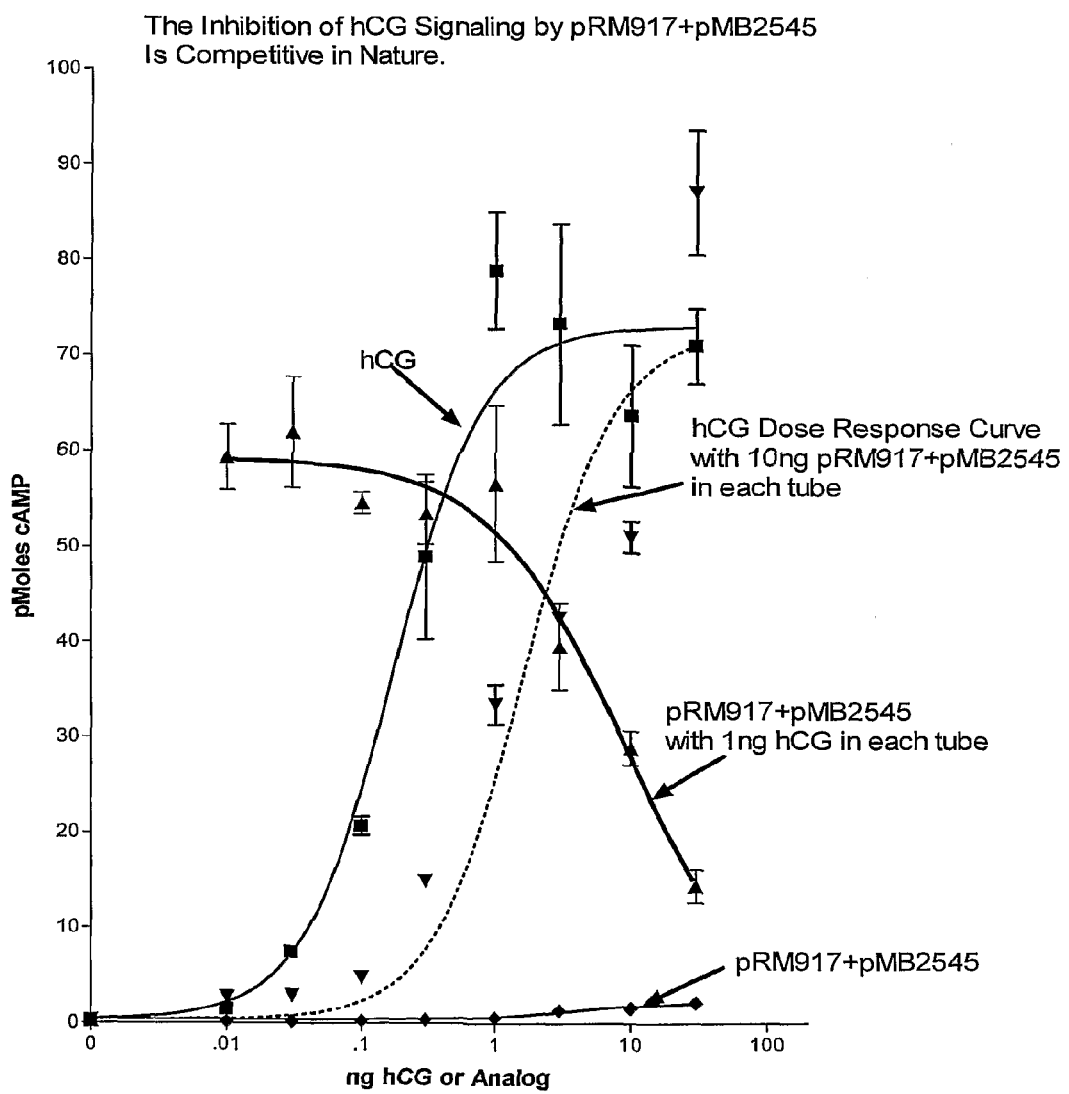
FIG. 20. The finding that pRM917+pMB2545 bound rat LH receptors with high affinity, but did not stimulate cyclic AMP accumulation nearly as well as hCG suggested that it would be a potent inhibitor of hCG induced activity. As shown here this analog blocked the response to hCG in a competitive fashion. Thus, the analog was able to block the activity of hCG and hCG was able to overcome the inhibitory influence of the analog.

Crosslinked heterodimers were formed that had the potential to contain two intersubunit disulfides. Co-expression of pRM917 with pMB2545 (FIGS. 16 & 17) and pMB2546 (FIGS. 18 & 19) yielded crosslinked heterodimers that had the potential ability to form disulfide bonds between α5-β8 and α86-β102 (pRM917+pMB2545) or between α5-β6 and α86-β102 (pRM917+pMB2546). Both crosslinked heterodimers had truncated aminoterminal β-subunits and bound rat LH receptors with high affinities (FIGS. 16 & 18). The presence of the additional potential crosslink did not enhance their efficacies; which were low (FIGS. 17 & 19). Their abilities to inhibit hCG induced signal transduction appeared to be competitive since hCG could overcome the effect of inhibition (FIG. 20).

Figure 21:
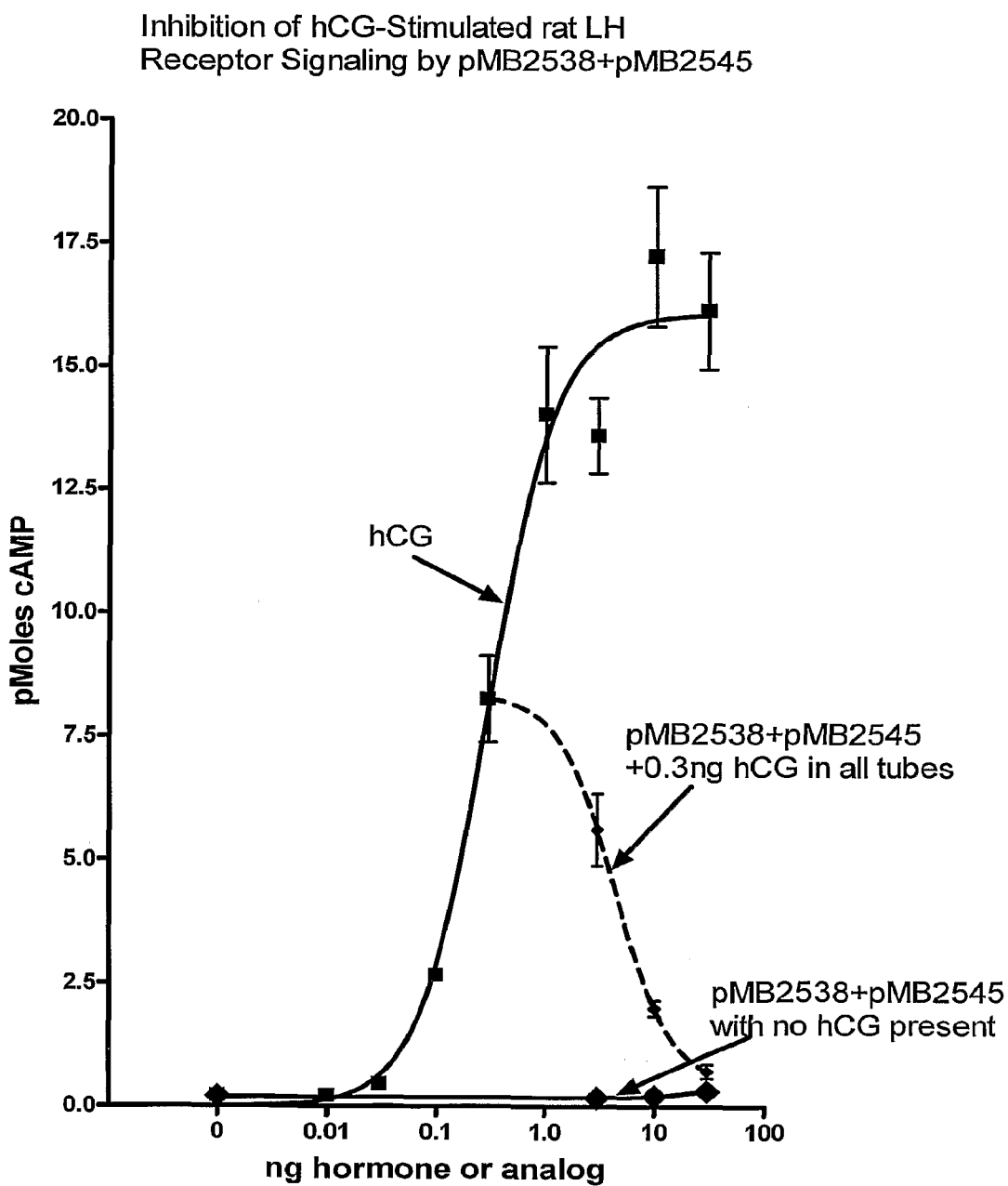
FIG. 21. Relative abilities of hCG and pMB2538+ pMB2545 to stimulate cyclic AMP accumulation in assays employing CHO cells that over express the rat LH receptor. This figure shows that the analog had much lower efficacy than hCG in this assay. In addition, it shows that the analog has high affinity for the rat LH receptor since it is capable of blocking the ability of hCG to initiate signal transduction. These data show that the potential to form two intersubunit crosslinks does not alter efficacy or receptor binding affinity when the two crosslinks are chosen as illustrated by the sequences of these analogs. The addition of the crosslink at the aminoterminal end of the subunits facilitated heterodimer production. Furthermore, the data show that truncation of the aminoterminal ends of both subunits does not alter their abilities to interact with rat LH receptors.
Figure 22:
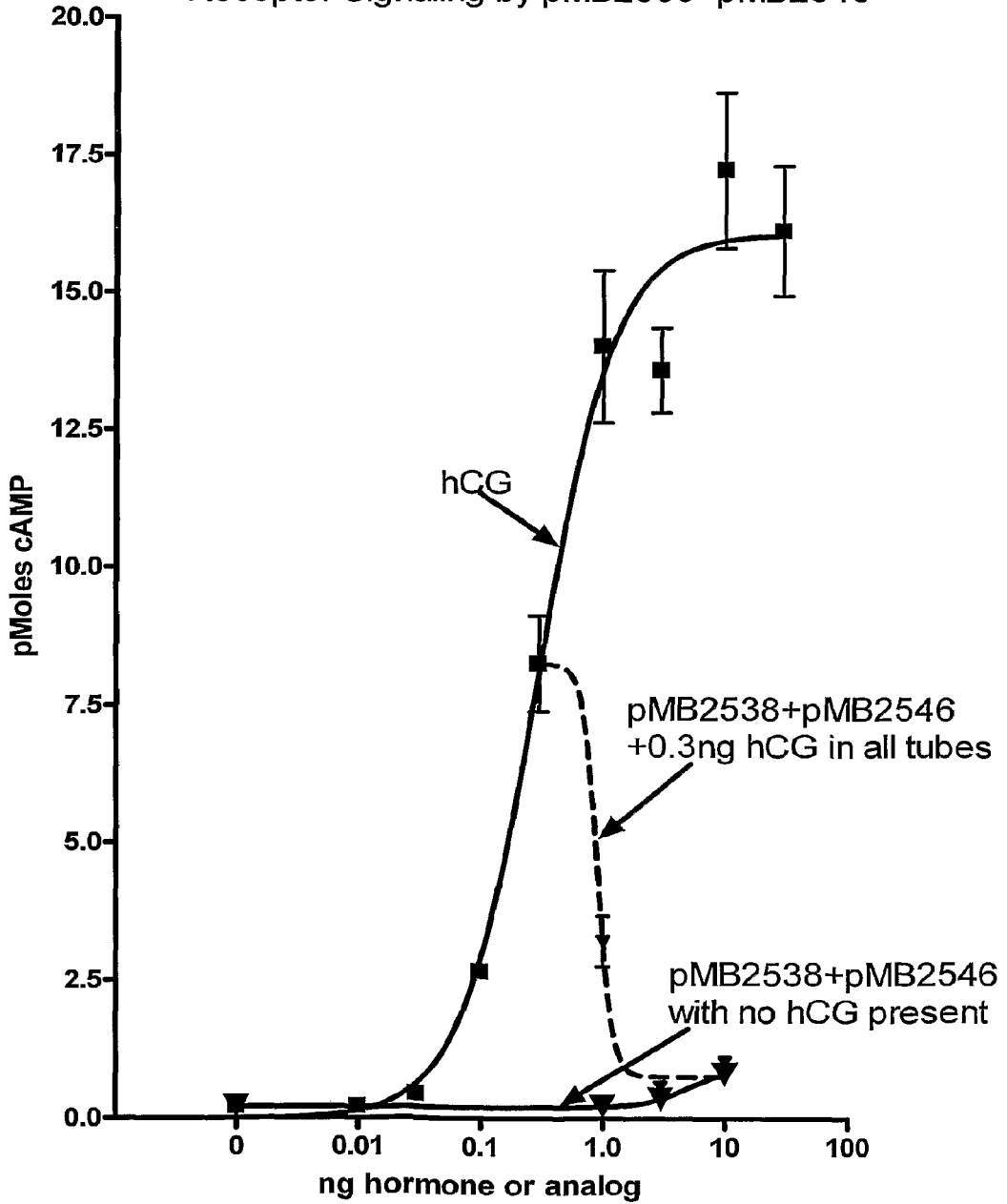
FIG. 22. Relative abilities of hCG and pMB2538+ pMB2546 to stimulate cyclic AMP accumulation in assays employing CHO cells that over express the rat LH receptor. This figure shows that the analog had much lower efficacy than hCG in this assay. In addition, it shows that the analog has high affinity for the rat LH receptor since it is capable of blocking the ability of hCG to initiate signal transduction. These data show that the potential to form two intersubunit crosslinks does not alter efficacy or receptor binding affinity when the two crosslinks are chosen as illustrated by the sequences of these analogs. The addition of the crosslink at the aminoterminal end of the subunits facilitated heterodimer production. Furthermore, the data show that truncation of the aminoterminal ends of both subunits does not alter their abilities to interact with rat LH receptors.
Figure 23:
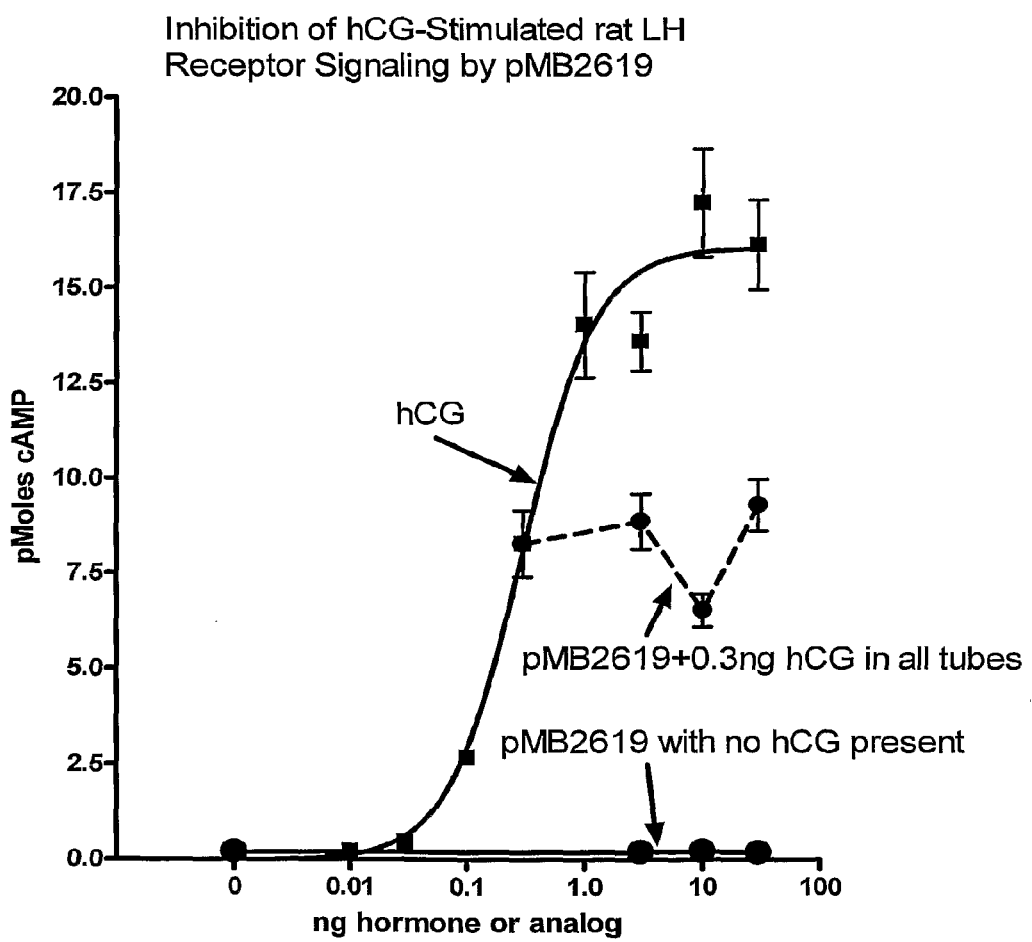
FIG. 23. Relative abilities of hCG and pMB2619, a single chain fusion protein containing a deletion of α-subunit residues Leu48 and Val49 to stimulate cyclic AMP accumulation in assays employing CHO cells that over express the rat LH receptor. This figure shows that the fusion protein has little ability to stimulate cyclic AMP accumulation or to inhibit the activity of hCG in this assay. Therefore, it appears to have reduced affinity for the receptor, a phenomenon that appears due to the deletion of a part of its α-subunit.
Figure 24:
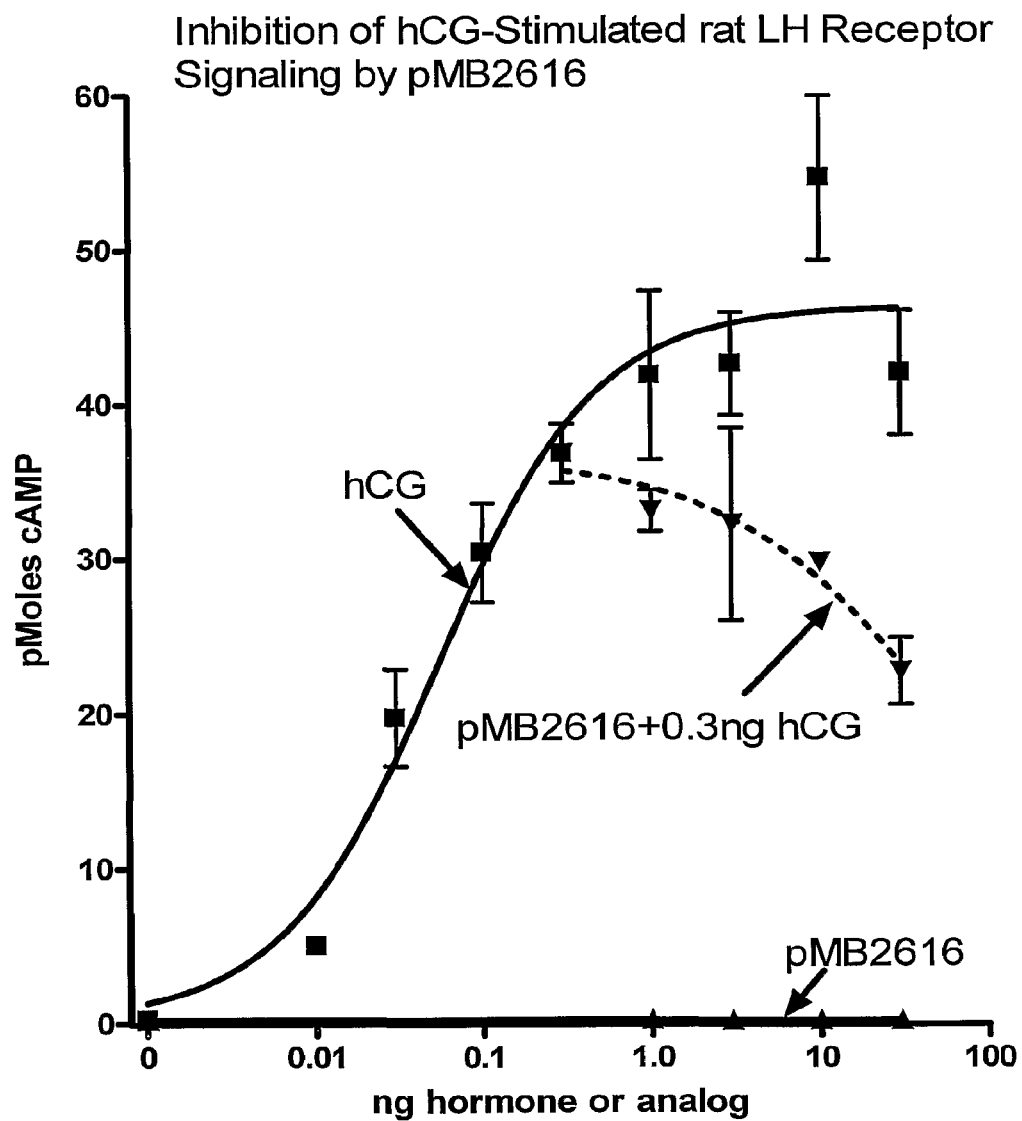
FIG. 24. Relative abilities of hCG and pMB2616, a single chain fusion protein containing a a substitution of hFSH β-subunit residues Asp-Ser-Asp-Ser for their hCG counterparts in the small seatbelt loop (FIG. 8) had low efficacy but was only a poor inhibitor of hCG stimulated cyclic AMP accumulation in rat LH receptor assays. This supported the notion that the small seatbelt loop has a key role in the interaction of these analogs with the LH receptor and that the use of a single chain construction does not alter receptor binding specificity.
Figure 26:
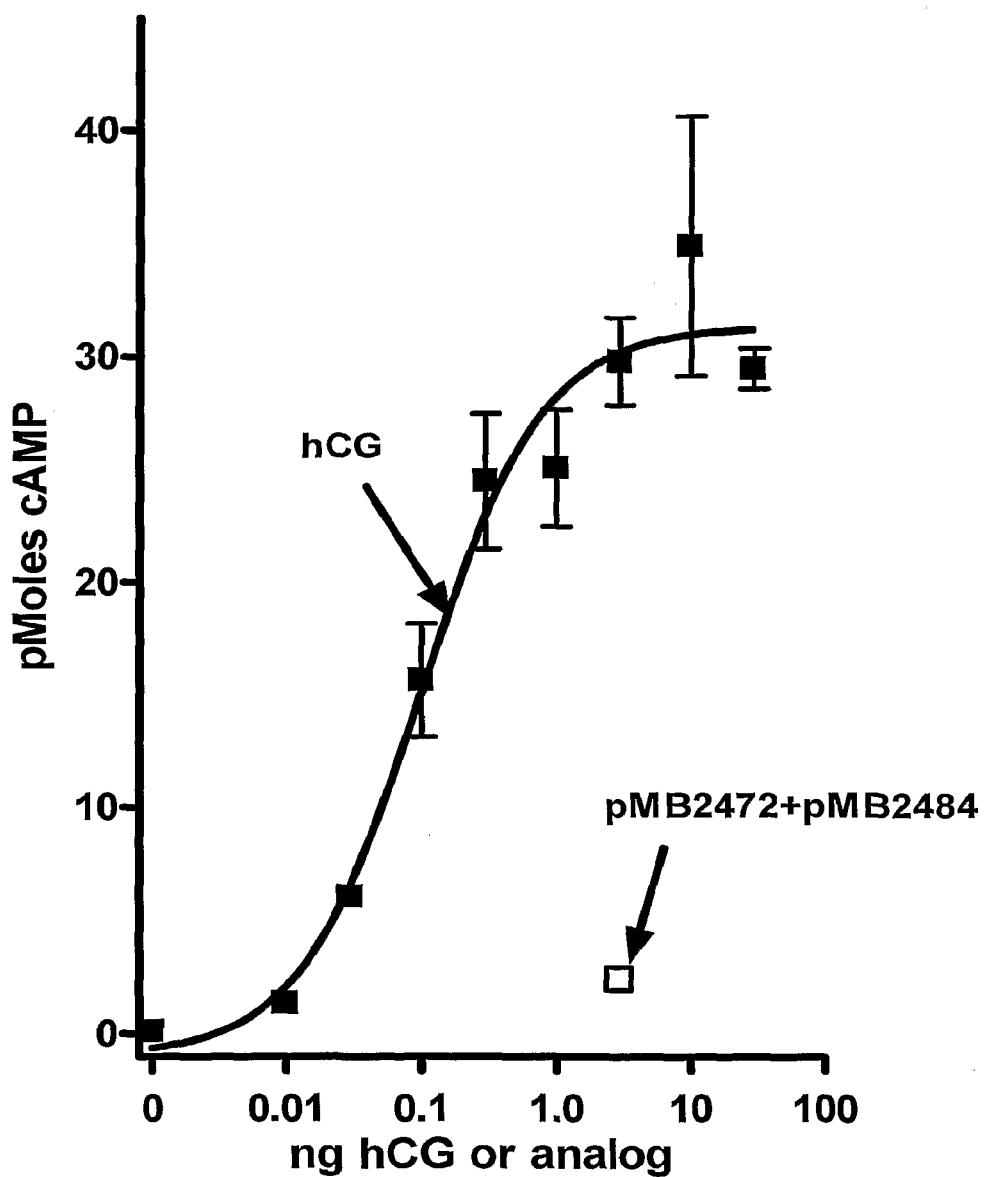
FIG. 26. Relative abilities of hCG and pMB2472+ pMB2484 to stimulate cyclic

The aminoterminal end of the α-subunit was also not required for LH receptor binding and did not appear to contribute to heterodimer efficacy in rat LH receptor assays. Heterodimers containing pMB2538+pMB2545 or pMB2538+pMB2546 were highly potent inhibitors of hCG signal transduction in signal transduction assays employing CHO cells that overexpress the rat LHR (FIGS. 21 & 22, respectively).

Crosslinks that disrupt the small seatbelt loop—i.e., that involve hCG β-subunit residues Cys93 or Cys100—reduced the affinity of the analog for LH receptors substantially (Xing et al., 2004a; Xing et al., 2004b). Thus, crosslinks to these cysteines would not be nearly as useful as those just described for producing antagonists or targeting vehicles. Crosslinks between α-subunit residue 86 and β-subunit residue cysteine 110, the natural end of the seatbelt, have been described (Xing et al., 2001a) and have low affinity for LH receptors. Thus, they would also not be as useful as antagonists or targeting vehicles.

These observations suggested that the most useful crosslinks involved cysteines that were located in regions of the heterodimer that would be capable of stabilizing the position of the small seatbelt more or less in the position it occupies in the heterodimer. Thus, it would also be expected that a crosslink between α86-β101 would also stabilize the seatbelt in a position in which it could form an antagonist. It would also be expected that crosslinks that involved α-subunit residue 85 rather than α-subunit residue 86 would also work.

Since heterodimers containing β-subunit analogs pMB2674, pMB2672, and pMB2673 contain a free cysteine at residue 26, it can be seen that removal of this cysteine is not essential for preparing this type of analog. In addition, it is possible to form a disulfide between hCG β-subunit Cys26 and a cysteine substituted for either hCG β-subunit residue Ala17 or hCG β-subunit residue Glu19. One of the first steps that takes place during the folding of the hCG β-subunit is the formation of loop 1. This causes Ala17 and Glu19 to become located near Cys26. A cysteine that is substituted for either Ala17 and Glu19 has been found to form a disulfide with Cys26, which makes this cysteine unavailable for other interactions. Examples of these sequences are pMB2567 and pMB2567, respectively (FIG. 8). This also shows that it is important that the other cysteines in the subunits be designed such that they will not be likely to interfere with formation of the intersubunit disulfide. This can be done by reference to the crystal structure (Lapthorn et al., 1994; Wu et al., 1994).

The addition of other cysteines to the amino terminal regions α- or β-subunits of the analogs of the types described in Example 1 did not interfere with heterodimer production or analog activity. Heterodimers containing a disulfide crosslink between α-subunit residue 5 (pRM917, FIG. 8) and β-subunit residues 5 or 8 (pMB2546 and pMB2545, respectively, FIG. 8) formed efficiently. In fact, the introduction of these additional aminoterminal disulfide bonds enhanced heterodimer production. These additional disulfides did not alter the efficacy of the antagonists and analogs containing pRM917 and pMB2546 as well as βRM917 and pMB2545 were potent inhibitors of LH receptor binding and activation (FIGS. 16, 17, 18, 19, & 20). This showed that it is possible to introduce additional disulfides into the antagonist and, when these are in parts of the molecule distant from the disulfides needed to produce an antagonist, they should be tolerated well. This suggests also that it will be possible to introduce disulfide bonds between residues α37 and β33 or between α35 and β35 in addition to those between α86 and β102. Since the former disulfides can reduce the efficacy of hCG analogs (Bernard et al., 2005), they might be expected to reduce the efficacy of analogs that contain the α86-β102 disulfide further. Note also that β-subunit analogs pMB2545 and pMB2546 are also truncated at their N-terminal ends, a phenomenon that did not alter their production. This shows that the N-terminal end of either subunit is not essential for its antagonist activity in these assays.

EXAMPLE 3

The Antagonist can be Made in a Single Chain Format

Single chain analogs of hCG and other glycoprotein hormones are often expressed better than the individual subunits. This is most likely because in the single chain format their subunit components are present at extremely high concentrations relative to one another. This phenomenon would be expected to facilitate heterodimer assembly in the endoplasmic reticulum, its normal site. Most hCG single chain constructs have a format in which the α-subunit component is linked to the carboxyterminal end of the β-subunit component. This is done to take advantage of the long disordered "tail" of the β-subunit, which facilitates assembly. It is also done because addition of residues to the α-subunit terminus can reduce receptor interactions (Furuhashi et al., 1995b). The antagonist analog described in Example 1 lacks much of the seatbelt and all of the β-subunit carboxyterminus. Therefore, it would not be expected that a single chain construct created by fusing the codons for the α-subunit directly to those of the β-subunit would be able to fold into a molecule that has many of the same structural properties as a glycoprotein hormone heterodimer. Furthermore, introduction of an artificial linker resulted in the production of an analog that retained significant efficacy (Heikoop et al., 1997a).

Proteins can be fused to the α-subunit C-terminus of hCG without reducing ligand-receptor interactions (Bernard et al., 2004) in spite of the notion that this region of the protein has long been thought to be required for receptor binding (Pierce and Parsons, 1981) and reports that fusions to this site reduce receptor binding (Furuhashi et al., 1995a). The key to making these types of analogs is to employ residues near the junction of α-subunit and the linker that are sufficiently hydrophilic to keep the C-terminal extension from folding back under the receptor binding surface of the heterodimer.

The orientation of the ligand in the putative LH receptor complex (Moyle et al., 2004) suggests that fusion of proteins to the carboxyterminal end of the α-subunit would be the most useful site for targeting cells that express LH receptor. This is because the additional residues that are downstream of this portion of the molecule would be least likely to enhance signal transduction. Efforts to express heterodimers containing pRM902 (FIG. 8) and pMB2419 (FIG. 8) were only marginally successful. These heterodimers would have had a β-subunit carboxyterminal extension on their α-subunits. Efforts to express heterodimers containing pMB2501 (FIG. 8) and pMB2419 (FIG. 8) were unsuccessful. These heterodimers would have had an α-subunit carboxyterminal extension containing the hCG (3-subunit carboxyterminus and β-lactamase, a much larger protein. pMB2501 contains a cysteine near the region derived from the hCG β-subunit carboxyterminus, but it was clear that this did not influence the formation of the crosslinked heterodimer. Replacing this cysteine with serine did not result in heterodimer formation. Thus, expression of pMB2531 (FIG. 8) with pMB2419 (FIG. 8) did not yield significant quantities of crosslinked heterodimer.

The difficulty of attaching proteins to the C-terminus of the α-subunit was eliminated by fabricating the molecule in a single-chain format wherein the C-terminal end of the α-subunit was connected to the N-terminal end of the β-subunit. Thus, the protein encoded by sequence pRM903 (FIG. 8) was expressed well. This type of construct was also quantified readily using a sandwich immunoassay composed of any monoclonal antibody that recognizes the α-subunit in hCG such as A113 and a radioiodinated antibody that recognizes an epitope on hCG β-subunit loops 1 and/or 3 such as 125I-B110. This fusion proteins was expressed efficiently. For example, typically 80-100 ng of hCG heterodimer is produced per ml of cell culture medium when COS-7 cells are transfected transiently with constructs encoding the natural hCG α- and β-subunits. Transient transfection with construct pRM903 (FIG. 8) that contained a linker having the sequence DDPRFQDSSSSKAPPPSLPSPSRLPGPSDTPILPQ (SEQ ID NO: 67) between the α- and (3-subunits, produced 62 ng/ml. (Stably transfected cells would be expected to produce at least 10-500 fold more than this depending on the system used.) This protein had a low efficacy and blocked the cyclic AMP response to hCG showing that it is a useful antagonist (Table 1).

TABLE 1

Activity of pRM903 (Cyclic AMP Accumulation Assay).

| Stimulator | No Single Chain Analog pMoles cyclic AMP | +10 ng Single Chain Analog pMoles cyclic AMP |
|---|---|---|
| None | 0.19 ± 0.05 | 0.21 ± 0.04 |
| 0.1 ng hCG | 5.06 ± 0.36 | 0.25 ± 0.08 |
| 30 ng hCG | 33.5 ± 1.2 | Not Tested |

Other useful fusion proteins can be made in a "cleavable" single chain format. These contain a furin (Trout et al., 1999) or other enzymatic cleavage sequence at the end of the linker that will enable them to be cleaved after they have folded and passed through the secretory machinery of the cell. One such protein having the sequence DDPRFQDSSSSKAP-PPSLPSPSRLPGPSDSGRRFKRRPR [SEQ ID NO: 68; underlined sequence is an optimized furin cleavage site (Matthews et al., 1994)] between the α- and β-subunits was also expressed well (81 ng/ml). This is shown as pMB2553 (FIG. 8). The advantage of cleaving the linker after the complex has formed is that it minimizes the size of the protein in the region that would be occupied normally by the end of the seatbelt. Keeping this region as small as possible is expected to minimize efficacy.

Fusion proteins were also useful for preparing hormone analogs that contained deletions in parts of the molecule that were not expressed efficiently. An example of this is the fusion construct pMB2619 (FIG. 8), which contains a deletion of part of α-subunit loop 2—i.e., residues Leu48 and Val49. Although it was possible to produce this analog using the fusion protein approach, this analog did not interact with rat LH receptors well and was a poor inhibitor of signaling (FIG. 23).

The use of a fusion protein for expression did not appear to alter the receptor binding specificity. Thus, a fusion protein that contained a small seatbelt loop that was derived from the hFSH βsubunit (pMB2616, FIG. 8) and that would not be expected to interact well with rat LH receptors (Campbell et al., 1991; Moyle et al., 1994), had low affinity for the rat LH receptor (FIG. 24). Although this analog had low efficacy, it was only a poor inhibitor of hCG-induced cyclic AMP accumulation.

EXAMPLE 4

Other Types of Fusion Proteins

It is expected that the ability of the antagonist analogs described in examples 1-4 to reverse the symptoms of PCOS will be potentiated by the addition of proteins that can help to promote apoptosis of unwanted ovarian tissues that contain lutropin receptors. These include nearly any apoptosis inducing protein, but a preferred protein is Interferonγ, a molecule that is already approved for clinical use. To facilitate production of the fusion proteins, they should be expressed as single chains having a cleavage site—i.e., furin—that permits cleavage of the linker between the components of the heterodimer. FIG. 25 provides an example of this type of protein. It should also be possible to prepare these proteins by use of a dimerization domain such as that illustrated by the use of the α5-β5 and α5-β8 crosslinks described in Example 2.

EXAMPLE 5

Crosslinked Heterodimers Lacking Additional Oligosaccharides

The importance of the oligosaccharides has long been known for the actions of the glycoprotein hormones (Moyle et al., 1975; Matzuk et al., 1989) and it is clear that efficacy is directly proportional to the extent of hormone glycosylation (Moyle et al., 1975; Matzuk et al., 1989). Although the efficacy of the antagonists is already lower than that of other hCG analogs of this type when tested in assays employing cells that overexpress LH receptors, studies were initiated to learn if the residual efficacy could be reduced further by removing some or all of the oligosaccharides on the β-subunit. The hCG β-subunit contains two N-linked oligosaccharides and that at $Asn^{13}$ is nearest the portion carboxyterminal portion of the seatbelt. Therefore, it seemed possible that disrupting this glycosylation signal would have the greatest influence on the efficacies of analogs that lack this region of the seatbelt and that lack the glycosylation signal at loop α2. All N-linked glycosylation signals have the sequence Asn-Xaa-Ser/Thr where Asn is the amino acid that is glycosylated, Xaa is any residue other than proline, and Ser/Thr are the residues serine or threonine. To disrupt the glycosylation signal one can change Asn to any other residue, Xaa to a proline, or Ser/Thr to a residue other than serine or threonine Heterodimers made by co-expressing pMB2472 and pMB2437 in COS-7 cells were monitored in sandwich immunoassays using antibody A113 for capture and $^{125I}$-B110 for detection. These interacted well with rat LH receptors and had similar efficacies as heterodimers prepared by co-expressing pMB2472 and pMB2419. This suggested that the dramatic reduction in efficacy caused by truncating the seatbelt, removing the α2 oligosaccharide, and introducing the α86-β02 disulfide may have obscured the potential role of the oligosaccharide at residue Asn13.

Conceivably, the presence of the oligosaccharide at β-subunit residue Asn30 was sufficient to overcome the influence of removing the oligosaccharide at β-subunit residue Asn13. This possibility was tested by removing both the Asn13 and Asn30 glycosylation signals, a phenomenon that would have removed all the oligosaccharides from the (3-subunit. The β-subunit oligosaccharides appear to have a role in its β-subunit folding, possibly by enabling the unfolded β-subunit to be a substrate for an endoplasmic reticulum oligosaccharide binding chaperone. This was overcome by creating a glycosylation site in the aminoterminal end of the β-subunit that would permit it to be glycosylated and thereby facilitate folding. This would create an oligosaccharide in a highly exposed portion of the β-subunit that might permit it to be removed after the protein had folded by the enzyme N-glycanase. COS-7 cell expression of pMB2472 with pMB2484 (FIG. 8), a construct that encoded a β-subunit that encodes a glycosylation signal at residue 2 and that lacks both the N15 and N30 glycosylation sites, led to the formation of a disulfide crosslinked heterodimer that was detected in the A113-125I-B110 sandwich immunoassay. The protein produced had low efficacy (FIG. 26), even though its N-linked oligosaccharide was not removed.

EXAMPLE 6

Introduction of a Crosslink Between the Seatbelt and the α-Subunit while the Seatbelt is Latched The cysteines that latch the seatbelt do not interfere with the formation of a disulfide between α-subunit residue 86 and β-subunit residue 102 and can lead to altered hormone activity. The seatbelt controls receptor binding specificity and seatbelt residues 11-20 have a greater influence on interactions with FSH receptors than LH receptors (Campbell et al., 1991; Moyle et al., 1994). Co-expression of pMB2472 (FIG. 8) with pMB2571 (FIG. 8) led to a heterodimer that was stable at pH 2 for 30 minutes at 37° C. indicating that it had a disulfide crosslink. This crosslinked heterodimer retained its ability to bind to LH and FSH receptors. It stimulated LH receptor signal transduction (FIG. 27) much better than FSH receptor signal transduction (FIG. 28). Remarkably, its ability to inhibit FSH-induced signaling was significantly greater than its ability to inhibit hCG-induced signaling (FIGS. 27 & 28).

EXAMPLE 7

Piscine Follitropins

Follitropin activity is needed to stimulate the production of female gametes from all vertebrate species, including fish. Piscine follitropins would be useful for stimulating the reproduction of endangered species as well as to facilitate the reproduction of captive animals such as those used in aquaculture. Many piscine follitropins, including those of salmon, trout, bass, bonito, sea bream, Conger eel, gourami, halibut, tilapia and tuna, among others have a structure in which their seatbelts are latched to a cysteine in the aminoterminal end of the β-subunit. Preparation of these analogs is often difficult, due largely to the location of the seatbelt latch site (Xing et al., 2004c). Initial efforts to prepare salmon FSH analogs involved obtaining vectors that encode the salmon αII subunit (PS1, FIG. 8) and salmon FSHβ subunit (PS2, FIG. 8) from Dr. Penny Swanson (Northwest Fisheries, National Oceanographic and Atmospheric Administration, Seattle, Wash.). That of PS1 was transferred into the pCI vector (Promega, Madison, Wis.) downstream of the cytomegalovirus intermediate early promoter. The salmon FSH α- and β-subunits were further modified by adding a Flag tag at their aminoterminal ends. The salmon FSH β-subunit was modified by adding the hCG β-subunit carboxyterminus to its carboxyterminal ends. This permitted heterodimers to be monitored using the Flag M1 antibody and a CTP antibody to the carboxyterminal portion of the hCG β-subunit (Birken et al., 2003) obtained from Dr. Steven Birken (Columbia University, New York City, N.Y.) All modifications of these coding sequences were done by standard methods of PCR and cassette mutagenesis, procedures that are well-known to persons familiar with mutagenesis techniques.

Co-expression of pMB575 and pRM783 (FIG. 8) in COS-7 cells led to only trace quantities of heterodimer as seen using a sandwich immunoassay (Moyle et al., 1982) employing a monoclonal antibody to the human α-subunit for capture (A113) and a radioiodinated CTP. The fact that pRM783 encoded a protein that has a Flag tag at its aminoterminal end also permitted the heterodimer to be detected in an assay employing A113 for capture and $^{125}$I-M1 antibody for detection. (The commercially available M1 antibody is specific for the Flag tag.) Again, only trace quantities of material were detected in the culture medium. Based on the difficulty of producing hCG analogs that contain the salmon FSH seatbelt (Xing et al., 2004c), it was assumed that the salmon seatbelt was responsible for the inefficient heterodimer formation.

Several methods have been developed to promote heterodimer assembly, one of which involves the use of an aminoterminal dimerization domain (Lin et al., 1999). This procedure works well for promoting the formation of most glycoprotein hormone heterodimers, including those that have altered tensor loops and/or that lack a seatbelt latch disulfide (Lin et al., 1999). Efforts to produce salmon FSH analogs by attaching the Fos dimerization domain to the human α-subunit to create the sequence that encoded pMB1197 (FIG. 8), the Jun dimerization domain to the salmon β-subunit to create the sequence that encoded pRM794 (FIG. 8), and co-expression of both in COS-7 cells yielded only small amounts of heterodimer when measured in the A113—radioiodinated SCTP sandwich immunoassay. The reasons for this is not understood, but might be due to the fact that neither the Fos or Jun dimerization domain contained a disulfide that crosslinks them. This disulfide was omitted so that it would be possible to distinguish heterodimers in which the seatbelt was wrapped around the α-subunit from those that were crosslinked by the presence of a disulfide stabilized Fos-Jun dimerization domain.

Another method for producing "heterodimers" involves expressing glycoprotein hormone analogs as fusion proteins in which the α-subunit is fused to the end of the (3-subunit or in which the β-subunit is fused to the end of the α-subunit. This procedure has been shown to enable the formation and secretion of heterodimers having altered disulfides (Ben-Menahem et al., 1997) and was expected to be useful for producing the salmon hormones efficiently. Expression of single chain constructs pRM784 or pRM787 separately in COS-7 cells led to the accumulation of somewhat more material in the culture medium, but this was deemed too small to be useful. These constructs encoded the salmon FSHβ-subunit upstream of an hCGβ-subunit tail and either lacking the α2 oligosaccharide or a human α-subunit having the α2 oligosaccharide, respectively. The reason for the low production of "heterodimer" was not clear, but might have been due to the possibility that the seatbelt became latched before the subunits had reached their normal position in the heterodimer in which the seatbelt is wrapped around α2. Expression of heterodimer from COS-7 cells that had been transfected with pRM798 (FIG. 8) was also low, indicating that expression was not enhanced by placing the salmon FSH β-subunit downstream of the α-subunit. During translation of this construct, the α-subunit would have begun to fold before the β-subunit had been finished being translated. Since the seatbelt would be the last part of the construct that is translated, it seemed less likely that premature latching of the seatbelt would be responsible for the low production of single chain heterodimer. Remarkably, this did not have a dramatic influence on production of the salmon construct.

The use of the human α-subunit in these constructs might have also been responsible for the low production of heterodimer. This possibility was tested using expression vectors that encode the Flag-tagged salmon α-subunit (pRM796, FIG. 8) and the fusion protein composed of the salmon FSH β-subunit and the hCG β-subunit carboxyterminus (pMB2376, FIG. 8). This combination did not result in efficient heterodimer production as monitored using the M1 antibodies to the Flag epitope and the CTP antibody to the carboxyterminus of the hCG β-subunit that was fused to the salmon β-subunit.

Together these data suggested that several factors might suppress the secretion of the salmon FSH heterodimer. Unlike the seatbelts of most vertebrate follitropins, those of salmon and several related species are latched to a cysteine in the aminoterminal end of the β-subunit. This places the carboxyterminal portion of these piscine follitropin seatbelts in a very different position than those of most vertebrate follitropins. If the salmon seatbelt reduces assembly, it seemed possible that production of this type of follitropin heterodimer would be enhanced by eliminating the piscine seatbelt latch site and replacing it with a disulfide comparable to that described in Example 1. The role of the salmon FSH seatbelt in hormone activity is unknown. In mammalian follitropins, the carboxyterminal portion of the follitropin seatbelt is known to be essential for its activity (Moyle et al., 1994; Campbell et al., 1991; Dias et al., 1994) and it is not possible to relocate the seatbelt latch site to a site in α-subunit loop 2 without disrupting follitropin activity. The fact that the salmon FSH seatbelt is located at a very different site than the mammalian FSH seatbelt suggested that the carboxyterminal portion of the salmon FSH seatbelt as well as those of other piscine species may not be required for follitropin activity in the same fashion as the mammalian FSH seatbelt. Therefore, salmon follitropin analogs having a folding pattern similar to those in Example 1 might activate the salmon FSH receptor.

To test this possibility, it was necessary to prepare a cell line that expressed the salmon FSH receptor. A vector that encoded the salmon FSH receptor was obtained from Dr. Penny Swanson (PS3, FIG. 8). The codons for the extracellular domain of this receptor, those for the transmembrane domain of the rat LH receptor, and those for neomycin phosphotransferase were used to prepare a fusion receptor construct that encoded a receptor analog (neo') containing the salmon FSHR extracellular domain, the rat LH receptor transmembrane domain and cytoplasmic domain, and a weakly active analog of neomycin phosphotransferase. This construct encoded the amino acid sequence shown as pMB2811 (FIG. 8). The presence of neo' at the carboxyterminus of this salmon FSH—rat LH receptor chimera was expected to confer resistance to the toxic antibiotic G418. By being attached to the receptor, neo' was expected to facilitate the selection of cell lines that express pMB2811 at the cell surface. Since the extracellular domain is known to determine receptor binding specificity (Segaloff and Ascoli, 1993), this receptor analog was expected to interact with salmon FSH. The binding of salmon FSH to this analog was expected to cause signal transduction as monitored by cyclic AMP accumulation. Furthermore, the presence of neo' would permit the membrane protein to be recognized by antibodies to neomycin phosphotransferase in Western blots. This provided a secondary screen for the presence of the receptor and was included to learn if portions of the cytoplasmic receptor became cleaved from the cells during receptor expression. If these retained hormone activity, they would have been expected to facilitate survival of the cell lines. Moreover, the finding of these might also indicate that the receptor had been cleaved during expression and/or plasma membrane turnover.

Following transfection of Chinese hamster ovary cells (CHO cells) with 6 μg of plasmid encoding pMB2811 and selection in the presence of 1 mg G418/ml of culture medium (DMEM), several G418 resistant cell lines were selected and tested for their abilities to express neo' in Western Blots using a polyclonal antibody prepared against neo that was purchased from Upstate USA, Inc. Charlottesville, Va. The presence of reactive material was determined by chemiluminescence using the BM Chemiluminescence Western Blotting Kit, Roche Diagnostics, Indianapolis, Ind. Several G418 resistant cell lines expressed the salmon follitropin receptor—rat lutropin receptor chimera—neo fusion protein—i.e., pMB2811 (FIG. 8). Those that expressed high amounts of neo' protein made cyclic AMP in response to a preparation that contained a mixture of salmon FSH and salmon LH that was obtained from Dr. Penny Swanson.

To determine if it was the LH or the FSH in the partially purified preparation of salmon gonadotropins, the sample was treated at pH 2, 37° C., for 30 minutes as described (Xing et al., 2004a). This procedure is known to disrupt heterodimers in which the seatbelt is latched to a cysteine in β-subunit loop 1 but not to a cysteine in the aminoterminal end of the β-subunit (Xing et al., 2004c). This treatment did not reduce the activity of the preparation. This showed that it was the FSH and not the LH in the preparation that interacted with the receptor to initiate signal transduction.

Preparations of heterodimer made by expressing pRM917 and pMB2827 in COS-7 cells stimulated cyclic AMP accumulation in CHO cells that expressed the salmon FSH receptor—rat LH receptor—neo' fusion protein. This analog would be expected to contain two disulfide crosslinks. One of these is between the cysteine found at the substitution of cysteine for $Gln^5$ in pRM917 and the normal salmon FSH β-subunit seatbelt latch site found in pMB2827. The other is between the cysteine substituted for human α-subunit residue Thr86 and that substituted for Arg98 in the portion of salmon FSH β-subunit that constitutes pMB2827. The amount of pRM917-pMB2827 produced by COS-7 cells was estimated in an A113-$^{125}$I-M1 sandwich immunoassay. The precise amount of heterodimer produced could not be quantified accurately in sandwich immunoassays due to the lack of an appropriate standard but was as high or higher than materials produced by expressing the human α-subunit with the Flag-tagged salmon FSHβ-subunit. The fact that it elicited a response in cells that expressed pMB2811 receptors (FIG. 29) revealed that it was active. This demonstrated that the salmon FSH seatbelt does not need to be latched in the same fashion as the mammalian FSH seatbelt for hormone analogs to interact with the salmon FSH receptor. Furthermore, since the pRM917-pMB2827 heterodimer lacks the glycosylation site on α-subunit loop 2 of pRM917, it would be expected that the fully glycosylated analog would be much higher in the same way that the efficacy of the heterodimer containing pMB1010 and pMB2419 is higher than that containing pMB2472 and pMB2419.

The fact that the heterodimer prepared by expressing pMB2472 and pMB2827 is active in COS-7 cells shows that several related analogs of this heterodimer will also be active salmon follitropins. These include those that have the α-subunit loop 2 oligosaccharide. It would be expected that analogs of pMB2472 that contain salmon α-subunit residues derived from α-subunit loop 2—i.e., FSRAYPTPLRSKQTMLVPKNITSEAT (SEQ ID NO: 69)—rather than their human counterparts found in loop 2 of pMB2472—i.e., FSRAYPTPLRSKKTMLVQKNVTSEST (SEQ ID NO: 70)—would enhance the activity of the analog. This α-subunit analog (pEX1, FIG. 8) would still be recognized by most monoclonal antibodies to the hCG α-subunit, which would also facilitate its quantification. A modification of pEX01 that is likely to facilitate its activity will be to add lysine residues to the portion of the molecule derived from the human α-subunit loop 1 to create pEX2 (FIG. 8). The introduction of positively charged residues in this region has been found to enhance the activities of other glycoprotein hormones (Grossmann et al., 1998). The disadvantage of this is that it will reduce or eliminate the abilities of many monoclonal antibodies to the human α-subunit to recognize the heterodimer. A modification of pMB2827 that should facilitate its utility involves the addition of hCG residues at sites that will facilitate its recognition by monoclonal antibodies to hCG. pEX3 (FIG. 8) is an example in which the residues derived from salmon FSH β-subunit loop 2 in pM2827 are replaced with their hCG counterparts. This will enable the protein to be recognized by monoclonal antibodies to hCG β-subunit loop 2—i.e., B101 (Moyle et al., 1990). Another modification of pMB2827 will facilitate the binding of hCG monoclonal antibodies to β-subunit loop 3 (pEX4, FIG. 8). Still other modifications of a molecule capable of stimulating the salmon FSH receptor will involve expressing it in a single chain format (pEX5, FIG. 8). Other modifications that will increase its efficacy involve addition of a glycosylation signal on β-subunit loop 3 (pEX6, FIG. 8). It would be obvious to one versed in the art of mutagenesis to combine the mutations described in pEX1, pEX2, pEX3, pEX4, pEX5, and/or pEX6 to create additional hormone analogs that are capable of stimulating the FSH receptors of salmon and other piscine species. These have the advantages of being highly potent, produced readily, and being monitored using existing monoclonal antibodies. By using these analogs to immunize rabbits or other species, it will also be possible to develop reagents that can be used to measure salmon FSH.

REFERENCES

1. Abell, A., X. Liu, and D. L. Segaloff. 1996. Deletions of portions of the extracellular loops of the lutropin/choriogonadotropin receptor decrease the binding affinity for ovine luteinizing hormone, but not human choriogonadotropin, by preventing the formation of mature cell surface receptor. *J. Biol. Chem.* 271:4518-4527.
2. Ascoli, M., R. A. Liddle, and D. Puett. 1976. Renal and hepatic lysosomal catabolism of luteinizing hormone. *Mol. Cell Endocrinol.* 4:297-310.
3. Baenziger, J. U. and E. D. Green. 1988. Pituitary glycoprotein hormone oligosaccharides: structure, synthesis and function of the asparagine-linked oligosaccharides on lutropin, follitropin and thyrotropin. *Biochim. Biophys. Acta* 947:287-306.
4. Baenziger, J. U., S. Kumar, R. M. Brodbeck, P. L. Smith, and M. C. Beranek. 1992. Circulatory half-life but not interaction with the lutropin/chorionic gonadotropin receptor is modulated by sulfation of bovine lutropin oligosaccharides. *Proc. Natl. Acad. Sci. (USA)* 89:334-338.
5. Balen, A. H., G. S. Conway, G. Kaltsas, K. Techatrasak, P. J. Manning, C. West, and H. S. Jacobs. 1995. Polycystic ovary syndrome: the spectrum of the disorder in 1741 patients. *Hum. Reprod.* 10:2107-2111.
6. Ben-Menahem, D., M. Kudo, M. R. Pixley, A. Sato, N. Suganuma, E. Perlas, A. J. Hsueh, and I. Boime. 1997. The biologic action of single-chain choriogonadotropin is not dependent on the individual disulfide bonds of the beta subunit. *J. Biol. Chem.* 272:6827-6830.
7. Bernard, M. P., W. Lin, D. Cao, R. V. Myers, Y. Xing, and W. R. Moyle. 2004. Only a portion of the small seatbelt loop in human choriogonadotropin appears capable of contacting the lutropin receptor. *J. Biol. Chem.* 279:44438-44441.
8. Bernard, M. P., W. Lin, R. V. Myers, D. Cao, Y. Xing, and W. R. Moyle. 2005. Crosslinked bifunctional gonadotropin analogs with reduced efficacy. *Mol. Cell. Endocrinol.* 233: 25-31.
9. Bernard, M. P., R. V. Myers, and W. R. Moyle. 1998. Lutropins Appear To Contact Two Independent Sites In The Extracellular Domain Of Their Receptors. *Biochem. J.* 335:611-617.
10. Birken, S., O. Yershova, R. V. Myers, M. P. Bernard, and W. R. Moyle. 2003. Analysis of human choriogonadotropin core 2 o-glycan isoforms. *Mol. Cell Endocrinol.* 204: 21-30.
11. Braun, T., P. R. Schofield, and R. Sprengel. 1991. Amino-terminal leucine-rich repeats in gonadotropin receptors determine hormone selectivity. *EMBO. J.* 10:1885-1890.
12. Brooker, J., J. F. Harper, W. L. Terasaki, and R. D. Moylan. 1979. Radioimmunoassay of cyclic AMP and cyclic GMP. *Adv. Cyclic Nucl. Res.* 10:1-33.
13. Buvat, J., M. Buvat-Herbaut, G. Marcolin, J. L. Dehaene, P. Verbecq, and O. Renouard. 1989. Purified follicle-stimulating hormone in polycystic ovary syndrome: slow administration is safer and more effective. *Fertil. Steril.* 52:553-559.
14. Campbell, R. K., E. R. Bergert, Y. Wang, J. C. Morris, and W. R. Moyle. 1997. Chimeric proteins can exceed the sum of their parts: implications for evolution and protein design. *Nature Biotech.* 15:439-443.
15. Campbell, R. K., D. M. Dean Emig, and W. R. Moyle. 1991. Conversion of human choriogonadotropin into a follitropin by protein engineering. *Proc. Natl. Acad. Sci. (USA)* 88:760-764.
16. Campo, S. 1998. Ovulatory cycles, pregnancy outcome and complications after surgical treatment of polycystic ovary syndrome. *Obstet. Gynecol. Surv.* 53:297-308.
17. Cardone, V. S. 2003. GnRH antagonists for treatment of polycystic ovarian syndrome. *Fertil. Steril.* 80 Suppl 1:S25-S31.
18. Cassels, J. W. J., K. Mann, D. L. Blithe, B. C. Nisula, and R. E. Wehmann. 1989. Reduced metabolic clearance of acidic variants of human choriogonadotropin from patients with testicular cancer. *Cancer* 64:2313-2318.
19. De, L. V., M. A. La, A. Ditto, G. Morgante, and A. Cianci. 1999. Effects of metformin on gonadotropin-induced ovulation in women with polycystic ovary syndrome. *Fertil. Steril.* 72:282-285.
20. Dias, J. A. 2005. Endocrinology: fertility hormone in repose. *Nature* 433:203-204.
21. Dias, J. A., Y. Zhang, and X. Liu. 1994. Receptor binding and functional properties of chimeric human follitropin prepared by an exchange between a small hydrophilic intercysteine loop of human follitropin and human lutropin. *J. Biol. Chem.* 269:25289-25294.
22. Dunaif, A. 1997. Insulin resistance and the polycystic ovary syndrome: mechanism and implications for pathogenesis. *Endocr. Rev* 18:774-800.
23. Dunaif, A., D. Scott, D. Finegood, B. Quintana, and R. Whitcomb. 1996. The insulin-sensitizing agent troglitazone improves metabolic and reproductive abnormalities in the polycystic ovary syndrome. *J. Clin. Endocrinol. Metab.* 81:3299-3306.
24. Ehrmann, D. A., M. K. Cavaghan, J. Imperial, J. Sturis, R. L. Rosenfield, and K. S. Polonsky. 1997. Effects of metformin on insulin secretion, insulin action, and ovarian steroidogenesis in women with polycystic ovary syndrome. *J. Clin. Endocrinol. Metab.* 82:524-530.
25. Elting, M. W., T. J. Korsen, L. T. Rekers-Mombarg, and J. Schoemaker. 2000. Women with polycystic ovary syndrome gain regular menstrual cycles when ageing. *Hum. Reprod.* 15:24-28.
26. Fan, Q. R. and W. A. Hendrickson. 2005. Structure of human follicle-stimulating hormone in complex with its receptor. *Nature* 433:269-277.
27. Fares, F. A., N. Gruener, and Z. Kraiem. 1996. The role of the asparagine-linked oligosaccharides of the alpha-subunit in human thyrotropin bioactivity. *Endocrinol.* 137: 555-560.
28. Fiddes, J. C. and K. Talmadge. 1984. Structure, Expression, and Evolution of the genes for the human glycoprotein hormones. In Recent Progress in Hormone Research. Vol 40. R. O. Greep, editor. Academic Press, New York. 43-78.
29. Flack, M. R., J. Froehlich, A. P. Bennet, J. Anasti, and B. C. Nisula. 1994. Site-directed mutagenesis defines the individual roles of the glycosylation sites on follicle-stimulating hormone. *J. Biol. Chem.* 269:14015-14020.
30. Fox, K. M., J. A. Dias, and P. Van Roey. 2001. Three-dimensional structure of human follicle-stimulating hormone. *Mol. Endocrinol.* 15:378-389.
31. Franks, S., C. Gilling-Smith, H. Watson, and D. Willis. 1999. Insulin action in the normal and polycystic ovary. *Endocrinol. Metab. Clin. North Am.* 28:361-378.
32. Furuhashi, M., T. Shikone, F. A. Fares, T. Sugahara, A. J. Hsueh, and I. Boime. 1995a. Fusing the carboxy-terminal peptide of the chorionic gonadotropin (CG) beta-subunit to the common alpha-subunit: retention of O-linked glycosylation and enhanced in vivo bioactivity of chimeric human CG. *Mol. Endocrinol.* 9:54-63.
33. Furuhashi, M., T. Shikone, F. A. Fares, T. Sugahara, A. J. W. Hsueh, and I. Boime. 1995b. Fusing the carboxy-terminal peptide of the chorionic gonadotropin (CG) b-subunit to the common α-subunit: Retention of O— linked glycosylation and enhanced in vivo bioactivity of chimeric human CG. *Mol. Endocrinol.* 9:54-63.
34. Greenblatt, E. and R. F. Casper. 1987. Endocrine changes after laparoscopic ovarian cautery in polycystic ovarian syndrome. *Am. J. Obstet. Gynecol.* 156:279-285.
35. Gromoll, J., U. Eiholzer, E. Nieschlag, and M. Simoni. 2000. Male hypogonadism caused by homozygous deletion of exon 10 of the luteinizing hormone (LH) receptor: differential action of human chorionic gonadotropin and LH. *J. Clin. Endocrinol. Metab* 85:2281-2286.
36. Gromoll, J., J. Wistuba, N. Terwort, M. Godmann, T. Muller, and M. Simoni. 2003. A new subclass of the luteinizing hormone/chorionic gonadotropin receptor lacking exon 10 messenger RNA in the New World monkey (Platyrrhini) lineage. *Biol. Reprod.* 69:75-80.
37. Grossmann, M., H. Leitolf, B. D. Weintraub, and M. W. Szkudlinski. 1998. A rational design strategy for protein hormone superagonists. *Nature Biotech.* 16:871-875.
38. Grossmann, M., M. W. Szkudlinski, R. Wong, J. A. Dias, T. H. Ji, and B. D. Weintraub. 1997. Substitution of the seat-belt region of the thyroid-stimulating hormone (TSH) beta-subunit with the corresponding regions of choriogonadotropin or follitropin confers luteotropic but not follitropic activity to chimeric TSH. *J. Biol. Chem.* 272:15532-15540.
39. Hall, J. E., A. E. Taylor, F. J. Hayes, and W. F. J. Crowley. 1998. Insights into hypothalamic-pituitary dysfunction in polycystic ovary syndrome. *J. Endocrinol. Invest.* 21:602-611.
40. Han, Y., M. P. Bernard, and W. R. Moyle. 1996. hCGb Residues 94-96 alter LH activity without appearing to make key receptor contacts. *Mol. Cell. Endocrinol.* 124: 151-161.
41. Hansel, W., C. Leuschner, B. Gawronska, and F. Enright. 2001. Targeted destruction of prostate cancer cells and xenografts by lytic peptide-betaLH conjugates. *Reprod. Biol.* 1:20-32.
42. Heikoop, J. C., M. M. van Beuningen-de Vaan, van den Boogaart, and P. D. Grootenhuis. 1997a. Evaluation of subunit truncation and the nature of the spacer for single chain human gonadotropins. *Eur. J. Biochem.* 245:656-662.
43. Heikoop, J. C., van den Boogaart, J. W. Mulders, and P. D. Grootenhuis. 1997b. Structure-based design and protein engineering of intersubunit disulfide bonds in gonadotropins. *Nature Biotech.* 15:658-662.
44. Hoelscher, S. R., M. R. Sairam, and M. Ascoli. 1991. The slow rate of internalization of deglycosylated human chorionic gonadotropin is not due to its inability to stimulate cyclic adenosine monophosphate accumulation. *Endocrinol.* 128:2837-2843.
45. Homburg, R. 2003. Ovulation induction. *Expert. Opin. Pharmacother.* 4:1995-2004.
46. Homburg, R. 2004. Management of infertility and prevention of ovarian hyperstimulation in women with polycystic ovary syndrome. *Best. Pract. Res. Clin. Obstet. Gynaecol.* 18:773-788.
47. Ji, I., C. Lee, Y. Song, P. M. Conn, and T. H. Ji. 2002. Cis- and trans-activation of hormone receptors: the LH receptor. *Mol. Endocrinol.* 16:1299-1308.
48. Jiang, X., M. Dreano, D. R. Buckler, S. Cheng, A. Ythier, H. Wu, W. A. Hendrickson, N. E. Tayar, and N. el Tayar. 1995. Structural predictions for the ligand-binding region of glycoprotein hormone receptors and the nature of hormone-receptor interactions. *Structure* 3:1341-1353.
49. Kajava, A. V., G. Vassart, and S. J. Wodak. 1995. Moldeling of the three-dimensional structure of proteins with the typical leucine-rich repeats. *Structure* 3:867-877.
50. Kobe, B. and J. Deisenhofer. 1993. Crystal structure of porcine ribonuclease inhibitor, a protein with leucine-rich repeats. *Nature* 366:751-756.
51. Lapthorn, A. J., D. C. Harris, A. Littlejohn, J. W. Lustbader, R. E. Canfield, K. J. Machin, F. J. Morgan, and N. W. Isaacs. 1994. Crystal structure of human chorionic gonadotropin. *Nature* 369:455-461.
52. Lee-Robichaud, P., M. E. Akhtar, J. N. Wright, Q. I. Sheikh, and M. Akhtar. 2004. The cationic charges on Arg347, Arg358 and Arg449 of human cytochrome P450c17 (CYP17) are essential for the enzyme's cytochrome b5-dependent acyl-carbon cleavage activities. *J. Steroid Biochem. Mol. Biol.* 92:119-130.
53. Li, M. D. and J. J. Ford. 1998. A comprehensive evolutionary analysis based on nucleotide and amino acid sequences of the alpha- and beta-subunits of glycoprotein hormone gene family. *Journal of Endocrinology* 156:529-542.
54. Liguori, G., A. Tolino, G. Moccia, G. Scognamiglio, and C. Nappi. 1996. Laparoscopic ovarian treatment in infertile patients with polycystic ovarian syndrome (PCOS): endocrine changes and clinical outcome. *Gynecol. Endocrinol.* 10:257-264.
55. Lin, W., M. X. Ransom, R. V. Myers, M. P. Bernard, and W. R. Moyle. 1999. Addition of an N-terminal dimerization domain promotes assembly of hCG analogs: implications for subunit combination and structure-function analysis. *Mol. Cell. Endocrinol.* 152:91-98.
56. Maciel, G. A., J. M. Soares Junior, E. L. ves da Motta, G. R. de Lima, and E. C. Baracat. 2004. Nonobese women with polycystic ovary syndrome respond better than obese women to treatment with metformin. *Fertil. Steril.* 81:355-360.
57. Marcil, J., N. Ravindranath, and M. R. Sairam. 1993. Cytotoxic activity of lutropin-gelonin conjugate in mouse Leydig tumor cells: potentiation of the hormonotoxin activity by different drugs. *Mol. Cell Endocrinol.* 92:83-90.
58. Matthews, D. J., L. J. Goodman, C. M. Gorman, and J. A. Wells. 1994. A survey of furin substrate specificity using substrate phage display. *Protein Sci.* 3:1197-1205.
59. Matzuk, M. M. and I. Boime. 1988. The role of the asparagine-linked oligosaccharides of the α-subunit in the secretion and assembly of human chorionic gonadotrophin. *J. Cell Biol.* 106:1049-1059.
60. Matzuk, M. M. and I. Boime. 1989. Mutagenesis and gene transfer define site-specific roles of the gonadotropin oligosaccharides. *Biol. Reprod.* 40:48-53.
61. Matzuk, M. M., J. L. Keene, and I. Boime. 1989. Site specificity of the chorionic gonadotropin N-linked oligosaccharides in signal transduction. *J. Biol. Chem.* 264: 2409-2414.
62. McFarland, KC., R. Sprengel, H. S. Phillips, M. Kohler, N. Rosemblit, K. Nikolics, D. L. Segaloff, and P. H. Seeburg. 1989. Lutropin-choriogonadotropin receptor: an unusual member of the G protein-coupled receptor family. *Science* 245:494-499.
63. Min, K. S., N. Hattori, J. Aikawa, K. Shiota, and T. Ogawa. 1996. Site-directed mutagenesis of recombinant equine chorionic gonadotropin/luteinizing hormone: differential role of oligosaccharides in luteinizing hormone- and follicle-stimulating hormone-like activities. *Endocr. J.* 43:585-593.
64. Morell, A. G., G. Gregoriadis, I. H. Scheinberg, J. Hickman, and G. Ashwell. 1971. The role of sialic acid in determining the survival of glycoproteins in the circulation. *J. Biol. Chem.* 246:1461-1467.
65. Moyle, W. R., O. P. Bahl, and L. Marz. 1975. Role of the carbohydrate of human choriogonadotropin in the mechanism of hormone action. *J. Biol. Chem.* 250:9163-9169.
66. Moyle, W. R., R. K. Campbell, R. V. Myers, M. P. Bernard, Y. Han, and X. Wang. 1994. Co-evolution of ligand-receptor pairs. *Nature* 368:251-255.
67. Moyle, W. R., R. K. Campbell, S. N. V. Rao, N. G. Ayad, M. P. Bernard, Y. Han, and Y. Wang. 1995. Model of human chorionic gonadotropin (hCG) and lutropin receptor (LHR) interaction that explains signal transduction of the glycoprotein hormones. *J. Biol. Chem.* 270:20020-20031.
68. Moyle, W. R., P. H. Ehrlich, and R. E. Canfield. 1982. Use of monoclonal antibodies to hCG subunits to examine the orientation of hCG in the hormone-receptor complex. *Proc. Natl. Acad. Sci. (USA)* 79:2245-2249.
69. Moyle, W. R., W. Lin, R. V. Myers, D. Cao, J. E. Kerrigan, and M. P. Bernard. 2005. Models of glycoprotein hormone receptor interaction. *Endocrine* 26:189-205.
70. Moyle, W. R., M. M. Matzuk, R. K. Campbell, E. Cogliani, D. M. Dean Emig, A. Krichevsky, R. W. Barnett, and I. Boime. 1990. Localization of residues that confer antibody binding specificity using human chorionic gonadotropin/luteinizing hormone beta subunit chimeras and mutants. *J. Biol. Chem.* 265:8511-8518.
71. Moyle, W. R., A. Pressey, D. Dean Emig, D. M. Anderson, M. Demeter, J. Lustbader, and P. Ehrlich. 1987. Detection of conformational changes in human chorionic gonadotropin upon binding to rat gonadal receptors. *J. Biol. Chem.* 262:16920-16926.
72. Moyle, W. R., Y. Xing, W. Lin, D. Cao, R. V. Myers, J. E. Kerrigan, and M. P. Bernard. 2004. Model of glycoprotein hormone receptor ligand binding and signaling. *J. Biol. Chem.* 279:44442-44459.
73. Muller, T., J. Gromoll, A. P. Simula, R. Norman, R. Sandhowe-Klayerkamp, and M. Simoni. 2004a. The carboxyterminal peptide of chorionic gonadotropin facilitates activation of the marmoset LH receptor. *Exp. Clin. Endocrinol. Diabetes* 112:574-579.
74. Muller, T., M. Simoni, E. Pekel, C. M. Luetjens, R. Chandolia, F. Amato, R. J. Norman, and J. Gromoll. 2004b. Chorionic gonadotrophin beta subunit mRNA but not luteinising hormone beta subunit mRNA is expressed in the pituitary of the common marmoset (Callithrix jacchus). *J. Mol. Endocrinol.* 32:115-128.
75. Murphy, B. D. and S. D. Martinuk. 1991. Equine chorionic gonadotropin. *Endocr. Rev.* 12:27-44.
76. Murray, R. D., R. M. Davison, R. C. Russell, and G. S. Conway. 2000. Clinical presentation of PCOS following development of an insulinoma: case report. *Hum. Reprod.* 15:86-88.
77. Nagayama, Y., K. D. Kaufman, P. Seto, and B. Rapoport. 1989. Molecular cloning sequence and functional expression of the cDNA for the human thyrotropin receptor. *Biochem. Biophys. Res. Commun.* 165:1184-1190.
78. Nagayama, Y., H. L. Wadsworth, G. D. Chazenbalk, D. Russo, P. Seto, and B. Rapoport. 1991. Thyrotropin-luteinizing hormone/chorionic gonadotropin receptor extracellular domain chimeras as probes for thyrotropin receptor function. *Proc. Natl. Acad. Sci. (USA)* 88:902-905.
79. Palczewski, K., T. Kumasaka, T. Hori, C. A. Behnke, H. Motoshima, B. A. Fox, I. LeTrong, D. C. Teller, T. Okada, R. E. Stenkamp, M. Yamamoto, and M. Miyano. 2000. Crystal structure of rhodopsin: A G protein-coupled receptor. *Science* 289:739-745.
80. Pierce, J. G. and T. F. Parsons. 1981. Glycoprotein hormones: structure and function. *Annu. Rev. Biochem.* 50:465-495.
81. Rapoport, B., G. D. Chazenbalk, J. C. Jaume, and S. M. McLachlan. 1998. The thyrotropin (TSH) receptor: interaction with TSH and autoantibodies. *Endocr. Rev.* 19:673-716.
82. Reddy, V. B., A. K. Beck, A. J. Garramone, V. Vellucci, J. Lustbader, and E. G. Bernstein. 1985. Expression of human choriogonadotropin in monkey cells using a single simian virus 40 vector. *Proc. Natl. Acad. Sci. (USA)* 82:3644-3648.
83. Remy, J.-J., L. Couture, J. Pantel, T. Haertle, H. Rabesona, V. Bozon, E. Pajot-Augy, P. Robert, F. Troalen, R. Salesse, and J.-M. Bidart. 1996. Mapping of hCG-receptor complexes. *Mol. Cell. Endocrinol.* 125:79-91.
84. Rosa, C., S. Amr, S. Birken, R. Wehmann, and B. Nisula. 1984. Effect of desialylation of human chorionic gonadotropin on its metabolic clearance rate in humans. *J. Clin. Endocrinol. Metab.* 59:1215-1219.
85. Rosenfield, R. L. 1999. Ovarian and adrenal function in polycystic ovary syndrome. *Endocrinol. Metab Clin. North Am.* 28:265-293.
86. Ruddon, R. W., S. A. Sherman, and E. Bedows. 1996. Protein folding in the endoplasmic reticulum: lessons from the human chorionic gonadotropin b-subunit. *Prot. Sci.* 8:1443-1452.
87. Sairam, M. R. and G. N. Bhargavi. 1985. A role for the glycosylation of the alpha-subunit in the transduction of biological signal in glycoprotein hormones. *Science* 229:65-67.
88. Sanchez-Yague, J., M. C. Rodriguez, D. L. Segaloff, and M. Ascoli. 1992. Truncation of the cytoplasmic tail of the lutropin/choriogonadotropin receptor prevents agonist-induced uncoupling. *J. Biol. Chem.* 267:7217-7220.
89. Segaloff, D. L. and M. Ascoli. 1993. The lutropin/choriogonadotropin receptor . . . 4 years later. *Endocr. Rev.* 14:324-347.
90. Shanti, A. and A. A. Murphy. 1997. Surgical approaches to ovulation induction. *Semin. Reprod Endocrinol.* 15:183-191.
91. Singh, V. and M. R. Sairam. 1989. Hormonotoxins: conjugation of human choriogonadotropin with the ribosome inactivating protein gelonin and comparison with a lutropin conjugate. *Mol. Cell Endocrinol.* 67:217-229.
92. Singh, V., M. R. Sairam, G. N. Bhargavi, and R. G. Akhras. 1989. Hormonotoxins. Preparation and characterization of ovine luteinizing hormone-gelonin conjugate. *J. Biol. Chem.* 264:3089-3095.
93. Sprengel, R., T. Braun, K. Nikolics, D. L. Segaloff, and P. H. Seeburg. 1990. The testicular receptor for follicle stimulating hormone: structure and functional expression of cloned cDNA. *Mol. Endocrinol.* 4:525-530.
94. Stein, I. and M. Leventhal. 1935. Amenorrhea associated with bilateral polycystic ovaries. *Am. J. Obstet. Gynecol.* 29:181-191.
95. Sugahara, T., P. D. Grootenhuis, A. Sato, M. Kudo, M. R. Pixley, A. J. Hsueh, and I. Boime. 1996a. Expression of biologically active fusion genes encoding the common alpha subunit and either the CG beta or FSH beta subunits: role of a linker sequence. *Mol. Cell. Endocrinol.* 125:71-77.

96. Sugahara, T., M. R. Pixley, S. Minami, E. Perlas, D. Ben-Menahem, A. J. Hsueh, and I. Boime. 1995. Biosynthesis of a biologically active single peptide chain containing the human common alpha and chorionic gonadotropin beta subunits in tandem. *Proc. Natl. Acad. Sci. (USA)* 92:2041-2045.

97. Sugahara, T., A. Sato, M. Kudo, D. Ben-Menahem, M. R. Pixley, A. J. W. Hsueh, and I. Boime. 1996b. Expression of biologically active fusion genes encoding the common alpha subunit and the follicle-stimulating hormone beta subunit. Role of a linker sequence. *J. Biol. Chem.* 271: 10445-10448.

98. Thomas, D., T. G. Rozell, X. Liu, and D. L. Segaloff. 1996. Mutational analyses of the extracellular domain of the full-length lutropin/choriogonadotropin receptor suggest leucine-rich repeats 1-6 are involved in hormone binding. *Mol. Endocrinol.* 10:760-768.

99. Trout, S. W., Y. Han, R. V. Myers, M. P. Bernard, and W. R. Moyle. 1999. Deglycosylation of a bifunctional lutropin-follitropin agonist reduced its follitropin activity more than its lutropin activity. *Fertil. Steril.* 72:1093-1099.

100. Valove, F. M., C. Finch, J. N. Anasti, J. Froehlich, and M. R. Flack. 1994. Receptor binding and signal transduction are dissociable functions requiring different sites on follicle-stimulating hormone. *Endocrinol.* 135:2657-2661.

101. Vendola, K., J. Zhou, O. O. Adesanya, S. J. Weil, and C. A. Bondy. 1998. Androgens Stimulate Early Stages of Follicular Growth in the Primate Ovary. *J. Clin. Invest.* 101: 2622-2629.

102. Wehmann, R. E., S. Amr, C. Rosa, and B. C. Nisula. 1984. Metabolism, distribution and excretion of purified human chorionic gonadotropin and its subunits in man. *Ann. Endocrinol. (Paris)* 45:291-295.

103. Wu, H., J. W. Lustbader, Y. Liu, R. E. Canfield, and W. A. Hendrickson. 1994. Structure of human chorionic gonadotropin at 2.6 Å resolution from MAD analysis of the selenomethionyl protein. *Structure* 2:545-558.

104. Xie, Y. B., H. Wang, and D. L. Segaloff. 1990. Extracellular domain of lutropin/choriogonadotropin receptor expressed in transfected cells binds choriogonadotropin with high affinity. *J. Biol. Chem.* 265:21411-21414.

105. Xing, Y., W. Lin, M. Jiang, R. V. Myers, D. Cao, M. P. Bernard, and W. R. Moyle. 2001a. Alternatively folded choriogonadotropin analogs. Implications for hormone folding and biological activity. *J. Biol. Chem.* 276:46953-46960.

106. Xing, Y. and W. R. Moyle. 2003. Efficient preparation of glycoprotein hormones lacking an alpha-subunit oligosaccharide. *Biochem. Biophys. Res. Commun.* 303:201-205.

107. Xing, Y., R. V. Myers, D. Cao, W. Lin, M. Jiang, M. P. Bernard, and W. R. Moyle. 2004a. Glycoprotein hormone assembly in the endoplasmic reticulum: I. The glycosylated end of human alpha-subunit loop 2 is threaded through a beta-subunit hole. *J. Biol. Chem.* 279:35426-35436.

108. Xing, Y., R. V. Myers, D. Cao, W. Lin, M. Jiang, M. P. Bernard, and W. R. Moyle. 2004b. Glycoprotein hormone assembly in the endoplasmic reticulum: II Multiple roles of a redox sensitive beta-subunit disulfide switch. *J. Biol. Chem.* 279:35437-35448.

109. Xing, Y., R. V. Myers, D. Cao, W. Lin, M. Jiang, M. P. Bernard, and W. R. Moyle. 2004c. Glycoprotein hormone assembly in the endoplasmic reticulum: III. The seatbelt and its latch site determine the assembly pathway. *J. Biol. Chem.* 279:35449-35457.

110. Xing, Y., R. V. Myers, D. Cao, W. Lin, M. Jiang, M. P. Bernard, and W. R. Moyle. 2004d. Glycoprotein hormone assembly in the endoplasmic reticulum: IV. Probable mechanism of subunit docking and completion of assembly. *J. Biol. Chem.* 279:35458-35468.

111. Xing, Y., C. Williams, R. K. Campbell, S. Cook, M. Knoppers, T. Addona, V. Altarocca, and W. R. Moyle. 2001b. Threading of a glycosylated protein loop through a protein hole: implications for combination of human chorionic gonadotropin subunits. *Protein Sci.* 10:226-235.

112. Yildiz, B. O., W. Chang, and R. Azziz. 2003. Polycystic ovary syndrome and ovulation induction. *Minerva Ginecol.* 55:425-439.

113. Zhang, F. P., A. S. Rannikko, P. R. Manna, H. M. Fraser, and Huhtaniemi. 1997. Cloning and functional expression of the luteinizing hormone receptor complementary deoxyribonucleic acid from the marmoset monkey testis: absence of sequences encoding exon 10 in other species. *Endocrinol.* 138:2481-2490.

114. Zhang, L. H., H. Rodriguez, S. Ohno, and W. L. Miller. 1995. Serine phosphorylation of human P450c17 increases 17,20-lyase activity: implications for adrenarche and the polycystic ovary syndrome. *Proc. Natl. Acad. Sci. U.S. A* 92:10619-10623.

115. Zhu, X., T. Gudermann, M. Birnbaumer, and L. Birnbaumer. 1993. A luteinizing hormone receptor with a severely truncated cytoplasmic tail (LHR-ct628) desensitizes to the same degree as the full-length receptor. *J. Biol. Chem.* 268:1723-1728.

I claim:

1. A biologically active salmon follitropin glycoprotein hormone analog, capable of binding to a follicle stimulating hormone receptor, said analog consisting essentially of a heterodimer comprising a glycosylated α subunit polypeptide and a glycosylated β subunit polypeptide, wherein:
   said α subunit polypeptide comprising the sequence set forth in SEQ ID NO: 66;
   said β subunit polypeptide comprising the sequence set forth in SEQ ID NO: 53;
   said α subunit polypeptide and β subunit polypeptide are linked by a peptide bond;
   said β subunit polypeptide comprises a seatbelt region that wraps around said alpha α subunit polypeptide;
   said α and β subunit polypeptides are covalently linked via two disulfide bonds consisting of a first disulfide bond and a second disulfide bond;
   said first disulfide bond is between cys29 of said α subunit polypeptide and a cysteine residue on the N-terminus end of said β subunit polypeptide; and
   said second disulfide bond is between cys110 of said α subunit polypeptide and cys98 of said β subunit polypeptide.

2. The analog of claim 1, wherein said α subunit polypeptide has reduced glycosylation relative to a native α subunit polypeptide.

3. The analog of claim 2, wherein said α subunit polypeptide comprises an α2 loop which has reduced glycosylation relative to an α2 loop of a native α subunit polypeptide.

4. The analog of claim 3 wherein said α subunit polypeptide comprises a mutation of at least one asparagine residue relative to a native α subunit polypeptide.

5. The analog of claim 1, wherein said α subunit polypeptide and β subunit polypeptide are linked by a peptide bond, wherein said peptide bond is between the C-terminus of said α subunit polypeptide and the N-terminus of said β subunit polypeptide.

6. The analog of claim 5, wherein said analog comprises a cleavage site in between said α subunit and said β subunit.

7. The analog of claim 6, wherein said cleavage site is selected from the group consisting of a furin cleavage site, thrombin cleavage site, Factor Xa cleavage site, and enterokinase cleavage site.

8. A nucleic acid comprising a polynucleotide encoding an α subunit polypeptide, wherein said α subunit polypeptide has an amino acid sequence comprising the sequence recited in SEQ ID NO: 66.

9. A nucleic acid comprising a polynucleotide encoding a β subunit polypeptide wherein said β subunit polypeptide has an amino acid sequence comprising the sequence recited in SEQ ID NO: 53.

10. A vector comprising a nucleic acid of claim 8.

11. A vector comprising a nucleic acid of claim 9.

12. An isolated host cell comprising, a nucleic acid of claim 8.

13. An isolated host cell comprising a nucleic acid of claim 9.

14. A method of inducing follicle development in fish comprising administering an effective dose of a formulation comprising an analog of claim 1 to said fish.

* * * * *

SEQUENCE LISTING

<160> NUMBER OF SEQ ID NOS: 286

<210> SEQ ID NO 1
<211> LENGTH: 116
<212> TYPE: PRT
<213> ORGANISM: Artificial Sequence
<220> FEATURE:
<223> OTHER INFORMATION: chimeric salmon-human alpha subunit analog

<400> SEQUENCE: 1

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Cys Asp Cys Pro
            20                  25                  30

```
Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
 50                  55                  60

Leu Arg Ser Lys Gln Thr Met Leu Val Pro Lys Asn Ile Thr Ser Glu
 65                  70                  75                  80

Ala Thr Cys Cys Val Ala Lys Ser Tyr Asn Arg Val Thr Val Met Gly
                 85                  90                  95

Gly Phe Lys Val Glu Asn His Thr Ala Cys His Cys Ser Cys Cys Tyr
                100                 105                 110

Tyr His Lys Ser
        115

<210> SEQ ID NO 2
<211> LENGTH: 116
<212> TYPE: PRT
<213> ORGANISM: Artificial Sequence
<220> FEATURE:
<223> OTHER INFORMATION: chimeric salmon-human alpha-subunit analog

<400> SEQUENCE: 2

Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Cys Asp Cys Pro
                 20                  25                  30

Glu Cys Lys Leu Lys Glu Asn Lys Phe Phe Ser Lys Pro Gly Ala Pro
        35                  40                  45

Ile Leu Gln Cys Met Gly Cys Cys Phe Ser Arg Ala Tyr Pro Thr Pro
 50                  55                  60

Leu Arg Ser Lys Gln Thr Met Leu Val Pro Lys Asn Ile Thr Ser Glu
 65                  70                  75                  80

Ala Thr Cys Cys Val Ala Lys Ser Tyr Asn Arg Val Thr Val Met Gly
                 85                  90                  95

Gly Phe Lys Val Glu Asn His Thr Ala Cys His Cys Ser Cys Cys Tyr
                100                 105                 110

Tyr His Lys Ser
        115

<210> SEQ ID NO 3
<211> LENGTH: 139
<212> TYPE: PRT
<213> ORGANISM: Artificial Sequence
<220> FEATURE:
<223> OTHER INFORMATION: chimeric salmon FSH hcG beta subunit analog

<400> SEQUENCE: 3

Met Glu Thr Asp Thr Leu Leu Leu Trp Val Leu Leu Leu Trp Val Pro
 1               5                  10                  15

Gly Ser Thr Gly Asp Tyr Lys Ala Lys Glu Leu Ala Ser Gly Thr Asp
                 20                  25                  30

Cys Arg Tyr Gly Cys Arg Leu Asn Asn Met Thr Ile Thr Val Glu Arg
        35                  40                  45

Glu Asp Cys His Gly Ser Ile Thr Ile Thr Thr Cys Ala Gly Leu Cys
 50                  55                  60

Pro Thr Met Thr Arg Val Leu Gln Gly Val Leu Pro Ala Leu Pro Gln
 65                  70                  75                  80

Val Val Cys Asn Phe Lys Glu Trp Ser Tyr Glu Lys Val Tyr Leu Glu
                 85                  90                  95
```

```
Gly Cys Pro Ser Gly Val Asp Pro Phe Phe Ile Pro Val Ala Lys Ser
                100                 105                 110

Cys Asp Cys Ile Lys Cys Lys Thr Asp Asn Thr Asp Cys Asp Cys Ile
            115                 120                 125

Ser Met Ala Thr Pro Gly Ser Phe Glu Gln Thr
        130                 135

<210> SEQ ID NO 4
<211> LENGTH: 139
<212> TYPE: PRT
<213> ORGANISM: Artificial Sequence
<220> FEATURE:
<223> OTHER INFORMATION: chimeric salmon FSH - hCG beta subunit

<400> SEQUENCE: 4

Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
            20                  25                  30

Cys Arg Tyr Gly Cys Arg Leu Asn Asn Met Thr Ile Thr Val Glu Arg
        35                  40                  45

Glu Asp Cys His Gly Ser Ile Thr Ile Thr Cys Ala Gly Leu Cys
    50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Ser Ile Arg Leu Pro
                85                  90                  95

Gly Cys Pro Arg Gly Val Asn Pro Val Phe Ile Pro Val Ala Lys Ser
                100                 105                 110

Cys Asp Cys Ile Lys Cys Lys Thr Asp Asn Thr Asp Cys Asp Cys Ile
            115                 120                 125

Ser Met Ala Thr Pro Gly Ser Phe Glu Gln Thr
        130                 135

<210> SEQ ID NO 5
<211> LENGTH: 249
<212> TYPE: PRT
<213> ORGANISM: Artificial Sequence
<220> FEATURE:
<223> OTHER INFORMATION: chimera human/salmon alpha subunit

<400> SEQUENCE: 5

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Gln Thr Met Leu Val Pro Lys Asn Ile Thr Ser Glu
65                  70                  75                  80

Ala Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
                100                 105                 110

Tyr His Lys Ser Asp Asp Pro Arg Phe Gln Asp Ser Ser Ser Ser Lys
            115                 120                 125
```

```
Ala Pro Pro Ser Leu Pro Ser Pro Ser Arg Leu Pro Gly Pro Ser
    130                 135                 140

Asp Thr Pro Ile Leu Pro Gln Arg Arg Phe Lys Arg Pro Arg Cys Arg
145                 150                 155                 160

Leu Asn Asn Met Thr Ile Thr Val Glu Arg Glu Asp Cys His Gly Ser
                165                 170                 175

Ile Thr Ile Thr Thr Cys Ala Gly Leu Cys Glu Thr Thr Asp Leu Asn
            180                 185                 190

Tyr Gln Ser Thr Trp Leu Pro Arg Ser Gln Gly Val Cys Asn Phe Lys
            195                 200                 205

Glu Trp Ser Tyr Glu Lys Val Tyr Leu Glu Gly Cys Pro Ser Gly Val
        210                 215                 220

Asp Pro Phe Phe Ile Pro Val Ala Lys Ser Cys Asp Cys Ile Lys Cys
225                 230                 235                 240

Lys Thr Asp Asn Thr Asp Cys Asp Cys
                245

<210> SEQ ID NO 6
<211> LENGTH: 139
<212> TYPE: PRT
<213> ORGANISM: Artificial Sequence
<220> FEATURE:
<223> OTHER INFORMATION: flag salmon FSH beta subunit

<400> SEQUENCE: 6

Met Glu Thr Asp Thr Leu Leu Leu Trp Val Leu Leu Trp Val Pro
1               5                   10                  15

Gly Ser Thr Gly Asp Tyr Lys Ala Lys Glu Leu Ala Ser Gly Thr Asp
                20                  25                  30

Cys Arg Tyr Gly Cys Arg Leu Asn Asn Met Thr Ile Thr Val Glu Arg
            35                  40                  45

Glu Asp Cys His Gly Ser Ile Thr Ile Thr Thr Cys Ala Gly Leu Cys
        50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asn Ser Thr Phe Ile Pro Val Ala Lys Ser
            100                 105                 110

Cys Asp Cys Ile Lys Cys Lys Thr Asp Asn Thr Asp Cys Asp Cys Ile
        115                 120                 125

Ser Met Ala Thr Pro Gly Ser Phe Glu Gln Thr
    130                 135

<210> SEQ ID NO 7
<211> LENGTH: 116
<212> TYPE: PRT
<213> ORGANISM: Homo sapiens

<400> SEQUENCE: 7

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60
```

```
Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
            100                 105                 110

Tyr His Lys Ser
        115

<210> SEQ ID NO 8
<211> LENGTH: 165
<212> TYPE: PRT
<213> ORGANISM: Homo sapiens

<400> SEQUENCE: 8

Met Glu Met Phe Gln Gly Leu Leu Leu Leu Leu Leu Leu Ser Met Gly
 1               5                  10                  15

Gly Thr Trp Ala Ser Lys Glu Pro Leu Arg Pro Arg Cys Arg Pro Ile
             20                  25                  30

Asn Ala Thr Leu Ala Val Glu Lys Glu Gly Cys Pro Val Cys Ile Thr
         35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 9
<211> LENGTH: 116
<212> TYPE: PRT
<213> ORGANISM: Homo sapiens

<400> SEQUENCE: 9

Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
             20                  25                  30

Glu Cys Thr Leu Gln Glu Asn Pro Phe Phe Ser Gln Pro Gly Ala Pro
         35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95
```

```
Gly Phe Lys Val Glu Asn His Thr Ala Cys His Cys Ser Cys Cys Tyr
                100                 105                 110

Tyr His Lys Ser
        115

<210> SEQ ID NO 10
<211> LENGTH: 149
<212> TYPE: PRT
<213> ORGANISM: Artificial Sequence
<220> FEATURE:
<223> OTHER INFORMATION: amino acid sequence encoded by the alpha
      subunit

<400> SEQUENCE: 10

Met Glu Met Phe Gln Gly Leu Leu Leu Leu Leu Leu Ser Met Gly
1               5                   10                  15

Gly Thr Trp Ala Ser Gly Leu Thr Asp Thr Leu Gln Ala Glu Thr Asp
                20                  25                  30

Gln Leu Glu Asp Lys Lys Ser Ala Leu Gln Thr Glu Ile Ala Asn Leu
            35                  40                  45

Leu Lys Glu Lys Glu Lys Leu Glu Phe Ile Leu Ala Gly Gln Asp Cys
50                  55                  60

Pro Glu Cys Thr Leu Gln Glu Asn Pro Phe Phe Ser Gln Pro Gly Ala
65                  70                  75                  80

Pro Ile Leu Gln Cys Met Gly Cys Cys Phe Ser Arg Ala Tyr Pro Thr
                85                  90                  95

Pro Leu Arg Ser Lys Lys Thr Met Leu Val Gln Lys Asn Val Thr Ser
            100                 105                 110

Glu Ser Thr Cys Cys Val Ala Lys Ser Tyr Asn Arg Val Thr Val Met
        115                 120                 125

Gly Gly Phe Lys Val Glu Asn His Thr Ala Cys His Cys Ser Thr Cys
    130                 135                 140

Tyr Tyr His Lys Ser
145

<210> SEQ ID NO 11
<211> LENGTH: 116
<212> TYPE: PRT
<213> ORGANISM: Homo sapiens

<400> SEQUENCE: 11

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Ala Tyr Pro Thr Pro
50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

```
<210> SEQ ID NO 12
<211> LENGTH: 116
<212> TYPE: PRT
<213> ORGANISM: Homo sapiens

<400> SEQUENCE: 12

Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Cys Pro Thr Pro
        50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 13
<211> LENGTH: 134
<212> TYPE: PRT
<213> ORGANISM: Artificial Sequence
<220> FEATURE:
<223> OTHER INFORMATION: chimeric beta subunit

<400> SEQUENCE: 13

Met Glu Met Phe Gln Gly Leu Leu Leu Leu Leu Leu Leu Ser Met Gly
 1               5                  10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Cys Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Thr Val Arg Gly Leu Gly Pro Ser
        115                 120                 125

Tyr Cys Asp Asp Pro Arg
        130

<210> SEQ ID NO 14
<211> LENGTH: 134
<212> TYPE: PRT
<213> ORGANISM: Artificial Sequence
<220> FEATURE:
<223> OTHER INFORMATION: chimeric beta subunit

<400> SEQUENCE: 14

Met Glu Met Phe Gln Gly Leu Leu Leu Leu Leu Leu Leu Ser Met Gly
 1               5                  10                  15
```

```
Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Cys Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Thr Val Arg Gly Leu Gly Pro Ser
                115                 120                 125

Tyr Cys Asp Asp Pro Arg
            130
```

<210> SEQ ID NO 15
<211> LENGTH: 164
<212> TYPE: PRT
<213> ORGANISM: Artificial Sequence
<220> FEATURE:
<223> OTHER INFORMATION: amino acid sequence encoded by the beta subunit

<400> SEQUENCE: 15

```
Met Glu Met Phe Gln Gly Leu Leu Leu Leu Leu Leu Leu Ser Met Gly
 1               5                   10                  15

Gly Thr Trp Ala Ser Gly Thr Asp Cys Arg Tyr Gly Cys Arg Leu Asn
            20                  25                  30

Asn Met Thr Ile Thr Val Glu Arg Glu Asp Cys His Gly Ser Ile Thr
            35                  40                  45

Ile Thr Thr Cys Ala Gly Leu Cys Glu Thr Thr Asp Leu Asn Tyr Gln
 50                  55                  60

Ser Thr Trp Leu Pro Arg Ser Gln Gly Val Cys Asn Phe Lys Glu Trp
 65                  70                  75                  80

Ser Tyr Glu Lys Val Tyr Leu Glu Gly Cys Pro Ser Gly Val Asp Pro
                85                  90                  95

Phe Phe Ile Pro Val Ala Lys Ser Cys Asp Cys Ile Lys Cys Lys Thr
                100                 105                 110

Asp Asn Thr Asp Cys Asp Arg Ile Ser Met Ala Thr Pro Ser Cys Ile
                115                 120                 125

Val Asn Pro Leu Glu Phe Gln Asp Ser Ser Ser Lys Ala Pro Pro
                130                 135                 140

Pro Ser Leu Pro Ser Pro Ser Arg Leu Pro Gly Pro Ser Asp Thr Pro
145                 150                 155                 160

Ile Leu Pro Gln
```

<210> SEQ ID NO 16
<211> LENGTH: 122
<212> TYPE: PRT
<213> ORGANISM: Artificial Sequence
<220> FEATURE:
<223> OTHER INFORMATION: amino acid sequence encoded by the beta subunit

<400> SEQUENCE: 16

```
Met Glu Met Phe Gln Gly Leu Leu Leu Leu Leu Leu Leu Ser Met Gly
 1               5                   10                  15
```

-continued

```
Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Ala Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                    85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Cys
            115                 120
```

<210> SEQ ID NO 17
<211> LENGTH: 116
<212> TYPE: PRT
<213> ORGANISM: Homo sapiens

<400> SEQUENCE: 17

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asp Val Thr Ser Glu
 65                  70                  75                  80

Ser Thr Cys Cys Val Ala Lys Ser Tyr Asn Arg Val Thr Val Met Gly
                    85                  90                  95

Gly Phe Lys Val Glu Asn His Thr Ala Cys His Cys Ser Cys Cys Tyr
                100                 105                 110

Tyr His Lys Ser
        115
```

<210> SEQ ID NO 18
<211> LENGTH: 164
<212> TYPE: PRT
<213> ORGANISM: Artificial Sequence
<220> FEATURE:
<223> OTHER INFORMATION: amino acid sequence encoded by beta subunit

<400> SEQUENCE: 18

```
Met Glu Met Phe Gln Gly Leu Leu Leu Leu Leu Leu Ser Met Gly
 1               5                  10                  15

Gly Thr Trp Ala Ser Gly Thr Asp Ala Arg Tyr Gly Cys Arg Leu Asn
            20                  25                  30

Asn Met Thr Ile Thr Val Glu Arg Glu Asp Cys His Gly Ser Ile Thr
            35                  40                  45

Ile Thr Thr Cys Ala Gly Leu Cys Glu Thr Thr Asp Leu Asn Tyr Gln
 50                  55                  60

Ser Thr Trp Leu Pro Arg Ser Gln Gly Val Cys Asn Phe Lys Glu Trp
 65                  70                  75                  80

Ser Tyr Glu Lys Val Tyr Leu Glu Gly Cys Pro Ser Gly Val Asp Pro
                    85                  90                  95
```

```
Phe Phe Ile Pro Val Ala Lys Ser Cys Asp Cys Ile Lys Cys Lys Thr
            100                 105                 110

Asp Asn Thr Asp Cys Asp Arg Ile Ser Met Ala Thr Pro Ser Cys Ile
        115                 120                 125

Val Asn Pro Leu Glu Phe Gln Asp Ser Ser Ser Lys Ala Pro Pro
    130                 135                 140

Pro Ser Leu Pro Ser Pro Ser Arg Leu Pro Gly Pro Ser Asp Thr Pro
145                 150                 155                 160

Ile Leu Pro Gln

<210> SEQ ID NO 19
<211> LENGTH: 122
<212> TYPE: PRT
<213> ORGANISM: Artificial Sequence
<220> FEATURE:
<223> OTHER INFORMATION: amino acid sequence encoded by beta subunit

<400> SEQUENCE: 19

Met Glu Met Phe Gln Gly Leu Leu Leu Leu Leu Leu Ser Met Gly
1               5                   10                  15

Gly Thr Trp Ala Ser Asn Glu Thr Leu Arg Pro Arg Cys Arg Pro Ile
            20                  25                  30

Asp Ala Thr Leu Ala Val Glu Lys Glu Gly Cys Pro Val Ala Ile Thr
        35                  40                  45

Val Asp Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Cys
        115                 120

<210> SEQ ID NO 20
<211> LENGTH: 172
<212> TYPE: PRT
<213> ORGANISM: Artificial Sequence
<220> FEATURE:
<223> OTHER INFORMATION: amino acid sequence encoded by beta subunit

<400> SEQUENCE: 20

Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
            20                  25                  30

Ala Arg Tyr Gly Cys Arg Leu Asn Asn Met Thr Ile Thr Val Glu Arg
        35                  40                  45

Glu Asp Cys His Gly Ser Ile Thr Ile Thr Cys Ala Gly Leu Cys
    50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asp Pro Phe Phe Ile Pro Val Ala Lys Ser
            100                 105                 110
```

```
Cys Asp Cys Ile Lys Cys Lys Thr Asp Asn Thr Asp Cys Asp Arg Ile
            115                 120                 125

Ser Met Ala Thr Pro Ser Cys Ile Val Asn Pro Leu Glu Phe Gln Asp
        130                 135                 140

Ser Ser Ser Ser Lys Ala Pro Pro Ser Leu Pro Ser Pro Ser Arg
145                 150                 155                 160

Leu Pro Gly Pro Ser Asp Thr Pro Ile Leu Pro Gln
                165                 170

<210> SEQ ID NO 21
<211> LENGTH: 127
<212> TYPE: PRT
<213> ORGANISM: Artificial Sequence
<220> FEATURE:
<223> OTHER INFORMATION: amino acid sequence encoded by beta subunit

<400> SEQUENCE: 21

Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
            20                  25                  30

Ala Arg Tyr Gly Cys Arg Leu Asn Asn Met Thr Ile Thr Val Glu Arg
        35                  40                  45

Glu Asp Cys His Gly Ser Ile Thr Ile Thr Thr Cys Ala Gly Leu Cys
    50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Cys
        115                 120                 125

<210> SEQ ID NO 22
<211> LENGTH: 165
<212> TYPE: PRT
<213> ORGANISM: Artificial Sequence
<220> FEATURE:
<223> OTHER INFORMATION: mutant beta subunit

<400> SEQUENCE: 22

Met Glu Met Phe Gln Gly Leu Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Ala Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Cys Pro Lys Asp His Pro Leu
        115                 120                 125
```

```
Thr Ala Asp Asp Pro Arg Phe Gln Asp Ser Ser Ser Lys Ala Pro
            130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 23
<211> LENGTH: 413
<212> TYPE: PRT
<213> ORGANISM: Artificial Sequence
<220> FEATURE:
<223> OTHER INFORMATION: chimeric alpha subunit

<400> SEQUENCE: 23

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
                100                 105                 110

Tyr His Lys Ser Asp Asp Pro Arg Phe Gln Asp Ser Ser Ser Ser Lys
            115                 120                 125

Ala Pro Pro Pro Ser Leu Pro Ser Pro Ser Arg Leu Gly Pro Cys Asp
130                 135                 140

Thr Pro Ile Leu Pro Gln His Pro Glu Thr Leu Val Lys Val Lys Asp
145                 150                 155                 160

Ala Glu Asp Gln Leu Gly Ala Arg Val Gly Tyr Ile Glu Leu Asp Leu
                165                 170                 175

Asn Ser Gly Lys Ile Leu Glu Ser Phe Arg Pro Glu Glu Arg Phe Pro
            180                 185                 190

Met Met Ser Thr Phe Lys Val Leu Leu Cys Gly Ala Val Leu Ser Arg
            195                 200                 205

Ile Asp Ala Gly Gln Glu Gln Leu Gly Arg Arg Ile His Tyr Ser Gln
210                 215                 220

Asn Asp Leu Val Glu Tyr Ser Pro Val Thr Glu Lys His Leu Thr Asp
225                 230                 235                 240

Gly Met Thr Val Arg Glu Leu Cys Ser Ala Ala Ile Thr Met Ser Asp
                245                 250                 255

Asn Thr Ala Ala Asn Leu Leu Leu Thr Thr Ile Gly Gly Pro Lys Glu
            260                 265                 270

Leu Thr Ala Phe Leu His Asn Met Gly Asp His Val Thr Arg Leu Asp
            275                 280                 285

Arg Trp Glu Pro Glu Leu Asn Glu Ala Ile Pro Asn Asp Glu Arg Asp
290                 295                 300

Thr Thr Met Pro Val Ala Met Ala Thr Leu Arg Lys Leu Leu Thr
305                 310                 315                 320

Gly Glu Leu Leu Thr Leu Ala Ser Arg Gln Gln Leu Ile Asp Trp Met
```

```
                    325                 330                 335
Glu Ala Asp Lys Val Ala Gly Pro Leu Leu Arg Ser Ala Leu Pro Ala
            340                 345                 350
Gly Trp Phe Ile Ala Asp Lys Ser Gly Ala Gly Glu Arg Gly Ser Arg
            355                 360                 365
Gly Ile Ile Ala Ala Leu Gly Pro Asp Gly Lys Pro Ser Arg Ile Val
            370                 375                 380
Val Ile Tyr Thr Thr Gly Ser Gln Ala Thr Met Asp Glu Arg Asn Arg
385                 390                 395                 400
Gln Ile Ala Glu Ile Gly Ala Ser Leu Ile Lys His Trp
            405                 410

<210> SEQ ID NO 24
<211> LENGTH: 413
<212> TYPE: PRT
<213> ORGANISM: Artificial Sequence
<220> FEATURE:
<223> OTHER INFORMATION: chimeric alpha subunit

<400> SEQUENCE: 24

Met Asp Tyr Tyr Arg Lys Tyr Ala Ala Ile Phe Leu Val Thr Leu Ser
1               5                   10                  15
Val Phe Leu His Val Leu His Ser Ala Pro Asp Val Gln Asp Cys Pro
            20                  25                  30
Glu Cys Thr Leu Gln Glu Asn Pro Phe Phe Ser Gln Pro Gly Ala Pro
            35                  40                  45
Ile Leu Gln Cys Met Gly Cys Cys Phe Ser Arg Ala Tyr Pro Thr Pro
50                  55                  60
Leu Arg Ser Lys Lys Thr Met Leu Val Gln Lys Asp Val Thr Ser Glu
65                  70                  75                  80
Ser Thr Cys Cys Val Ala Lys Ser Tyr Asn Arg Val Thr Val Met Gly
                85                  90                  95
Gly Phe Lys Val Glu Asn His Thr Ala Cys His Cys Ser Cys Cys Tyr
            100                 105                 110
Tyr His Lys Ser Asp Asp Pro Arg Phe Gln Asp Ser Ser Ser Ser Lys
            115                 120                 125
Ala Pro Pro Pro Ser Leu Pro Ser Pro Ser Arg Leu Gly Pro Ser Asp
            130                 135                 140
Thr Pro Ile Leu Pro Gln His Pro Glu Thr Leu Val Lys Val Lys Asp
145                 150                 155                 160
Ala Glu Asp Gln Leu Gly Ala Arg Val Gly Tyr Ile Glu Leu Asp Leu
                165                 170                 175
Asn Ser Gly Lys Ile Leu Glu Ser Phe Arg Pro Glu Glu Arg Phe Pro
            180                 185                 190
Met Met Ser Thr Phe Lys Val Leu Leu Cys Gly Ala Val Leu Ser Arg
            195                 200                 205
Ile Asp Ala Gly Gln Glu Gln Leu Gly Arg Arg Ile His Tyr Ser Gln
            210                 215                 220
Asn Asp Leu Val Glu Tyr Ser Pro Val Thr Glu Lys His Leu Thr Asp
225                 230                 235                 240
Gly Met Thr Val Arg Glu Leu Cys Ser Ala Ala Ile Thr Met Ser Asp
                245                 250                 255
Asn Thr Ala Ala Asn Leu Leu Leu Thr Thr Ile Gly Gly Pro Lys Glu
            260                 265                 270
Leu Thr Ala Phe Leu His Asn Met Gly Asp His Val Thr Arg Leu Asp
            275                 280                 285
```

```
Arg Trp Glu Pro Glu Leu Asn Glu Ala Ile Pro Asn Asp Glu Arg Asp
        290                 295                 300

Thr Thr Met Pro Val Ala Met Ala Thr Thr Leu Arg Lys Leu Leu Thr
305                 310                 315                 320

Gly Glu Leu Leu Thr Leu Ala Ser Arg Gln Gln Leu Ile Asp Trp Met
                325                 330                 335

Glu Ala Asp Lys Val Ala Gly Pro Leu Leu Arg Ser Ala Leu Pro Ala
            340                 345                 350

Gly Trp Phe Ile Ala Asp Lys Ser Gly Ala Gly Glu Arg Gly Ser Arg
        355                 360                 365

Gly Ile Ile Ala Ala Leu Gly Pro Asp Gly Lys Pro Ser Arg Ile Val
    370                 375                 380

Val Ile Tyr Thr Thr Gly Ser Gln Ala Thr Met Asp Glu Arg Asn Arg
385                 390                 395                 400

Gln Ile Ala Glu Ile Gly Ala Ser Leu Ile Lys His Trp
            405                 410

<210> SEQ ID NO 25
<211> LENGTH: 122
<212> TYPE: PRT
<213> ORGANISM: Artificial Sequence
<220> FEATURE:
<223> OTHER INFORMATION: mutant beta subunit

<400> SEQUENCE: 25

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asp Ala Thr Leu Ala Val Glu Lys Glu Gly Cys Pro Val Ala Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Cys
        115                 120

<210> SEQ ID NO 26
<211> LENGTH: 108
<212> TYPE: PRT
<213> ORGANISM: Artificial Sequence
<220> FEATURE:
<223> OTHER INFORMATION: mutant alpha subunit

<400> SEQUENCE: 26

Met Glu Met Phe Gln Gly Leu Leu Leu Leu Leu Leu Ser Met Gly
1               5                   10                  15

Gly Thr Trp Ala Ser Asp Cys Pro Glu Cys Thr Leu Gln Glu Asn Pro
            20                  25                  30

Phe Phe Ser Gln Pro Gly Ala Pro Ile Leu Gln Cys Met Gly Cys Cys
        35                  40                  45

Phe Ser Arg Ala Tyr Pro Thr Pro Leu Arg Ser Lys Lys Thr Met Leu
    50                  55                  60
```

```
Val Gln Lys Asp Val Thr Ser Glu Ser Thr Cys Cys Val Ala Lys Ser
 65                  70                  75                  80

Tyr Asn Arg Val Thr Val Met Gly Gly Phe Lys Val Glu Asn His Thr
                 85                  90                  95

Ala Cys His Cys Ser Cys Cys Tyr His Lys Ser
                100                 105
```

<210> SEQ ID NO 27
<211> LENGTH: 116
<212> TYPE: PRT
<213> ORGANISM: Artificial Sequence
<220> FEATURE:
<223> OTHER INFORMATION: mutant alpha subunit

<400> SEQUENCE: 27

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asp Val Thr Ser Cys
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
        115
```

<210> SEQ ID NO 28
<211> LENGTH: 116
<212> TYPE: PRT
<213> ORGANISM: Homo sapiens

<400> SEQUENCE: 28

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Lys Thr Met Leu Val Gln Lys Asp Val Cys Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
                100                 105                 110

Tyr His Lys Ser
        115
```

<210> SEQ ID NO 29
<211> LENGTH: 116
<212> TYPE: PRT

<213> ORGANISM: Homo sapiens

<400> SEQUENCE: 29

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Cys Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

<210> SEQ ID NO 30
<211> LENGTH: 118
<212> TYPE: PRT
<213> ORGANISM: Artificial Sequence
<220> FEATURE:
<223> OTHER INFORMATION: mutant beta subunit

<400> SEQUENCE: 30

Met Glu Met Phe Gln Gly Leu Leu Leu Leu Leu Leu Ser Met Gly
1               5                   10                  15

Gly Thr Trp Ala Ser Arg Pro Cys Cys Arg Pro Ile Asn Ala Thr Leu
            20                  25                  30

Ala Val Glu Lys Glu Gly Cys Pro Val Ala Ile Thr Val Asn Thr Thr
        35                  40                  45

Ile Cys Ala Gly Tyr Cys Pro Thr Met Thr Arg Val Leu Gln Gly Val
    50                  55                  60

Leu Pro Ala Leu Pro Gln Val Val Cys Asn Tyr Arg Asp Val Arg Phe
65                  70                  75                  80

Glu Ser Ile Arg Leu Pro Gly Cys Pro Arg Gly Val Asn Pro Val Val
                85                  90                  95

Ser Tyr Ala Val Ala Leu Ser Cys Gln Cys Ala Leu Cys Arg Arg Ser
            100                 105                 110

Thr Thr Asp Cys Gly Cys
        115

<210> SEQ ID NO 31
<211> LENGTH: 119
<212> TYPE: PRT
<213> ORGANISM: Artificial Sequence
<220> FEATURE:
<223> OTHER INFORMATION: mutant beta subunit

<400> SEQUENCE: 31

Met Glu Met Phe Gln Gly Leu Leu Leu Leu Leu Leu Ser Met Gly
1               5                   10                  15

Gly Thr Trp Ala Ser Cys Arg Pro Arg Cys Arg Pro Ile Asn Ala Thr
            20                  25                  30

Leu Ala Val Glu Lys Glu Gly Cys Pro Val Ala Ile Thr Val Asn Thr
        35                  40                  45

```
Thr Ile Cys Ala Gly Tyr Cys Pro Thr Met Thr Arg Val Leu Gln Gly
    50                  55                  60

Val Leu Pro Ala Leu Pro Gln Val Val Cys Asn Tyr Arg Asp Val Arg
65                  70                  75                  80

Phe Glu Ser Ile Arg Leu Pro Gly Cys Pro Arg Gly Val Asn Pro Val
                85                  90                  95

Val Ser Tyr Ala Val Ala Leu Ser Cys Gln Cys Ala Leu Cys Arg Arg
            100                 105                 110

Ser Thr Thr Asp Cys Gly Cys
        115

<210> SEQ ID NO 32
<211> LENGTH: 122
<212> TYPE: PRT
<213> ORGANISM: Artificial Sequence
<220> FEATURE:
<223> OTHER INFORMATION: mutant beta subunit

<400> SEQUENCE: 32

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Ala Ile Thr
            35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Asp Ser Asp Ser Thr Asp Cys Gly Cys
        115                 120

<210> SEQ ID NO 33
<211> LENGTH: 130
<212> TYPE: PRT
<213> ORGANISM: Artificial Sequence
<220> FEATURE:
<223> OTHER INFORMATION: mutant beta subunit

<400> SEQUENCE: 33

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asp Ala Thr Leu Ala Val Glu Lys Glu Gly Cys Pro Val Cys Ile Thr
            35                  40                  45

Val Asn Thr Thr Cys Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110
```

-continued

Cys Arg Arg Ser Thr Thr Asp Cys Thr Val Arg Gly Leu Gly Pro Ser
            115                 120                 125

Tyr Cys
    130

<210> SEQ ID NO 34
<211> LENGTH: 252
<212> TYPE: PRT
<213> ORGANISM: Artificial Sequence
<220> FEATURE:
<223> OTHER INFORMATION: fused mutant alpha/beta subunit

<400> SEQUENCE: 34

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser Asp Glu Pro Arg Phe Gln Asp Ser Ser Ser Ser Lys
        115                 120                 125

Ala Pro Pro Pro Ser Leu Pro Ser Pro Ser Arg Leu Pro Gly Pro Ser
    130                 135                 140

Asp Thr Pro Ile Leu Pro Gln Arg Arg Phe Lys Arg Pro Arg Cys Arg
145                 150                 155                 160

Pro Ile Asn Ala Thr Leu Ala Val Glu Lys Glu Gly Cys Pro Val Ala
                165                 170                 175

Ile Thr Val Asn Thr Thr Ile Cys Ala Gly Tyr Cys Pro Thr Met Thr
            180                 185                 190

Arg Val Leu Gln Gly Val Leu Pro Ala Leu Pro Gln Val Val Cys Asn
        195                 200                 205

Tyr Arg Asp Val Arg Phe Glu Ser Ile Arg Leu Pro Gly Cys Pro Arg
    210                 215                 220

Gly Val Asn Pro Val Val Ser Tyr Ala Val Ala Leu Ser Cys Gln Cys
225                 230                 235                 240

Ala Leu Cys Arg Arg Ser Thr Thr Asp Cys Gly Cys
                245                 250

<210> SEQ ID NO 35
<211> LENGTH: 122
<212> TYPE: PRT
<213> ORGANISM: Artificial Sequence
<220> FEATURE:
<223> OTHER INFORMATION: mutant beta subunit

<400> SEQUENCE: 35

Met Glu Met Phe Gln Gly Leu Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Cys Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Cys
            115                 120

<210> SEQ ID NO 36
<211> LENGTH: 122
<212> TYPE: PRT
<213> ORGANISM: Artificial Sequence
<220> FEATURE:
<223> OTHER INFORMATION: mutant beta subunit

<400> SEQUENCE: 36

Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
                20                  25                  30

Asn Ala Thr Leu Cys Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Cys
            115                 120

<210> SEQ ID NO 37
<211> LENGTH: 130
<212> TYPE: PRT
<213> ORGANISM: Artificial Sequence
<220> FEATURE:
<223> OTHER INFORMATION: mutant beta subunit

<400> SEQUENCE: 37

Met Glu Met Phe Gln Gly Leu Leu Leu Leu Leu Leu Ser Met Gly
 1               5                  10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

-continued

Asn Pro Val Val Ser Tyr Ala Val Ala Leu Ser Cys Gln Cys Ala Leu
            100                 105                 110

Cys Asp Ser Asp Ser Thr Asp Cys Gly Cys Arg Gly Leu Gly Pro Ser
            115                 120                 125

Tyr Cys
    130

<210> SEQ ID NO 38
<211> LENGTH: 250
<212> TYPE: PRT
<213> ORGANISM: Artificial Sequence
<220> FEATURE:
<223> OTHER INFORMATION: mutant alpha/beta subunit

<400> SEQUENCE: 38

Met Asp Tyr Tyr Arg Lys Tyr Ala Ala Ile Phe Leu Val Thr Leu Ser
1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser Asp Glu Pro Arg Phe Gln Asp Ser Ser Ser Ser Lys
            115                 120                 125

Ala Pro Pro Pro Ser Leu Pro Ser Pro Ser Arg Leu Pro Gly Pro Ser
        130                 135                 140

Asp Thr Pro Ile Leu Pro Ser Lys Glu Pro Leu Arg Pro Arg Cys Arg
145                 150                 155                 160

Pro Ile Asn Ala Thr Leu Ala Val Glu Lys Glu Gly Cys Pro Val Ala
                165                 170                 175

Ile Thr Val Asn Thr Thr Ile Cys Ala Gly Tyr Cys Pro Thr Met Thr
            180                 185                 190

Arg Val Leu Gln Gly Val Leu Pro Ala Leu Pro Gln Val Val Cys Asn
        195                 200                 205

Tyr Arg Asp Val Arg Phe Glu Ser Ile Arg Leu Pro Gly Cys Pro Val
    210                 215                 220

Asn Pro Val Val Ser Tyr Ala Val Ala Leu Ser Cys Gln Cys Ala Leu
225                 230                 235                 240

Cys Arg Arg Ser Thr Thr Asp Cys Gly Cys
                245                 250

<210> SEQ ID NO 39
<211> LENGTH: 116
<212> TYPE: PRT
<213> ORGANISM: Artificial Sequence
<220> FEATURE:
<223> OTHER INFORMATION: mutant alpha subunit

<400> SEQUENCE: 39

Met Asp Tyr Tyr Arg Lys Tyr Ala Ala Ile Phe Leu Val Thr Leu Ser
1               5                  10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Thr Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser
        115

<210> SEQ ID NO 40
<211> LENGTH: 116
<212> TYPE: PRT
<213> ORGANISM: Homo sapiens

<400> SEQUENCE: 40

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Ala Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser
        115

<210> SEQ ID NO 41
<211> LENGTH: 116
<212> TYPE: PRT
<213> ORGANISM: Homo sapiens

<400> SEQUENCE: 41

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

```
Gly Phe Lys Val Glu Asn His Thr Ala Cys His Cys Ser Cys Cys Asp
                100                 105                 110
Tyr His Lys Ser
        115

<210> SEQ ID NO 42
<211> LENGTH: 252
<212> TYPE: PRT
<213> ORGANISM: Artificial Sequence
<220> FEATURE:
<223> OTHER INFORMATION: mutant alpha/beta subunit

<400> SEQUENCE: 42

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
                100                 105                 110

Tyr His Lys Ser Asp Glu Pro Arg Phe Gln Asp Ser Ser Ser Ser Lys
            115                 120                 125

Ala Pro Pro Pro Ser Leu Pro Ser Pro Ser Arg Leu Pro Gly Pro Ser
        130                 135                 140

Asp Thr Pro Ile Leu Pro Gln Arg Arg Phe Lys Arg Pro Arg Cys Arg
145                 150                 155                 160

Pro Ile Asn Ala Thr Leu Ala Val Glu Lys Glu Gly Cys Pro Val Ala
                165                 170                 175

Ile Thr Val Asn Thr Thr Ile Cys Ala Gly Tyr Cys Pro Thr Met Thr
            180                 185                 190

Arg Val Leu Gln Gly Val Leu Pro Ala Leu Pro Gln Val Val Cys Asn
        195                 200                 205

Tyr Arg Asp Val Arg Phe Glu Ser Ile Arg Leu Pro Gly Cys Pro Arg
    210                 215                 220

Gly Val Asn Pro Val Val Ser Tyr Ala Val Ala Leu Ser Cys Gln Cys
225                 230                 235                 240

Ala Leu Cys Asp Ser Asp Ser Thr Asp Cys Gly Cys
                245                 250

<210> SEQ ID NO 43
<211> LENGTH: 252
<212> TYPE: PRT
<213> ORGANISM: Artificial Sequence
<220> FEATURE:
<223> OTHER INFORMATION: mutant alpha/beta subunit

<400> SEQUENCE: 43

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30
```

-continued

```
Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Thr Thr Met Leu Val Gln Lys Asp Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Cys Cys Tyr
                100                 105                 110

Tyr His Lys Ser Asp Glu Pro Arg Phe Gln Asp Ser Ser Ser Ser Lys
                115                 120                 125

Ala Pro Pro Pro Ser Leu Pro Ser Pro Ser Arg Leu Pro Gly Pro Ser
130                 135                 140

Asp Thr Pro Ile Leu Pro Gln Arg Arg Phe Lys Arg Pro Arg Cys Arg
145                 150                 155                 160

Pro Ile Asn Ala Thr Leu Ala Val Glu Lys Glu Gly Cys Pro Val Ala
                165                 170                 175

Ile Thr Val Asn Thr Thr Ile Cys Ala Gly Tyr Cys Pro Thr Met Thr
                180                 185                 190

Arg Val Leu Gln Gly Val Leu Pro Ala Leu Pro Gln Val Val Cys Asn
                195                 200                 205

Tyr Arg Asp Val Arg Phe Glu Ser Ile Arg Leu Pro Gly Cys Pro Arg
210                 215                 220

Gly Val Asn Pro Val Val Ser Tyr Ala Val Ala Leu Ser Cys Gln Cys
225                 230                 235                 240

Ala Leu Cys Arg Arg Ser Thr Thr Asp Cys Gly Cys
                245                 250
```

<210> SEQ ID NO 44
<211> LENGTH: 252
<212> TYPE: PRT
<213> ORGANISM: Artificial Sequence
<220> FEATURE:
<223> OTHER INFORMATION: mutant alpha/beta subunit

<400> SEQUENCE: 44

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
                 20                  25                  30

Glu Cys Thr Leu Gln Glu Asn Pro Phe Phe Ser Gln Pro Gly Ala Pro
             35                  40                  45

Ile Leu Gln Cys Met Gly Cys Cys Phe Ser Arg Ala Tyr Pro Thr Pro
 50                  55                  60

Leu Arg Ser Lys Ala Thr Met Leu Val Gln Lys Asp Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Cys Cys Tyr
                100                 105                 110

Tyr His Lys Ser Asp Glu Pro Arg Phe Gln Asp Ser Ser Ser Ser Lys
                115                 120                 125

Ala Pro Pro Pro Ser Leu Pro Ser Pro Ser Arg Leu Pro Gly Pro Ser
130                 135                 140

Asp Thr Pro Ile Leu Pro Gln Arg Arg Phe Lys Arg Pro Arg Cys Arg
```

```
                145                 150                 155                 160
Pro Ile Asn Ala Thr Leu Ala Val Glu Lys Glu Gly Cys Pro Val Ala
                    165                 170                 175

Ile Thr Val Asn Thr Thr Ile Cys Ala Gly Tyr Cys Pro Thr Met Thr
                    180                 185                 190

Arg Val Leu Gln Gly Val Leu Pro Ala Leu Pro Gln Val Val Cys Asn
                    195                 200                 205

Tyr Arg Asp Val Arg Phe Glu Ser Ile Arg Leu Pro Gly Cys Pro Arg
                    210                 215                 220

Gly Val Asn Pro Val Val Ser Tyr Ala Val Ala Leu Ser Cys Gln Cys
225                 230                 235                 240

Ala Leu Cys Arg Arg Ser Thr Thr Asp Cys Gly Cys
                    245                 250

<210> SEQ ID NO 45
<211> LENGTH: 250
<212> TYPE: PRT
<213> ORGANISM: Artificial Sequence
<220> FEATURE:
<223> OTHER INFORMATION: mutant alpha/beta subunit

<400> SEQUENCE: 45

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
                35                  40                  45

Ile Leu Gln Cys Met Gly Cys Cys Phe Ser Arg Ala Tyr Pro Thr Pro
50                  55                  60

Leu Arg Ser Lys Lys Thr Met Gln Lys Asp Val Thr Ser Glu Ser Thr
65                  70                  75                  80

Cys Cys Val Ala Lys Ser Tyr Asn Arg Val Thr Val Met Gly Gly Phe
                85                  90                  95

Lys Val Glu Asn His Thr Ala Cys His Cys Ser Cys Tyr Tyr His
                100                 105                 110

Lys Ser Asp Glu Pro Arg Phe Gln Asp Ser Ser Ser Ser Lys Ala Pro
                115                 120                 125

Pro Pro Ser Leu Pro Ser Pro Ser Arg Leu Pro Gly Pro Ser Asp Thr
                130                 135                 140

Pro Ile Leu Pro Ser Lys Glu Pro Leu Arg Pro Arg Cys Arg Pro Ile
145                 150                 155                 160

Asn Ala Thr Leu Ala Val Glu Lys Glu Gly Cys Pro Val Ala Ile Thr
                    165                 170                 175

Val Asn Thr Thr Ile Cys Ala Gly Tyr Cys Pro Thr Met Thr Arg Val
                    180                 185                 190

Leu Gln Gly Val Leu Pro Ala Leu Pro Gln Val Val Cys Asn Tyr Arg
                    195                 200                 205

Asp Val Arg Phe Glu Ser Ile Arg Leu Pro Gly Cys Pro Arg Gly Val
                    210                 215                 220

Asn Pro Val Val Ser Tyr Ala Val Ala Leu Ser Cys Gln Cys Ala Leu
225                 230                 235                 240

Cys Arg Arg Ser Thr Thr Asp Cys Gly Cys
                    245                 250

<210> SEQ ID NO 46
```

```
<211> LENGTH: 126
<212> TYPE: PRT
<213> ORGANISM: Artificial Sequence
<220> FEATURE:
<223> OTHER INFORMATION: mutant beta subunit

<400> SEQUENCE: 46

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp Cys
        115                 120                 125

<210> SEQ ID NO 47
<211> LENGTH: 128
<212> TYPE: PRT
<213> ORGANISM: Artificial Sequence
<220> FEATURE:
<223> OTHER INFORMATION: mutant beta subunit

<400> SEQUENCE: 47

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Cys
        115                 120                 125

<210> SEQ ID NO 48
<211> LENGTH: 123
<212> TYPE: PRT
<213> ORGANISM: Artificial Sequence
<220> FEATURE:
<223> OTHER INFORMATION: mutant beta subunit

<400> SEQUENCE: 48

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
```

```
                       20                   25                  30
Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
65                   70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Cys
                115                 120

<210> SEQ ID NO 49
<211> LENGTH: 258
<212> TYPE: PRT
<213> ORGANISM: Artificial Sequence
<220> FEATURE:
<223> OTHER INFORMATION: mutant beta/alpha subunit

<400> SEQUENCE: 49

Met Glu Met Phe Gln Gly Leu Leu Leu Leu Leu Leu Leu Ser Met Gly
1               5                   10                  15

Gly Thr Trp Ala Ser Gly Thr Glu Cys Gly Tyr Gly Arg Cys Arg Pro
                20                  25                  30

Ile Asn Ala Thr Leu Ala Val Glu Lys Glu Gly Cys Pro Val Cys Ile
                35                  40                  45

Thr Val Asn Thr Thr Ile Cys Ala Gly Tyr Cys Pro Thr Met Thr Arg
 50                  55                  60

Val Leu Gln Gly Val Leu Pro Ala Leu Pro Gln Val Val Cys Asn Tyr
65                   70                  75                  80

Arg Asp Val Arg Phe Glu Ser Ile Arg Leu Pro Gly Cys Pro Arg Gly
                85                  90                  95

Val Asn Pro Val Val Ser Tyr Ala Val Ala Leu Ser Cys Gln Cys Ser
                100                 105                 110

Leu Cys Asn Met Ser Thr Ser Asp Cys Thr Ile Glu Ser Leu Gln Pro
                115                 120                 125

Asp Phe Cys Ile Thr Pro Arg Phe Gln Asp Ser Ser Ser Ser Lys Ala
                130                 135                 140

Pro Pro Pro Ser Leu Pro Ser Pro Ser Arg Leu Pro Gly Pro Ser Asp
145                 150                 155                 160

Thr Pro Ile Leu Pro Gln Ala Pro Asp Val Gln Asp Cys Pro Glu Cys
                165                 170                 175

Thr Leu Gln Glu Asn Pro Phe Phe Ser Gln Pro Gly Ala Pro Ile Leu
                180                 185                 190

Gln Cys Met Gly Cys Cys Phe Ser Arg Ala Tyr Pro Thr Pro Leu Arg
                195                 200                 205

Ser Lys Lys Thr Met Leu Val Gln Lys Asn Val Thr Ser Glu Ser Thr
                210                 215                 220

Cys Cys Val Ala Lys Ser Tyr Asn Arg Val Thr Val Met Gly Gly Phe
225                 230                 235                 240

Lys Val Glu Asn His Thr Ala Cys His Cys Ser Thr Cys Tyr Tyr His
                245                 250                 255

Lys Ser
```

-continued

```
<210> SEQ ID NO 50
<211> LENGTH: 957
<212> TYPE: PRT
<213> ORGANISM: Artificial Sequence
<220> FEATURE:
<223> OTHER INFORMATION: chimera of salmon FSH receptor, the rat LH
      receptor, and Neo

<400> SEQUENCE: 50

Met Met Lys Met Lys Lys Ile Met Lys Met Leu Leu Cys Val Leu Gly
1               5                   10                  15

Cys Val Ser Met Ser Gln Ala Glu Val Ala Met Val Asn Ser Gly Thr
            20                  25                  30

Thr Phe Thr Tyr Leu Cys Met Gly Asn Thr Ile Thr His Met Pro Thr
        35                  40                  45

His Ile Pro Lys Asn Thr Thr Asp Leu Glu Phe Lys Gln Thr His Ile
    50                  55                  60

Arg Val Phe Pro Gln Glu Ala Phe Thr Asn Leu Gln Gln Leu Thr Ala
65                  70                  75                  80

Ile Val Leu Thr Glu Asn Gly Met Leu Glu Ser Ile Gly Ala Phe Ala
                85                  90                  95

Phe Ala Asn Leu Pro Arg Leu Thr Glu Ile Thr Ile Thr Lys Ser Lys
            100                 105                 110

His Leu Val Ile Ile His His Gln Ala Phe Ile Gly Leu Pro Lys Leu
        115                 120                 125

Ser His Leu Thr Ile Cys Asn Thr Gly Leu Arg Val Leu Pro Asn Phe
    130                 135                 140

Ser Arg Ile His Ser Ala Ala Met Thr Phe Leu Leu Asp Leu Gln Asp
145                 150                 155                 160

Asn Val His Ile Val Ile Pro Ser Asn Ala Phe Leu Gly Leu Thr
                165                 170                 175

Thr Asn Thr Ile Asp Glu Leu Arg Leu Thr Lys Asn Gly Ile Ser Glu
            180                 185                 190

Val Glu Ser His Ala Phe Asn Gly Thr Lys Ile His Lys Leu Tyr Leu
        195                 200                 205

Met Gly Asn Leu Gln Leu Ser His Met His Asn Asn Ser Phe Lys Gly
    210                 215                 220

Ala Glu Gly Pro Gly Phe Leu Asp Ile Ser Arg Thr Ala Leu Ser Ser
225                 230                 235                 240

Leu Pro Glu Ser Val Leu Gly Glu Val Glu His Leu Ser Ala Val Ser
                245                 250                 255

Val Phe Ser Leu Arg Thr Leu Pro Pro Leu Ser Leu Phe Thr Lys Leu
            260                 265                 270

Arg Gln Ala Asn Leu Thr Tyr Pro Ser His Cys Cys Ala Phe His Lys
        275                 280                 285

His Gln Arg Asn Arg Thr Phe Arg Met Thr Ser Ala Cys Phe Lys Pro
    290                 295                 300

Gly Ala Gln Asn Leu His Phe Phe Met Asp Phe Cys Leu Asn Trp
305                 310                 315                 320

Thr Ser Val Ala Cys Ser Pro Ala Pro Asp Ala Phe Asn Pro Cys Glu
                325                 330                 335

Asp Ile Met Gly Ser Ala Pro Leu Arg Val Leu Ile Trp Leu Ile Asn
            340                 345                 350

Ile Leu Ala Ile Phe Gly Asn Leu Thr Val Leu Phe Val Leu Leu Thr
        355                 360                 365
```

```
Ser Arg Tyr Lys Leu Thr Val Pro Arg Phe Leu Met Cys Asn Leu Ser
    370                 375                 380

Phe Ala Asp Phe Cys Met Gly Leu Tyr Leu Leu Ile Ala Ser Val
385                 390                 395                 400

Asp Ser Gln Thr Lys Gly Gln Tyr Tyr Asn His Ala Ile Asp Trp Gln
                405                 410                 415

Thr Gly Ser Gly Cys Gly Ala Ala Gly Phe Phe Thr Val Phe Ala Ser
                420                 425                 430

Glu Leu Ser Val Tyr Thr Leu Thr Val Ile Thr Leu Glu Arg Trp His
            435                 440                 445

Thr Ile Thr Tyr Ala Val Gln Leu Asp Gln Lys Leu Arg Leu Arg His
        450                 455                 460

Ala Ile Pro Ile Met Leu Gly Gly Trp Leu Phe Ser Thr Leu Ile Ala
465                 470                 475                 480

Thr Met Pro Leu Val Gly Ile Ser Asn Tyr Met Lys Val Ser Ile Cys
                485                 490                 495

Leu Pro Met Asp Val Glu Ser Thr Leu Ser Gln Val Tyr Ile Leu Ser
            500                 505                 510

Ile Leu Ile Leu Asn Val Ala Phe Val Ile Cys Ala Cys Tyr
        515                 520                 525

Ile Arg Ile Tyr Phe Ala Val Gln Asn Pro Glu Leu Thr Ala Pro Asn
    530                 535                 540

Lys Asp Thr Lys Ile Ala Lys Lys Met Ala Ile Leu Ile Phe Thr Asp
545                 550                 555                 560

Phe Thr Cys Met Ala Pro Ile Ser Phe Phe Ala Ile Ser Ala Ala Phe
                565                 570                 575

Lys Val Pro Leu Ile Thr Val Thr Asn Ser Lys Ile Leu Leu Val Leu
            580                 585                 590

Phe Tyr Pro Val Asn Ser Cys Ala Asn Pro Phe Leu Tyr Ala Ile Phe
        595                 600                 605

Thr Lys Ala Phe Gln Arg Asp Phe Leu Leu Leu Leu Ser Arg Phe Gly
    610                 615                 620

Cys Cys Lys Arg Arg Ala Glu Leu Tyr Arg Arg Lys Glu Phe Ser Ala
625                 630                 635                 640

Tyr Thr Ser Asn Cys Lys Asn Gly Phe Pro Gly Ala Ser Lys Pro Ser
                645                 650                 655

Gln Ala Thr Leu Lys Leu Ser Thr Val His Cys Gln Gln Pro Ile Pro
            660                 665                 670

Pro Arg Ala Leu Thr His Gly Gln Phe Cys Arg Tyr Pro Ala Gln Trp
        675                 680                 685

Arg Pro Leu Glu Phe Met Ile Glu Gln Asp Gly Leu His Ala Gly Ser
    690                 695                 700

Pro Ala Ala Trp Val Glu Arg Leu Phe Gly Tyr Asp Trp Ala Gln Gln
705                 710                 715                 720

Thr Ile Gly Cys Ser Asp Ala Ala Val Phe Arg Leu Ser Ala Gln Gly
                725                 730                 735

Arg Pro Val Leu Phe Val Lys Thr Asp Leu Ser Gly Ala Leu Asn Glu
            740                 745                 750

Leu Gln Asp Glu Ala Ala Arg Leu Ser Trp Leu Ala Thr Thr Gly Val
        755                 760                 765

Pro Cys Ala Ala Val Leu Asp Val Val Thr Glu Ala Gly Arg Asp Trp
    770                 775                 780

Leu Leu Leu Gly Glu Val Pro Gly Gln Asp Leu Leu Ser Ser His Leu
785                 790                 795                 800
```

```
Ala Pro Ala Glu Lys Val Ser Ile Met Ala Asp Ala Met Arg Arg Leu
            805                 810                 815

His Thr Leu Asp Pro Ala Thr Cys Pro Phe Asp His Gln Ala Lys His
        820                 825                 830

Arg Ile Glu Arg Ala Arg Thr Arg Met Glu Ala Gly Leu Val Asp Gln
835                 840                 845

Asp Asp Leu Asp Glu Glu His Gln Gly Leu Ala Pro Ala Glu Leu Phe
        850                 855                 860

Ala Arg Leu Lys Ala Arg Met Pro Asp Gly Glu Asp Leu Val Val Thr
865                 870                 875                 880

His Gly Asp Ala Cys Leu Pro Asn Ile Met Val Glu Asn Gly Arg Phe
                885                 890                 895

Ser Gly Phe Ile Asp Cys Gly Arg Leu Gly Val Ala Asp Arg Tyr Gln
            900                 905                 910

Asp Ile Ala Leu Ala Thr Arg Asp Ile Ala Glu Glu Leu Gly Gly Glu
        915                 920                 925

Trp Ala Asp Arg Phe Leu Val Leu Tyr Gly Ile Ala Ala Pro Asp Ser
        930                 935                 940

Gln Arg Ile Ala Phe Tyr Arg Leu Leu Gly Glu Phe Phe
945                 950                 955
```

<210> SEQ ID NO 51
<211> LENGTH: 172
<212> TYPE: PRT
<213> ORGANISM: Artificial Sequence
<220> FEATURE:
<223> OTHER INFORMATION: mutant beta subunit

<400> SEQUENCE: 51

```
Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
            20                  25                  30

Ser Arg Tyr Gly Cys Arg Leu Asn Asn Met Thr Ile Thr Val Glu Arg
        35                  40                  45

Glu Asp Cys His Gly Ser Ile Thr Ile Thr Cys Ala Gly Leu Cys
    50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Cys Ile
        115                 120                 125

Ser Met Ala Thr Pro Gly Ser Ile Val Asn Pro Leu Glu Phe Gln Asp
    130                 135                 140

Ser Ser Ser Ser Lys Ala Pro Pro Ser Leu Pro Ser Pro Ser Arg
145                 150                 155                 160

Leu Pro Gly Pro Ser Asp Thr Pro Ile Leu Pro Gln
                165                 170
```

<210> SEQ ID NO 52
<211> LENGTH: 257
<212> TYPE: PRT
<213> ORGANISM: Artificial Sequence
<220> FEATURE:

<223> OTHER INFORMATION: mutant beta/alpha subunit

<400> SEQUENCE: 52

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
            50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
                100                 105                 110

Cys Arg Arg Ser Thr Thr Asp Cys Thr Ile Glu Ser Leu Gln Pro Asp
                115                 120                 125

Phe Cys Ile Thr Pro Arg Phe Gln Asp Ser Ser Ser Ser Lys Ala Pro
            130                 135                 140

Pro Pro Ser Leu Pro Ser Pro Ser Arg Leu Pro Gly Pro Ser Asp Thr
145                 150                 155                 160

Pro Ile Leu Pro Gln Ala Pro Asp Val Gln Asp Cys Pro Glu Cys Thr
                165                 170                 175

Leu Gln Glu Asn Pro Phe Phe Ser Gln Pro Gly Ala Pro Ile Leu Gln
                180                 185                 190

Cys Met Gly Cys Cys Phe Ser Arg Ala Tyr Pro Thr Pro Leu Arg Ser
                195                 200                 205

Lys Lys Thr Met Leu Val Gln Lys Asn Val Thr Ser Glu Ser Thr Cys
            210                 215                 220

Cys Val Ala Lys Ser Tyr Asn Arg Val Thr Val Met Gly Gly Phe Lys
225                 230                 235                 240

Val Glu Asn His Thr Ala Cys His Cys Ser Thr Cys Tyr Tyr His Lys
                245                 250                 255

Ser
```

<210> SEQ ID NO 53
<211> LENGTH: 139
<212> TYPE: PRT
<213> ORGANISM: Artificial Sequence
<220> FEATURE:
<223> OTHER INFORMATION: mutant beta subunit

<400> SEQUENCE: 53

```
Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
                20                  25                  30

Cys Arg Tyr Gly Cys Arg Leu Asn Asn Met Thr Ile Thr Val Glu Arg
            35                  40                  45

Glu Asp Cys His Gly Ser Ile Thr Ile Thr Cys Ala Gly Leu Cys
            50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
```

```
                    85                  90                  95
Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Cys Ile
            115                 120                 125

Ser Met Ala Thr Pro Gly Ser Phe Glu Gln Thr
            130                 135

<210> SEQ ID NO 54
<211> LENGTH: 116
<212> TYPE: PRT
<213> ORGANISM: Artificial Sequence
<220> FEATURE:
<223> OTHER INFORMATION: mutant alpha subunit

<400> SEQUENCE: 54

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Cys Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser
            115

<210> SEQ ID NO 55
<211> LENGTH: 137
<212> TYPE: PRT
<213> ORGANISM: Artificial Sequence
<220> FEATURE:
<223> OTHER INFORMATION: mutant  beta subunit contruct used to express
      salmon

<400> SEQUENCE: 55

Met Tyr Cys Thr His Leu Lys Thr Leu Gln Leu Val Met Ala Thr
1               5                   10                  15

Leu Trp Val Thr Pro Val Arg Ala Gly Thr Asp Cys Arg Tyr Gly Cys
            20                  25                  30

Arg Leu Asn Asn Met Thr Ile Thr Val Glu Arg Glu Asp Cys His Gly
        35                  40                  45

Ser Ile Thr Ile Thr Thr Cys Ala Gly Leu Cys Glu Thr Thr Asp Leu
    50                  55                  60

Asn Tyr Gln Ser Thr Trp Leu Pro Arg Ser Gln Gly Val Cys Asn Phe
65                  70                  75                  80

Lys Glu Trp Ser Tyr Glu Lys Val Tyr Leu Glu Gly Cys Pro Ser Gly
                85                  90                  95

Val Asp Pro Phe Phe Ile Pro Val Ala Lys Ser Cys Asp Cys Ile Lys
            100                 105                 110

Cys Lys Thr Asp Asn Thr Asp Cys Asp Arg Ile Ser Met Ala Thr Pro
            115                 120                 125
```

```
Ser Cys Ile Val Asn Pro Leu Glu Met
    130                 135
```

```
<210> SEQ ID NO 56
<211> LENGTH: 114
<212> TYPE: PRT
<213> ORGANISM: Artificial Sequence
<220> FEATURE:
<223> OTHER INFORMATION: mutant alpha subunit construct used to express
      salmon

<400> SEQUENCE: 56
```

```
Met Cys Leu Leu Lys Ser Thr Gly Leu Ser Leu Ile Leu Ser Ala Leu
1               5                   10                  15

Leu Val Ile Gly Asp Ser Tyr Pro Asn Ser Asp Lys Thr Asn Met Gly
            20                  25                  30

Cys Glu Glu Cys Thr Leu Lys Pro Asn Thr Ile Phe Pro Asn Ile Met
        35                  40                  45

Gln Cys Thr Gly Cys Cys Phe Ser Arg Ala Tyr Pro Thr Pro Leu Arg
    50                  55                  60

Ser Lys Gln Thr Met Leu Val Pro Lys Asn Ile Thr Ser Glu Ala Thr
65                  70                  75                  80

Cys Cys Val Ala Lys Glu Gly Glu Arg Val Thr Thr Lys Asp Gly Phe
                85                  90                  95

Pro Val Thr Asn His Thr Glu Cys His Cys Ser Thr Cys Tyr Tyr His
            100                 105                 110

Lys Ser
```

```
<210> SEQ ID NO 57
<211> LENGTH: 172
<212> TYPE: PRT
<213> ORGANISM: Artificial Sequence
<220> FEATURE:
<223> OTHER INFORMATION: mutant beta subunit

<400> SEQUENCE: 57
```

```
Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Ala Ser Gly Thr Asp
            20                  25                  30

Cys Arg Tyr Gly Cys Arg Leu Asn Asn Met Thr Ile Thr Val Glu Arg
        35                  40                  45

Glu Asp Cys His Gly Ser Ile Thr Ile Thr Cys Ala Gly Leu Cys
    50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Arg Ile
        115                 120                 125

Ser Met Ala Thr Pro Ser Cys Ile Val Asn Pro Leu Glu Phe Gln Asp
    130                 135                 140

Ser Ser Ser Ser Lys Ala Pro Pro Ser Leu Pro Ser Pro Ser Arg
145                 150                 155                 160

Leu Pro Gly Pro Ser Asp Thr Pro Ile Leu Pro Gln
                165                 170
```

-continued

```
<210> SEQ ID NO 58
<211> LENGTH: 264
<212> TYPE: PRT
<213> ORGANISM: Artificial Sequence
<220> FEATURE:
<223> OTHER INFORMATION: mutant beta/alpha subunit

<400> SEQUENCE: 58

Met Glu Thr Asp Thr Leu Leu Leu Trp Val Leu Leu Trp Val Pro
1               5                   10                  15

Gly Ser Thr Gly Asp Tyr Lys Ala Lys Glu Leu Ala Ser Gly Thr Asp
                20                  25                  30

Cys Arg Tyr Gly Cys Arg Leu Asn Asn Met Thr Ile Thr Val Glu Arg
            35                  40                  45

Glu Asp Cys His Gly Ser Ile Thr Ile Thr Thr Cys Ala Gly Leu Cys
        50                  55                  60

Glu Thr Thr Asp Leu Asn Tyr Gln Ser Thr Trp Leu Pro Arg Ser Gln
65                  70                  75                  80

Gly Val Cys Asn Phe Lys Glu Trp Ser Tyr Glu Lys Val Tyr Leu Glu
                85                  90                  95

Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Arg Ile
        115                 120                 125

Ser Met Ala Thr Pro Ser Cys Ile Val Asn Pro Leu Glu Phe Gln Asp
    130                 135                 140

Ser Ser Ser Ser Lys Ala Pro Pro Ser Leu Pro Ser Pro Ser Arg
145                 150                 155                 160

Leu Pro Gly Pro Ser Asp Thr Pro Ile Leu Pro Gln Ala Pro Asp Val
                165                 170                 175

Gln Asp Cys Pro Glu Cys Thr Leu Gln Glu Asn Pro Phe Phe Ser Gln
            180                 185                 190

Pro Gly Ala Pro Ile Leu Gln Cys Met Gly Cys Cys Phe Ser Arg Ala
        195                 200                 205

Tyr Pro Thr Pro Leu Arg Ser Lys Lys Thr Met Leu Val Gln Lys Asp
    210                 215                 220

Val Thr Ser Glu Ser Thr Cys Cys Val Ala Lys Ser Tyr Asn Arg Val
225                 230                 235                 240

Thr Val Met Gly Gly Phe Lys Val Glu Asn His Thr Ala Cys His Cys
                245                 250                 255

Ser Thr Cys Tyr Tyr His Lys Ser
            260

<210> SEQ ID NO 59
<211> LENGTH: 264
<212> TYPE: PRT
<213> ORGANISM: Artificial Sequence
<220> FEATURE:
<223> OTHER INFORMATION: mutant beta/alpha subunit

<400> SEQUENCE: 59

Met Glu Thr Asp Thr Leu Leu Leu Trp Val Leu Leu Trp Val Pro
1               5                   10                  15

Gly Ser Thr Gly Asp Tyr Lys Ala Lys Glu Leu Ala Ser Gly Thr Asp
                20                  25                  30

Cys Arg Tyr Gly Cys Arg Leu Asn Asn Met Thr Ile Thr Val Glu Arg
            35                  40                  45
```

```
Glu Asp Cys His Gly Ser Ile Thr Ile Thr Thr Cys Ala Gly Leu Cys
 50                  55                  60

Glu Thr Thr Asp Leu Asn Tyr Gln Ser Thr Trp Leu Pro Arg Ser Gln
 65                  70                  75                  80

Gly Val Cys Asn Phe Lys Glu Trp Ser Tyr Glu Lys Val Tyr Leu Glu
                 85                  90                  95

Gly Cys Pro Ser Gly Val Asp Pro Phe Phe Ile Pro Val Ala Lys Ser
            100                 105                 110

Cys Asp Cys Ile Lys Cys Lys Thr Asp Asn Thr Asp Cys Asp Arg Ile
            115                 120                 125

Ser Met Ala Thr Pro Ser Cys Ile Val Asn Pro Leu Glu Phe Gln Asp
130                 135                 140

Ser Ser Ser Ser Lys Ala Pro Pro Ser Leu Pro Ser Pro Ser Arg
145                 150                 155                 160

Leu Pro Gly Pro Ser Asp Thr Pro Ile Leu Pro Gln Ala Pro Asp Val
                165                 170                 175

Gln Asp Cys Pro Glu Cys Thr Leu Gln Glu Asn Pro Phe Phe Ser Gln
            180                 185                 190

Pro Gly Ala Pro Ile Leu Gln Cys Met Gly Cys Cys Phe Ser Arg Ala
            195                 200                 205

Tyr Pro Thr Pro Leu Arg Ser Lys Lys Thr Met Leu Val Gln Lys Asn
            210                 215                 220

Val Thr Ser Glu Ser Thr Cys Cys Val Ala Lys Ser Tyr Asn Arg Val
225                 230                 235                 240

Thr Val Met Gly Gly Phe Lys Val Glu Asn His Thr Ala Cys His Cys
                245                 250                 255

Ser Thr Cys Tyr Tyr His Lys Ser
            260

<210> SEQ ID NO 60
<211> LENGTH: 208
<212> TYPE: PRT
<213> ORGANISM: Artificial Sequence
<220> FEATURE:
<223> OTHER INFORMATION: mutant beta subunit

<400> SEQUENCE: 60

Met Glu Met Phe Gln Gly Leu Leu Leu Leu Leu Leu Leu Ser Met Gly
 1               5                  10                  15

Gly Thr Trp Ala Ser Gly Arg Ile Ala Arg Leu Glu Glu Lys Val Lys
                 20                  25                  30

Thr Leu Lys Ala Gln Asn Ser Glu Leu Ala Ser Thr Ala Asn Met Leu
            35                  40                  45

Arg Glu Gln Val Ala Gln Leu Lys Gln Lys Val Met Gly Leu Arg Pro
 50                  55                  60

Ser Gly Thr Asp Cys Arg Tyr Gly Cys Arg Leu Asn Asn Met Thr Ile
 65                  70                  75                  80

Thr Val Glu Arg Glu Asp Cys His Gly Ser Ile Thr Ile Thr Thr Cys
                 85                  90                  95

Ala Gly Leu Cys Glu Thr Thr Asp Leu Asn Tyr Gln Ser Thr Trp Leu
            100                 105                 110

Pro Arg Ser Gln Gly Val Cys Asn Phe Lys Glu Trp Ser Tyr Glu Lys
            115                 120                 125

Val Tyr Leu Glu Gly Cys Pro Ser Gly Val Asp Pro Phe Phe Ile Pro
130                 135                 140

Val Ala Lys Ser Cys Asp Cys Ile Lys Cys Lys Thr Asp Asn Thr Asp
```

-continued

```
                145                 150                 155                 160
Cys Asp Arg Ile Ser Met Ala Thr Pro Ser Cys Ile Val Asn Pro Leu
                165                 170                 175

Glu Phe Gln Asp Ser Ser Ser Lys Ala Pro Pro Ser Leu Pro
            180                 185                 190

Ser Pro Ser Arg Leu Pro Gly Pro Ser Asp Thr Pro Ile Leu Pro Gln
            195                 200                 205

<210> SEQ ID NO 61
<211> LENGTH: 119
<212> TYPE: PRT
<213> ORGANISM: Artificial Sequence
<220> FEATURE:
<223> OTHER INFORMATION: mutant alpha subunit

<400> SEQUENCE: 61

Met Glu Thr Asp Thr Leu Leu Leu Trp Val Leu Leu Leu Trp Val Pro
1               5                   10                  15

Gly Ser Thr Gly Asp Tyr Lys Ala Lys Glu Leu Tyr Pro Asn Ser Asp
            20                  25                  30

Lys Thr Asn Met Gly Cys Glu Glu Cys Thr Leu Lys Pro Asn Thr Ile
        35                  40                  45

Phe Pro Asn Ile Met Gln Cys Thr Gly Cys Cys Phe Ser Arg Ala Tyr
    50                  55                  60

Pro Thr Pro Leu Arg Ser Lys Gln Thr Met Leu Val Pro Lys Asn Ile
65                  70                  75                  80

Thr Ser Glu Ala Thr Cys Cys Val Ala Lys Glu Gly Glu Arg Val Thr
                85                  90                  95

Thr Lys Asp Gly Phe Pro Val Thr Asn His Thr Glu Cys His Cys Ser
            100                 105                 110

Thr Cys Tyr Tyr His Lys Ser
        115

<210> SEQ ID NO 62
<211> LENGTH: 282
<212> TYPE: PRT
<213> ORGANISM: Artificial Sequence
<220> FEATURE:
<223> OTHER INFORMATION: mutant alpha/beta subunit

<400> SEQUENCE: 62

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser Asp Asp Pro Arg Phe Gln Asp Ser Ser Ser Ala Lys
        115                 120                 125

Ala Pro Pro Pro Ser Leu Pro Ser Pro Ser Ser Gly Thr Asp Cys Arg
```

```
                130                 135                 140
Tyr Gly Cys Arg Leu Asn Asn Met Thr Ile Thr Val Glu Arg Glu Asp
145                 150                 155                 160

Cys His Gly Ser Ile Thr Ile Thr Thr Cys Ala Gly Leu Cys Glu Thr
                165                 170                 175

Thr Asp Leu Asn Tyr Gln Ser Thr Trp Leu Pro Arg Ser Gln Gly Val
            180                 185                 190

Cys Asn Phe Lys Glu Trp Ser Tyr Glu Lys Val Tyr Leu Glu Gly Cys
        195                 200                 205

Pro Ser Gly Val Asp Pro Phe Phe Ile Pro Val Ala Lys Ser Cys Asp
    210                 215                 220

Cys Ile Lys Cys Lys Thr Asp Asn Thr Asp Cys Asp Arg Ile Ser Met
225                 230                 235                 240

Ala Thr Pro Ser Cys Ile Val Asn Pro Leu Glu Phe Gln Asp Ser Ser
                245                 250                 255

Ser Ser Lys Ala Pro Pro Ser Leu Pro Ser Pro Ser Arg Leu Pro
            260                 265                 270

Gly Pro Ser Asp Thr Pro Ile Leu Pro Gln
        275                 280
```

<210> SEQ ID NO 63
<211> LENGTH: 261
<212> TYPE: PRT
<213> ORGANISM: Artificial Sequence
<220> FEATURE:
<223> OTHER INFORMATION: mutant beta/alpha subunit

<400> SEQUENCE: 63

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln Lys Asp Glu Leu Tyr Pro Asn Ser Asp Lys Thr
                165                 170                 175

Asn Met Gly Cys Glu Glu Cys Thr Leu Lys Pro Asn Thr Ile Phe Pro
            180                 185                 190

Asn Ile Met Gln Cys Thr Gly Cys Cys Phe Ser Arg Ala Tyr Pro Thr
        195                 200                 205

Pro Leu Arg Ser Lys Gln Thr Met Leu Val Pro Lys Asn Ile Thr Ser
    210                 215                 220
```

```
Glu Ala Thr Cys Cys Val Ala Lys Glu Gly Glu Arg Val Thr Lys
225                 230                 235                 240

Asp Gly Phe Pro Val Thr Asn His Thr Glu Cys His Cys Ser Thr Cys
                245                 250                 255

Tyr Tyr His Lys Ser
            260

<210> SEQ ID NO 64
<211> LENGTH: 151
<212> TYPE: PRT
<213> ORGANISM: Artificial Sequence
<220> FEATURE:
<223> OTHER INFORMATION: mutant alpha subunit

<400> SEQUENCE: 64

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110

Tyr His Lys Ser Asp Glu Pro Arg Phe Gln Asp Ser Ser Ser Ser Lys
        115                 120                 125

Ala Pro Pro Pro Ser Leu Pro Ser Pro Ser Arg Leu Pro Gly Pro Ser
    130                 135                 140

Asp Thr Pro Ile Leu Pro Gln
145                 150

<210> SEQ ID NO 65
<211> LENGTH: 252
<212> TYPE: PRT
<213> ORGANISM: Artificial Sequence
<220> FEATURE:
<223> OTHER INFORMATION: mutant alpha/beta subunit

<400> SEQUENCE: 65

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asp Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
            100                 105                 110
```

```
Tyr His Lys Ser Asp Glu Pro Arg Phe Gln Asp Ser Ser Ser Ser Lys
            115                 120                 125

Ala Pro Pro Ser Leu Pro Ser Pro Ser Arg Leu Pro Gly Pro Ser
        130                 135                 140

Asp Thr Pro Ile Leu Pro Ser Lys Glu Pro Leu Arg Pro Arg Cys Arg
145                 150                 155                 160

Pro Ile Asn Ala Thr Leu Ala Val Glu Lys Glu Gly Cys Pro Val Ala
                165                 170                 175

Ile Thr Val Asn Thr Thr Ile Cys Ala Gly Tyr Cys Pro Thr Met Thr
                180                 185                 190

Arg Val Leu Gln Gly Val Leu Pro Ala Leu Pro Gln Val Val Cys Asn
            195                 200                 205

Tyr Arg Asp Val Arg Phe Glu Ser Ile Arg Leu Pro Gly Cys Pro Arg
        210                 215                 220

Gly Val Asn Pro Val Val Ser Tyr Ala Val Ala Leu Ser Cys Gln Cys
225                 230                 235                 240

Ala Leu Cys Arg Arg Ser Thr Thr Asp Cys Gly Cys
                245                 250

<210> SEQ ID NO 66
<211> LENGTH: 116
<212> TYPE: PRT
<213> ORGANISM: Artificial Sequence
<220> FEATURE:
<223> OTHER INFORMATION: mutant alpha subunit

<400> SEQUENCE: 66

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Cys Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Cys Cys Tyr
                100                 105                 110

Tyr His Lys Ser
        115

<210> SEQ ID NO 67
<211> LENGTH: 35
<212> TYPE: PRT
<213> ORGANISM: Artificial Sequence
<220> FEATURE:
<223> OTHER INFORMATION: linker

<400> SEQUENCE: 67

Asp Asp Pro Arg Phe Gln Asp Ser Ser Ser Ser Lys Ala Pro Pro Pro
1               5                   10                  15

Ser Leu Pro Ser Pro Ser Arg Leu Pro Gly Pro Ser Asp Thr Pro Ile
                20                  25                  30

Leu Pro Gln
        35
```

<210> SEQ ID NO 68
<211> LENGTH: 39
<212> TYPE: PRT
<213> ORGANISM: Artificial Sequence
<220> FEATURE:
<223> OTHER INFORMATION: liner and cleavage sequence

<400> SEQUENCE: 68

Asp Asp Pro Arg Phe Gln Asp Ser Ser Ser Lys Ala Pro Pro Pro
1               5                   10                  15

Ser Leu Pro Ser Pro Ser Arg Leu Pro Gly Pro Ser Asp Ser Gly Arg
            20                  25                  30

Arg Phe Lys Arg Arg Pro Arg
        35

<210> SEQ ID NO 69
<211> LENGTH: 26
<212> TYPE: PRT
<213> ORGANISM: Artificial Sequence
<220> FEATURE:
<223> OTHER INFORMATION: salmon alpha subunit loop 2

<400> SEQUENCE: 69

Phe Ser Arg Ala Tyr Pro Thr Pro Leu Arg Ser Lys Gln Thr Met Leu
1               5                   10                  15

Val Pro Lys Asn Ile Thr Ser Glu Ala Thr
            20                  25

<210> SEQ ID NO 70
<211> LENGTH: 26
<212> TYPE: PRT
<213> ORGANISM: Artificial Sequence
<220> FEATURE:
<223> OTHER INFORMATION: human alpha subunit loop 2

<400> SEQUENCE: 70

Phe Ser Arg Ala Tyr Pro Thr Pro Leu Arg Ser Lys Lys Thr Met Leu
1               5                   10                  15

Val Gln Lys Asn Val Thr Ser Glu Ser Thr
            20                  25

<210> SEQ ID NO 71
<211> LENGTH: 20
<212> TYPE: PRT
<213> ORGANISM: Cavia porcellus

<400> SEQUENCE: 71

Gly Thr Cys Arg Leu Ser Asn Ser Asp Cys Gly Gly Leu Arg Gly Gln
1               5                   10                  15

Pro Ser Ala Cys
            20

<210> SEQ ID NO 72
<211> LENGTH: 20
<212> TYPE: PRT
<213> ORGANISM: Homo sapiens

<400> SEQUENCE: 72

Ala Leu Cys Arg Arg Ser Thr Thr Asp Cys Gly Gly Pro Lys Asp His
1               5                   10                  15

Pro Leu Thr Cys
            20

<210> SEQ ID NO 73
<211> LENGTH: 20
<212> TYPE: PRT
<213> ORGANISM: Homo sapiens

<400> SEQUENCE: 73

Ala Leu Cys Arg Arg Ser Thr Thr Asp Cys Gly Gly Pro Lys Asp His
1               5                   10                  15

Pro Leu Thr Cys
            20

<210> SEQ ID NO 74
<211> LENGTH: 20
<212> TYPE: PRT
<213> ORGANISM: Macaca mulatta

<400> SEQUENCE: 74

Ala Leu Cys Arg Arg Ser Thr Ser Asp Cys Gly Gly Pro Lys Asp His
1               5                   10                  15

Pro Leu Ala Cys
            20

<210> SEQ ID NO 75
<211> LENGTH: 20
<212> TYPE: PRT
<213> ORGANISM: Callithrix jacchus

<400> SEQUENCE: 75

Gly Leu Cys Arg Arg Ser Tyr Ser Asp Cys Gly Ser Leu Arg Asn Glu
1               5                   10                  15

Pro Leu Gly Cys
            20

<210> SEQ ID NO 76
<211> LENGTH: 20
<212> TYPE: PRT
<213> ORGANISM: Aotus trivirgatus

<400> SEQUENCE: 76

Ala Leu Cys Arg Arg Ser Tyr Ser Asp Cys Gly Asn Leu Lys Ser Glu
1               5                   10                  15

Pro Leu Gly Cys
            20

<210> SEQ ID NO 77
<211> LENGTH: 20
<212> TYPE: PRT
<213> ORGANISM: Callicebus moloch

<400> SEQUENCE: 77

Gly Leu Cys Arg Arg Ser Tyr Ser Asp Cys Gly Ser Leu Arg Asn Glu
1               5                   10                  15

Pro Leu Gly Cys
            20

<210> SEQ ID NO 78
<211> LENGTH: 20
<212> TYPE: PRT
<213> ORGANISM: Colobus guereza

<400> SEQUENCE: 78

Gly Leu Cys Arg Arg Ser Thr Ser Asp Cys Gly Gly Pro Lys Asp His
1               5                   10                  15

-continued

Pro Leu Thr Cys
            20

<210> SEQ ID NO 79
<211> LENGTH: 20
<212> TYPE: PRT
<213> ORGANISM: Colobus guereza

<400> SEQUENCE: 79

Gly Leu Cys Arg Arg Ser Thr Ser Asp Cys Gly Gly Pro Lys Asp His
1               5                   10                  15

Pro Leu Thr Cys
            20

<210> SEQ ID NO 80
<211> LENGTH: 20
<212> TYPE: PRT
<213> ORGANISM: Colobus guereza

<400> SEQUENCE: 80

Gly Leu Cys Arg Arg Ser Thr Thr Asp Cys Gly Gly Pro Lys Asp His
1               5                   10                  15

Pro Leu Thr Cys
            20

<210> SEQ ID NO 81
<211> LENGTH: 20
<212> TYPE: PRT
<213> ORGANISM: Colobus guereza

<400> SEQUENCE: 81

Gly Leu Cys Arg Arg Ser Thr Thr Asp Cys Gly Gly Pro Lys Asp His
1               5                   10                  15

Pro Leu Thr Cys
            20

<210> SEQ ID NO 82
<211> LENGTH: 20
<212> TYPE: PRT
<213> ORGANISM: Macaca fascicularis

<400> SEQUENCE: 82

Gly Leu Cys Arg Arg Ser Thr Ser Asp Cys Gly Gly Pro Lys Asp His
1               5                   10                  15

Pro Leu Thr Cys
            20

<210> SEQ ID NO 83
<211> LENGTH: 20
<212> TYPE: PRT
<213> ORGANISM: Macaca fascicularis

<400> SEQUENCE: 83

Gly Leu Cys Arg Arg Ser Thr Ser Asp Cys Gly Gly Pro Lys Asp His
1               5                   10                  15

Pro Leu Thr Cys
            20

<210> SEQ ID NO 84
<211> LENGTH: 20
<212> TYPE: PRT
<213> ORGANISM: Macaca mulatta

<400> SEQUENCE: 84

Ala Leu Cys Arg Arg Ser Thr Ser Asp Cys Gly Gly Pro Lys Asp His
1               5                   10                  15

Pro Leu Thr Cys
            20

<210> SEQ ID NO 85
<211> LENGTH: 20
<212> TYPE: PRT
<213> ORGANISM: Macaca mulatta

<400> SEQUENCE: 85

Ala Leu Cys Arg Arg Ser Thr Ser Asp Cys Gly Gly Pro Lys Asp His
1               5                   10                  15

Pro Leu Thr Cys
            20

<210> SEQ ID NO 86
<211> LENGTH: 20
<212> TYPE: PRT
<213> ORGANISM: papio cynocephalus anubis

<400> SEQUENCE: 86

Ala Leu Cys Arg Arg Ser Thr Ser Asp Cys Gly Gly Pro Lys Asp His
1               5                   10                  15

Pro Leu Thr Cys
            20

<210> SEQ ID NO 87
<211> LENGTH: 20
<212> TYPE: PRT
<213> ORGANISM: Pongo pygmaeus

<400> SEQUENCE: 87

Ala Leu Cys Arg Arg Ser Thr Thr Asp Cys Gly Gly Pro Lys Asp His
1               5                   10                  15

Pro Leu Thr Cys
            20

<210> SEQ ID NO 88
<211> LENGTH: 20
<212> TYPE: PRT
<213> ORGANISM: Pongo pygmaeus

<400> SEQUENCE: 88

Ala Leu Cys Arg Arg Ser Thr Thr Asp Cys Gly Gly Pro Lys Asp His
1               5                   10                  15

Pro Leu Thr Cys
            20

<210> SEQ ID NO 89
<211> LENGTH: 20
<212> TYPE: PRT
<213> ORGANISM: Presbytis obscura

<400> SEQUENCE: 89

Gly Leu Cys Arg Arg Ser Thr Thr Asp Cys Gly Gly Pro Lys Asp His
1               5                   10                  15

Pro Leu Thr Cys
            20

<210> SEQ ID NO 90

```
<210> SEQ ID NO 90
<211> LENGTH: 20
<212> TYPE: PRT
<213> ORGANISM: Presbytis obscura

<400> SEQUENCE: 90

Gly Leu Cys Arg Arg Ser Thr Thr Asp Cys Gly Gly Pro Lys Asp His
1               5                   10                  15

Pro Leu Thr Cys
            20

<210> SEQ ID NO 91
<211> LENGTH: 20
<212> TYPE: PRT
<213> ORGANISM: Presbytis obscura

<400> SEQUENCE: 91

Gly Leu Cys Arg Arg Ser Thr Thr Asp Cys Gly Gly Pro Lys Asp His
1               5                   10                  15

Pro Leu Thr Cys
            20

<210> SEQ ID NO 92
<211> LENGTH: 20
<212> TYPE: PRT
<213> ORGANISM: Presbytis obscura

<400> SEQUENCE: 92

Gly Leu Cys Arg Arg Ser Thr Thr Asp Cys Gly Gly Pro Lys Asp His
1               5                   10                  15

Pro Leu Thr Cys
            20

<210> SEQ ID NO 93
<211> LENGTH: 20
<212> TYPE: PRT
<213> ORGANISM: Presbytis obscura

<400> SEQUENCE: 93

Gly Leu Cys Arg Arg Ser Thr Thr Asp Cys Gly Gly Pro Lys Asp His
1               5                   10                  15

Pro Leu Thr Cys
            20

<210> SEQ ID NO 94
<211> LENGTH: 20
<212> TYPE: PRT
<213> ORGANISM: Pongo pygmaeus

<400> SEQUENCE: 94

Ala Leu Cys Arg Arg Ser Thr Thr Asp Cys Gly Gly Pro Lys Asp His
1               5                   10                  15

Pro Leu Thr Cys
            20

<210> SEQ ID NO 95
<211> LENGTH: 20
<212> TYPE: PRT
<213> ORGANISM: Homo sapiens

<400> SEQUENCE: 95

Ala Leu Cys Arg Arg Ser Thr Thr Asp Cys Gly Gly Pro Lys Asp His
1               5                   10                  15

Pro Leu Thr Cys
```

```
<210> SEQ ID NO 96
<211> LENGTH: 20
<212> TYPE: PRT
<213> ORGANISM: Homo sapiens

<400> SEQUENCE: 96

Ala Leu Cys Arg Arg Ser Thr Thr Asp Cys Gly Gly Pro Lys Asp His
1               5                   10                  15

Pro Leu Thr Cys
            20

<210> SEQ ID NO 97
<211> LENGTH: 20
<212> TYPE: PRT
<213> ORGANISM: Coregonus autumnalis

<400> SEQUENCE: 97

Ile Lys Cys Lys Thr Asp Asn Thr Asp Cys Asp Arg Ile Ser Met Ala
1               5                   10                  15

Thr Pro Ser Cys
            20

<210> SEQ ID NO 98
<211> LENGTH: 20
<212> TYPE: PRT
<213> ORGANISM: Morone saxatilis

<400> SEQUENCE: 98

Thr Thr Cys Asn Thr Glu Asn Thr Asp Cys Gly Arg Phe Pro Glu Asp
1               5                   10                  15

Ile Pro Ser Cys
            20

<210> SEQ ID NO 99
<211> LENGTH: 20
<212> TYPE: PRT
<213> ORGANISM: Katsuwonus plelamis

<400> SEQUENCE: 99

Thr Val Cys Asn Thr Gly Asn Thr Tyr Cys Gly Arg Leu Pro Gly Tyr
1               5                   10                  15

Thr Pro Ser Cys
            20

<210> SEQ ID NO 100
<211> LENGTH: 20
<212> TYPE: PRT
<213> ORGANISM: Bovine

<400> SEQUENCE: 100

Ser Lys Cys Asp Ser Asp Ser Thr Asp Cys Thr Val Arg Gly Leu Gly
1               5                   10                  15

Pro Ser Tyr Cys
            20

<210> SEQ ID NO 101
<211> LENGTH: 20
<212> TYPE: PRT
<213> ORGANISM: Pagrus pagrus

<400> SEQUENCE: 101
```

```
Thr Val Cys Asp Thr Gly Asn Met Asp Cys Gly Arg Phe Pro Gly Asn
1               5                   10                  15

Ile Pro Lys Cys
            20

<210> SEQ ID NO 102
<211> LENGTH: 20
<212> TYPE: PRT
<213> ORGANISM: catfish

<400> SEQUENCE: 102

Ser Gln Cys Asn Thr Glu Ile Thr Asp Cys Gly Ala Phe Ser Met Gln
1               5                   10                  15

Pro Ser Ser Cys
            20

<210> SEQ ID NO 103
<211> LENGTH: 20
<212> TYPE: PRT
<213> ORGANISM: Mylopharyngodon piceus

<400> SEQUENCE: 103

Ser Lys Cys Asn Ser Asp Ile Ala Asp Cys Gly Val Leu Ser Gln Gln
1               5                   10                  15

Thr Ser Ser Cys
            20

<210> SEQ ID NO 104
<211> LENGTH: 20
<212> TYPE: PRT
<213> ORGANISM: Cyprinus carpio

<400> SEQUENCE: 104

Ser Lys Cys Asn Ser Asp Ile Thr Asp Cys Gly Ala Leu Ser Gln Gln
1               5                   10                  15

Thr Leu Ser Cys
            20

<210> SEQ ID NO 105
<211> LENGTH: 20
<212> TYPE: PRT
<213> ORGANISM: Ictalurus punctatus

<400> SEQUENCE: 105

Ser Gln Cys Asn Thr Glu Ile Thr Asp Cys Gly Ala Phe Ser Met Gln
1               5                   10                  15

Pro Ser Ser Cys
            20

<210> SEQ ID NO 106
<211> LENGTH: 20
<212> TYPE: PRT
<213> ORGANISM: Gallus gallus

<400> SEQUENCE: 106

Glu Thr Cys Asp Thr Asp Ser Thr Asp Cys Thr Val Arg Gly Leu Gly
1               5                   10                  15

Pro Ser Tyr Cys
            20

<210> SEQ ID NO 107
<211> LENGTH: 20
<212> TYPE: PRT
```

```
<213> ORGANISM: Anguilla anguilla

<400> SEQUENCE: 107

Ser Arg Cys Asn Thr Asn Ser Thr Asp Cys Gly Gln Leu Asn Thr Glu
1               5                   10                  15

Ala Ser Gly Cys
            20

<210> SEQ ID NO 108
<211> LENGTH: 20
<212> TYPE: PRT
<213> ORGANISM: Conger myriaster

<400> SEQUENCE: 108

Ser Arg Cys Asn Thr Asn Ser Thr Asp Cys Gly Gln Leu Asn Thr Glu
1               5                   10                  15

Ala Ser Gly Cys
            20

<210> SEQ ID NO 109
<211> LENGTH: 20
<212> TYPE: PRT
<213> ORGANISM: Anguilla japonica

<400> SEQUENCE: 109

Ser Lys Cys Asn Thr Asp Ser Thr Asp Cys Gly Pro Leu Asn Thr Glu
1               5                   10                  15

Val Ser Gly Cys
            20

<210> SEQ ID NO 110
<211> LENGTH: 20
<212> TYPE: PRT
<213> ORGANISM: Rana catesbeiana

<400> SEQUENCE: 110

Gly Arg Cys Asp Ser Glu Thr Thr Asp Cys Thr Val Arg Ala Leu Gly
1               5                   10                  15

Pro Thr Tyr Cys
            20

<210> SEQ ID NO 111
<211> LENGTH: 20
<212> TYPE: PRT
<213> ORGANISM: Rana ridibunda

<400> SEQUENCE: 111

Gly Arg Cys Asn Ser Glu Thr Thr Asp Cys Thr Val Arg Ala Leu Gly
1               5                   10                  15

Pro Thr Tyr Cys
            20

<210> SEQ ID NO 112
<211> LENGTH: 20
<212> TYPE: PRT
<213> ORGANISM: Fundulus heteroclitus

<400> SEQUENCE: 112

Ser Ala Cys Asn Thr Lys Asp Thr Tyr Cys Thr Arg Leu Tyr Ala His
1               5                   10                  15

Ile Pro Ser Cys
            20
```

```
<210> SEQ ID NO 113
<211> LENGTH: 20
<212> TYPE: PRT
<213> ORGANISM: Capra hircus

<400> SEQUENCE: 113

Gly Lys Cys Asp Arg Asp Ser Thr Asp Cys Thr Val Arg Gly Leu Gly
1               5                   10                  15

Pro Ser Tyr Cys
            20

<210> SEQ ID NO 114
<211> LENGTH: 20
<212> TYPE: PRT
<213> ORGANISM: Carassius auratus

<400> SEQUENCE: 114

Ser Lys Cys Asn Ser Asp Ile Thr Asp Cys Gly Val Leu Ser Gln Gln
1               5                   10                  15

Thr Leu Gly Cys
            20

<210> SEQ ID NO 115
<211> LENGTH: 20
<212> TYPE: PRT
<213> ORGANISM: Carassius auratus

<400> SEQUENCE: 115

Ser Lys Cys Asn Ser Asp Val Thr Asp Cys Gly Val Leu Ser Gln Gln
1               5                   10                  15

Thr Ile Ser Cys
            20

<210> SEQ ID NO 116
<211> LENGTH: 20
<212> TYPE: PRT
<213> ORGANISM: Trichogaster trichopterus

<400> SEQUENCE: 116

Thr Ala Cys Asn Ala Gly Asn Thr Tyr Cys Gly His Phe His Gly Tyr
1               5                   10                  15

Ile Pro Ser Cys
            20

<210> SEQ ID NO 117
<211> LENGTH: 20
<212> TYPE: PRT
<213> ORGANISM: Cavia porcellus

<400> SEQUENCE: 117

Gly Lys Cys Asp Ser Asp Ser Thr Asp Cys Thr Val Arg Gly Leu Gly
1               5                   10                  15

Pro Ser Tyr Cys
            20

<210> SEQ ID NO 118
<211> LENGTH: 20
<212> TYPE: PRT
<213> ORGANISM: Hippoglossus hippoglossus

<400> SEQUENCE: 118

Ser Ile Cys Asn Leu Asp Asp Thr Asp Cys Ser Pro Phe Pro Gly Asp
1               5                   10                  15
```

Ile Pro Gly Cys
            20

<210> SEQ ID NO 119
<211> LENGTH: 20
<212> TYPE: PRT
<213> ORGANISM: Equus caballus

<400> SEQUENCE: 119

Gly Lys Cys Asn Ser Asp Ser Thr Asp Cys Thr Val Arg Gly Leu Gly
1               5                   10                  15

Pro Ser Tyr Cys
            20

<210> SEQ ID NO 120
<211> LENGTH: 20
<212> TYPE: PRT
<213> ORGANISM: Homo sapiens

<400> SEQUENCE: 120

Gly Lys Cys Asp Ser Asp Ser Thr Asp Cys Thr Val Arg Gly Leu Gly
1               5                   10                  15

Pro Ser Tyr Cys
            20

<210> SEQ ID NO 121
<211> LENGTH: 20
<212> TYPE: PRT
<213> ORGANISM: Homo sapiens

<400> SEQUENCE: 121

Gly Lys Cys Asp Ser Asp Ser Thr Asp Cys Thr Val Arg Gly Leu Gly
1               5                   10                  15

Pro Ser Tyr Cys
            20

<210> SEQ ID NO 122
<211> LENGTH: 20
<212> TYPE: PRT
<213> ORGANISM: Salamandra salamandra

<400> SEQUENCE: 122

Gly Thr Cys His Thr Glu Thr Thr Asp Cys Thr Val Gly Gly Leu Gly
1               5                   10                  15

Pro Ser Tyr Cys
            20

<210> SEQ ID NO 123
<211> LENGTH: 20
<212> TYPE: PRT
<213> ORGANISM: Japanese crested ibis

<400> SEQUENCE: 123

Glu Thr Cys Asp Thr Asp Ser Thr Asp Cys Thr Val Arg Gly Leu Gly
1               5                   10                  15

Pro Ser Tyr Cys
            20

<210> SEQ ID NO 124
<211> LENGTH: 20
<212> TYPE: PRT
<213> ORGANISM: Monodelphis domestica -continued

```
<400> SEQUENCE: 124

Gly Ser Cys Asp Thr Asp Ser Thr Asp Cys Thr Val Arg Gly Leu Gly
1               5                   10                  15

Pro Ser Tyr Cys
            20

<210> SEQ ID NO 125
<211> LENGTH: 7
<212> TYPE: PRT
<213> ORGANISM: Macaca mulatta

<400> SEQUENCE: 125

Gly Lys Cys Asp Ser Asp Ser
1               5

<210> SEQ ID NO 126
<211> LENGTH: 20
<212> TYPE: PRT
<213> ORGANISM: Mus musculus

<400> SEQUENCE: 126

Gly Lys Cys Asp Ser Asp Ser Thr Asp Cys Thr Val Arg Gly Leu Gly
1               5                   10                  15

Pro Ser Tyr Cys
            20

<210> SEQ ID NO 127
<211> LENGTH: 20
<212> TYPE: PRT
<213> ORGANISM: Cynops pyrrhogaster

<400> SEQUENCE: 127

Gly Ala Cys Asp Thr Asp His Thr Asp Cys Thr Val Arg Gly Leu Gly
1               5                   10                  15

Pro Asn Tyr Cys
            20

<210> SEQ ID NO 128
<211> LENGTH: 20
<212> TYPE: PRT
<213> ORGANISM: Oncorhynchus masou

<400> SEQUENCE: 128

Ile Lys Cys Lys Thr Asp Asn Thr Asp Cys Asp Arg Lys Ser Met Ala
1               5                   10                  15

Thr Pro Ser Cys
            20

<210> SEQ ID NO 129
<211> LENGTH: 20
<212> TYPE: PRT
<213> ORGANISM: Rainbow Trout

<400> SEQUENCE: 129

Ile Lys Cys Lys Thr Asp Asn Thr Asp Cys Asp Arg Ile Ser Met Ala
1               5                   10                  15

Thr Pro Ser Cys
            20

<210> SEQ ID NO 130
<211> LENGTH: 20
<212> TYPE: PRT
<213> ORGANISM: Struthio camelus
```

<400> SEQUENCE: 130

Glu Thr Cys Asp Thr Asp Ser Thr Asp Cys Thr Val Arg Gly Leu Gly
1               5                   10                  15

Pro Ser Tyr Cys
            20

<210> SEQ ID NO 131
<211> LENGTH: 20
<212> TYPE: PRT
<213> ORGANISM: Ailuropoda melanoleuca

<400> SEQUENCE: 131

Gly Lys Cys Asp Ser Asp Ser Thr Asp Cys Thr Val Arg Gly Leu Gly
1               5                   10                  15

Pro Ser Tyr Cys
            20

<210> SEQ ID NO 132
<211> LENGTH: 20
<212> TYPE: PRT
<213> ORGANISM: Sus barbatus

<400> SEQUENCE: 132

Gly Lys Cys Asp Ser Asp Ser Thr Asp Cys Thr Val Arg Gly Leu Gly
1               5                   10                  15

Pro Ser Tyr Cys
            20

<210> SEQ ID NO 133
<211> LENGTH: 20
<212> TYPE: PRT
<213> ORGANISM: Trichosurus vulpecula

<400> SEQUENCE: 133

Gly Ser Cys Asp Thr Asp Ser Thr Asp Cys Thr Val Arg Gly Leu Gly
1               5                   10                  15

Pro Ser Tyr Cys
            20

<210> SEQ ID NO 134
<211> LENGTH: 20
<212> TYPE: PRT
<213> ORGANISM: Coturnix japonica

<400> SEQUENCE: 134

Glu Thr Cys Asp Thr Asp Ser Thr Asp Cys Thr Val Arg Gly Leu Gly
1               5                   10                  15

Pro Ser Tyr Cys
            20

<210> SEQ ID NO 135
<211> LENGTH: 20
<212> TYPE: PRT
<213> ORGANISM: Rattus rattus

<400> SEQUENCE: 135

Gly Lys Cys Asp Ser Asp Ser Thr Asp Cys Thr Val Arg Gly Leu Gly
1               5                   10                  15

Pro Ser Tyr Cys
            20

```
<210> SEQ ID NO 136
<211> LENGTH: 20
<212> TYPE: PRT
<213> ORGANISM: Oncorhynchus keta

<400> SEQUENCE: 136

Ile Lys Cys Lys Thr Asp Asn Thr Asp Cys Asp Arg Ile Ser Met Ala
1               5                   10                  15

Thr Pro Ser Cys
            20

<210> SEQ ID NO 137
<211> LENGTH: 20
<212> TYPE: PRT
<213> ORGANISM: Osmeridae

<400> SEQUENCE: 137

Thr Thr Cys Ser Ile Ala Ser Thr Glu Cys Asp Pro Met His Met Asp
1               5                   10                  15

Met Ala Ser Cys
            20

<210> SEQ ID NO 138
<211> LENGTH: 20
<212> TYPE: PRT
<213> ORGANISM: Salmo salar

<400> SEQUENCE: 138

Ile Lys Cys Glu Thr Asp Asn Thr Asp Cys Asp Arg Ile Ser Met Ala
1               5                   10                  15

Thr Pro Ser Cys
            20

<210> SEQ ID NO 139
<211> LENGTH: 20
<212> TYPE: PRT
<213> ORGANISM: Scyliorhinus canicula

<400> SEQUENCE: 139

Gly Met Cys Asn Thr Glu Thr Thr Asp Cys Thr Val Ser Ala Met Glu
1               5                   10                  15

Pro Thr His Cys
            20

<210> SEQ ID NO 140
<211> LENGTH: 20
<212> TYPE: PRT
<213> ORGANISM: Ovis aries

<400> SEQUENCE: 140

Gly Lys Cys Asp Arg Asp Ser Thr Asp Cys Thr Val Arg Gly Leu Gly
1               5                   10                  15

Pro Ser Tyr Cys
            20

<210> SEQ ID NO 141
<211> LENGTH: 20
<212> TYPE: PRT
<213> ORGANISM: Phodopus sungorus

<400> SEQUENCE: 141

Gly Lys Cys Asp Ser Asp Ser Thr Asp Cys Thr Val Arg Gly Leu Gly
1               5                   10                  15
```

```
Pro Ser Tyr Cys
            20

<210> SEQ ID NO 142
<211> LENGTH: 20
<212> TYPE: PRT
<213> ORGANISM: Acipenser baeri

<400> SEQUENCE: 142

Gly Gln Cys Ala Thr Asp Tyr Thr Asp Cys Gly Thr Leu Ser Leu Gly
1               5                   10                  15

Pro Ser Asp Cys
            20

<210> SEQ ID NO 143
<211> LENGTH: 20
<212> TYPE: PRT
<213> ORGANISM: Panthera tigris

<400> SEQUENCE: 143

Gly Lys Cys Asp Ser Asp Ser Thr Asp Cys Thr Val Gln Gly Leu Gly
1               5                   10                  15

Pro Ser Tyr Cys
            20

<210> SEQ ID NO 144
<211> LENGTH: 19
<212> TYPE: PRT
<213> ORGANISM: Tilapia mossambica

<400> SEQUENCE: 144

Thr Ala Cys Asn Ala Asn Thr Asp Cys Gly Thr Leu Ser Gly Tyr Ile
1               5                   10                  15

Pro Ser Cys

<210> SEQ ID NO 145
<211> LENGTH: 20
<212> TYPE: PRT
<213> ORGANISM: Bufo japonicus

<400> SEQUENCE: 145

Gly Arg Cys Asn Ser Glu Thr Thr Asp Cys Thr Val Arg Gly Leu Gly
1               5                   10                  15

Pro Thr His Cys
            20

<210> SEQ ID NO 146
<211> LENGTH: 19
<212> TYPE: PRT
<213> ORGANISM: Thunnus obesus

<400> SEQUENCE: 146

Thr Ala Cys Asn Thr Gly Asn Thr Tyr Cys Gly Arg Leu Pro Gly Tyr
1               5                   10                  15

Val Pro Ser

<210> SEQ ID NO 147
<211> LENGTH: 20
<212> TYPE: PRT
<213> ORGANISM: Chinemys reevesii

<400> SEQUENCE: 147

Glu Ser Cys Asp Thr Asp Asn Thr Asp Cys Thr Val Arg Gly Leu Gly
```

```
                1               5                  10                  15

Pro Ser Tyr Cys
            20

<210> SEQ ID NO 148
<211> LENGTH: 20
<212> TYPE: PRT
<213> ORGANISM: Danio rerio

<400> SEQUENCE: 148

Asn Gln Val Asn Ser Asp Thr Thr Asp Trp Gly Ala Ile Ser Pro Gln
1               5                   10                  15

Thr Thr Ser Cys
            20

<210> SEQ ID NO 149
<211> LENGTH: 20
<212> TYPE: PRT
<213> ORGANISM: Acanthopagrus latus

<400> SEQUENCE: 149

Gly Leu Cys Ala Met Asp Thr Ser Asp Cys Thr Phe Glu Ser Leu Gln
1               5                   10                  15

Pro Asn Phe Cys
            20

<210> SEQ ID NO 150
<211> LENGTH: 20
<212> TYPE: PRT
<213> ORGANISM: Ailuropoda melanoleuca

<400> SEQUENCE: 150

Gly Pro Cys Arg Leu Ser Asn Ser Asp Cys Gly Gly Pro Arg Ala Gln
1               5                   10                  15

Pro Leu Ala Cys
            20

<210> SEQ ID NO 151
<211> LENGTH: 20
<212> TYPE: PRT
<213> ORGANISM: Anguilla anguilla

<400> SEQUENCE: 151

Asn Leu Cys Thr Met Asp Thr Ser Asp Cys Ala Ile Gln Ser Leu Arg
1               5                   10                  15

Pro Asp Phe Cys
            20

<210> SEQ ID NO 152
<211> LENGTH: 19
<212> TYPE: PRT
<213> ORGANISM: Anguilla anguilla

<400> SEQUENCE: 152

Asn Leu Cys Thr Met Asp Thr Ser Asp Cys Ala Ile Gln Ser Leu Arg
1               5                   10                  15

Pro Asp Phe

<210> SEQ ID NO 153
<211> LENGTH: 20
<212> TYPE: PRT
<213> ORGANISM: Anguilla celebesensis
```

```
<400> SEQUENCE: 153

Asn Leu Cys Thr Met Asp Thr Ser Asp Cys Ala Ile Gln Ser Leu Arg
1               5                   10                  15

Pro Asp Phe Cys
            20

<210> SEQ ID NO 154
<211> LENGTH: 20
<212> TYPE: PRT
<213> ORGANISM: Anguilla marmorata

<400> SEQUENCE: 154

Asn Leu Cys Thr Met Asp Thr Ser Asp Cys Ala Ile Gln Ser Leu Arg
1               5                   10                  15

Pro Asp Phe Cys
            20

<210> SEQ ID NO 155
<211> LENGTH: 36
<212> TYPE: DNA
<213> ORGANISM: Coregonus autumnalis
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 155
srcysasnmt asthrsrasc ysthrgsrgn rascys                           36

<210> SEQ ID NO 156
<211> LENGTH: 20
<212> TYPE: PRT
<213> ORGANISM: Osmeridae

<400> SEQUENCE: 156

Asn Met Cys Thr Met Asp Thr Ser Asp Cys Thr Ile Gln Ser Leu Asn
1               5                   10                  15

Pro Asp Phe Cys
            20

<210> SEQ ID NO 157
<211> LENGTH: 20
<212> TYPE: PRT
<213> ORGANISM: Balaenoptera acutorostrata

<400> SEQUENCE: 157

Gly Pro Cys Arg Leu Ser Ser Ser Asx Cys Gly Pro Gly Arg Ala Glx
1               5                   10                  15

Pro Leu Ala Cys
            20

<210> SEQ ID NO 158
<211> LENGTH: 20
<212> TYPE: PRT
<213> ORGANISM: Morone saxatilis

<400> SEQUENCE: 158

Gly Arg Cys Ala Met Asp Thr Ser Asp Cys Thr Phe Glu Ser Leu Gln
1               5                   10                  15

Pro Asn Phe Cys
```

<210> SEQ ID NO 159
<211> LENGTH: 20
<212> TYPE: PRT
<213> ORGANISM: Morone saxatilis

<400> SEQUENCE: 159

Gly Arg Cys Ala Met Asp Thr Ser Asp Cys Thr Phe Glu Ser Leu Gln
1               5                   10                  15

Pro Asn Phe Cys
            20

<210> SEQ ID NO 160
<211> LENGTH: 20
<212> TYPE: PRT
<213> ORGANISM: Trichogaster trichopterus

<400> SEQUENCE: 160

Ser Arg Cys Val Met Asp Thr Ser Asp Cys Thr Phe Glu Ser Leu Gln
1               5                   10                  15

Pro Asp Phe Cys
            20

<210> SEQ ID NO 161
<211> LENGTH: 20
<212> TYPE: PRT
<213> ORGANISM: Katsuwonus plelamis

<400> SEQUENCE: 161

Gly Arg Cys Ala Met Asp Thr Ser Asp Cys Thr Phe Glu Ser Leu Gln
1               5                   10                  15

Pro Asp Phe Cys
            20

<210> SEQ ID NO 162
<211> LENGTH: 20
<212> TYPE: PRT
<213> ORGANISM: Bovine

<400> SEQUENCE: 162

Gly Pro Cys Arg Leu Ser Ser Thr Asp Cys Gly Gly Pro Arg Thr Gln
1               5                   10                  15

Pro Leu Ala Cys
            20

<210> SEQ ID NO 163
<211> LENGTH: 20
<212> TYPE: PRT
<213> ORGANISM: Bos taurus

<400> SEQUENCE: 163

Gly Ser Cys Arg Leu Ser Ser Thr Asp Cys Gly Gly Pro Arg Thr Gln
1               5                   10                  15

Pro Leu Ala Cys
            20

<210> SEQ ID NO 164
<211> LENGTH: 20
<212> TYPE: PRT
<213> ORGANISM: Canis familiaris

<400> SEQUENCE: 164

```
Gly Pro Cys Arg Leu Ser Asn Ser Asp Cys Gly Gly Pro Arg Ala Gln
1               5                   10                  15

Ser Leu Ala Cys
            20

<210> SEQ ID NO 165
<211> LENGTH: 20
<212> TYPE: PRT
<213> ORGANISM: Mylopharyngodon piceus

<400> SEQUENCE: 165

Ser Leu Cys Thr Met Asp Thr Ser Asp Cys Thr Ile Glu Ser Leu Gln
1               5                   10                  15

Pro Asp Tyr Cys
            20

<210> SEQ ID NO 166
<211> LENGTH: 20
<212> TYPE: PRT
<213> ORGANISM: Clarias gariepinus

<400> SEQUENCE: 166

Ser Leu Cys Thr Met Asp Thr Ser Asp Cys Thr Ile Glu Ser Leu Asn
1               5                   10                  15

Pro Asp Phe Cys
            20

<210> SEQ ID NO 167
<211> LENGTH: 20
<212> TYPE: PRT
<213> ORGANISM: Cyprinus carpio

<400> SEQUENCE: 167

Ser Leu Cys Thr Met Asp Thr Ser Asp Cys Thr Ile Glu Ser Leu Gln
1               5                   10                  15

Pro Asp Phe Cys
            20

<210> SEQ ID NO 168
<211> LENGTH: 20
<212> TYPE: PRT
<213> ORGANISM: Hypophthalmichthys molitrix

<400> SEQUENCE: 168

Ser Leu Cys Thr Met Asp Thr Ser Asp Cys Thr Ile Glu Ser Leu Gln
1               5                   10                  15

Pro Asp Tyr Cys
            20

<210> SEQ ID NO 169
<211> LENGTH: 20
<212> TYPE: PRT
<213> ORGANISM: Clarias gariepinus

<400> SEQUENCE: 169

Ser Leu Cys Thr Met Asp Thr Ser Asp Cys Thr Ile Glu Ser Leu Asn
1               5                   10                  15

Pro Asp Phe Cys
            20

<210> SEQ ID NO 170
<211> LENGTH: 20
<212> TYPE: PRT
```

```
<213> ORGANISM: Clarias gariepinus

<400> SEQUENCE: 170

Ser Leu Cys Thr Met Asp Thr Ser Asp Cys Thr Ile Glu Ser Leu Asn
1               5                   10                  15

Pro Asp Phe Cys
            20

<210> SEQ ID NO 171
<211> LENGTH: 20
<212> TYPE: PRT
<213> ORGANISM: Ceratotherium simum

<400> SEQUENCE: 171

Gly Pro Cys Arg Leu Ser Ser Ser Asp Cys Gly Gly Pro Arg Ala Gln
1               5                   10                  15

Pro Leu Ala Cys
            20

<210> SEQ ID NO 172
<211> LENGTH: 20
<212> TYPE: PRT
<213> ORGANISM: Ictalurus punctatus

<400> SEQUENCE: 172

Thr Leu Cys Thr Met Asp Thr Ser Asp Cys Thr Ile Glu Ser Leu Asn
1               5                   10                  15

Pro Asp Phe Cys
            20

<210> SEQ ID NO 173
<211> LENGTH: 20
<212> TYPE: PRT
<213> ORGANISM: Gallus gallus

<400> SEQUENCE: 173

Ala Arg Cys Pro Met Ala Thr Ser Asp Cys Thr Val Gln Gly Leu Gly
1               5                   10                  15

Pro Ala Phe Cys
            20

<210> SEQ ID NO 174
<211> LENGTH: 20
<212> TYPE: PRT
<213> ORGANISM: Ctenopharyngodon idella

<400> SEQUENCE: 174

Ser Leu Cys Thr Met Asp Thr Ser Asp Cys Thr Ile Glu Ser Leu Gln
1               5                   10                  15

Pro Asp Phe Cys
            20

<210> SEQ ID NO 175
<211> LENGTH: 20
<212> TYPE: PRT
<213> ORGANISM: Cynocephalus variegatus

<400> SEQUENCE: 175

Gly Pro Cys Arg Leu Ser Ser Ser Asp Cys Gly Gly Pro Arg Thr Gln
1               5                   10                  15

Pro Leu Ala Cys
            20
```

<210> SEQ ID NO 176
<211> LENGTH: 20
<212> TYPE: PRT
<213> ORGANISM: Daubentonia madagascariensis

<400> SEQUENCE: 176

Gly Ala Cys Arg Leu Ser Ser Asp Cys Gly Gly Pro Arg Ala Gln
1               5                   10                  15

Pro Phe Ala Cys
            20

<210> SEQ ID NO 177
<211> LENGTH: 20
<212> TYPE: PRT
<213> ORGANISM: Equus asinus

<400> SEQUENCE: 177

Gly Pro Cys Arg Leu Lys Thr Thr Asp Cys Gly Gly Pro Arg Asp His
1               5                   10                  15

Pro Leu Ala Cys
            20

<210> SEQ ID NO 178
<211> LENGTH: 20
<212> TYPE: PRT
<213> ORGANISM: Anguilla anguilla

<400> SEQUENCE: 178

Asn Leu Cys Thr Met Asp Thr Ser Asp Cys Ala Ile Gln Ser Leu Arg
1               5                   10                  15

Pro Asp Phe Cys
            20

<210> SEQ ID NO 179
<211> LENGTH: 20
<212> TYPE: PRT
<213> ORGANISM: Anguilla marmorata

<400> SEQUENCE: 179

Asn Leu Cys Thr Met Asp Thr Ser Asp Cys Ala Ile Gln Ser Leu Arg
1               5                   10                  15

Pro Asp Phe Cys
            20

<210> SEQ ID NO 180
<211> LENGTH: 20
<212> TYPE: PRT
<213> ORGANISM: Conger myriaster

<400> SEQUENCE: 180

Asn Leu Cys Thr Met Glu Thr Ser Asp Cys Thr Ile Gln Ser Leu Arg
1               5                   10                  15

Pro Asp Phe Cys
            20

<210> SEQ ID NO 181
<211> LENGTH: 20
<212> TYPE: PRT
<213> ORGANISM: Epinephelus coioides

<400> SEQUENCE: 181

Gly Arg Cys Ala Met Asp Thr Ser Asp Cys Thr Phe Glu Ser Leu Gln
1               5                   10                  15

```
Pro Asn Phe Cys
        20

<210> SEQ ID NO 182
<211> LENGTH: 20
<212> TYPE: PRT
<213> ORGANISM: Equus burchelli

<400> SEQUENCE: 182

Gly Pro Cys Arg Leu Lys Thr Thr Asp Cys Gly Gly Pro Arg Asp His
1               5                   10                  15

Pro Leu Ala Cys
        20

<210> SEQ ID NO 183
<211> LENGTH: 20
<212> TYPE: PRT
<213> ORGANISM: Felis catus

<400> SEQUENCE: 183

Gly Pro Cys Arg Leu Ser Ser Ser Asp Cys Gly Gly Pro Arg Ala Gln
1               5                   10                  15

Pro Leu Ala Cys
        20

<210> SEQ ID NO 184
<211> LENGTH: 20
<212> TYPE: PRT
<213> ORGANISM: Paralichthys olivaceus

<400> SEQUENCE: 184

Gly Arg Cys Ala Leu Asn Thr Ser Asp Cys Thr Phe Gln Ser Leu Gln
1               5                   10                  15

Pro Asp Phe Cys
        20

<210> SEQ ID NO 185
<211> LENGTH: 20
<212> TYPE: PRT
<213> ORGANISM: Rana catesbeiana

<400> SEQUENCE: 185

Asp Leu Cys Lys Met Asp Tyr Ser Asp Cys Thr Val Glu Ser Ser Glu
1               5                   10                  15

Pro Asp Val Cys
        20

<210> SEQ ID NO 186
<211> LENGTH: 20
<212> TYPE: PRT
<213> ORGANISM: Rana ridibunda

<400> SEQUENCE: 186

Asp Phe Cys Lys Met Asp Tyr Ser Asp Cys Thr Val Glu Ser Ser Glu
1               5                   10                  15

Pro Asp Val Cys
        20

<210> SEQ ID NO 187
<211> LENGTH: 20
<212> TYPE: PRT
<213> ORGANISM: Galago senegalensis
```

-continued

```
<400> SEQUENCE: 187

Gly Pro Cys Arg Leu Ser Ser Ser Asp Cys Gly Gly Pro Arg Ala Gln
1               5                   10                  15

Pro Leu Ala Cys
            20

<210> SEQ ID NO 188
<211> LENGTH: 20
<212> TYPE: PRT
<213> ORGANISM: Carassius auratus

<400> SEQUENCE: 188

Ser Leu Cys Thr Met Asp Thr Ser Asp Cys Thr Ile Glu Ser Leu Gln
1               5                   10                  15

Pro Asp Phe Cys
            20

<210> SEQ ID NO 189
<211> LENGTH: 20
<212> TYPE: PRT
<213> ORGANISM: Cavia porcellus

<400> SEQUENCE: 189

Gly Thr Cys Arg Leu Ser Asn Ser Asp Cys Gly Gly Leu Arg Gly Gln
1               5                   10                  15

Pro Ser Ala Cys
            20

<210> SEQ ID NO 190
<211> LENGTH: 20
<212> TYPE: PRT
<213> ORGANISM: Cavia porcellus

<400> SEQUENCE: 190

Gly Thr Cys Arg Leu Ser Asn Ser Asp Cys Gly Gly Leu Arg Gly Gln
1               5                   10                  15

Pro Ser Ala Cys
            20

<210> SEQ ID NO 191
<211> LENGTH: 20
<212> TYPE: PRT
<213> ORGANISM: Hippoglossus hippoglossus

<400> SEQUENCE: 191

Gly Arg Cys Ala Leu Asn Thr Ser Asp Cys Thr Phe Glu Ser Leu Gln
1               5                   10                  15

Pro Asp Phe Cys
            20

<210> SEQ ID NO 192
<211> LENGTH: 18
<212> TYPE: PRT
<213> ORGANISM: Phodopus sungorus

<400> SEQUENCE: 192

Gly Pro Cys Arg Leu Ser Thr Ser Asp Cys Gly Gly Pro Arg Thr Gln
1               5                   10                  15

Pro Met

<210> SEQ ID NO 193
<211> LENGTH: 20
```

```
<212> TYPE: PRT
<213> ORGANISM: Clupea pallasi

<400> SEQUENCE: 193

Ser Leu Cys Ser Met Asp Thr Ser Asp Cys Thr Ile Glu Ser Val Glu
1               5                   10                  15

Pro Asp Phe Cys
            20

<210> SEQ ID NO 194
<211> LENGTH: 20
<212> TYPE: PRT
<213> ORGANISM: Equus caballus

<400> SEQUENCE: 194

Gly Pro Cys Gln Ile Lys Thr Thr Asp Cys Gly Val Phe Arg Asp Gln
1               5                   10                  15

Pro Leu Ala Cys
            20

<210> SEQ ID NO 195
<211> LENGTH: 20
<212> TYPE: PRT
<213> ORGANISM: Equus caballus

<400> SEQUENCE: 195

Gly Pro Cys Gln Ile Lys Thr Thr Asp Cys Gly Val Phe Arg Asp Gln
1               5                   10                  15

Pro Leu Ala Cys
            20

<210> SEQ ID NO 196
<211> LENGTH: 20
<212> TYPE: PRT
<213> ORGANISM: Equus hemionus

<400> SEQUENCE: 196

Gly Pro Cys Arg Leu Lys Thr Thr Asp Cys Gly Gly Pro Arg Asp His
1               5                   10                  15

Pro Leu Ala Cys
            20

<210> SEQ ID NO 197
<211> LENGTH: 20
<212> TYPE: PRT
<213> ORGANISM: Homo sapiens

<400> SEQUENCE: 197

Gly Pro Cys Arg Arg Ser Thr Ser Asp Cys Gly Gly Pro Lys Asp His
1               5                   10                  15

Pro Leu Thr Cys
            20

<210> SEQ ID NO 198
<211> LENGTH: 20
<212> TYPE: PRT
<213> ORGANISM: Homo sapiens

<400> SEQUENCE: 198

Gly Pro Cys Arg Arg Ser Thr Ser Asp Cys Gly Gly Pro Lys Asp His
1               5                   10                  15

Pro Leu Thr Cys
            20
```

```
<210> SEQ ID NO 199
<211> LENGTH: 20
<212> TYPE: PRT
<213> ORGANISM: Macropus rufus

<400> SEQUENCE: 199

Gly Ser Cys Arg Leu Ser His Ser Asp Cys Gly Gly Pro Arg Ala Gln
1               5                   10                  15

Pro His Leu Cys
            20

<210> SEQ ID NO 200
<211> LENGTH: 20
<212> TYPE: PRT
<213> ORGANISM: Fundulus heteroclitus

<400> SEQUENCE: 200

Gly Gly Cys Ala Met Ala Thr Ser Asp Cys Thr Phe Glu Ser Leu Gln
1               5                   10                  15

Pro Asp Phe Cys
            20

<210> SEQ ID NO 201
<211> LENGTH: 20
<212> TYPE: PRT
<213> ORGANISM: Fundulus heteroclitus

<400> SEQUENCE: 201

Gly Gly Gly Ala Met Ala Thr Ser Asp Cys Thr Phe Glu Ser Leu Gln
1               5                   10                  15

Pro Asp Phe Cys
            20

<210> SEQ ID NO 202
<211> LENGTH: 20
<212> TYPE: PRT
<213> ORGANISM: Loris tardigradus

<400> SEQUENCE: 202

Gly Pro Cys Arg Leu Ser Ser Ser Asp Cys Gly Gly Pro Arg Ala Gln
1               5                   10                  15

Ala Leu Ala Cys
            20

<210> SEQ ID NO 203
<211> LENGTH: 20
<212> TYPE: PRT
<213> ORGANISM: Colobus guereza

<400> SEQUENCE: 203

Gly Pro Cys Arg Arg Ser Thr Ser Asp Cys Gly Gly Pro Lys Asp His
1               5                   10                  15

Pro Leu Thr Cys
            20

<210> SEQ ID NO 204
<211> LENGTH: 20
<212> TYPE: PRT
<213> ORGANISM: Macaca mulatta

<400> SEQUENCE: 204

Gly Pro Cys His Arg Ser Thr Ser Asp Cys Gly Gly Pro Lys Asp His
```

```
                    1               5                   10                  15

Pro Leu Thr Cys
            20

<210> SEQ ID NO 205
<211> LENGTH: 20
<212> TYPE: PRT
<213> ORGANISM: Presbytis obscura

<400> SEQUENCE: 205

Gly Pro Cys Arg Arg Ser Thr Ser Asp Cys Gly Gly Pro Arg Asp His
1               5                   10                  15

Pro Leu Thr Cys
            20

<210> SEQ ID NO 206
<211> LENGTH: 20
<212> TYPE: PRT
<213> ORGANISM: Monodelphis domestica

<400> SEQUENCE: 206

Gly Ser Cys Arg Leu Ser His Ser Asp Cys Gly Gly Pro Arg Ala Arg
1               5                   10                  15

Pro His Leu Cys
            20

<210> SEQ ID NO 207
<211> LENGTH: 20
<212> TYPE: PRT
<213> ORGANISM: Mus musculus

<400> SEQUENCE: 207

Gly Pro Cys Arg Leu Ser Ser Ser Asp Cys Gly Gly Pro Arg Thr Gln
1               5                   10                  15

Pro Met Ala Cys
            20

<210> SEQ ID NO 208
<211> LENGTH: 20
<212> TYPE: PRT
<213> ORGANISM: Cynops pyrrhogaster

<400> SEQUENCE: 208

Asn Met Cys Lys Met Asp Tyr Ser Asp Cys Thr Val Gln Ser Ile Gly
1               5                   10                  15

Pro Glu Phe Cys
            20

<210> SEQ ID NO 209
<211> LENGTH: 20
<212> TYPE: PRT
<213> ORGANISM: Struthio camelus

<400> SEQUENCE: 209

Ala Arg Cys Pro Met Ala Thr Ala Asp Cys Thr Val Ala Gly Leu Gly
1               5                   10                  15

Pro Ala Phe Cys
            20

<210> SEQ ID NO 210
<211> LENGTH: 20
<212> TYPE: PRT
<213> ORGANISM: Panthera tigris
```

```
<400> SEQUENCE: 210

Gly Pro Cys Arg Leu Ser Ser Ser Asp Cys Gly Gly Pro Arg Ala Gln
1               5                   10                  15

Pro Leu Ala Cys
            20

<210> SEQ ID NO 211
<211> LENGTH: 20
<212> TYPE: PRT
<213> ORGANISM: Paralichthys olivaceus

<400> SEQUENCE: 211

Gly Arg Cys Ala Leu Asn Thr Ser Asp Cys Thr Phe Gln Ser Leu Gln
1               5                   10                  15

Pro Asp Phe Cys
            20

<210> SEQ ID NO 212
<211> LENGTH: 20
<212> TYPE: PRT
<213> ORGANISM: porcine

<400> SEQUENCE: 212

Gly Pro Cys Arg Leu Ser Ser Ser Asp Cys Gly Gly Pro Arg Ala Gln
1               5                   10                  15

Pro Leu Ala Cys
            20

<210> SEQ ID NO 213
<211> LENGTH: 20
<212> TYPE: PRT
<213> ORGANISM: Pongo pygmaeus

<400> SEQUENCE: 213

Gly Leu Cys Arg Arg Ser Thr Ser Asp Cys Gly Gly Pro Lys Asp His
1               5                   10                  15

Pro Leu Thr Cys
            20

<210> SEQ ID NO 214
<211> LENGTH: 20
<212> TYPE: PRT
<213> ORGANISM: Trichosurus vulpecula

<400> SEQUENCE: 214

Gly Ser Cys Arg Leu Ser His Ser Asp Cys Gly Gly Pro Arg Ala Arg
1               5                   10                  15

Pro His Leu Cys
            20

<210> SEQ ID NO 215
<211> LENGTH: 20
<212> TYPE: PRT
<213> ORGANISM: Pteropus alecto

<400> SEQUENCE: 215

Gly Pro Cys Arg Leu Ser Ser Ser Asp Cys Gly Cys Pro Arg Ala Gln
1               5                   10                  15

Ser Leu Ala Cys
            20
```

-continued

```
<210> SEQ ID NO 216
<211> LENGTH: 20
<212> TYPE: PRT
<213> ORGANISM: Coturnix japonica

<400> SEQUENCE: 216

Ala Arg Cys Pro Ile Ala Thr Ser Asp Cys Thr Val Gln Gly Leu Gly
1               5                   10                  15

Pro Ala Phe Cys
            20

<210> SEQ ID NO 217
<211> LENGTH: 20
<212> TYPE: PRT
<213> ORGANISM: Oryctolagus cuniculus

<400> SEQUENCE: 217

Gly Pro Cys Arg Leu Ser Ser Ser Asp Cys Gly Gly Pro Arg Ala Glu
1               5                   10                  15

Pro Leu Ala Cys
            20

<210> SEQ ID NO 218
<211> LENGTH: 20
<212> TYPE: PRT
<213> ORGANISM: Rattus rattus

<400> SEQUENCE: 218

Gly Pro Cys Arg Leu Ser Ser Ser Asp Cys Gly Gly Pro Arg Thr Gln
1               5                   10                  15

Pro Met Thr Cys
            20

<210> SEQ ID NO 219
<211> LENGTH: 20
<212> TYPE: PRT
<213> ORGANISM: Ceratotherium simum

<400> SEQUENCE: 219

Gly Pro Cys Arg Leu Ser Ser Ser Asp Cys Gly Gly Pro Arg Ala Gln
1               5                   10                  15

Pro Leu Ala Cys
            20

<210> SEQ ID NO 220
<211> LENGTH: 20
<212> TYPE: PRT
<213> ORGANISM: Oncorhynchus keta

<400> SEQUENCE: 220

Ser Leu Cys Asn Met Asp Thr Ser Asp Cys Thr Ile Glu Ser Leu Gln
1               5                   10                  15

Pro Asp Phe Cys
            20

<210> SEQ ID NO 221
<211> LENGTH: 20
<212> TYPE: PRT
<213> ORGANISM: Oncorhynchus masou

<400> SEQUENCE: 221

Ser Leu Cys Asn Met Asp Thr Ser Asp Cys Thr Ile Glu Ser Leu Gln
1               5                   10                  15
```

-continued

Pro Asp Phe Cys
            20

<210> SEQ ID NO 222
<211> LENGTH: 20
<212> TYPE: PRT
<213> ORGANISM: Oncorhynchus tshawytscha

<400> SEQUENCE: 222

Ser Leu Cys Asn Met Asp Thr Ser Asp Cys Thr Ile Glu Ser Leu Gln
1               5                   10                  15

Pro Asp Phe Cys
            20

<210> SEQ ID NO 223
<211> LENGTH: 20
<212> TYPE: PRT
<213> ORGANISM: Pagrus pagrus

<400> SEQUENCE: 223

Gly Leu Cys Ala Met Asp Thr Ser Asp Cys Thr Phe Glu Ser Leu Glu
1               5                   10                  15

Pro Asn Phe Cys
            20

<210> SEQ ID NO 224
<211> LENGTH: 20
<212> TYPE: PRT
<213> ORGANISM: Scyliorhinus canicula

<400> SEQUENCE: 224

Asn Leu Cys Arg Met Asp Tyr Thr Asp Cys Thr Val Gln Ser Ile Lys
1               5                   10                  15

Pro Asp Phe Cys
            20

<210> SEQ ID NO 225
<211> LENGTH: 20
<212> TYPE: PRT
<213> ORGANISM: Ovis aries

<400> SEQUENCE: 225

Gly Pro Cys Arg Leu Ser Ser Thr Asp Cys Gly Gly Pro Arg Thr Gln
1               5                   10                  15

Pro Leu Ala Cys
            20

<210> SEQ ID NO 226
<211> LENGTH: 20
<212> TYPE: PRT
<213> ORGANISM: Ovis aries

<400> SEQUENCE: 226

Gly Pro Cys Arg Leu Ser Ser Thr Asp Cys Gly Gly Pro Arg Thr Gln
1               5                   10                  15

Pro Leu Ala Cys
            20

<210> SEQ ID NO 227
<211> LENGTH: 20
<212> TYPE: PRT
<213> ORGANISM: Ovis aries

<400> SEQUENCE: 227

Gly Pro Cys Arg Leu Ser Ser Thr Asp Cys Gly Gly Pro Arg Thr Gln
1               5                   10                  15

Pro Leu Ala Cys
            20

<210> SEQ ID NO 228
<211> LENGTH: 20
<212> TYPE: PRT
<213> ORGANISM: Acipenser baeri

<400> SEQUENCE: 228

Ser Leu Cys Arg Met Glu Ser Ser Asp Cys Thr Ile Gln Ser Val Gly
1               5                   10                  15

Pro Ser Asp Cys
            20

<210> SEQ ID NO 229
<211> LENGTH: 20
<212> TYPE: PRT
<213> ORGANISM: Acipenser baeri

<400> SEQUENCE: 229

Ser Leu Cys Arg Met Glu Ser Ser Asp Cys Thr Ile Gln Gly Val Gly
1               5                   10                  15

Pro Ser Asp Cys
            20

<210> SEQ ID NO 230
<211> LENGTH: 20
<212> TYPE: PRT
<213> ORGANISM: Tarsius bancanus

<400> SEQUENCE: 230

Gly Pro Cys Arg Leu Ser Ser Ser Asp Cys Gly Gly Pro Arg Ala Gln
1               5                   10                  15

Pro Leu Ala Cys
            20

<210> SEQ ID NO 231
<211> LENGTH: 20
<212> TYPE: PRT
<213> ORGANISM: Tilapia nilotica

<400> SEQUENCE: 231

Gly Arg Cys Ala Met Asp Thr Ser Asp Cys Thr Phe Glu Ser Met Gln
1               5                   10                  15

Pro Asp Phe Cys
            20

<210> SEQ ID NO 232
<211> LENGTH: 21
<212> TYPE: PRT
<213> ORGANISM: Bufo japonicus

<400> SEQUENCE: 232

Asp Leu Cys Lys Met Asp Tyr Ser Asp Cys Thr Val Glu Ser Ser Ser
1               5                   10                  15

Glu Pro Asp Val Cys
            20

<210> SEQ ID NO 233
<211> LENGTH: 21

```
<212> TYPE: PRT
<213> ORGANISM: Bufo japonicus

<400> SEQUENCE: 233

Asp Leu Cys Lys Met Asp Tyr Ser Asp Cys Thr Val Glu Ser Ser Ser
1               5                   10                  15

Glu Pro Asp Val Cys
            20

<210> SEQ ID NO 234
<211> LENGTH: 21
<212> TYPE: PRT
<213> ORGANISM: Bufo japonicus

<400> SEQUENCE: 234

Asp Leu Cys Lys Met Asp Tyr Ser Asp Cys Thr Val Glu Ser Ser Ser
1               5                   10                  15

Glu Pro Asp Val Cys
            20

<210> SEQ ID NO 235
<211> LENGTH: 20
<212> TYPE: PRT
<213> ORGANISM: Rainbow Trout

<400> SEQUENCE: 235

Ser Leu Cys Asn Met Asp Thr Ser Asp Cys Thr Ile Glu Ser Leu Gln
1               5                   10                  15

Pro Asp Phe Cys
            20

<210> SEQ ID NO 236
<211> LENGTH: 20
<212> TYPE: PRT
<213> ORGANISM: Thunnus obesus

<400> SEQUENCE: 236

Gly Arg Cys Ala Met Asp Thr Ser Asp Cys Thr Phe Glu Ser Leu Gln
1               5                   10                  15

Pro Asp Phe Cys
            20

<210> SEQ ID NO 237
<211> LENGTH: 20
<212> TYPE: PRT
<213> ORGANISM: Meleagris gallopavo

<400> SEQUENCE: 237

Ala Arg Cys Pro Ile Ala Thr Ser Asp Cys Thr Val Gln Gly Leu Gly
1               5                   10                  15

Pro Ala Phe Cys
            20

<210> SEQ ID NO 238
<211> LENGTH: 20
<212> TYPE: PRT
<213> ORGANISM: Chinemys reevesii

<400> SEQUENCE: 238

Ser Leu Cys Pro Met Asp Ser Ser Asp Cys Thr Val His Ser Ile Gly
1               5                   10                  15

Pro Asp Phe Cys
            20
```

```
<210> SEQ ID NO 239
<211> LENGTH: 20
<212> TYPE: PRT
<213> ORGANISM: Varecia variegata

<400> SEQUENCE: 239

Gly Ala Cys Arg Leu Ser Ser Ser Asp Cys Gly Gly Pro Arg Ala Gln
1               5                   10                  15

Pro Phe Ala Cys
            20

<210> SEQ ID NO 240
<211> LENGTH: 20
<212> TYPE: PRT
<213> ORGANISM: Physeter catodon

<400> SEQUENCE: 240

Gly Pro Cys Arg Leu Ser Ser Ser Asp Cys Gly Pro Gly Arg Ala Gln
1               5                   10                  15

Pro Leu Ala Cys
            20

<210> SEQ ID NO 241
<211> LENGTH: 20
<212> TYPE: PRT
<213> ORGANISM: Physeter catodon

<400> SEQUENCE: 241

Gly Pro Cys Arg Leu Ser Ser Ser Asp Cys Gly Pro Gly Arg Ala Gln
1               5                   10                  15

Pro Leu Ala Cys
            20

<210> SEQ ID NO 242
<211> LENGTH: 20
<212> TYPE: PRT
<213> ORGANISM: Xenopus laevis

<400> SEQUENCE: 242

Asn Gln Cys Lys Met Asp Tyr Ser Asp Cys Thr Val Gln Ser Ile Gly
1               5                   10                  15

Pro Asp Phe Cys
            20

<210> SEQ ID NO 243
<211> LENGTH: 20
<212> TYPE: PRT
<213> ORGANISM: Equus zebra

<400> SEQUENCE: 243

Gly Pro Cys Arg Leu Lys Thr Thr Asp Cys Gly Gly Pro Arg Asp His
1               5                   10                  15

Pro Leu Ala Cys
            20

<210> SEQ ID NO 244
<211> LENGTH: 20
<212> TYPE: PRT
<213> ORGANISM: Salmo salar

<400> SEQUENCE: 244

Ser Leu Cys Asn Met Asp Thr Ser Asp Cys Thr Ile Glu Ser Leu Gln
```

```
1               5                   10                  15

Pro Glu Phe Cys
            20

<210> SEQ ID NO 245
<211> LENGTH: 20
<212> TYPE: PRT
<213> ORGANISM: Muraenesox cinereus

<400> SEQUENCE: 245

Asn Leu Cys Thr Met Asp Thr Ser Asp Cys Ala Ile Gln Ser Leu Arg
1               5                   10                  15

Pro Asp Phe Cys
            20

<210> SEQ ID NO 246
<211> LENGTH: 20
<212> TYPE: PRT
<213> ORGANISM: Oncorhynchus keta

<400> SEQUENCE: 246

Ser Leu Cys Asn Met Asp Thr Ser Asp Cys Thr Ile Glu Ser Leu Gln
1               5                   10                  15

Pro Asp Phe Cys
            20

<210> SEQ ID NO 247
<211> LENGTH: 21
<212> TYPE: PRT
<213> ORGANISM: Salmo salar

<400> SEQUENCE: 247

Gly Thr Cys Asn Thr Asp Ser Asp Glu Cys Ala His Lys Ala Ser Ser
1               5                   10                  15

Gly Asp Gly Ala Arg
            20

<210> SEQ ID NO 248
<211> LENGTH: 20
<212> TYPE: PRT
<213> ORGANISM: Bovine

<400> SEQUENCE: 248

Gly Lys Cys Asn Thr Asp Tyr Ser Asp Cys Ile His Glu Ala Ile Lys
1               5                   10                  15

Thr Asn Tyr Cys
            20

<210> SEQ ID NO 249
<211> LENGTH: 21
<212> TYPE: PRT
<213> ORGANISM: Hypophthalmichthys nobilis

<400> SEQUENCE: 249

Ser Thr Cys Asn Thr His Ser Asp Glu Cys Ala His Lys Thr Ser Asn
1               5                   10                  15

Ala Ala Arg Lys Cys
            20

<210> SEQ ID NO 250
<211> LENGTH: 20
<212> TYPE: PRT
<213> ORGANISM: Gallus gallus
```

<400> SEQUENCE: 250

Gly Lys Cys Asn Thr Asp Tyr Ser Asp Cys Val His Glu Lys Val Arg
1               5                   10                  15

Thr Asn Tyr Cys
            20

<210> SEQ ID NO 251
<211> LENGTH: 21
<212> TYPE: PRT
<213> ORGANISM: Ctenopharyngodon idella

<400> SEQUENCE: 251

Ser Thr Cys Asn Thr His Ser Asp Glu Cys Ala His Lys Thr Ser Asn
1               5                   10                  15

Ala Ala Arg Lys Cys
            20

<210> SEQ ID NO 252
<211> LENGTH: 21
<212> TYPE: PRT
<213> ORGANISM: Cyprinus carpio

<400> SEQUENCE: 252

Ser Thr Cys Asn Thr His Ser Asp Glu Cys Ala His Arg Thr Ser Asn
1               5                   10                  15

Ala Gly Met Lys Cys
            20

<210> SEQ ID NO 253
<211> LENGTH: 20
<212> TYPE: PRT
<213> ORGANISM: Canis familiaris

<400> SEQUENCE: 253

Gly Lys Cys Asn Thr Asp Tyr Ser Asp Cys Ile His Glu Ala Ile Lys
1               5                   10                  15

Thr Asn Tyr Cys
            20

<210> SEQ ID NO 254
<211> LENGTH: 21
<212> TYPE: PRT
<213> ORGANISM: Anguilla anguilla

<400> SEQUENCE: 254

Arg Ala Cys Asp Pro Ala Arg Asp Glu Cys Thr His Arg Ala Ser Ala
1               5                   10                  15

Asp Gly Asp Arg Cys
            20

<210> SEQ ID NO 255
<211> LENGTH: 21
<212> TYPE: PRT
<213> ORGANISM: Anguilla anguilla

<400> SEQUENCE: 255

Arg Ala Cys Asp Pro Ala Arg Asp Glu Cys Thr His Arg Ala Ser Ala
1               5                   10                  15

Asp Gly Asp Arg Cys
            20

```
<210> SEQ ID NO 256
<211> LENGTH: 21
<212> TYPE: PRT
<213> ORGANISM: Carassius auratus

<400> SEQUENCE: 256

Ser Thr Cys Asn Thr Asn Ser Asp Glu Cys Ala His Lys Thr Asn Asn
1               5                   10                  15

Ala Gly Met Lys Cys
            20

<210> SEQ ID NO 257
<211> LENGTH: 21
<212> TYPE: PRT
<213> ORGANISM: Carassius auratus

<400> SEQUENCE: 257

Ser Thr Cys Asn Thr Asn Ser Asp Glu Cys Ala His Lys Thr Asn Asn
1               5                   10                  15

Ala Gly Met Lys Cys
            20

<210> SEQ ID NO 258
<211> LENGTH: 20
<212> TYPE: PRT
<213> ORGANISM: Phodopus sungorus

<400> SEQUENCE: 258

Gly Lys Cys Asn Thr Asp Tyr Ser Asp Cys Ile His Glu Ala Val Lys
1               5                   10                  15

Thr Asn Tyr Cys
            20

<210> SEQ ID NO 259
<211> LENGTH: 20
<212> TYPE: PRT
<213> ORGANISM: Equus caballus

<400> SEQUENCE: 259

Gly Lys Cys Asn Thr Asp Tyr Ser Asp Cys Ile His Glu Ala Ile Lys
1               5                   10                  15

Ala Asn Tyr Cys
            20

<210> SEQ ID NO 260
<211> LENGTH: 20
<212> TYPE: PRT
<213> ORGANISM: Homo sapiens

<400> SEQUENCE: 260

Gly Lys Cys Asn Thr Asp Tyr Ser Asp Cys Ile His Glu Ala Ile Lys
1               5                   10                  15

Thr Asn Tyr Cys
            20

<210> SEQ ID NO 261
<211> LENGTH: 20
<212> TYPE: PRT
<213> ORGANISM: Homo sapiens

<400> SEQUENCE: 261

Gly Lys Cys Asn Thr Asp Tyr Ser Asp Cys Ile His Glu Ala Ile Lys
1               5                   10                  15
```

-continued

Thr Asn Tyr Cys
         20

<210> SEQ ID NO 262
<211> LENGTH: 20
<212> TYPE: PRT
<213> ORGANISM: Homo sapiens

<400> SEQUENCE: 262

Gly Lys Cys Asn Thr Asp Tyr Ser Asp Cys Thr His Glu Ala Val Lys
1               5                   10                  15

Thr Asn Tyr Cys
         20

<210> SEQ ID NO 263
<211> LENGTH: 20
<212> TYPE: PRT
<213> ORGANISM: Japanese crested ibis

<400> SEQUENCE: 263

Gly Lys Cys Asn Thr Asp Tyr Ser Asp Cys Val His Glu Lys Val Arg
1               5                   10                  15

Thr Asn Tyr Cys
         20

<210> SEQ ID NO 264
<211> LENGTH: 20
<212> TYPE: PRT
<213> ORGANISM: Lama glama

<400> SEQUENCE: 264

Gly Lys Cys Asp Thr Asp Tyr Ser Asp Cys Ile Gln Glu Ala Val Lys
1               5                   10                  15

Met Asn Tyr Cys
         20

<210> SEQ ID NO 265
<211> LENGTH: 20
<212> TYPE: PRT
<213> ORGANISM: Monodelphis domestica

<400> SEQUENCE: 265

Gly Lys Cys Asn Thr Asp Tyr Ile Asp Cys Ile His Glu Ser Val Thr
1               5                   10                  15

Thr Asn Tyr Cys
         20

<210> SEQ ID NO 266
<211> LENGTH: 20
<212> TYPE: PRT
<213> ORGANISM: Mus musculus

<400> SEQUENCE: 266

Gly Lys Cys Asn Thr Asp Asn Ser Asp Cys Ile His Glu Ala Val Arg
1               5                   10                  15

Thr Asn Tyr Cys
         20

<210> SEQ ID NO 267
<211> LENGTH: 20
<212> TYPE: PRT
<213> ORGANISM: porcine

<400> SEQUENCE: 267

Gly Lys Cys Asp Thr Asp Tyr Ser Asp Cys Ile His Glu Ala Ile Lys
1               5                   10                  15

Thr Asn Tyr Cys
            20

<210> SEQ ID NO 268
<211> LENGTH: 20
<212> TYPE: PRT
<213> ORGANISM: porcine

<400> SEQUENCE: 268

Gly Lys Cys Asn Thr Asp Tyr Ser Asp Cys Ile His Glu Ala Ile Lys
1               5                   10                  15

Thr Asn Tyr Cys
            20

<210> SEQ ID NO 269
<211> LENGTH: 22
<212> TYPE: PRT
<213> ORGANISM: Oncorhynchus mykiss

<400> SEQUENCE: 269

Gly Thr Cys Asn Thr Asp Ser Asp Glu Cys Ala His Lys Ala Ser Ser
1               5                   10                  15

Gly Asp Gly Ala Arg Cys
            20

<210> SEQ ID NO 270
<211> LENGTH: 20
<212> TYPE: PRT
<213> ORGANISM: Rattus rattus

<400> SEQUENCE: 270

Gly Lys Cys Asn Thr Asp Tyr Ser Asp Cys Thr His Glu Ala Val Lys
1               5                   10                  15

Thr Asn Tyr Cys
            20

<210> SEQ ID NO 271
<211> LENGTH: 20
<212> TYPE: PRT
<213> ORGANISM: Rattus rattus

<400> SEQUENCE: 271

Gly Lys Cys Asn Thr Asp Tyr Ser Asp Cys Thr His Glu Ala Val Lys
1               5                   10                  15

Thr Asn Tyr Cys
            20

<210> SEQ ID NO 272
<211> LENGTH: 20
<212> TYPE: PRT
<213> ORGANISM: Rattus rattus

<400> SEQUENCE: 272

Gly Lys Cys Asn Thr Asp Tyr Ser Asp Cys Thr His Glu Ala Val Lys
1               5                   10                  15

Thr Asn Tyr Cys
            20

<210> SEQ ID NO 273
<211> LENGTH: 20

<212> TYPE: PRT
<213> ORGANISM: Acipenser baeri

<400> SEQUENCE: 273

Arg Lys Cys Asn Thr Asp Tyr Ser Glu Cys Thr Met Glu Pro Leu Arg
1               5                   10                  15

Pro Ser Pro Cys
            20

<210> SEQ ID NO 274
<211> LENGTH: 20
<212> TYPE: PRT
<213> ORGANISM: Bufo japonicus

<400> SEQUENCE: 274

Glu Lys Cys Asn Thr Glu Tyr Ile Asp Cys Val Gln Asp Arg Ile Asp
1               5                   10                  15

Ser Asn Tyr Cys
            20

<210> SEQ ID NO 275
<211> LENGTH: 20
<212> TYPE: PRT
<213> ORGANISM: Bufo japonicus

<400> SEQUENCE: 275

Glu Lys Cys Asn Thr Glu Tyr Ile Asp Cys Val Gln Asp Arg Ile Asp
1               5                   10                  15

Ser Asn Tyr Cys
            20

<210> SEQ ID NO 276
<211> LENGTH: 20
<212> TYPE: PRT
<213> ORGANISM: Bufo japonicus

<400> SEQUENCE: 276

Glu Lys Cys Asn Thr Glu Tyr Ile Asp Cys Val Gln Asp Arg Ile Asp
1               5                   10                  15

Ser Asn Tyr Cys
            20

<210> SEQ ID NO 277
<211> LENGTH: 96
<212> TYPE: PRT
<213> ORGANISM: Ovine

<400> SEQUENCE: 277

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
                20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
        50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

```
<210> SEQ ID NO 278
<211> LENGTH: 96
<212> TYPE: PRT
<213> ORGANISM: porcine

<400> SEQUENCE: 278

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

<210> SEQ ID NO 279
<211> LENGTH: 96
<212> TYPE: PRT
<213> ORGANISM: Bovine

<400> SEQUENCE: 279

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95

<210> SEQ ID NO 280
<211> LENGTH: 96
<212> TYPE: PRT
<213> ORGANISM: Equus asinus

<400> SEQUENCE: 280

Phe Pro Asp Gly Glu Phe Thr Thr Gln Asp Cys Pro Glu Cys Lys Leu
1               5                   10                  15

Arg Glu Asn Lys Tyr Phe Phe Lys Leu Gly Val Pro Ile Tyr Gln Cys
            20                  25                  30

Lys Gly Cys Cys Phe Ser Arg Ala Tyr Pro Thr Pro Ala Arg Ser Arg
        35                  40                  45

Lys Thr Met Leu Val Pro Lys Asn Ile Thr Ser Glu Ser Thr Cys Cys
    50                  55                  60

Val Ala Lys Ala Phe Ile Arg Val Thr Val Met Gly Asn Ile Lys Leu
65                  70                  75                  80

Glu Asn His Thr Gln Cys Tyr Cys Ser Thr Cys Tyr His His Lys Ile
                85                  90                  95

<210> SEQ ID NO 281
<211> LENGTH: 95
```

```
<212> TYPE: PRT
<213> ORGANISM: Carassius auratus

<400> SEQUENCE: 281

Tyr Pro Arg Asn Tyr Met Asn Asn Phe Gly Cys Glu Glu Cys Glu Leu
1               5                   10                  15

Lys Glu Asn Asn Ile Phe Ser Lys Pro Gly Ala Pro Val Tyr Gln Cys
            20                  25                  30

Met Gly Cys Cys Phe Ser Arg Ala Tyr Pro Thr Pro Leu Arg Ser Lys
        35                  40                  45

Lys Thr Met Leu Val Pro Lys Asn Ile Thr Ser Glu Ala Thr Cys Cys
    50                  55                  60

Val Ala Lys Glu Val Lys Arg Val Leu Val Asn Asp Val Arg Leu Val
65                  70                  75                  80

Asn His Thr Asp Cys His Cys Ser Thr Cys Tyr Tyr His Lys Ser
                85                  90                  95

<210> SEQ ID NO 282
<211> LENGTH: 91
<212> TYPE: PRT
<213> ORGANISM: Scaphirhynchus albus

<400> SEQUENCE: 282

Tyr Pro Asp Gly Asp Met Thr Gln Gly Cys His Glu Cys Lys Leu Lys
1               5                   10                  15

Leu Asn Lys Tyr Phe Ser Thr Pro Arg Asp Gln Ile Phe Gln Cys Val
            20                  25                  30

Gly Cys Cys Phe Ser Arg Ala Tyr Pro Thr Pro Leu Arg Ser Lys Lys
        35                  40                  45

Thr Met Leu Val Pro Lys Asn Ile Thr Ser Glu Ala Thr Cys Cys Val
    50                  55                  60

Ala Lys Asp Phe Lys Arg Ile Asn Gln Lys Leu Glu Asn His Thr Asp
65                  70                  75                  80

Cys His Cys Ser Thr Cys Tyr Tyr His Lys Thr
                85                  90

<210> SEQ ID NO 283
<211> LENGTH: 94
<212> TYPE: PRT
<213> ORGANISM: Danio rerio

<400> SEQUENCE: 283

Tyr Ser Arg Asn Asp Val Ser Asn Tyr Gly Cys Glu Glu Cys Lys Leu
1               5                   10                  15

Lys Met Asn Glu Arg Phe Ser Lys Pro Gly Ala Pro Val Tyr Gln Cys
            20                  25                  30

Val Gly Cys Cys Phe Ser Arg Ala Tyr Pro Thr Pro Leu Arg Ser Lys
        35                  40                  45

Lys Thr Met Leu Val Pro Lys Asn Ile Thr Ser Glu Ala Thr Cys Cys
    50                  55                  60

Val Ala Lys Glu Ser Lys Met Val Ala Thr Asn Ile Pro Leu Tyr Asn
65                  70                  75                  80

His Thr Asp Cys His Cys Ser Thr Cys Tyr Tyr His Lys Ser
                85                  90

<210> SEQ ID NO 284
<211> LENGTH: 92
<212> TYPE: PRT
<213> ORGANISM: catfish
```

```
<400> SEQUENCE: 284

Tyr Pro Asn Asn Asp Phe Gly Cys Glu Cys Lys Leu Lys Glu Asn
1               5                   10                  15

Asn Ile Phe Ser Lys Pro Gly Ala Pro Val Tyr Gln Cys Met Gly Cys
            20                  25                  30

Cys Phe Ser Arg Ala Tyr Pro Thr Pro Leu Arg Ser Lys Lys Thr Met
        35                  40                  45

Leu Val Pro Lys Asn Ile Thr Ser Glu Ala Thr Cys Cys Val Ala Lys
    50                  55                  60

Glu Val Lys Arg Val Ile Val Asn Asp Val Lys Leu Val Asn His Thr
65                  70                  75                  80

Asp Cys His Cys Ser Thr Cys Tyr Tyr His Lys Phe
                85                  90

<210> SEQ ID NO 285
<211> LENGTH: 95
<212> TYPE: PRT
<213> ORGANISM: salmon I

<400> SEQUENCE: 285

Tyr Pro Asn Ser Asp Met Thr Asn Val Gly Cys Glu Glu Cys Lys Leu
1               5                   10                  15

Lys Glu Asn Lys Leu Phe Ser Asn Pro Gly Ala Pro Val Tyr Gln Cys
            20                  25                  30

Thr Gly Cys Cys Phe Ser Arg Ala Tyr Pro Thr Pro Leu Gln Ser Lys
        35                  40                  45

Lys Ala Met Leu Val Pro Lys Asn Ile Thr Ser Glu Ala Thr Cys Cys
    50                  55                  60

Val Ala Lys Glu Gly Glu Arg Val Val Asp Asn Ile Lys Leu Thr
65                  70                  75                  80

Asn His Thr Glu Cys Trp Cys Asn Thr Cys Tyr His His Lys Ser
                85                  90                  95

<210> SEQ ID NO 286
<211> LENGTH: 92
<212> TYPE: PRT
<213> ORGANISM: Salmon II

<400> SEQUENCE: 286

Tyr Pro Asn Ser Asp Lys Thr Asn Met Gly Cys Glu Glu Cys Thr Leu
1               5                   10                  15

Lys Pro Asn Thr Ile Phe Pro Asn Ile Met Gln Cys Thr Gly Cys Cys
            20                  25                  30

Phe Ser Arg Ala Tyr Pro Thr Pro Leu Arg Ser Lys Gln Thr Met Leu
        35                  40                  45

Val Pro Lys Asn Ile Thr Ser Glu Ala Thr Cys Cys Val Ala Lys Glu
    50                  55                  60

Gly Glu Arg Val Thr Thr Lys Asp Gly Phe Pro Val Thr Asn His Thr
65                  70                  75                  80

Glu Cys His Cys Ser Thr Cys Tyr Tyr His Lys Ser
                85                  90
```